United States Patent
Srivastava et al.

(10) Patent No.: US 10,081,842 B2
(45) Date of Patent: Sep. 25, 2018

(54) PROSTATE CANCER GENE EXPRESSION PROFILES

(71) Applicant: The Henry M. Jackson Foundation for the Advancement of Military Medicine, Inc., Bethesda, MD (US)

(72) Inventors: Shiv K. Srivastava, Potomac, MD (US); Gyorgy Petrovics, Bethesda, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 375 days.

(21) Appl. No.: 14/419,861

(22) PCT Filed: Aug. 6, 2013

(86) PCT No.: PCT/US2013/053836
§ 371 (c)(1),
(2) Date: Feb. 5, 2015

(87) PCT Pub. No.: WO2014/025810
PCT Pub. Date: Feb. 13, 2014

(65) Prior Publication Data
US 2015/0176078 A1    Jun. 25, 2015

Related U.S. Application Data

(60) Provisional application No. 61/680,633, filed on Aug. 7, 2012.

(51) Int. Cl.
*C12Q 1/68* (2018.01)
*C12Q 1/6886* (2018.01)
*G01N 33/574* (2006.01)

(52) U.S. Cl.
CPC ..... *C12Q 1/6886* (2013.01); *G01N 33/57434* (2013.01); *C12Q 2600/118* (2013.01); *C12Q 2600/158* (2013.01); *G01N 2800/60* (2013.01)

(58) Field of Classification Search
None
See application file for complete search history.

(56) References Cited

U.S. PATENT DOCUMENTS

| | | |
|---|---|---|
| 2008/0131883 A1 | 6/2008 | Adams et al. |
| 2009/0170075 A1 | 7/2009 | Petrovics et al. |
| 2010/0215638 A1 | 8/2010 | Iljin et al. |
| 2010/0261617 A1 | 10/2010 | Poustka et al. |
| 2011/0136683 A1 | 6/2011 | Davicioni |
| 2011/0224089 A1 | 9/2011 | Ried et al. |
| 2011/0236903 A1 | 9/2011 | McClelland et al. |
| 2011/0294684 A1 | 12/2011 | Baty et al. |
| 2012/0039811 A1 | 2/2012 | Admon et al. |
| 2012/0046185 A1 | 2/2012 | Chan et al. |
| 2012/0157344 A1 | 6/2012 | Rosenfeld et al. |
| 2012/0178642 A1 | 7/2012 | Salomon et al. |
| 2012/0184454 A1 | 7/2012 | Kalady et al. |

FOREIGN PATENT DOCUMENTS

WO    2008/067065 A2    6/2008

OTHER PUBLICATIONS

Handbook of Chemistry and Physics, 49th Edition, 1968, Weast (ed.), The Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Extended International Search Report dated Mar. 17, 2016 from European Patent Application No. 13827277.8, pp. 1-9.
Brassell et al., "The center for prostate disease research (CPDR): A multidisciplinary approach to translational research", Urologic Oncology, Sep. 1, 2009, vol. 27, No. 5, pp. 562-569.
Vainio et al., "Arachidonic Acid Pathway Members PLA2G7, HPGD, EPHX2, and CYP4F8 Identified as Putative Novel Therapeutic Targets in Prostate Cancer", Feb. 1, 2011, vol. 178, No. 2, pp. 525-536.
International Search Report dated Nov. 27, 2013 from International Application No. PCT/US2013/053836, pp. 1-9.

* cited by examiner

*Primary Examiner* — James Martinell
(74) *Attorney, Agent, or Firm* — MH2 Technology Law Group, LLP

(57) ABSTRACT

The present disclosure provides gene expression profiles that are associated with prostate cancer. The gene expression profiles can be used to detect prostate cancer cells in a sample and to distinguish between well differentiated (WD) prostate cancer and poorly differentiated (PD) prostate cancer. Also provided is an array comprising oligonucleotide probes for detecting the unique gene signature associated with WD and/or PD prostate cancer.

11 Claims, 13 Drawing Sheets
Specification includes a Sequence Listing.

SEQUENCE LISTING

<160> NUMBER OF SEQ ID NOS: 51

<210> SEQ ID NO 1
<211> LENGTH: 3352
<212> TYPE: DNA

<213> ORGANISM: Homo sapiens

<400> SEQUENCE: 1

| | | | | | |
|---|---|---|---|---|---|
| ggggcgtggc | gccggggatt | gggagggctt | cttgcaggct | gctgggctgg | ggctaagggc | 60 |
| tgctcagttt | ccttcagcgg | ggcactggga | agcgccatgg | cactgcaggg | catctcggtc | 120 |
| gtggagctgt | ccggcctggc | cccgggcccg | ttctgtgcta | tggtcctggc | tgacttcggg | 180 |
| gcgcgtgtgg | tacgcgtgga | ccggcccggc | tcccgctacg | acgtgagccg | cttgggccgg | 240 |
| ggcaagcgct | cgctagtgct | ggacctgaag | cagccgcggg | gagccgccgt | gctgcggcgt | 300 |
| ctgtgcaagc | ggtcggatgt | gctgctgag | cccttccgcc | gcggtgtcat | ggagaaactc | 360 |
| cagctgggcc | cagagattct | gcagcgggaa | aatccaaggc | ttatttatgc | caggctgagt | 420 |
| ggatttggcc | agtcaggaag | cttctgccgg | ttagctggcc | acgatatcaa | ctatttggct | 480 |
| tgtcaggtg | ttctctcaaa | aattggcaga | agtggtgaga | atccgtatgc | cccgctgaat | 540 |
| ctcctggctg | actttgctgg | tggtggcctt | atgtgtgcac | tggcattat | aatggctctt | 600 |
| tttgaccgca | cacgcactgg | caaggtcag | gtcattgatg | caaatatggt | ggaaggaaca | 660 |
| gcatatttaa | gttcttttct | gtggaaaact | cagaaattga | gtctgtggga | agcacctcga | 720 |
| ggacagaaca | tgttggatgg | tggagcacct | ttctatacga | cttacaggac | agcagatggg | 780 |
| gaattcatgg | ctgttggagc | aatagaaccc | cagttctacg | agctgctgat | caaaggactt | 840 |
| ggactaaagt | ctgatgaact | tcccaatcag | atgagcatgg | atgattggcc | agaaatgaag | 900 |
| aagaagtttg | cagatgtatt | tgcagagaag | acgaaggcag | agtggtgtca | aatctttgac | 960 |
| ggcacagatg | cctgtgtgac | tccggttctg | acttttgagg | aggttgttca | tcatgatcac | 1020 |
| aacaaggaac | ggggctcgtt | tatccaccagt | gaggagcagg | acgtgagccc | ccgccctgca | 1080 |
| cctctgctgt | taaacacccc | agccatccct | tctttcaaaa | gggatccttt | cataggagaa | 1140 |
| cacactgagg | agatacttga | agaatttgga | ttcagccgcg | aagagattta | tcagcttaac | 1200 |
| tcagataaaa | tcattgaaag | taataaggta | aaagctagtc | tctaacttcc | aggcccacgg | 1260 |
| ctcaagtgaa | tttgaatact | gcatttacag | tgtagagtaa | cacataacat | tgtatgcatg | 1320 |
| gaaacatgga | ggaacagtat | tacagtgtcc | taccactcta | atcaagaaaa | gaattacaga | 1380 |
| ctctgattct | acagtgatga | ttgaattcta | aaaatggtta | tcattagggc | ttttgattta | 1440 |
| taaaactttg | ggtacttata | ctaaattatg | gtagttattc | tgccttccag | tttgcttgat | 1500 |
| atatttgttg | atattaagat | tcttgactta | tattttgaat | gggttctagt | gaaaaggaa | 1560 |
| tgatatattc | ttgaagacat | cgatatacat | ttatttacac | tcttgattct | acaatgtaga | 1620 |
| aaatgaggaa | atgccacaaa | ttgtatggtg | ataaaagtca | cgtgaaacag | agtgattggt | 1680 |
| tgcatccagg | cctttgtct | tggtgttcat | gatctccctc | taagcacatt | ccaaactta | 1740 |
| gcaacagtta | tcacactttg | taatttgcaa | agaaaagttt | cacctgtatt | gaatcagaat | 1800 |
| gccttcaact | gaaaaaaaca | tatccaaaat | aatgaggaaa | tgtgttggct | cactacgtag | 1860 |
| agtccagagg | gacagtcagt | tttagggttg | cctgtatcca | gtaactcggg | gcctgtttcc | 1920 |
| ccgtgggtct | ctgggctgtc | agctttcctt | tctccatgtg | tttgatttct | cctcaggctg | 1980 |
| gtagcaagtt | ctggatctta | tacccaacac | acagcaacat | ccagaaataa | agatctcagg | 2040 |
| accccccagc | aagtcgtttt | tgtgtctcct | tggactgagtt | aagttacaag | cctttcttat | 2100 |
| acctgtcttt | gacaaagaag | acgggattgt | ctttacataa | aaccagcctg | ctcctggagc | 2160 |
| ttccctggac | tcaacttcct | aaaggcatgt | gaggaagggg | tagattccac | aatctaatcc | 2220 |
| gggtgccatc | agagtagagg | gagtagagaa | tggatgttgg | gtaggccatc | aataaggtcc | 2280 |

```
attctgcgca gtatctcaac tgccgttcaa caatcgcaag aggaaggtgg agcaggtttc    2340
ttcatcttac agttgagaaa acagagactc agaagggctt cttagttcat gtttcccttc    2400
gcgcctcagt gattttttca tggtggctta ggccaaaaga aatatctaac cattcaattt    2460
ataaataatt aggtccccaa cgaattaaat attatgtcct accaacttat tagctgcttg    2520
aaaaatataa tacacataaa taaaaaaata tattttcat ttctatttca ttgttaatca    2580
caactactta ctaaggagat gtatgcacct attggacact gtgcaacttc tcacctggaa    2640
tgagattgga cactgctgcc ctcattttct gctccatgtt ggtgtccata tagtacttga    2700
ttttttatca gatggcctgg aaaacccagt ctcacaaaaa tatgaaatta tcagaaggat    2760
tatagtgcaa tcttatgttg aaagaatgaa ctacctcact agtagttcac gtgatgtctg    2820
acagatgttg agtttcattg tgtttgtgtg ttcaaatttt taaatattct gagatactct    2880
tgtgaggtca ctctaatgcc ctgggtgcct tggcacagtt ttagaaatac cagttgaaaa    2940
tatttgctca ggaatatgca actaggaagg ggcagaatca gaatttaagc tttcatattc    3000
tagccttcag tcttgttctt caaccatttt taggaacttt cccataaggt tatgttttcc    3060
agcccaggca tggaggatca cttgaggcca agagttcgag accagcctgg ggaacttggc    3120
tggacctccg tttctacgaa ataaaaataa aaaaattatc caggtatggt ggtgtgtgcc    3180
tgtagtccta tctactcaag ggtgggggcag gaggatcact tgagcccagg aatttgaggc    3240
cacagtgaat taggattgca ccactgcact ctagcccagg caacagaaca agaacctgtc    3300
tctaaataaa taaataaaaa taataataat aaaaagatg ttttccctac aa              3352

<210> SEQ ID NO 2
<211> LENGTH: 4945
<212> TYPE: DNA
<213> ORGANISM: Homo sapiens

<400> SEQUENCE: 2
ttcatttccc agacttagca caatctcatc cgctctaaac aacctcatca aaactacttt      60
ctggtcagag agaagcaata attattatta acatttatta acgatcaata aacttgatcg     120
cattatggcc agcactatta aggaagcctt atcagttgtg agtgaggacc agtcgttgtt     180
tgagtgtgcc tacggaacgc cacacctggc taagacagag atgaccgcgt cctcctccag     240
cgactatgga cagacttcca agatgagccc acgcgtccct cagcaggatt ggctgtctca     300 accccccagcc agggtcacca tcaaaatgga atgtaaccct agccaggtga atggctcaag     360
gaactctcct gatgaatgca gtgtggccaa aggcgggaag atggtgggca gcccagacac     420
cgttgggatg aactacggca gctacatgga ggagaagcac atgccacccc caaacatgac     480
cacgaacgag cgcagagtta tcgtgccagc agatcctacg ctatggagta cagaccatgt     540
gcggcagtgg ctggagtggg cggtgaaaga atatggcctt ccagacgtca acatcttgtt     600
attccagaac atcgatggga aggaactgtg caagatgacc aaggacgact tccagaggct     660 caccccccagc tacaacgccg acatccttct ctcacatctc cactacctca gagagactcc     720
tcttccacat ttgacttcag atgatgttga taaagcctta caaaactctc acggttaat      780 gcatgctaga aacacagggg gtgcagcttt tatttcccca aatacttcag tatatcctga     840
agctacgcaa agaattacaa ctaggccaga tttaccatat gagcccccca ggagatcagc     900
ctggaccggt cacggccacc ccacgcccca gtcgaaagct gctcaaccat ctccttccac     960
agtgcccaaa actgaagacc agcgtcctca gttagatcct tatcagattc ttggaccaac    1020
```

```
aagtagccgc cttgcaaatc caggcagtgg ccagatccag ctttggcagt tcctcctgga    1080
gctcctgtcg gacagctcca actccagctg catcacctgg gaaggcacca acggggagtt    1140
caagatgacg gatcccgacg aggtggcccg gcgctggggga gagcggaaga gcaaacccaa    1200
catgaactac gataagctca gccgcgccct ccgttactac tatgacaaga acatcatgac    1260
caaggtccat gggaagcgct acgcctacaa gttcgacttc cacgggatcg cccaggccct    1320
ccagccccac cccccggagt catctctgta caagtacccc tcagacctcc cgtacatggg    1380
ctcctatcac gcccacccac agaagatgaa ctttgtggcg ccccacccte cagccctccc    1440 cgtgacatct tccagttttt ttgctgcccc aaacccatac tggaattcac caactggggg    1500 tatataccccc aacactaggc tccccaccag ccatatgcct tctcatctgg gcacttacta    1560
ctaaagacct ggcggaggct tttcccatca gcgtgcattc accagcccat cgccacaaac    1620
tctatcggag aacatgaatc aaaagtgcct caagaggaat gaaaaaagct ttactggggc    1680
tggggaagga agccggggaa gagatccaaa gactcttggg agggagttac tgaagtctta    1740
ctacagaaat gaggaggatg ctaaaaatgt cacgaatatg gacatatcat ctgtggactg    1800
accttgtaaa agacagtgta tgtagaagca tgaagtctta aggacaaagt gccaaagaaa    1860
gtggtcttaa gaaatgtata aacttttagag tagagtttgg aatcccacta atgcaaactg    1920
ggatgaaact aaagcaatag aaacaacaca gttttgacct aacataccgt ttataatgcc    1980
attttaagga aaactacctg tatttaaaaa tagaaacata tcaaaacaa gagaaaagac    2040 acgagagaga ctgtggccca tcaacagacg ttgatatgca actgcatggc atgtgctgtt    2100
ttggttgaaa tcaaatacat tccgtttgat ggacagctgt cagctttctc aaactgtgaa    2160
gatgacccaa agtttccaac tcctttacag tattaccggg actatgaact aaaaggtggg    2220
actgaggatg tgtatagagt gagcgtgtga ttgtagacag aggggtgaag aaggaggagg    2280
aagaggcaga gaaggaggag accagggctg ggaaagaaac ttctcaagca atgaagactg    2340
gactcaggac atttggggac tgtgtacaat gagttatgga gactcgaggg ttcatgcagt    2400
cagtgttata ccaaacccag tgttaggaga aaggacacag cgtaatggag aaaggggaag    2460
tagtagaatt cagaaacaaa aatgcgcatc tctttctttg tttgtcaaat gaaaattta    2520 actggaattg tctgatattt aagagaaaca ttcaggacct catcattatg tgggggcttt    2580
gttctccaca gggtcaggta agagatggcc ttcttggctg ccacaatcag aaatcacgca    2640
ggcattttgg gtaggcggcc tccagttttc ctttgagtcg cgaacgctgt gcgtttgtca    2700
gaatgaagta tacaagtcaa tgttttttccc ccttttttata taataattat ataacttatg    2760
catttataca ctacgagttg atctcggcca gccaaagaca cacgacaaaa gagacaatcg    2820
atataatgtg gccttgaatt ttaactctgt atgcttaatg tttacaatat gaagttatta    2880
gttcttagaa tgcagaatgt atgtaataaa ataagcttgg cctagcatgg caaatcagat    2940
ttatacagga gtctgcattt gcactttttt tagtgactaa agttgcttaa tgaaaacatg    3000
tgctgaatgt tgtggatttt gtgttataat ttactttgtc caggaacttg tgcaagggag    3060
agccaaggaa ataggatgtt tggcacccaa atggcgtcag cctctccagg tccttcttgc    3120
ctcccctcct gtcttttatt tctagcccct tttggaacag aaggacccg ggtttcacat    3180 tggagcctcc atatttatgc ctggaatgga aagaggccta tgaagctggg gttgtcattg    3240
agaaattcta gttcagcacc tggtcacaaa tcacccttaa ttcctgctat gattaaaata    3300
catttgttga acagtgaaca agctaccact cgtaaggcaa actgtattat tactggcaaa    3360
taaagcgtca tggatagctg caatttctca ctttacagaa acaagggata acgtctagat    3420
```

```
ttgctgcggg gtttctcttt caggagctct cactaggtag acagctttag tcctgctaca    3480
tcagagttac ctgggcactg tggcttggga ttcactagcc ctgagcctga tgttgctggc    3540
tatcccttga agacaatgtt tatttccata atctagagtc agtttccctg ggcatctttt    3600
cttttgaatca caaatgctgc caaccttggt ccaggtgaag gcaactcaaa aggtgaaaat    3660
acaaggtgac cgtgcgaagg cgctagccga aacatcttag ctgaataggt ttctgaactg    3720
gccctttca tagctgtttc agggcctgtt ttttcacgt tgcagtcctt ttgctatgat    3780
tatgtgaagt tgccaaacct ctgtgctgtg gatgttttgg cagtgggctt tgaagtcggc    3840
aggacacgat taccaatgct cctgacaccc cgtgtcattt ggattagacg gagcccaacc    3900
atccatcatt ttgcagcagc ctgggaaggc ccacaaagtg cccgtatctc cttagggaaa    3960
ataaataaat acaatcatga aagctggcag ttaggctgac ccaaactgtg ctaatggaaa    4020
agatcagtca ttttattttt ggaatgcaaa gtcaagacac acctacattc ttcatagaaa    4080
tacacattta cttggataat cactcagttc tctcttcaag actgtctcat gagcaagatc    4140
ataaaaacaa gacatgatta tcatattcaa ttttaacaga tgttttccat tagatccctc    4200
aaccctccac ccccagtcca ggttattagc aagtcttatg agcaactggg ataattttgg    4260
ataacatgat aatactgagt tccttcaaat acataattct taaattgttt caaaatggca    4320
ttaactctct gttactgttg taatctaatt ccaaagcccc ctccaggtca tattcataat    4380
tgcatgaacc tttttctctct gttgtccct gtctcttggc ttgccctgat gtatactcag    4440
actcctgtac aatcttactc ctgctggcaa gagatttgtc ttcttttctt gtcttcaatt    4500
ggctttcggg ccttgtatgt ggtaaaatca ccaaatcaca gtcaagactg tgttttttgtt    4560
cctagtttga tgcccttatg tcccggaggg gttcacaaag tgctttgtca ggactgctgc    4620
agttagaagg ctcactgctt ctcctaagcc ttctgcacag atgtggcacc tgcaacccag    4680
gagcaggagc cggaggagct gccctctgac agcaggtgca gcagagatgg ctacagctca    4740
ggagctggga aggtgatggg gcacagggaa agcacagatg ttctgcagcg ccccaaagtg    4800
acccattgcc tggagaaaga gaagaaaata tttttttaaaa agctagttta tttagcttct    4860
cattaattca ttcaaataaa gtcgtgaggt gactaattag agaataaaaa ttactttgga    4920
ctactcaaaa ataccaccaaa aaaaa                                         4945
```

<210> SEQ ID NO 3
<211> LENGTH: 5042
<212> TYPE: DNA
<213> ORGANISM: Homo sapiens

<400> SEQUENCE: 3

```
gttttcactt ggtcggaatg gggagagtgt gcaagagatc gctgcgggac aggttcctag      60
agatcgctcc gggacggtcg tgacggcccc cgagggacat gagagaagag gagcggcgct    120
caggttattc caggatcttt ggagacccga ggaaagccgt gttgaccaaa agcaagacaa    180
atgactcaca gagaaaaaag atggcagaac caagggcaac taaagccgtc aggttctgaa    240
cagctggtag atgggctggc ttactgaagg acatgattca gactgtcccg gacccagcag    300
ctcatatcaa ggaagcctta tcagttgtga gtgaggacca gtcgttgttt gagtgtgcct    360
acggaacgcc acacctggct aagacagaga tgaccgcgtc ctcctccagc gactatggac    420
agacttccaa gatgagccca cgcgtccctc agcaggattg gctgtctcaa cccccagcca    480
gggtcaccat caaaatggaa tgtaacccta gccaggtgaa tggctcaagg aactctcctg    540
```

```
atgaatgcag tgtggccaaa ggcgggaaga tggtgggcag cccagacacc gttgggatga      600
actacggcag ctacatggag gagaagcaca tgccaccccc aaacatgacc acgaacgagc      660
gcagagttat cgtgccagca gatcctacgc tatggagtac agaccatgtg cggcagtggc      720
tggagtgggc ggtgaaagaa tatggccttc cagacgtcaa catcttgtta ttccagaaca      780
tcgatgggaa ggaactgtgc aagatgacca aggacgactt ccagaggctc acccccagct      840
acaacgccga catccttctc tcacatctcc actacctcag agagactcct cttccacatt      900
tgacttcaga tgatgttgat aaagccttac aaaactctcc acggttaatg catgctagaa      960
acacagattt accatatgag ccccccagga gatcagcctg gaccggtcac ggccacccca     1020
cgccccagtc gaaagctgct caaccatctc cttccacagt gcccaaaact gaagaccagc     1080
gtcctcagtt agatccttat cagattcttg gaccaacaag tagccgcctt gcaaatccag     1140
gcagtggcca gatccagctt tggcagttcc tcctggagct cctgtcggac agctccaact     1200
ccagctgcat cacctgggaa ggcaccaacg gggagttcaa gatgacggat cccgacgagg     1260
tggcccggcg ctggggagag cggaagagca acccaacat gaactacgat aagctcagcc     1320
gcgccctccg ttactactat gacaagaaca tcatgaccaa ggtccatggg aagcgctacg     1380
cctacaagtt cgacttccac gggatcgccc aggccctcca gccccacccc cggagtcat     1440 ctctgtacaa gtacccctca gacctcccgt acatgggctc ctatcacgcc cacccacaga     1500
agatgaactt tgtggcgccc cacctccag ccctccccgt gacatcttcc agttttttg      1560 ctgccccaaa cccatactgg aattcaccaa ctgggggtat ataccccaac actaggctcc     1620
ccaccagcca tatgccttct catctgggca cttactacta aagacctggc ggaggctttt     1680
cccatcagcg tgcattcacc agcccatcgc cacaaactct atcggagaac atgaatcaaa     1740
agtgcctcaa gaggaatgaa aaaagcttta ctggggctgg ggaaggaagc cggggaagag     1800
atccaaagac tcttgggagg gagttactga agtcttacta cagaaatgag gaggatgcta     1860
aaaatgtcac gaatatggac atatcatctg tggactgacc ttgtaaaaga cagtgtatgt     1920
agaagcatga agtcttaagg acaaagtgcc aaagaaagtg gtcttaagaa atgtataaac     1980
tttagagtag agtttggaat cccactaatg caaactggga tgaaactaaa gcaatagaaa     2040
caacacagtt ttgacctaac ataccgttta taatgccatt ttaaggaaaa ctacctgtat     2100
ttaaaaatag aaacatatca aaaacaagag aaaagacacg agagagactg tggcccatca     2160
acagacgttg atatgcaact gcatggcatg tgctgttttg gttgaaatca aatacattcc     2220
gtttgatgga cagctgtcag ctttctcaaa ctgtgaagat gacccaaagt ttccaactcc     2280
tttacagtat taccgggact atgaactaaa aggtgggact gaggatgtgt atagagtgag     2340
cgtgtgattg tagacagagg ggtgaagaag gaggaggaag aggcagagaa ggaggagacc     2400
agggctggga agaaaacttc tcaagcaatg aagactggac tcaggacatt tggggactgt     2460
gtacaatgag ttatggagac tcgagggttc atgcagtcag tgttatacca aacccagtgt     2520
taggagaaag gacacagcgt aatggagaaa ggggaagtag tagaattcag aaacaaaaat     2580
gcgcatctct ttctttgttt gtcaaatgaa aatttaact ggaattgtct gatatttaag      2640
agaaacattc aggacctcat cattatgtgg gggctttgtt ctccacaggg tcaggtaaga     2700
gatggccttc ttggctgcca caatcagaaa tcacgcaggc attttgggta ggcggcctcc     2760
agttttcctt tgagtcgcga acgctgtgcg tttgtcagaa tgaagtatac aagtcaatgt     2820 ttttcccccct ttttatataa taattatata acttatgcat ttatacacta cgagttgatc     2880
tcggccagcc aaagacacac gacaaaagag acaatcgata taatgtggcc ttgaatttta     2940
```

-continued

```
actctgtatg cttaatgttt acaatatgaa gttattagtt cttagaatgc agaatgtatg    3000
taataaaata agcttggcct agcatggcaa atcagattta tacaggagtc tgcatttgca    3060 cttttttag tgactaaagt tgcttaatga aaacatgtgc tgaatgttgt ggattttgtg     3120
ttataattta ctttgtccag gaacttgtgc aagggagagc caaggaaata ggatgttgg     3180 cacccaaatg gcgtcagcct ctccaggtcc ttcttgcctc ccctcctgtc ttttatttct    3240 agccccttt ggaacagaag gaccccgggt tcacattgg agcctccata tttatgcctg      3300
gaatggaaag aggcctatga agctggggtt gtcattgaga aattctagtt cagcacctgg    3360
tcacaaatca cccttaattc ctgctatgat taaaatacat tgttgaaca gtgaacaagc     3420 taccactcgt aaggcaaact gtattattac tggcaaataa agcgtcatgg atagctgcaa    3480
tttctcactt tacagaaaca agggataacg tctagatttg ctgcggggtt tctcttttcag   3540 gagctctcac taggtagaca gctttagtcc tgctacatca gagttacctg gcactgtgg    3600 cttgggattc actagccctg agcctgatgt tgctggctat cccttgaaga caatgtttat    3660
ttccataatc tagagtcagt ttccctgggc atcttttctt tgaatcacaa atgctgccaa    3720
ccttggtcca ggtgaaggca actcaaaagg tgaaaataca aggtgaccgt gcgaaggcgc    3780
tagccgaaac atcttagctg aataggtttc tgaactggcc cttttcatag ctgtttcagg    3840
gcctgttttt ttcacgttgc agtccttttg ctatgattat gtgaagttgc caaacctctg    3900
tgctgtggat gttttggcag tgggctttga agtcggcagg acacgattac caatgctcct    3960
gacaccccgt gtcatttgga ttagacgag cccaaccatc catcattttg cagcagcctg     4020
ggaaggccca caaagtgccc gtatctcctt agggaaaata aataaataca atcatgaaag    4080
ctggcagtta ggctgaccca aactgtgcta atggaaaaga tcagtcattt ttattttgga    4140
atgcaaagtc aagacacacc tacattcttc atagaaatac acatttactt ggataatcac    4200
tcagttctct cttcaagact gtctcatgag caagatcata aaaacaagac atgattatca    4260
tattcaattt taacagatgt tttccattag atccctcaac cctccacccc cagtccaggt    4320
tattagcaag tcttatgagc aactgggata attttggata acatgataat actgagttcc    4380
ttcaaataca taattcttaa attgtttcaa aatggcatta actctctgtt actgttgtaa    4440
tctaattcca aagcccctc caggtcatat tcataattgc atgaacctttt tctctctgtt    4500 tgtccctgtc tcttggcttg ccctgatgta tactcagact cctgtacaat cttactcctg    4560
ctggcaagag atttgtcttc ttttcttgtc ttcaattggc tttcgggcct tgtatgtggt    4620
aaaatcacca aatcacagtc aagactgtgt ttttgttcct agtttgatgc ccttatgtcc    4680 cggagggtt cacaaagtgc tttgtcagga ctgctgcagt tagaaggctc actgcttctc     4740
ctaagccttc tgcacagatg tggcacctgc aacccaggag caggagccgg aggagctgcc    4800
ctctgacagc aggtgcagca gagatggcta cagctcagga gctgggaagg tgatggggca    4860
cagggaaagc acagatgttc tgcagcgccc caaagtgacc cattgcctgg agaaagagaa    4920
gaaaatattt tttaaaaagc tagtttattt agcttctcat taattcattc aaataaagtc    4980
gtgaggtgac taattagaga ataaaaatta ctttggacta ctcaaaaata caccaaaaaa    5040
aa                                                                   5042
```

<210> SEQ ID NO 4
<211> LENGTH: 1460
<212> TYPE: DNA
<213> ORGANISM: Homo sapiens

<400> SEQUENCE: 4

```
cccccgaggg acatgagaga agaggagcgg cgctcaggtt attccaggat ctttggagac    60
ccgaggaaag ccgtgttgac caaaagcaag acaaatgact cacagagaaa aaagatggca   120
gaaccaaggg caactaaagc cgtcaggttc tgaacagctg gtagatgggc tggcttactg   180
aaggacatga ttcagactgt cccggaccca gcagctcata tcaaggaagc cttatcagtt   240
gtgagtgagg accagtcgtt gtttgagtgt gcctacggaa cgccacacct ggctaagaca   300
gagatgaccg cgtcctcctc cagcgactat ggacagactt ccaagatgag cccacgcgtc   360
cctcagcagg attggctgtc tcaaccccca gccagggtca ccatcaaaat ggaatgtaac   420
cctagccagg tgaatggctc aaggaactct cctgatgaat gcagtgtggc caaaggcggg   480
aagatggtgg gcagcccaga caccgttggg atgaactacg gcagctacat ggaggagaag   540
cacatgccac ccccaaacat gaccacgaac gagcgcagag ttatcgtgcc agcagatcct   600
acgctatgga gtacagacca tgtgcggcag tggctggagt gggcggtgaa agaatatggc   660
cttccagacg tcaacatctt gttattccag aacatcgatg gaaggaact gtgcaagatg   720
accaaggacg acttccagag gctcaccccc agctacaacg ccgacatcct tctctcacat   780
ctccactacc tcagagagac tcctcttcca catttgactt cagatgatgt tgataaagcc   840
ttacaaaact ctccacggtt aatgcatgct agaaacacag gggtgcagc ttttattttc   900
ccaaatactt cagtatatcc tgaagctacg caaagaatta caactaggcc aggtacgaaa   960
acacccctgt gtgatctctt cattgagaga catcccagat gtcctgctga gatccgtgcc  1020
ctaagtcacg tgatacaaag agagctgatc ccggagctga gccagtccc agacagtctt  1080
attctgcctc tgttgatttg gagactaaat ccactcaaac catttcattc aaagaccaca  1140
ctaaaggaat taagagcaga ttagcccttt aactagcttt tcagaaagac agatgggcaa  1200
agaaggcatc ctggatgcct ggcagttagg aataggccga cttttgaact aacagaagga  1260
tctgtccctc ctcggggaa gagcacaaaa caaggacact ccccagattc acagtgaccg  1320
attatcagta tgtcacaaga agccagtctt gcagagcaga agcatgcaac cagtagtatt  1380
tacatctgaa tcttactgcc tgtcctccaa atgatttaat taggtaataa atttacatgc  1440
cattcatgca aaaaaaaaa                                                1460
```

<210> SEQ ID NO 5
<211> LENGTH: 2147
<212> TYPE: DNA
<213> ORGANISM: Homo sapiens

<400> SEQUENCE: 5

```
gatttgtaag tttacctgtt gcagccaata gcagggccat tcagccagc cagcactgga    60
tactatctgg ccagaagtag caaagcagct cttatttgaa aaaccactgg gttccgagtt   120
cattactaca ggaaaaactg ttctcttctg tggcacagag aaccctgctt caaagcagaa   180
gtagcagttc cggagtccag ctggctaaaa ctcatcccag aggataatgg caacccatgc   240
cttagaaatc gctgggctgt tcttggtgg tgttggaatg gtgggcacag tggctgtcac   300
tgtcatgcct cagtggagag tgtcggcctt cattgaaaac aacatcgtgg tttttgaaaa   360
cttctgggaa ggactgtgga tgaattgcgt gaggcaggct aacatcagga tgcagtgcaa   420
aatctatgat tccctgctgg ctctttctcc ggacctacag gcagccagag gactgatgtg   480
tgctgcttcc gtgatgtcct tcttggcttt catgatggcc atccttggca tgaaatgcac   540
caggtgcacg ggggacaatg agaaggtgaa ggctcacatt ctgctgacgg ctggaatcat   600
```

-continued

```
cttcatcatc acgggcatgg tggtgctcat ccctgtgagc tgggttgcca atgccatcat     660
cagagatttc tataactcaa tagtgaatgt tgcccaaaaa cgtgagcttg agaagctct      720 ctacttagga tggaccacgg cactggtgct gattgttgga ggagctctgt tctgctgcgt    780
tttttgttgc aacgaaaaga gcagtagcta cagatactcg ataccttccc atcgcacaac    840
ccaaaaaagt tatcacaccg gaaagaagtc accgagcgtc tactccagaa gtcagtatgt    900
gtagttgtgt atgtttttttt aactttacta taaagccatg caaatgacaa aaatctatat    960
tactttctca aaatggaccc caagaaaact ttgatttact gttcttaact gcctaatctt    1020
aattacagga actgtgcatc agctatttat gattctataa gctatttcag cagaatgaga   1080
tattaaaccc aatgctttga ttgttctaga aagtatagta atttgttttc taaggtggtt   1140
caagcatcta ctctttttat catttacttc aaaatgacat tgctaaagac tgcattattt    1200
tactactgta atttctccac gacatagcat tatgtacata gatgagtgta acatttatat    1260
ctcacataga gacatgctta tatggtttta tttaaaatga aatgccagtc cattacactg    1320
aataaataga actcaactat tgcttttcag ggaaatcatg gatagggttg aagaaggtta    1380
ctattaattg ttttaaaaaca gcttagggat taatgtcctc catttataat gaagattaaa   1440
atgaaggctt taatcagcat tgtaaaggaa attgaatggc tttctgatat gctgtttttt    1500
agcctaggag ttagaaatcc taacttcttt atcctcttct cccagaggct tttttttct     1560 tgtgtattaa attaacattt ttaaaaagca gatattttgt caaggggctt tgcattcaaa   1620
ctgcttttcc agggctatac tcagaagaaa gataaaagtg tgatctaaga aaaagtgatg   1680
gttttaggaa agtgaaaata tttttgtttt tgtatttgaa gaagaatgat gcattttgac    1740
aagaaatcat atatgtatgg atatattttta ataagtattt gagtacagac tttgaggttt    1800
catcaatata aataaaagag cagaaaaata tgtcttggtt ttcatttgct taccaaaaaa    1860
acaacaacaa aaaagttgt cctttgagaa cttcacctgc tcctatgtgg gtacctgagt    1920
caaaattgtc attttttgttc tgtgaaaaat aaatttcctt cttgtaccat ttctgtttag    1980
ttttactaaa atctgtaaat actgtatttt tctgtttatt ccaaatttga tgaaactgac    2040
aatccaattt gaaagtttgt gtcgacgtct gtctagctta aatgaatgtg ttctatttgc    2100
tttatacatt tatattaata aattgtacat ttttctaatt atttgaa                  2147
```

<210> SEQ ID NO 6
<211> LENGTH: 7771
<212> TYPE: DNA
<213> ORGANISM: Homo sapiens

<400> SEQUENCE: 6

```
tttctgttat ttgtccccgt ccctccccac cccctgctg aagcgagaat aagggcaggg      60
accgcggctc ctacctcttg gtgatccct tccccattcc gccccgcct caacgcccag      120 cacagtgccc tgcacacagt agtcgctcaa taaatgttcg tggatgatga tgatgatgat    180
gatgaaaaaa atgcagcatc aacggcagca gcaagcggac cacgcgaacg aggcaaacta    240
tgcaagaggc accagacttc ctctttctgg tgaaggacca acttctcagc cgaatagctc    300
caagcaaact gtcctgtctt ggcaagctgc aatcgatgct gctagacagg ccaaggctgc    360
ccaaactatg agcacctctg caccccacc tgtaggatct ctctcccaaa gaaaacgtca    420
gcaatacgcc aagagcaaaa aacagggtaa ctcgtccaac agccgacctg cccgcgccct    480
tttctgttta tcactcaata accccatccg aagagcctgc attagtatag tggaatggaa    540
```

```
accatttgac atatttatat tattggctat ttttgccaat tgtgtggcct tagctattta    600
catcccattc cctgaagatg attctaattc aacaaatcat aacttggaaa agtagaata     660
tgccttcctg attattttta cagtcgagac attttttgaag attatagcgt atggattatt  720
gctacatcct aatgcttatg ttaggaatgg atggaattta ctggattttg ttatagtaat   780
agtaggattg tttagtgtaa ttttggaaca attaaccaaa gaaacagaag gcgggaacca   840
ctcaagcggc aaatctggag cttttgatgt caaagccctc cgtgcctttc gagtgttgcg   900
accacttcga ctagtgtcag gagtgcccag tttacaagtt gtcctgaact ccattataaa   960
agccatggtt cccctccttc acatagccct tttggtatta tttgtaatca taatctatgc  1020
tattatagga ttggaacttt ttattggaaa aatgcacaaa acatgttttt ttgctgactc  1080
agatatcgta gctgaagagg acccagctcc atgtgcgttc tcagggaatg gacgccagtg  1140
tactgccaat ggcacggaat gtaggagtgg ctgggttggc ccgaacggag gcatcaccaa  1200
ctttgataac tttgcctttg ccatgcttac tgtgtttcag tgcatcacca tggagggctg  1260
gacagatgtg ctctactggg taaatgatgc gataggatgg gaatggccat gggtgtattt  1320
tgttagtctg atcatccttg gctcattttt cgtccttaac ctggttcttg gtgtccttag  1380
tggagaattc tcaaaggaaa gagagaaggc aaaagcacgg ggagatttcc agaagctccg  1440
ggagaagcag cagctggagg aggatctaaa gggctacttg gattggatca cccaagctga  1500
ggacatcgat ccggagaatg aggaagaagg aggagaggaa ggcaaacgaa atactagcat  1560
gcccaccagc gagactgagt ctgtgaacac agagaacgtc agcggtgaag gcgagaaccg  1620
aggctgctgt ggaagtctct ggtgctggtg gagacggaga ggcgcggcca aggcggggcc  1680
ctctgggtgt cggcggtggg gtcaagccat ctcaaaatcc aaactcagcc gacgctggcg  1740
tcgctggaac cgattcaatc gcagaagatg tagggccgcc gtgaagtctg tcacgtttta  1800
ctggctggtt atcgtcctgg tgtttctgaa caccttaacc atttcctctg agcactacaa  1860
tcagccagat tggttgacac agattcaaga tattgccaac aaagtcctct ggctctgtt   1920
cacctgcgag atgctggtaa aaatgtacag cttgggcctc caagcatatt tcgtctctct  1980
tttcaaccgg tttgattgct tcgtggtgtg tggtggaatc actgagacga tcttggtgga  2040
actggaaatc atgtctcccc tggggatctc tgtgtttcgg tgtgtgcgcc tcttaagaat  2100
cttcaaagtg accaggcact ggacttccct gagcaactta gtggcatcct tattaaactc  2160
catgaagtcc atcgcttcgc tgttgcttct gcttttttctc ttcattatca tcttttcctt  2220
gcttgggatt cagctgtttg gcggcaagtt taattttgat gaaacgcaaa ccaagcggag  2280
caccttttgac aatttccctc aagcacttct cacagtgttc cagatcctga caggcgaaga  2340
ctggaatgct gtgatgtacg atggcatcat ggcttacggg ggcccatcct cttcaggaat  2400
gatcgtctgc atctacttca tcatcctctt catttgtggt aactatattc tactgaatgt  2460
cttcttggcc atcgctgtag acaatttggc tgatgctgaa agtctgaaca ctgctcagaa  2520
agaagaagcg gaagaaaagg agaggaaaaa gattgccaga aaagagagcc tagaaaataa  2580
aaagaacaac aaaccagaag tcaaccagat agccaacagt gacaacaagg ttacaattga  2640
tgactataga gaagaggatg aagacaagga cccctatccg ccttgcgatg tgccagtagg  2700
ggaagaggaa gaggaagagg aggaggatga acctgaggtt cctgccggac ccgtcctcg   2760
aaggatctcg gagttgaaca tgaaggaaaa aattgcccccc atccctgaag ggagcgcttt  2820
cttcattctt agcaagacca acccgatccg cgtaggctgc cacaagctca tcaaccacca  2880
catcttcacc aacctcatcc ttgtcttcat catgctgagc agcgctgccc tggccgcaga  2940
```

```
ggaccccatc cgcagccact ccttccggaa cacgatactg ggttactttg actatgcctt    3000
cacagccatc tttactgttg agatcctgtt gaagatgaca acttttggag ctttcctcca    3060
caaaggggcc ttctgcagga actacttcaa tttgctggat atgctggtgg ttggggtgtc    3120
tctggtgtca tttgggattc aatccagtgc catctccgtt gtgaagattc tgagggtctt    3180
aagggtcctg cgtcccctca gggccatcaa cagagcaaaa ggacttaagc acgtggtcca    3240
gtgcgtcttc gtggccatcc ggaccatcgg caacatcatg atcgtcacca ccctcctgca    3300
gttcatgttt gcctgtatcg gggtccagtt gttcaagggg aagttctatc gctgtacgga    3360
tgaagccaaa agtaaccctg aagaatgcag gggactttc atcctctaca aggatgggga     3420
tgttgacagt cctgtggtcc gtgaacggat ctggcaaaac agtgatttca acttcgacaa    3480
cgtcctctct gctatgatgg cgctcttcac agtctccacg tttgagggct ggcctgcgtt    3540
gctgtataaa gccatcgact cgaatggaga aacatcggc ccaatctaca accaccgcgt     3600
ggagatctcc atcttcttca tcatctacat catcattgta gctttcttca tgatgaacat    3660 cttgtgggc tttgtcatcg ttacatttca ggaacaagga gaaaagagt ataagaactg      3720 tgagctggac aaaaatcagc gtcagtgtgt tgaatacgcc ttgaaagcac gtccttgcg     3780 gagatacatc cccaaaaacc cctaccagta caagttctgg tacgtggtga actcttcgcc    3840
tttcgaatac atgatgtttg tcctcatcat gctcaacaca ctctgcttgg ccatgcagca    3900
ctacgagcag tccaagatgt tcaatgatgc catggacatt ctgaacatgg tcttcaccgg    3960
ggtgttcacc gtcgagatgg ttttgaaagt catcgcattt aagcctaagg ggtattttag    4020
tgacgcctgg aacacgtttg actccctcat cgtaatcggc agcattatag acgtggccct    4080
cagcgaagca gacccaactg aaagtgaaaa tgtccctgtc ccaactgcta cacctgggaa    4140
ctctgaagag agcaatagaa tctccatcac cttttttccgt cttttccgag tgatgcgatt    4200
ggtgaagctt ctcagcaggg gggaaggcat ccggacattg ctgtggactt ttattaagtc    4260
ctttcaggcg ctcccgtatg tggccctcct catagccatg ctgttcttca tctatgcggt    4320
cattggcatg cagatgtttg ggaaagttgc catgagagat aacaaccaga tcaataggaa    4380
caataacttc cagacgtttc cccaggcggt gctgctgctc ttcaggtgtg caacaggtga    4440
ggcctggcag gagatcatgc tggcctgtct cccagggaag ctctgtgacc ctgagtcaga    4500
ttacaacccc ggggaggagt atacatgtgg gagcaacttt gccattgtct atttcatcag    4560
tttttacatg ctctgtgcat ttctgatcat caatctgttt gtggctgtca tcatggataa    4620
tttcgactat ctgaccgggg actggtctat tttggggcct caccatttag atgaattcaa    4680
aagaatatgg tcagaatatg accctgaggc aaagggaagg ataaaacacc ttgatgtggt    4740
cactctgctt cgacgcatcc agcctcccct ggggtttggg aagttatgtc cacacagggt    4800
agcgtgcaag agattagttg ccatgaacat gcctctcaac agtgacggga cagtcatgtt    4860
taatgcaacc ctgtttgctt tggttcgaac ggctcttaag atcaagaccg aagggaacct    4920
ggagcaagct aatgaagaac ttcgggctgt gataaagaaa atttggaaga aaccagcat     4980 gaaattactt gaccaagttg tccctccagc tggtgatgat gaggtaaccg tggggaagtt    5040
ctatgccact ttcctgatac aggactactt taggaaattc aagaacgga aagaacaagg     5100 actggtggga aagtaccctg cgaagaacac cacaattgcc ctacaggcgg gattaaggac    5160
actgcatgac attgggccag aaatccggcg tgctatatcg tgtgatttgc aagatgacga    5220
gcctgaggaa acaaaacgag aagaagaaga tgatgtgttc aaaagaaatg gtgccctgct    5280
```

```
tggaaaccat gtcaatcatg ttaatagtga taggagagat tcccttcagc agaccaatac    5340
cacccaccgt cccctgcatg tccaaaggcc ttcaattcca cctgcaagtg atactgagaa    5400
accgctgttt cctccagcag gaaattcggt gtgtcataac catcataacc ataattccat    5460
aggaaagcaa gttcccacct caacaaatgc caatctcaat aatgccaata tgtccaaagc    5520
tgcccatgga aagcggccca gcattgggaa ccttgagcat gtgtctgaaa atgggcatca    5580
ttcttcccac aagcatgacc gggagcctca gagaaggtcc agtgtgaaaa gaacccgcta    5640
ttatgaaact tacattaggt ccgactcagg agatgaacag ctcccaacta tttgccggga    5700
agacccagag atacatggct atttcaggga cccccactgc ttgggggagc aggagtattt    5760
cagtagtgag gaatgctacg aggatgacag ctcgcccacc tggagcaggc aaaactatgg    5820
ctactacagc agatacccag gcagaaacat cgactctgag aggccccgag gctaccatca    5880
tccccaagga ttcttggagg acgatgactc gcccgtttgc tatgattcac ggagatctcc    5940
aaggagacgc ctactacctc ccaccccagc atcccaccgg agatcctcct tcaactttga    6000
gtgcctgcgc cggcagagca gccaggaaga ggtcccgtcg tctcccatct tccccccatcg   6060 cacggccctg cctctgcatc taatgcagca acagatcatg gcagttgccg gcctagattc    6120
aagtaaagcc cagaagtact caccgagtca ctcgacccgg tcgtgggcca ccctccagc    6180 aaccccctccc taccgggact ggacaccgtg ctacacccc ctgatccaag tggagcagtc    6240
agaggccctg gaccaggtga acggcagcct gccgtccctg caccgcagct cctggtacac    6300
agacgagccc gacatctcct accggacttt cacaccagcc agcctgactg tccccagcag    6360
cttccggaac aaaaacagcg acaagcagag gagtgcggac agcttggtgg aggcagtcct    6420
gatatccgaa ggcttgggac gctatgcaag ggacccaaaa tttgtgtcag caacaaaaca    6480
cgaaatcgct gatgcctgtg acctcaccat cgacgagatg gagagtgcag ccagcaccct    6540
gcttaatggg aacgtgcgtc cccgagccaa cggggatgtg ggcccctct cacaccggca    6600 ggactatgag ctacaggact tggtcctgg ctacagcgac gaagagccag accctgggag    6660
ggatgaggag gacctggcgg atgaaatgat atgcatcacc accttgtagc ccccagcgag    6720
gggcagactg gctctggcct caggtgggggc gcaggagagc caggggaaaa gtgcctcata    6780
gttaggaaag tttaggcact agttgggagt aatattcaat taattagact tttgtataag    6840
agatgtcatg cctcaagaaa gccataaacc tggtaggaac aggtcccaag cggttgagcc    6900
tggcagagta ccatgcgctc ggccccagct gcaggaaaca gcaggccccg ccctctcaca    6960
gaggatgggt gaggaggcca gacctgccct gccccattgt ccagatgggc actgctgtgg    7020
agtctgcttc tccatgtac cagggcacca ggcccaccca actgaaggca tggcggcggg    7080
gtgcagggga aagttaaagg tgatgacgat catcacacct gtgtcgttac ctcagccatc    7140
ggtctagcat atcagtcact gggcccaaca tatccatttt taaacccttt ccccaaata    7200 cactgcgtcc tggttcctgt ttagctgttc tgaaatacgg tgtgtaagta agtcagaacc    7260
cagctaccag tgattattgc gagggcaatg ggacctcata aataaggttt tctgtgatgt    7320
gacgccagtt tacataagag aatatcactc cgatggtcgg tttctgactg tcacgctaag    7380
ggcaactgta aactggaata ataatgcact cgcaaccagg taaacttaga tacactagtt    7440
tgtttaaaat tatagattta ctgtacatga cttgtaatat actataattt gtatttgtaa    7500
agagatggtc tatattttgt aattactgta ttgtatttga actgcagcaa tatccatggg    7560
tcctaataat tgtagttccc cactaaaatc tagaaattat tagtattttt actcgggcta    7620
tccagaagta gaagaaatag agccaattct catttattca gcgaaaatcc tctggggtta    7680
```

```
aaatttttaag tttgaaagaa cttgacacta cagaaatttt tctaaaatat tttgagtcac   7740
tataaaccta tcatctttcc acaagataaa a                                   7771

<210> SEQ ID NO 7
<211> LENGTH: 2072
<212> TYPE: DNA
<213> ORGANISM: Homo sapiens

<400> SEQUENCE: 7
ttattgtggt ttgtccgttc cgagcgctcc gcagaacagt cctccctgta agagcctaac     60
cattgccagg gaaacctgcc ctgggcgctc ccttcattag cagtattttt tttaaattaa    120
tctgattaat aattattttt cccccattta attttttttc ctcccaggtg gagttgccga    180 agctggggc agctgggag ggtggggatg ggaggggaga acagaagtt gagggcatct       240 ctctcttcct tcccgaccct ctggccccca aggggcagga ggaatgcagg agcaggagtt    300
gagcttggga gctgcagatg cctccgcccc tcctctctcc caggctcttc ctcctgcccc    360
cttcttgcaa ctctccttaa ttttgtttgg cttttggatg attataatta tttttatttt    420
tgaatttata taaagtatat gtgtgtgtgt gtggagctga acaggctcg gcagcggcac     480 agaatgaggg aagacgagaa agagagtggg agagagagag gcagagaggg agagagggag    540
agtgacagca gcgctcggac gtcctcccca acgtcgccct caattccacc gcctatgatc    600
cagtgaggca tttctcgacc tatggagcgg ccgttgccca gaaccggatc tactcgactc    660
ccttttattc gccacaggag aatgtcgtgt tcagttccag ccgggggccg tatgactatg    720
gatctaattc cttttaccag gagaaagaca tgctctcaaa ctgcagacaa aacaccttag    780
gacataacac acagacctca atcgctcagg attttagttc tgagcagggc aggactgcgc    840
cccaggacca gaaagccagt atccagattt acccctggat gcagcgaatg aattcgcaca    900
gtggggtcgg ctacggagcg gaccggaggc gcggccgcca gatctactcg cggtaccaga    960
ccctggaact ggagaaggaa tttcacttca atcgctacct aacgcggcgc cggcgcatcg   1020
agatcgccaa cgcgctttgc ctgaccgagc gacagatcaa aatctggttc cagaaccgcc   1080
ggatgaagtg gaaaaagaa tctaatctca catccactct ctcggggggc ggcggagggg    1140
ccaccgccga cagcctgggc ggaaaagagg aaaagcggga agagacagaa gaggagaagc   1200
agaaagagtg accaggactg tccctgccac ccctctctcc ctttctccct cgctccccac    1260
caactctccc ctaatcacac actctgtatt tatcactggc acaattgatg tgttttgatt    1320
ccctaaaaca aaattaggga gtcaaacgtg gacctgaaag tcagctctgg accccctccc    1380
tcaccgcaca actctctttc accacgcgcc tcctcctcct cgctcccttg ctagctcgtt    1440
ctcggcttgt ctacaggccc ttttcccgt ccaggcttg ggggctcgga ccctgaactc     1500
agactctaca gattgccctc caagtgagga cttggctccc ccactccttc gacgccccca    1560 ccccgcccc ccgtgcagag agccggctcc tgggcctgct ggggcctctg ctccagggcc    1620
tcagggcccg gcctggcagc cggggagggc cggaggccca aggagggcgc gccttggccc    1680
cacaccaacc cccagggcct ccccgcagtc cctgcctagc ccctctgccc cagcaaatgc    1740
ccagcccagg caaattgtat ttaaagaatc ctggggggtca ttatggcatt ttacaaactg    1800
tgaccgtttc tgtgtgaaga ttttttagctg tatttgtggt ctctgtattt atatttatgt    1860
ttagcaccgt cagtgttcct atccaatttc aaaaaaggaa aaaaaagagg gaaaattaca    1920 aaagagaga aaaaagtga atgacgtttg tttagccagt aggagaaaat aaataaataa     1980
```

| | |
|---|---|
| ataaatccct tcgtgttacc ctcctgtata aatccaacct ctgggtccgt tctcgaatat | 2040 |
| ttaataaaac tgatattatt tttaaaactt ta | 2072 |

<210> SEQ ID NO 8
<211> LENGTH: 1814
<212> TYPE: DNA
<213> ORGANISM: Homo sapiens

<400> SEQUENCE: 8

| | |
|---|---|
| gcagagctcg agaggcggct gccgggctgc ggggcgcctt gactctccct ccaccctgcc | 60 |
| tcctcgggct ccactcgtct gccctggac tcccgtctcc tcctgtcctc cggcttccca | 120 |
| gagctccctc cttatggcag cagcttcccg cgtctccggc gcagcttctc agcggacgac | 180 |
| cctctcgctc cggggctgag cccagtccct ggatgttgct gaaactctcg agatcatgcg | 240 |
| cgggtttggc tgctgcttcc ccgccgggtg ccactgccac cgccgccgcc tctgctgccg | 300 |
| ccgtccgcgg gatgctcagt agcccgctgc ccggccccg cgatcctgtg ttcctcggaa | 360 |
| gccgtttgct gctgcagagt tgcacgaact agtcatggtg ctgtgggagt cccgcggca | 420 |
| gtgcagcagc tggacacttt gcgagggctt ttgctggctg ctgctgctgc ccgtcatgct | 480 |
| actcatcgta gcccgcccgg tgaagctcgc tgctttccct acctccttaa gtgactgcca | 540 |
| aacgcccacc ggctggaatt gctctggtta tgatgacaga gaaaatgatc tcttcctctg | 600 |
| tgacaccaac acctgtaaat ttgatgggga atgtttaaga attggagaca ctgtgacttg | 660 |
| cgtctgtcag ttcaagtgca acaatgacta tgtgcctgtg tgtggctcca atggggagag | 720 |
| ctaccagaat gagtgttacc tgcgacaggc tgcatgcaaa cagcagagtg agatacttgt | 780 |
| ggtgtcagaa ggatcatgtg ccacagatgc aggatcagga tctggagatg gagtccatga | 840 |
| aggctctgga gaaactagtc aaaaggagac atccacctgt gatatttgcc agtttggtgc | 900 |
| agaatgtgac gaagatgccg aggatgtctg gtgtgtgtgt aatattgact gttctcaaac | 960 |
| caacttcaat cccctctgcg cttctgatgg gaaatcttat gataatgcat gccaaatcaa | 1020 |
| agaagcatcg tgtcagaaac aggagaaaat tgaagtcatg tctttgggtc gatgtcaaga | 1080 |
| taacacaact acaactacta gtctgaaga tgggcattat gcaagaacag attatgcaga | 1140 |
| gaatgctaac aaattagaag aaagtgccag agaacaccac ataccttgtc cggaacatta | 1200 |
| caatggcttc tgcatgcatg gaagtgtga gcattctatc aatatgcagg agccatcttg | 1260 |
| caggtgtgat gctggttata ctggacaaca ctgtgaaaaa aaggactaca gtgttctata | 1320 |
| cgttgttccc ggtcctgtac gatttcagta tgtcttaatc gcagctgtga ttggaacaat | 1380 |
| tcagattgct gtcatctgtg tggtggtcct ctgcatcaca aggaaatgcc ccagaagcaa | 1440 |
| cagaattcac agacagaagc aaaatacagg gcactacagt tcagacaata caacaagagc | 1500 |
| gtccacgagg ttaatctaaa gggagcatgt ttcacagtgg ctggactacc gagagcttgg | 1560 |
| actacacaat acagtattat agacaaaaga ataagacaag atctacac atgttgcctt | 1620 |
| gcatttgtgg taatctacac caatgaaaac atgtactaca gctatatttg attatgtatg | 1680 |
| gatatatttg aaatagtata cattgtcttg atgttttttc tgtaatgtaa ataaactatt | 1740 |
| tatatcacac aatatagttt tttctttccc atgtatttgt tatatataat aaatactcag | 1800 |
| tgatgagaaa aaaa | 1814 |

<210> SEQ ID NO 9
<211> LENGTH: 576
<212> TYPE: DNA
<213> ORGANISM: Homo sapiens

<400> SEQUENCE: 9

```
gcaccccatc cgctggctct cacccctcgg agacgctcgc ccgacagcat agtacttgcc    60
gcccagccac gcccgcgcgc cagccaccat gctaggtaac aagcgactgg ggctgtccgg   120
actgaccctc gccctgtccc tgctcgtgtg cctgggtgcg ctggccgagg cgtacccctc   180
caagccggac aacccgggcg aggacgcacc agcggaggac atggccagat actactcggc   240
gctgcgacac tacatcaacc tcatcaccag gcagagatat ggaaaacgat ccagcccaga   300
gacactgatt tcagacctct tgatgagaga agcacagaa aatgttccca gaactcggct   360
tgaagaccct gcaatgtggt gatgggaaat gagacttgct ctctggcctt ttcctatttt   420
cagcccatat ttcatcgtgt aaaacgagaa tccacccatc ctaccaatgc atgcagccac   480
tgtgctgaat tctgcaatgt tttcctttgt catcattgta tatatgtgtg tttaaataaa   540
gtatcatgca ttcaaaagtg aaaaaaaaaa aaaaaa                             576
```

<210> SEQ ID NO 10
<211> LENGTH: 2774
<212> TYPE: DNA
<213> ORGANISM: Homo sapiens

<400> SEQUENCE: 10

```
attgtttgct tgttttgttc cggagtcggg gccgggaggg agtgcaggag gagggatcca    60
agcttccaag cctctgctcc gctctccttc tatccagttg gtctttaggg cactgaagga   120
aactcttctt cagaaataac cttttaactt ttcttctgtc agctgcctgc caatcacgga   180
gccagaggct gaggggaggc tttgagccgg tctgcgagtc cggaaggcaa agatcgcgaa   240
gcttggcgct ccagaacgct caggggggcag gtagcgctgg tggattggaa tcttgaagca   300
ggtgtacagt gtaaagctgc cctggatgag cagtttgaac ctcagaagac tctgttcatc   360
cagtgcgatg tggctgacca gcaacaactg agagacactt ttagaaaagt tgtagaccac   420
tttggaagac tggacatttt ggtcaataat gctggagtga ataatgagaa aaactgggaa   480
aaaactctgc aaattaattt ggtttctgtt atcagtggaa cctatcttgg tttggattac   540
atgagtaagc aaaatggagg tgaaggcggc atcattatca atatgtcatc tttagcagga   600
ctcatgcccg ttgcacagca gccggtttat tgtgcttcaa agcatggcat agttggattc   660
acacgctcag cagcgttggc tgctaatctt atgaacagtg gtgtgagact gaatgccatt   720
tgtccaggct tgttaacac agccatcctt gaatcaattg aaaagaaga aacatggga   780
caatatatag aatataagga tcatatcaag gatatgatta aatactatgg aattttggac   840
ccaccattga ttgccaatgg attgataaca ctcattgaag atgatgcttt aaatggtgct   900
attatgaaga tcacaacttc taagggaatt cattttcaag actatgatac aactccattt   960
caagcaaaaa cccaatgaac agcttatgtg ttagccatag ctgaaaataa gcacaaatag  1020
cttatattca gatcctatct tcatttgaat atagctttta aatgaaatgt acagtttga  1080
agttttcctt catgcacttg gtgataaacg ttttctaaat ttttagttaa gtatatggat  1140
aaaaagttat gaactattaa aaatgtgatg tggaccaaag gctaggttgt aatcttgata  1200
gtctaaaaaa tgatcaaaac aaatgatttt caaggaatat tcaatattct gcctttcaga  1260
aagtgtattt atatctgtgc ttcataaata ttaatgttct tcagaacatc attttaaagg  1320
agatacttga attgttattt aaatcaaacc agatgtaaaa cactcacata caagttcata  1380
ctttaaaaga ggaaagctac ttaacaatga caaatatttc acaataataa tttttactta  1440
```

```
tataccatct ttcaactgaa catttcagtt cttccaagag cttcttagag tagtatattt    1500
tgggggcagt caaggaataa actacagtgt aaacatatcc cagatgaaaa ctgctgtatg    1560
gaaaaatgac agaaagtaac tgattgacac tgttgattca cagttcagcc tcctatctgg    1620
gaaagacatt tctttcctct gctcacttta agaactttta ccgactccaa aaatctcagg    1680
aattaaactt ttaacagtta cagcaataaa gaatagttag tactccaaaa atattatatt    1740
taagatgctc aacaagaaaa aaatgcaaat gtaatatttt tttcaaatta cttctttatt    1800
gacttgtcca aatttcaaaa gtgcctaccc ttcaataaaa cttttttatt ctgatctcca    1860
taaattactt agtcttctat gtatagctat caaggaaata aaaccaattt tgccacagcc    1920
acaactgtaa atgttttttgt acccatgctg aaactcataa caacacagac ataaaaatag    1980
ctgtgaggtt ttgcttttttt tgttgtcagc tatcttaaga atcattaaat acacctgctt    2040
tgggtaaaac tctttgcaag cagtaattaa cactagtaac agtgaaagca caagatttcc    2100
aaatcagtcg ttttctcaaa aaatatcgt ataagtgact catcctgtct gctaactcca    2160
gacctcccag cttgaagcca aatctttcca tgtgagattg atatgattt cctagaagta    2220 ctggaatgtt gtcatatctt gccctatttt aattctgcta tagaaaacaa ttgccttcac    2280
ttttaaggag taatttgaat attaataact ctggtctaga ttttcatata atgtattaaa    2340
gacaaagtag tgaacatcaa tgaacatctg atagagataa actgtaatca ggcataagct    2400
tgtttgtatg ttctggcagt gactaatcag taaatgatgt cggtttgccc agtatcactt    2460
atcttctgta ttttcctct gtcgtgtaaa tagtataacc ttttcattta tggacaattt    2520
tttggactag tagccttcaa tatacattct gctttgaatt aattttttca aatcaataaa    2580
ttatgtagac atttaaaatc aaatatcaag tagaattgaa aaatgtgagt tacataagtt    2640
aaaaacttac tttaaatctt accttctata ggtagctcta aataaattca tatggttata    2700
tggcatctct ggtgtatact gattgagaaa ataattaaac tgaagttagg ggaggggaaa    2760
aaaaaaaaaa aaaa                                                     2774

<210> SEQ ID NO 11
<211> LENGTH: 3589
<212> TYPE: DNA
<213> ORGANISM: Homo sapiens

<400> SEQUENCE: 11
atttccttct cccttttcccc gccagcttcg catccatctc ccccaccccg taacccctc     60 ctgcctccat ccaccggggc tatggccgca gaagaggtat tgcagacggt ggaccattat   120
aagactgaga tagagaggct aaccaaggag ctcacggaga ccacccacga aagatccag    180 gctgccgagt acgggctggt ggtgctggag agaagctga ccctcaaaca gcagtatgat    240
gaactggagg ctgagtacga cagcctcaaa caggagctgg agcagctcaa agaggcattt    300
gggcagtcct tctccatcca ccggaaggtt gctgaagatg agagactcg ggaggaaacg    360 cttctgcagg agtcagcatc gaaggaggct tactatctgg ggaagatctt ggagatgcag    420
aacgagctga acagagccg ggctgtggtc actaatgtac aggcagaaaa cgagaggctc    480
accgcagtcg tgcaggatct gaaggagaac aatgagatgg tggagctaca gagaatacgg    540
atgaaggatg aaatccgaga atataagttc cgggaggcac ggctccttca ggactatact    600
gaattggaag aagaaaatat cacattgcag aaactagtgt ccacgttgaa gcagaaccag    660
gttgaatacg aaggcttaaa gcatgagatt aagcgatttg aggaggagac ggtactgctg    720
aacagccagc tggaagatgc catccgattg aaagagattg ctgagcacca actggaagaa    780
```

```
gccctcgaga ctttaaaaaa tgaaagagag caaaagaaca acctgcggaa ggagctctcc      840
cagtatatca gcctcaatga taaccatatc agcatctcag tagatggact caaatttgcc      900
gaggatggga gtgaaccaaa caatgatgac aaaatgaacg gtcatatcca tgggcctctt      960
gtgaaactga atggagacta tcggactccc accttaagga aaggagagtc tctgaaccct     1020
gtctctgact tattcagtga gctgaacatt tcagaaatac agaagttgaa gcagcagctt     1080
atgcaggtag agcgggaaaa ggccattctt ttggccaacc tacaggagtc acagacacag     1140
ctggaacaca ccaaggggc actgacggag cagcatgagc gggtgcaccg gctcacagag      1200
cacgtcaatg ccatgagggg cctgcaaagc agcaaggagc tcaaggctga gctggacggg     1260
gagaagggcc gggactcagg ggaggaggcc catgactatg aggtggacat caatggttta     1320
gagatccttg aatgcaaata cagggtggca gtaactgagg tgattgatct gaaagctgaa     1380
attaaggcct taaggagaaa atataataaa tctgtagaaa actacactga tgagaaggcc     1440
aagtatgaga gtaaaatcca gatgtatgat gagcaggtga caagccttga gaagaccacc     1500
aaggagagtg gtgagaagat ggcccacatg gagaaggagt tgcaaaagat gaccagcata     1560
gccaacgaaa atcacagtac ccttaatacg gcccaggatg agttagtgac attcagtgag     1620
gagttagctc agcttttacca ccatgtgtgt ctatgtaata atgaaactcc caacagggtc     1680
atgctggatt actataggca gagcagagtc acccgcagtg gcagcctgaa agggcccgat     1740
gatcccagag acttttgtc cccacgatta gccaggcggg gtgtgtcatc cccggtagaa      1800
acaaggacct catctgaacc agttgcaaaa gaaagcacag aggccagcaa agaaccaagt     1860
ccaactaaga cccccacaat ctctcctgtt attactgccc caccgtcatc tccagtattg     1920
gatacaagtg acatccgcaa agagccaatg aatatctaca accttaatgc cataatccgg     1980
gaccaaatca agcatctgca gaaagctgtg gaccggtcct gcaactgtc tcgtcaaaga      2040 gcagcggctc gggagctagc ccccatgatt gataaagaca aggaagcctt aatggaagag     2100
atcctcaagc taaagtccct gctgagcacc aaacgggagc agatcgccac attgagggcg     2160
gtgttgaaag ccaacaagca gacagctgag gtggcgctag ctaatctcaa gaacaaaatat    2220 gaaaatgaaa aagcaatggt gactgaaacc atgacgaagc ttagaaatga actgaaggct     2280
ttgaaagaag atgctgcaac cttctcatcc ctgagagcaa tgtttgcaac aagatgtgat     2340
gaatatgtca cccagttgga tgagatgcag agacagttag cagctgcaga ggatgagaag     2400
aagactctga acactttgtt acgaatggct atccagcaaa aactcgccct gacccagagg     2460
ctggaggact tagagtttga ccatgagcag tcccgacgca gcaaaggcaa acttggaaag     2520
agcaagatcg gcagccctaa agtaagtggg gaggcatcag tcaccgtgcc caccatagac     2580
acttacctcc tgcatagtca gggcccacag acacccaaca ttcgggtcag cagtggcact     2640
cagaggaaaa gacaattttc accttccctt tgtgatcaga gccgtcccag gacttcaggg     2700
gcttcctacc tacagaattt attaagagtt cccctgatc ccacctccac agaatcattt      2760
cttctgaagg gccccccttc catgagtgaa ttcatccaag ggcaccggct cagcaaggaa     2820
aaaaggttaa ccgtggctcc accagattgt cagcagcctg ctgcctccgt accgccacag     2880
tgctcacaac tagccgggag gcaagactgc ccaactgtca gtcctgacac agctctccct     2940
gaggagcagc cacattccag ctcccagtgc gcccctctcc actgtctctc caagcctcct     3000
cacccctagt cttcatctcc tgtggacgaa catctggggt ggaagttttg tagccacaca     3060
caggatactg cccaagatcc agcgggtgtt ttcttctcgg ttgttagatg tacaattgga     3120
```

| | |
|---|---:|
| ttaatgtcca tcgttttgga agacgagaga aagttgagaa gaacacgaag cacagaccct | 3180 |
| gatgtgataa acattttgt ggtttctctg agtcacagat aaacttctgc catcaaatgg | 3240 |
| ctacagttca tttaaattta aaaaaagaa aaaagaaaca gaaaacgtgt ctcagatggc | 3300 |
| tggctttacc tcgatagcat aagagagacc taagacatgt aaaatacgta tattgcagta | 3360 |
| tcatctttcc tcacactcca aattcagcta gggaagttga ttccaatatg tttgtcattg | 3420 |
| atatttattt tgtactttat ttgctacatg atttatgtct atacaaataa tttctctgag | 3480 |
| gtgaatttaa ttcatttatt ttcaaataag cataatttgc tcaattaagt atgagtttga | 3540 |
| atttagtttg aaatctggaa ttggccagac tgtggtcatt tttcttgca | 3589 |

<210> SEQ ID NO 12
<211> LENGTH: 3130
<212> TYPE: DNA
<213> ORGANISM: Homo sapiens

<400> SEQUENCE: 12

| | |
|---|---:|
| gggagtaggc ggagacagag aggctgtatt tcagtgcagc ctgccagacc tcttctggag | 60 |
| gaagactgga caaggggt cacacattcc ttccatacgg ttgagcctct acctgcctgg | 120 |
| tgctggtcac agttcagctt cttcatgatg gtggatccca atggcaatga atccagtgct | 180 |
| acatacttca tcctaatagg cctccctggt ttagaagagg ctcagttctg gttggccttc | 240 |
| ccattgtgct ccctctacct tattgctgtg ctaggtaact tgacaatcat ctacattgtg | 300 |
| cggactgagc acagcctgca tgagcccatg tatatatttc tttgcatgct ttcaggcatt | 360 |
| gacatcctca tctccacctc atccatgccc aaaatgctgg ccatcttctg gttcaattcc | 420 |
| actaccatcc agtttgatgc ttgtctgcta cagatgtttg ccatccactc cttatctggc | 480 |
| atggaatcca cagtgctgct ggccatggct tttgaccgct atgtggccat ctgtcaccca | 540 |
| ctgcgccatg ccacagtact tacgttgcct cgtgtcacca aaattggtgt ggctgctgtg | 600 |
| gtgcgggggg ctgcactgat ggcacccctt cctgtcttca tcaagcagct gcccttctgc | 660 |
| cgctccaata tccttttccca ttcctactgc ctacaccaag atgtcatgaa gctggcctgt | 720 |
| gatgatatcc gggtcaatgt cgtctatggc cttatcgtca tcatctccgc cattggcctg | 780 |
| gactcacttc tcatctcctt ctcatatctg cttattctta agactgtgtt gggcttgaca | 840 |
| cgtgaagccc aggccaaggc atttggcact tgcgtctctc atgtgtgtgc tgtgttcata | 900 |
| ttctatgtac ctttcattgg attgtccatg gtgcatcgct ttagcaagcg gcgtgactct | 960 |
| ccgctgcccg tcatcttggc caatatctat ctgctggttc ctcctgtgct caacccaatt | 1020 |
| gtctatggag tgaagacaaa ggagattcga cagcgcatcc ttcgactttt ccatgtggcc | 1080 |
| acacacgctt cagagcccta ggtgtcagtg atcaaacttc ttttccattc agagtccctct | 1140 |
| gattcagatt ttaatgttaa cattttggaa gacagtattc agaaaaaaa tttccttaat | 1200 |
| aaaaatacaa ctcagatcct tcaaatatga aactggttgg ggaatctcca ttttttcaat | 1260 |
| attattttct tctttgtttt cttgctacat ataattatta ataccctgac taggttgtgg | 1320 |
| ttggagggtt attacttttc attttaccat gcagtccaaa tctaaactgc ttctactgat | 1380 |
| ggtttacagc attctgagat aagaatggta catctagaga acatttgcca aaggcctaag | 1440 |
| cacggcaaag gaaaataaac acagaatata ataaaatgag ataatctagc ttaaaactat | 1500 |
| aacttcctct tcagaactcc caaccacatt ggatctcaga aaaatgctgt cttcaaaatg | 1560 |
| acttctacag agaagaaata atttttcctc tggacactag cacttaaggg gaagattgga | 1620 |
| agtaaagcct tgaaaagagt acatttacct acgttaatga aagttgacac actgttctga | 1680 |

```
gagttttcac agcatatgga ccctgttttt cctatttaat tttcttatca acccttaat      1740
taggcaaaga tattattagt accctcattg tagccatggg aaaattgatg ttcagtgggg      1800
atcagtgaat taaatgggt catacaagta taaaaattaa aaaaaaaga cttcatgccc       1860
aatctcatat gatgtggaag aactgttaga gagaccaaca gggtagtggg ttagagattt    1920
ccagagtctt acattttcta gaggaggtat ttaatttctt ctcactcatc cagtgttgta    1980
tttaggaatt tcctggcaac agaactcatg gctttaatcc cactagctat tgcttattgt    2040
cctggtccaa ttgccaatta cctgtgtctt ggaagaagtg atttctaggt tcaccattat    2100
ggaagattct tattcagaaa gtctgcatag ggcttatagc aagttattta ttttttaaaag   2160
ttccataggt gattctgata ggcagtgagg ttagggagcc accagttatg atgggaagta    2220
tggaatggca ggtcttgaag ataacattgg cctttgagt gtgactcgta gctgaaaagt     2280
gagggaatct tcaggaccat gctttatttg gggctttgtg cagtatggaa cagggacttt    2340
gagaccagga aagcaatctg acttaggcat gggaatcagg catttttgct tctgaggggc    2400
tattaccaag ggttaatagg tttcatcttc aacaggatat gacaacagtg ttaaccaaga    2460
aactcaaatt acaaatacta aaacatgtga tcatatatgt ggtaagtttc attttctttt    2520
tcaatcctca ggttccctga tatggattcc tataacatgc tttcatcccc ttttgtaatg   2580
gatatcatat ttggaaatgc ctatttaata cttgtatttg ctgctggact gtaagcccat    2640
gagggcactg tttattattg aatgtcatct ctgttcatca ttgactgctc tttgctcatc    2700
attgaatccc ccagcaaagt gcctagaaca taatagtgct tatgcttgac accggttatt    2760
tttcatcaaa cctgattcct tctgtcctga acacatagcc aggcaatttt ccagccttct    2820
ttgagttggg tattattaaa ttctggccat tacttccaat gtgagtggaa gtgacatgtg    2880
caatttctat acctggctca taaaaccctc ccatgtgcag cctttcatgt tgacattaaa    2940
tgtgacttgg gaagctatgt gttacacaga gtaaatcacc agaagcctgg atttctgaaa    3000
aaactgtgca gagccaaacc tctgtcattt gcaactccca cttgtatttg tacgaggcag    3060
ttggataagt gaaaataaa gtactattgt gtcaagtctc tgaaaaaaaa aaaaaaaaa    3120
aaaaaaaaaa                                                             3130
```

<210> SEQ ID NO 13
<211> LENGTH: 2785
<212> TYPE: DNA
<213> ORGANISM: Homo sapiens

<400> SEQUENCE: 13

```
gaatctccac accctgaaga cacagtgagt tagcaccacc accaggaatt ggcctttcag      60
ctctgtgcct gtctccagtc aggctggaat aagtctcctc atatttgcaa gctcggccct    120
cccctggaat ctaaagcctc ctcagccttc tgagtcagcc tgaaaggaac aggccgaact    180
gctgtatggg ctctactgcc agtgtgacct caccctctcc agtcacccct cctcagttcc    240
agctatgagt tcctgcaact tcacacatgc cacctttgtg cttattggta tcccaggatt    300
agagaaagcc catttctggg ttggcttccc cctcctttcc atgtatgtag tggcaatgtt    360
tggaaactgc atcgtggtct tcatcgtaag gacggaacgc agcctgcacg ctccgatgta    420
cctcttttctc tgcatgcttg cagccattga cctggcctta ccacatccca catgcctaa    480
gatccttgcc cttttctggt ttgattcccg agagattagc tttgaggcct gtcttaccca    540
gatgttcttt attcatgccc tctcagccat tgaatccacc atcctgctgg ccatggcctt    600
```

```
tgaccgttat gtggccatct gccacccact gcgccatgct gcagtgctca acaatacagt    660
aacagcccag attggcatcg tggctgtggt ccgcggatcc ctcttttttt tcccactgcc    720
tctgctgatc aagcggctgg ccttctgcca ctccaatgtc ctctcgcact cctattgtgt    780
ccaccaggat gtaatgaagt tggcctatgc agacactttg cccaatgtgg tatatggtct    840
tactgccatt ctgctggtca tgggcgtgga cgtaatgttc atctccttgt cctatttcct    900
gataatacga acggttctgc aactgccttc caagtcagag cgggccaagg cctttggaac    960
ctgtgtgtca cacattggtg tggtactcgc cttctatgtg ccacttattg gcctctcagt   1020
ggtacaccgc tttggaaaca gccttcatcc cattgtgcgt gttgtcatgg gtgacatcta   1080
cctgctgctg cctcctgtca tcaatcccat catctatggt gccaaaacca aacagatcag   1140
aacacgggtg ctggctatgt tcaagatcag ctgtgacaag gacttgcagg ctgtgggagg   1200
caagtgaccc ttaacactac acttctcctt atctttattg gcttgataaa cataattatt   1260
tctaacacta gcttatttcc agttgcccat aagcacatca gtacttttct ctggctggaa   1320
tagtaaacta agtatggta catctaccta aaggactatt atgtggaata atacatacta   1380
atgaagtatt acatgattta aagactacaa taaaaccaaa catgcttata acattaagaa   1440
aaacaataaa gatacatgat tgaaaccaag ttgaaaaata gcatatgcct tggaggaaat   1500
gtgctcaaat tactaatgat ttagtgttgt ccctactttc tctctcttt ttctttcttt   1560 ttttttatt atggttagct gtcacataca actttttttt tttttgagat ggggtctcgc   1620
tctgtcacca ggctggagtg cagtggcgcg atctcggctc actgcaacct ccacatccca   1680
tgttgaagta attcttctgc ctcagcctcc cgagtagctg ggactagagg aacgtgccac   1740
catgactggc taattttctg tattttttag tagagacaga gtttcaccat gttggccagg   1800
atggtctcga tctcctgacc ttgtgatcca cccgcctcag cctcccaaag tgttgggatt   1860
acaggtgtga accactgtgc ccggcctgtg tacaactttt taaataggga atatgatagc   1920
ttcgcatggt ggtgtgcacc tatagccccc actgcctgga agctgaggt gggagaatcg   1980 cttgagtcca ggagtttgag gttacagtga tccacgatcg taccactaca ctccagcctg   2040
ggcaacagag caagaccctg tctcaaagca taaaatggaa taacatatca aatgaaacag   2100
ggaaaatgaa gctgacaatt tatggaagcc agggcttgtc acagtctcta ctgttattat   2160
gcattacctg ggaatttata taagccctta ataataatgc caatgaacat ctcatgtgtg   2220
ctcacaatgt tctggcacta ttataagtgc ttcacaggtt ttatgtgttc ttcgtaactt   2280
tatggagtag gtaccatttg tgtctctta ttataagtga gagaaatgaa gtttatatta   2340
tcaaggggac taaagtcaca cggcttgtgg gcactgtgcc aagatttaaa attaaatttg   2400
atggttgaat acagttactt aatgaccatg ttatattgct tcctgtgtaa catctgccat   2460
ttatttcctc agctgtacaa atcctctgtt ttctctctgt tacacactaa catcaatggc   2520
tttgtacttg tgatgagaga taaccttgcc ctagttgtgg gcaacacatg cagaataatc   2580
ctgttttaca gctgcctttc gtgatcttat tgcttgcttt tttccagatt cagggagaat   2640
gttgttgtct atttgtctct tacatctcct tgatcatgtc ttcattttt aatgtgctct   2700 gtacctgtca aaattttga atgtacacca catgctattg tctgaacttg agtataagat   2760
aaaataaaat tttattttaa atttt                                         2785
```

<210> SEQ ID NO 14
<211> LENGTH: 2653
<212> TYPE: DNA
<213> ORGANISM: Homo sapiens

<400> SEQUENCE: 14

```
ctcaaaaggg gccggatttc cttctcctgg aggcagatgt tgcctctctc tctcgctcgg        60
attggttcag tgcactctag aaacactgct gtggtggaga aactggaccc caggtctgga       120
gcgaattcca gcctgcaggg ctgataagcg aggcattagt gagattgaga gagactttac       180
cccgccgtgg tggttggagg gcgcgcagta gagcagcagc acaggcgcgg gtcccgggag       240
gccggctctg ctcgcgccga gatgtggaat ctccttcacg aaaccgactc ggctgtggcc       300
accgcgcgcc gcccgcgctg gctgtgcgct ggggcgctgg tgctggcggg tggcttcttt       360
ctcctcggct tcctcttcgg gtggtttata aaatcctcca atgaagctac taacattact       420
ccaaagcata atatgaaagc attttggat gaattgaaag ctgagaacat caagaagttc       480
ttatataatt ttacacagat accacattta gcaggaacag aacaaaactt tcagcttgca       540
aagcaaattc aatcccagtg aaagaatttt ggcctggatt ctgttgagct agcacattat       600
gatgtcctgt tgtcctaccc aaataagact catcccaact acatctcaat aattaatgaa       660
gatggaaatg agattttcaa cacatcatta tttgaaccac ctcctccagg atatgaaaat       720
gtttcggata ttgtaccacc tttcagtgct ttctctcctc aaggaatgcc agagggcgat       780
ctagtgtatg ttaactatgc acgaactgaa gacttcttta aattggaacg ggacatgaaa       840
atcaattgct ctgggaaaat tgtaattgcc agatatggga aagttttcag aggaaataag       900
gttaaaaatg cccagctggc aggggccaaa ggagtcattc tctactccga ccctgctgac       960
tactttgctc ctggggtgaa gtcctatcca gatggttgga atcttcctgg aggtggtgtc      1020
cagcgtggaa atatcctaaa tctgaatggt gcaggagacc ctctcacacc aggttaccca      1080
gcaaatgaat atgcttatag gcgtggaatt cagaggctg ttggtcttcc aagtattcct      1140
gttcatccaa ttggatacta tgatgcacag aagctcctag aaaaaatggg tggctcagca      1200
ccaccagata gcagctggag aggaagtctc aaagtgccct acaatgttgg acctggcttt      1260
actgaaaact tttctacaca aaaagtcaag atgcacatcc actctaccaa tgaagtgaca      1320
agaatttaca atgtgatagg tactctcaga ggagcagtgg aaccagacag atatgtcatt      1380
ctgggaggtc accgggactc atgggtgttt ggtggtattg accctcagag tggagcagct      1440
gttgttcatg aaattgtgag gagctttgga acactgaaaa aggaagggtg gagacctaga      1500
agaacaattt tgtttcaag ctgggatgca gaagaatttg gtcttcttgg ttctactgag      1560
tgggcagagg agaattcaag actccttcaa gagcgtggcg tggcttatat taatgctgac      1620
tcatctatag aaggaaacta cactctgaga gttgattgta caccgctgat gtacagcttg      1680
gtacacaacc taacaaaaga gctgaaaagc cctgatgaag ctttgaagg caaatctctt      1740
tatgaaagtt ggactaaaaa aagtccttcc ccagagttca gtggcatgcc caggataagc      1800
aaattgggat ctggaaatga ttttgaggtg ttcttccaac gacttggaat tgcttcaggc      1860
agagcacggt atactaaaaa ttgggaaaca aacaaattca gcggctatcc actgtatcac      1920
agtgtctatg aaacatatga gttggtggaa aagttttatg atccaatgtt taaatatcac      1980
ctcactgtgg cccaggttcg aggagggatg tgtttgagc tagccaattc catagtgctc      2040
ccttttgatt gtcgagatta tgctgtagtt ttaagaaagt atgctgacaa aatctacagt      2100
atttctatga acatccaca ggaaatgaag acatacagtg tatcatttga ttcacttttt      2160
tctgcagtaa agaattttac agaaattgct tccaagttca gtgagagact ccaggacttt      2220
gacaaaagca acccaatagt attaagaatg atgaatgatc aactcatgtt tctggaaaga      2280
```

```
gcatttattg atccattagg gttaccagac aggccttttt ataggcatgt catctatgct    2340
ccaagcagcc acaacaagta tgcaggggag tcattcccag gaatttatga tgctctgttt    2400
gatattgaaa gcaaagtgga cccttccaag gcctgggag aagtgaagag acagatttat    2460
gttgcagcct tcacagtgca ggcagctgca gagactttga gtgaagtagc ctaagaggat    2520
tctttagaga atccgtattg aatttgtgtg gtatgtcact cagaaagaat cgtaatgggt    2580
atattgataa attttaaaat tggtatattt gaaataaagt tgaatattat atataaaaaa    2640
aaaaaaaaaa aaa                                                       2653

<210> SEQ ID NO 15
<211> LENGTH: 3604
<212> TYPE: DNA
<213> ORGANISM: Homo sapiens

<400> SEQUENCE: 15
gggagaagga ggaggccggg ggaaggagga gacaggagga ggagggacca cggggtggag      60
gggagataga cccagcccag agctctgagt ggtttcctgt tgcctgtctc taaacccctc     120
cacattcccg cggtccttca gactgcccgg agagcgcgct ctgcctgccg cctgcctgcc     180
tgccactgag ggttcccagc accatgaggg cctggatctt ctttctcctt tgcctggccg     240
ggagggcctt ggcagcccct cagcaagaag ccctgcctga tgagacagag gtggtggaag     300
aaactgtggc agaggtgact gaggtatctg tgggagctaa tcctgtccag gtggaagtag     360
gagaatttga tgatggtgca gaggaaaccg aagaggaggt ggtggcggaa atccctgcc     420 agaaccacca ctgcaaacac ggcaaggtgt gcgagctgga tgagaacaac accccccatgt    480 gcgtgtgcca ggaccccacc agctgcccag ccccccattgg cgagtttgag aaggtgtgca    540
gcaatgacaa caagaccttc gactcttcct gccacttctt tgccacaaag tgcaccctgg     600
agggcaccaa gaagggccac aagctccacc tggactacat cgggccttgc aaatacatcc     660
cccccttgcc tggactctgag ctgaccgaat tccccctgcg catgcgggac tggctcaaga     720
acgtcctggt caccctgtat gagagggatg aggacaacaa ccttctgact gagaagcaga     780
agctgcgggt gaagaagatc catgagaatg agaagcgcct ggaggcagga gaccacccccg    840 tggagctgct ggcccgggac ttcgagaaga actataacat gtacatcttc cctgtacact     900
ggcagttcgg ccagctggac cagcacccca ttgacgggta cctctcccac accgagctgg     960
ctccactgcg tgctcccctc atccccatgg agcattgcac caccgctttt tcgagacct    1020 gtgacctgga caatgacaag tacatcgccc tggatgagtg ggcggctgc ttcggcatca    1080 agcagaagga tatcgacaag gatcttgtga tctaaatcca ctccttccac agtaccggat    1140 tctctctta accctcccct tcgtgttttcc cccaatgttt aaaatgtttg atggtttgt    1200 tgttctgcct ggagacaagg tgctaacata gatttaagtg aatacattaa cggtgctaaa    1260
aatgaaaatt ctaacccaag acatgacatt cttagctgta acttaactat taaggccttt    1320
tccacacgca ttaatagtcc catttttctc ttgccatttg tagctttgcc cattgtctta    1380
ttggcacatg ggtggacacg gatctgctgg gctctgcctt aaacacacat tgcagcttca    1440
acttttctct ttagtgttct gtttgaaact aatacttacc gagtcagact ttgtgttcat    1500
ttcatttcag ggtcttggct gcctgtgggc ttccccaggt ggcctggagg tgggcaaagg    1560
gaagtaacag acacacgatg ttgtcaagga tggttttggg actagaggct cagtggtggg    1620
agagatccct gcagaaccca ccaaccagaa cgtggtttgc ctgaggctgt aactgagaga    1680
aagattctgg ggctgtgtta tgaaaatata gacattctca cataagccca gttcatcacc    1740
```

| | | | | |
|---|---|---|---|---|
| atttcctcct | ttacctttca | gtgcagtttc | ttttcacatt | aggctgttgg | ttcaaacttt | 1800 |
| tgggagcacg | gactgtcagt | tctctgggaa | gtggtcagcg | catcctgcag | ggcttctcct | 1860 |
| cctctgtctt | ttggagaacc | agggctcttc | tcagggctc | tagggactgc | caggctgttt | 1920 |
| cagccaggaa | ggccaaaatc | aagagtgaga | tgtagaaagt | tgtaaaatag | aaaaagtgga | 1980 |
| gttggtgaat | cggttgttct | ttcctcacat | ttggatgatt | gtcataaggt | ttttagcatg | 2040 |
| ttcctccttt | tcttcaccct | ccccttttt | cttctattaa | tcaagagaaa | cttcaaagtt | 2100 |
| aatgggatgg | tcggatctca | caggctgaga | actcgttcac | ctccaagcat | ttcatgaaaa | 2160 |
| agctgcttct | tattaatcat | acaaactctc | accatgatgt | gaagagtttc | acaaatcctt | 2220 |
| caaaataaaa | agtaatgact | tagaaactgc | cttcctgggt | gatttgcatg | tgtcttagtc | 2280 |
| ttagtcacct | tattatcctg | acacaaaaac | acatgagcat | acatgtctac | acatgactac | 2340 |
| acaaatgcaa | acctttgcaa | acacattatg | cttttgcaca | cacacacctg | tacacacaca | 2400 |
| ccggcatgtt | tatacacagg | gagtgtatgg | ttcctgtaag | cactaagtta | gctgttttca | 2460 |
| tttaatgacc | tgtggtttaa | cccttttgat | cactaccacc | attatcagca | ccagactgag | 2520 |
| cagctatatc | cttttattaa | tcatggtcat | tcattcattc | attcattcac | aaaatattta | 2580 |
| tgatgtattt | actctgcacc | aggtcccatg | ccaagcactg | gggacacagt | tatggcaaag | 2640 |
| tagacaaagc | atttgttcat | ttggagctta | gagtccagga | ggaatacatt | agataatgac | 2700 |
| acaatcaaat | ataaattgca | agatgtcaca | ggtgtgatga | agggagagta | ggagagacca | 2760 |
| tgagtatgtg | taacaggagg | acacagcatt | attctagtgc | tgtactgttc | cgtacggcag | 2820 |
| ccactaccca | catgtaactt | tttaagattt | aaatttaaat | tagttaacat | tcaaaacgca | 2880 |
| gctccccaat | cacactagca | acatttcaag | tgcttgagag | ccatgcatga | ttagtggtta | 2940 |
| ccctattgaa | taggtcagaa | gtagaatctt | ttcatcatca | cagaaagttc | tattggacag | 3000 |
| tgctcttcta | gatcatcata | agactacaga | gcacttttca | aagctcatgc | atgttcatca | 3060 |
| tgttagtgtc | gtattttgag | ctggggtttt | gagactcccc | ttagagatag | agaaacagac | 3120 |
| ccaagaaatg | tgctcaattg | caatgggcca | catacctaga | tctccagatg | tcatttcccc | 3180 |
| tctcttattt | taagttatgt | taagattact | aaaacaataa | aagctcctaa | aaaatcaaac | 3240 |
| tgtattctgg | tgttctcttc | tacacagtgg | gagggcgagc | agtaggagag | attggcccat | 3300 |
| ttggtgctgg | ccatttgagg | aatgcaagcc | cagcactagt | ctcataatct | ctaggaatct | 3360 |
| gtagagagag | gaattgaagt | aaatttcagc | attggctcat | tcagtcattc | ggcgacattc | 3420 |
| atcaggtacc | tgcaatgtgt | taggggatct | tatgagtagg | cagcgtgcgt | gatccttgct | 3480 |
| cccctggagc | tttctaacat | tctagcaggc | agaccacaca | taaatttgca | atactgtttc | 3540 |
| tgataaaaac | gtgctgtaaa | ggaaataaag | cagagaacta | tcatggaaaa | aaaaaaaaa | 3600 |
| aaaa | | | | | | 3604 |

<210> SEQ ID NO 16
<211> LENGTH: 1789
<212> TYPE: DNA
<213> ORGANISM: Homo sapiens

<400> SEQUENCE: 16

| | | | | | | |
|---|---|---|---|---|---|---|
| ggaaaaccgg | cctgactggg | gggtgaattc | agcagggagt | aaatctgatc | ggcatcaggt | 60 |
| ctgcggaaag | gagctggtga | gcacgacacc | acccaggcat | tgcctggctc | tctccgcggc | 120 |
| gggctaagtt | aaccgcgggt | ccaggagact | aagctgaaac | tgctgctcag | ctcccaagat | 180 |

| | |
|---|---|
| ggtgccaccc aaattgcatg tgcttttctg cctctgcggc tgcctggctg tggtttatcc | 240 |
| ttttgactgg caatacataa atcctgttgc ccatatgaaa tcatcagcat gggtcaacaa | 300 |
| aatacaagta ctgatggctg ctgcaagctt tggccaaact aaaatccccc ggggaaatgg | 360 |
| gccttattcc gttggttgta cagacttaat gtttgatcac actaataagg caccttctt | 420 |
| gcgtttatat tatccatccc aagataatga tcgccttgac acccttttgga tcccaaataa | 480 |
| agaatatttt tggggtctta gcaaatttct tggaacacac tggcttatgg caacatttt | 540 |
| gaggttactc tttggttcaa tgacaactcc tgcaaactgg aattcccctc tgaggcctgg | 600 |
| tgaaaaatat ccacttgttg ttttttctca tggtcttggg gcattcagga cactttattc | 660 |
| tgctattggc attgacctgg catctcatgg gtttatagtt gctgctgtag aacacagaga | 720 |
| tagatctgca tctgcaactt actatttcaa ggaccaatct gctgcagaaa taggggacaa | 780 |
| gtcttggctc taccttagaa ccctgaaaca agaggaggag acacatatac gaaatgagca | 840 |
| ggtacggcaa agagcaaaag aatgttccca agctctcagt ctgattcttg acattgatca | 900 |
| tggaaagcca gtgaagaatg cattagattt aaagtttgat atggaacaac tgaaggactc | 960 |
| tattgatagg gaaaaaatag cagtaattgg acattctttt ggtggagcaa cggttattca | 1020 |
| gactcttagt gaagatcaga gattcagatg tggtattgcc ctggatgcat ggatgtttcc | 1080 |
| actgggtgat gaagtatatt ccagaattcc tcagcccctc ttttttatca actctgaata | 1140 |
| tttccaatat cctgctaata tcataaaaat gaaaaaatgc tactcacctg ataaagaaag | 1200 |
| aaagatgatt acaatcaggg gttcagtcca ccagaatttt gctgacttca cttttgcaac | 1260 |
| tggcaaaata attggacaca tgctcaaatt aaagggagac atagattcaa atgtagctat | 1320 |
| tgatcttagc aacaaagctt cattagcatt cttacaaaag catttaggac ttcataaaga | 1380 |
| ttttgatcag tgggactgct tgattgaagg agatgatgag aatcttattc cagggaccaa | 1440 |
| cattaacaca accaatcaac acatcatgtt acagaactct tcaggaatag agaaatacaa | 1500 |
| ttaggattaa aataggtttt ttaaaagtct tgtttcaaaa ctgtctaaaa ttatgtgtgt | 1560 |
| gtgtgtgtgt gtgtgtgtgt gtgtgagaga gagagagaga gagagagaga gagagagaga | 1620 |
| gaatttaat gtattttccc aaaggactca tattttaaaa tgtaggctat actgtaatcg | 1680 |
| tgattgaagc ttggactaag aatttttttcc ctttagatgt aaagaaagaa tacagtatac | 1740 |
| aatattcaaa aaaaaaaaaa aaaaaaaaaa aaaaaaaaaa aaaaaaaa | 1789 |

<210> SEQ ID NO 17
<211> LENGTH: 8662
<212> TYPE: DNA
<213> ORGANISM: Homo sapiens

<400> SEQUENCE: 17

| | |
|---|---|
| gtgcacgccg cagtgccggg gactcggcgg ggcgccggcc ggcgggcgga gaccgactcg | 60 |
| ggatctgtcc gagcaggaag ccagcctcag cccggccgct gtcgccgccc tgtcctggtg | 120 |
| cccgtccgcg tcgtcgccct cttcactggc cctcatcact tctcaccgcg ccctccagct | 180 |
| tcacccgtac aggtagcccc gccgccgcgc acctgccttc gctcccgcac cggtgacagt | 240 |
| ggatagtgga acaggagat cgtggatcct ccttcaaaaa tggaggatgg aaagcccgtt | 300 |
| tgggcgccac accctacaga tggatttcag atgggcaata ttgtggatat tggccccgac | 360 |
| agcttaacaa ttgaacccctt gaatcagaaa ggcaagacat ttttggctct cataaaccaa | 420 |
| gtgtttcctg cagaagagga cagtaaaaaa gatgtggaag ataactgttc actaatgtat | 480 |
| ttaaatgaag ccacactgct ccataatatc aaagttcgat atagtaaaga cagaatttat | 540 |

```
acatatgtcg ccaacattct gattgcagtg aatccatact ttgacatacc taaaatatat    600
tcttcagaag caataaagtc atatcaagga aaatctcttg ggacaagacc acctcatgtc    660
tttgcaattg ctgataaagc ttttcgagac atgaaggtgc tcaagatgag tcagtctatc    720
attgtatctg gagaatcagg agccggcaaa acagaaaata caaaatttgt tctaagatac    780
ctgactgaat cctatggaac aggtcaagat attgatgaca gaattgttga agctaaccca    840
ctcctagaag cctttggaaa tgcgaagact gttcgcaaca ataatagcag tcgatttggg    900
aaatttgtag aaatacattt taatgaaaag agctcagttg ttggaggatt tgtttcacat    960
tatctcctag agaaatctag gatctgtgtt caaggcaaag aggaaagaaa ttatcatatc   1020
ttttataggt tgtgtgctgg tgcttctgaa gatattagag aaaaacttca tttgagttca   1080
ccagataatt ttcggtattt aaaccgaggc tgcactagta ctttgctaa caaagaaact   1140 gacaaacaga ttttacagaa ccgcaaaagt cctgagtacc ttaaggcagg ttctatgaaa   1200
gatcctctgc tagatgacca tggtgatttt attagaatgt gcacggctat gaaaaaaatt   1260
ggtttggatg atgaagaaaa gcttgatctc ttccgggtag tagctggcgt cctgcacctt   1320
ggaaatattg attttgagga agctggcagc acttcaggtg gttgtaatct gaagaataaa   1380
tctgctcagt ctttggaata ttgtgctgaa ttactgggtt tggaccaaga tgatcttcga   1440
gtaagtttga ccacaagagt catgctaaca acagcagggg gcaccaaagg aacagttata   1500
aaggtacctc tgaaagtgga gcaagcaaac aatgctcgtg atgccctggc aaagacagtg   1560
tatagccatc tttttgatca tgtggtaaac agagtaaatc agtgtttttcc ttttgaaaca   1620 tcatcctatt ttattggagt cctagatatt gctggttttg agtactttga gcataacagt   1680
tttgaacaat tttgcatcaa ctattgcaat gaaaaacttc aacattttt taatgaaagg   1740 attctgaagg aggaacaaga actctatcaa aaagaaggtt taggtgttaa tgaagtgcat   1800
tatgtggata tcaggactg tatagattta attgaagcca aattagtggg aatactggat   1860
attttggatg aagaaaatcg ccttccccag ccaagtgatc aacactttac atctgcagtt   1920
caccaaaagc acaaggatca ttttcgactc actattccca gaaaatctaa gctggcagtt   1980
cataggaata tcagagacga cgaaggcttc attatcaggc attttgcggg ggcagtgtgc   2040
tatgaaacaa cccagtttgt ggagaaaaat aatgatgctt tacatatgtc tcttgaatcc   2100
ttaatatgtg aatccagaga taagtttata cgggaattat ttgaatcatc cacaaataac   2160
aacaaagata ctaaacaaaa agcaggaaaa cttagcttca tcagcgtggg aaacaagttt   2220
aagacacagt taaatttgct tctgataaa cttcgaagta ctggagcaag ctttattcgt   2280
tgcatcaaac ctaacttaaa gatgacaagc caccactttg aaggtgctca aattctgtct   2340
cagcttcagt gttcagggat ggtgtctgtt ttggacttga tgcagggtgg ttacccatca   2400
cgagcttcat ttcatgaact ctacaacatg tacaaaaagt atatgccaga taaacttgca   2460
agattggatc caagactatt ttgtaaggct ttgtttaaag ctttgggctt aaatgaaaat   2520
gactacaagt ttgggttaac caaagtattt tttagacctg gcaagtttgc agaatttgat   2580
cagatcatga gtctgacccc tgaccactta gcagagttgg ttaaaagagt caatcactgg   2640
ctcacatgca gtcgctggaa gaaagttcag tggtgctcac tctcagtcat caaattgaaa   2700
aacaaaataa aatatcgagc tgaagcctgc attaaaatgc aaaaaactat tcgaatgtgg   2760
ctttgcaaga ggagacacaa acctcgcatt gatggtctgg ttaaggtggg cacactgaaa   2820
aaacgacttg ataaatttaa tgaggtagtc agtgtgttga agatggaaa acccgagatg   2880
```

```
aataaacaga tcaagaatct ggaaatttct attgatactt tgatggccaa aattaagtcc    2940
actatgatga cgcaggaaca aatccagaaa gaatatgatg cactggttaa aagctcagag    3000
gaactcctca gtgcattaca gaaaaaaaaa cagcaggaag aggaagcaga aaggctgagg    3060
cgtattcaag aagaaatgga aaaggaaaga aaaagacgtg aagaagacga aaaacgtcga    3120
agaaaggaag aggaggaaag gcggatgaaa cttgagatgg aagcaaagag aaaacaagaa    3180
gaagaagaga gaaagaaaag ggaagatgat gaaaaacgca ttcaagctga agtggaggca    3240
cagctggccc gacagaagga ggaggaatcc aacagcaag cagttctgga gcaggagcgc    3300
agggaccggg agctggccct gaggattgcc cagagtgaag ccgagctcat cagtgatgag    3360
gcccaggccg acctggcgct gcggagaaat gatggaacaa gacccaaaat gacaccggaa    3420
caaatggcca agaaatgtc agaattttg agtagaggtc ctgctgtact agccaccaaa    3480
gcagctgctg gtactaagaa atatgatctt agtaaatgga aatatgcaga actacgtgat    3540
accatcaata cttcttgtga tattgagctc ctggcagctt gcagagaaga atttcatagg    3600
agactaaaag tgtatcatgc ttggaaatct aagaacaaga agaaatac tgaaacagag    3660 caacgtgctc caaagtctgt tactgattat gattttgcac cattttgaa caattcacct    3720 cagcaaaacc cagcagctca gattcctgcc aggcagcggg agattgaaat gaaccgacag    3780
caacgcttct tccgcatccc attcatccgc cctgccgacc agtacaaaga ccctcagagt    3840
aagaaaaaag gctggtggta tgcccatttt gatggaccat ggattgcccg gcaaatggaa    3900
ctccatcctg acaagccacc catcctactt gtggctggta aggacgacat ggagatgtgt    3960
gagctgaatc ttgaggagac tggcctgact cggaagcgtg gtgctgagat cttgccaaga    4020
cagtttgaag aaatctggga acgctgtgga ggcatccagt accttcagaa tgcgattgag    4080
agcagacagg ctcggcccac ctatgcaaca gccatgctgc agagtctgtt aaagtagatg    4140
ttgcacacca gccttacagc tgggagcctt gccatggta cttaggtagg gtgtgtgccc    4200
ccagatttaa ccattccata atcatgttag agttacttct ataaagtgaa cagattttat    4260
taatcacggc ttttggtgaa tttgtttaag gttaattatg gtagcaaatt ttggacctaa    4320
acattatttt tctgtatccc gctgtaattc ccaaaactct cattattctc taactattac    4380
acatgggcat attctgatgt ttctcatcct ttgccagaag actaccttac atccatcgta    4440
attgttctct aggaaaagag aacttttttc aaaattcaaa atacttttta aggatggcac    4500
agtaccatat aactggagta ataaaacatg agcttacatt cttacaataa ctaaaccact    4560
taaaatgatc aaggcactaa tgttttggtc tgaaaagctg tgtactttat agacatttc    4620 agacattttt ggaaatttcc attaaggtg gaaaatctat ttttttcctc ctttgcagtg    4680
tcttagtttg aatgaaacac ttcgaagttc tagaattcta gaaagagcct taatgtattt    4740
gatgtattct gtgataagag gtactaatag tatccagcac agatttgctt ttctttgcta    4800
gcacaatgtg tgttgctgtc agaatattct ttttatattc tgtggaaaaa taaggaaat    4860 tcagattgtt taaatgccta aaagttttga gataagtttt gtttcaatta gaaaggaaa    4920 taggttttag gtggcatagt ggcttaactg gactgaattc aaatattctt tcaacttcat    4980
ctcaatagtt atttttgtat cagaatcttg tccaagttgt ttcattgatt tagtaagtgt    5040
tctgcttcca acatctttct ttttaagaaa ttcctagtgt cttttttggc ctttgaggtt    5100
ttggtaattg tagacctgtt tcataagctt tgtaattcag aaatccttgt atttagtaag    5160
tgcttgtttt acataactga taattttaaa atgttttctt tgtgtgctgt tagtattgat    5220
tcaaatgtca gcagctttaa gcctaatatt tatgactttc acatttggaa tttaaagaca    5280
```

| | |
|---|---|
| aaaatacatc aaggagttat gctgacataa ttctaaggag ttttgttgta ttttagaata | 5340 |
| aaattataaa gtaaaatgat tctctgtact gcttttttccc ccagttttta gagaccctaa | 5400 |
| cctttgaaat gaaattccag tgatttcttt tttccctaga aagattacct cagttaggga | 5460 |
| agtatttccc agctgactag tgtttgtgag ccacagacac tgtcttcaga attgcttctc | 5520 |
| tcatgtctta gtagagaaat atttatttat tatgatacat tcaaatgatt gtcaagttaa | 5580 |
| attaaatggt tgtgtctgtg ctattgagaa tgcaaatgtg attatctttt gaaggctgta | 5640 |
| ttactgcata gcttcaccca ccctcgggtc atttcgtccc tgtgattggg gacagaaggt | 5700 |
| gtagctactg aagtaaatga cctattctct ctcttccatc tctcgccttt aactggtgtt | 5760 |
| tttatttgtg taggatagtg aatgataagc ttttttccta accagtagtg agtaaagttc | 5820 |
| ttgaacaaaa tttagtagcc aaattgtttt ttaatgacat gtctctttag tacaatagtt | 5880 |
| ttgtgtatct tttagataca ttaataggca ctagatggaa aattaaagag ttaaacatat | 5940 |
| ttaaatgaga gaatctaatg tttcagaaat ttgtaagaaa tgtatcacag caaagggttg | 6000 |
| ttataagtcc ttagtttttg actctaatag ttaatacaat tatagttaat cttaagccat | 6060 |
| aatgtttcta atcatgtcac acagctgtcc tagaacttat ctatttaaaa tagttttcctg | 6120 |
| agttaatttt ggccagcagg gcaactgccc taattcagat agatttacag taacctacgt | 6180 |
| acagtagatg cacatacaca cagacacccc tttgctggag aaacttagga ccctgtcagc | 6240 |
| cttttaaagg aaacagcagg agtggtgtcc taaatgatgt tcatgcagct gctttaccat | 6300 |
| gttcacagtc aagcccatgc atgccaggtt aaaactgtgg aaatcaaaag taaattcact | 6360 |
| catatttaa tcatttaac tgagatttaa aattagaagt ttaaaccact atatataaag | 6420 |
| aactaatctt ttcttaatac cagttctttc catagcatat gctttgcaaa ggcagcatgc | 6480 |
| ataaaatatt taaatgaga ggacagaatg ttttcacatt tgattcaatt ttaatataat | 6540 |
| tcctaattgt ggtaacacag ttgagatatg tattatgagt tatgggaact aattgagaaa | 6600 |
| aggaagttac tctaatccac gtatgttaag agaatattga gttttcttag ttgtaaagtt | 6660 |
| ggggagatgg caccttctca gaggattgtg aaaatatgag gaagaaacaa aacagtgcat | 6720 |
| gtaggagcac agggccacac aaaggcattc tattgttatg ctcattctgc ttctgtaatg | 6780 |
| acttttcata ggtcattctt gtgaaccatt ttgttttgca agcaaccaag gaaagaacat | 6840 |
| cttaagtgga aaatcagtgg tggttgtgaa cacttagaga atagcaatcc acaggcaaga | 6900 |
| ataatggtat tgtttgtaga gctttattaa ttggatattt tttaaaagac attttcattc | 6960 |
| acaggtcatt actatggttc tcagcgatcc aaatatgtag atcattggtt ttttttttta | 7020 |
| cctgaagtag cttaagagta cttggatcag tagaataaat atttattgaa tcaatcagtc | 7080 |
| agccaattaa tatgatgtta gtgatagacc tgcctccttt tatggaagag gtaacagatc | 7140 |
| cagagaggtc aagtaattta gttgtagact gaaaaatata tcaaagcctt tgctgcaatc | 7200 |
| atatgtaaca aaaagaacca aaacaaacac tttttagtgg cacctgtgga tttacaaagg | 7260 |
| gttgcctctc tgtcattcca caacttcaga aggtgtgaca ggttttccct atttatcatt | 7320 |
| accaataata acaagtattg agagttttaa aatttctccc agaagataaa ctaacaagga | 7380 |
| tggaagggga gggcaaagga tatctaaaca tgagaataag gacatgttag agggggggaa | 7440 |
| acagttgtaa caataaggaa agagaagagc aacagtggaa gagacaggtt gtgtgcccct | 7500 |
| aaagattctg cacccccagt ttggaaacac tgatacattt taggacacag agcactccta | 7560 |
| gatctctacg aaatttttaga atgaataatg tgtaatttat aggatcagaa cgtatggtta | 7620 |

| | |
|---|---:|
| ttaaaacttg gatcaagata tgcccggtgt atacattctt agcacatagg aatggcactg | 7680 |
| ccatactgga gaaggtcagc agtaaatagg cattctgtac ataagcctca tggaagggta | 7740 |
| agatggagag actggcagaa gtagcaccta ctctgctggg agcacttctc tgagtacgct | 7800 |
| ttagttcaat tcaaatcact gtattctttc cccattgcta acctaatata tgaaacaagc | 7860 |
| ttagctgtct cagaagtttt tcaagagatg atcaggaaaa attaatgcac attcaaaagg | 7920 |
| agaatcttca gtacaaattt gttttttttaa aaatagattt agggctgggc gcggtggctc | 7980 |
| acgcctgtaa tcccagcact tgggaggcc gaggcgggtg gatcacgagg tcaagacttc | 8040 |
| gagaccagcc tggccaacat ggtgaaaccc tgtctctact aaaaatacaa aacattagcc | 8100 |
| aggcgtggta gtgggtgcct gtaatccctg ctacttggga ggctgaggca ggagaatcac | 8160 |
| ttgaacgcgg gaggcagagg ttgcaggag ccgagatggc gccattgcac tccatcctgg | 8220 |
| gcaacaagag cgaaattcca tctcaaaaaa taaaatagat ttagggggta caagtgcagt | 8280 |
| tttgttacat gggtatattg catagtggta aaatgtgggc ttttagtgta cctaacaccc | 8340 |
| agagaagcat acattgtgcc cagtaggtaa ttttcatcc ctaaaccttt tctcagcctc | 8400 |
| ccactttctg gagtctccaa tgtcggttat tccactcttt atgtccatat ctacacattc | 8460 |
| aatcctaatt tgtaccaagt agcatctcac ctttaaatca caggcttatt agttgggtgt | 8520 |
| tttctttta cttatgaaaa ttcatctagt caaactgtca attaattttt cctcatttca | 8580 |
| ttaaaagtgt atatctaatg ctttctctaa aaattgatgt actggaaata caaataaata | 8640 |
| aatgctccct gtgtagaatt tc | 8662 |

<210> SEQ ID NO 18
<211> LENGTH: 2219
<212> TYPE: DNA
<213> ORGANISM: Homo sapiens

<400> SEQUENCE: 18

| | |
|---|---:|
| gcacaaccag aatttgccaa aacaggaaat aggtgtttca tatatacggc tctaaccttc | 60 |
| tctctctgca ccttccttct gtcaatagat gaaacaaata cttcatcctg ctctggaaac | 120 |
| cactgcaatg acattattcc cagtgctgtt gttcctggtt gctgggctgc ttccatcttt | 180 |
| tccagcaaat gaagataagg atcccgcttt tactgctttg ttaaccaccc aaacacaagt | 240 |
| gcaaagggag attgtgaata agcacaatga actgaggaga gcagtatctc cccctgccag | 300 |
| aaacatgctg aagatggaat ggaacaaaga ggctgcagca aatgcccaaa agtgggcaaa | 360 |
| ccagtgcaat tacagacaca gtaacccaaa ggatcgaatg acaagtctaa aatgtggtga | 420 |
| gaatctctac atgtcaagtg cctccagctc atggtcacaa gcaatccaaa gctggtttga | 480 |
| tgagtacaat gattttgact ttggtgtagg gccaaagact cccaacgcag tggttggaca | 540 |
| ttatacacag gttgtttggt actcttcata cctcgttgga tgtggaaatg cctactgtcc | 600 |
| caatcaaaaa gttctaaaat actactatgt ttgccaatat tgtcctgctg gtaattgggc | 660 |
| taatagacta tatgtccctt atgaacaagg agcaccttgt gccagttgcc cagataactg | 720 |
| tgacgatgga ctatgcacca atggttgcaa gtacgaagat ctctatagta actgtaaaag | 780 |
| tttgaagctc acattaacct gtaaacatca gttggtcagg acagttgca aggcctcctg | 840 |
| caattgttca aacagcattt attaaatacg cattacacac cgagtagggc tatgtagaga | 900 |
| ggagtcagat tatctactta gatttggcat ctacttagat ttaacatata ctagctgaga | 960 |
| aattgtaggc atgtttgata cacatttgat ttcaaatgtt tttcttctgg atctgctttt | 1020 |
| tattttacaa aaatattttt catacaaatg gttaaaaaga aacaaaatct ataacaacaa | 1080 |

```
ctttggattt ttatatataa actttgtgat ttaaatttac tgaatttaat tagggtgaaa    1140
attttgaaag ttgtattctc atatgactaa gttcactaaa accctggatt gaaagtgaaa    1200
attatgttcc tagaacaaaa tgtacaaaaa gaacaatata attttcacat gaacccttgg    1260
ctgtagttgc ctttcctagc tccactctaa ggctaagcat cttcaaagac gttttcccat    1320
atgctgtctt aattcttttc actcattcac ccttcttccc aatcatctgg ctggcatcct    1380
cacaattgag ttgaagctgt tcctcctaaa acaatcctga cttttatttt gccaaaatca    1440
atacaatcct ttgaattttt tatctgcata aattttacag tagaatatga tcaaaccttc    1500 attttaaac ctctcttctc tttgacaaaa cttccttaaa aaagaataca agataatata    1560
ggtaaatacc ctccactcaa ggaggtagaa ctcagtcctc tcccttgtga gtcttcacta    1620
aaatcagtga ctcacttcca aagagtggag tatggaaagg gaaacatagt aactttacag    1680
gggagaaaaa tgacaaatga cgtcttcacc aagtgatcaa aattaacgtc accagtgata    1740
agtcattcag atttgttcta gataatcttt ctaaaaattc ataatcccaa tctaattatg    1800
agctaaaaca tccagcaaac tcaagttgaa ggacattcta caaaatatcc ctggggtatt    1860
ttagagtatt cctcaaaact gtaaaaatca tggaaaataa gggaatcctg agaaacaatc    1920
acagaccaca tgagactaag gagacatgtg agccaaatgc aatgtgcttc ttggatcaga    1980
tcctggaaca gaaaaagatc agtaatgaaa aaactgatga agtctgaata gaatctggag    2040 tattttttaac agtagtgttg atttcttaat cttgataaat atagcagggt aatgtaagat    2100
gataacgtta gagaaactga aactgggtga gggctatcta ggaattctct gtactatctt    2160
accaaatttt cggtaagtct aagaaagcaa tgcaaaataa aaagtgtctt gaaaaaaaa    2219

<210> SEQ ID NO 19
<211> LENGTH: 1669
<212> TYPE: DNA
<213> ORGANISM: Homo sapiens

<400> SEQUENCE: 19
gaggtataag agcctccaag tctgcagctc tcgcccaact cccagacacc tcgcgggctc      60
tgcagcaccg gcaccgtttc caggaggcct ggcggggtgt gcgtccagcc gttgggcgct     120 ttcttttttgg acctcggggc catccacacc gtccctccc cctcccgcct ccctcccgc     180 ctccccgcg cgccctcccc gcggaggtcc ctcccgtccg tcctcctgct ctctcctccg     240
cgggccgcat cgcccgggcc ggcgccgcgc gcggggaag ctggcgggct gaggcgcccc     300
gctcttctcc tctgccccgg gcccgcgagg ccacgcgtcg ccgctcgaga gatgatgcag     360
gacgtgtcca gctcgccagt ctcgccggcc gacgacagcc tgagcaacag cgaggaagag     420
ccagaccggc agcagccgcc gagcggcaag gcgggggac gcaagcggcg cagcagcagg     480
cgcagcgcgg gcggcggcgc ggggcccggc ggagccgcgg gtggggcgt cggaggcggc     540 gacgagccgg gcagcccggc ccagggcaag gcggcaaga agtctgcggg ctgtggcggc     600
ggcggcggcg cgggcggcgg cggcggcagc agcagcggcg gcgggagtcc gcagtcttac     660
gaggagctgc agacgcagcg ggtcatggcc aacgtgcggg agcgccagcg cacccagtcg     720
ctgaacgagg cgttcgccgc gctgcggaag atcatcccca cgctgccctc ggacaagctg     780
agcaagattc agaccctcaa gctggcggcc aggtacatcg acttcctcta ccaggtcctc     840
cagagcgacg agctggactc caagatggca agctgcagct atgtggctca cgagcggctc     900
agctacgcct tctcggtctg gaggatggag ggggcctggt ccatgtccgc gtcccactag     960
```

| | |
|---|---|
| caggcggagc cccccacccc ctcagcaggg ccggagacct agatgtcatt gtttccagag | 1020 |
| aaggagaaaa tggacagtct agagactctg gagctggata actaaaaata aaaatatatg | 1080 |
| ccaaagattt tcttggaaat tagaagagca aaatccaaat tcaaagaaac agggcgtggg | 1140 |
| gcgcactttt aaaagagaaa gcgagacagg cccgtggaca gtgattccca gacgggcagc | 1200 |
| ggcaccatcc tcacacctct gcattctgat agaagtctga acagttgttt gtgttttttt | 1260 |
| ttttttttt tttgacgaag aatgttttta ttttatttt tttcatgcat gcattctcaa | 1320 |
| gaggtcgtgc caatcagcca ctgaaaggaa aggcatcact atggactttc tctattttaa | 1380 |
| aatggtaaca atcagaggaa ctataagaac acctttagaa ataaaaatac tgggatcaaa | 1440 |
| ctggcctgca aaaccatagt cagttaattc ttttttttcat ccttcctctg aggggaaaaa | 1500 |
| caaaaaaaaa cttaaaatac aaaaaacaac attctattta tttattgagg acccatggta | 1560 |
| aaatgcaaat agatccggtg tctaaatgca ttcatatttt tatgattgtt ttgtaaatat | 1620 |
| ctttgtatat ttttctgcaa taaataaata taaaaatttt agagaaaaa | 1669 |

<210> SEQ ID NO 20
<211> LENGTH: 5988
<212> TYPE: DNA
<213> ORGANISM: Homo sapiens

<400> SEQUENCE: 20

| | |
|---|---|
| ctgcccggcg tgctgggtag aggtggccag ccccggccgc tgctgccaga cgggctctcc | 60 |
| gggtccttct ccgagagccg ggcgggcacg cgtcattgtg ttacctgcgg ccggcccgcg | 120 |
| agctaggctg gttttttttt ttctcccctc cctcccccct ttttccatgc agctgatcta | 180 |
| aaagggaata aaaggctgcg cataatcata ataataaaag aaggggagcg cgagagaagg | 240 |
| aaagaaagcc gggaggtgga agaggagggg gagcgtctca aagaagcgat cagaataata | 300 |
| aaaggaggcc gggctctttg ccttctggaa cgggccgctc ttgaaagggc ttttgaaaag | 360 |
| tggtgttgtt ttccagtcgt gcatgctcca atcggcggag tatattagag ccgggacgcg | 420 |
| gcggccgcag gggcagcggc gacggcagca ccggcggcag caccagcgcg aacagcagcg | 480 |
| gcggcgtccc gagtgcccgc ggcgcgcggc gcagcgatgc gttccccacg gacgcgcggc | 540 |
| cggtccgggc gcccctaag cctcctgctc gccctgctct gtgccctgcg agccaaggtg | 600 |
| tgtgggggcct cgggtcagtt cgagttggag atcctgtcca tgcagaacgt gaacggggag | 660 |
| ctgcagaacg ggaactgctg cggcggcgcc cggaacccgg agaccgcaa gtgcacccgc | 720 |
| gacgagtgtg acacatactt caagtgtgc ctcaaggagt atcagtcccg cgtcacggcc | 780 |
| gggggggccct gcagcttcgg ctcagggtcc acgcctgtca tcggggcaa caccttcaac | 840 |
| ctcaaggcca gccgcggcaa cgaccgcaac cgcatcgtgc tgcctttcag tttcgcctgg | 900 |
| ccgaggtcct atacgttgct tgtggaggcg tgggattcca gtaatgacac cgttcaacct | 960 |
| gacagtatta ttgaaaaggc ttctcactcg gcatgatca accccagccg gcagtggcag | 1020 |
| acgctgaagc agaacacggg cgttgcccac tttgagtatc agatccgcgt gacctgtgat | 1080 |
| gactactact atggctttgg ctgcaataag ttctgccgcc ccagagatga cttctttgga | 1140 |
| cactatgcct gtgaccagaa tggcaacaaa acttgcatgg aaggctggat gggccccgaa | 1200 |
| tgtaacagag ctatttgccg acaaggctgc agtcctaagc atgggtcttg caaactccca | 1260 |
| ggtgactgca gtgccagta cggctggcaa ggcctgtact gtgataagtg catcccacac | 1320 |
| ccgggatgcg tccacggcat ctgtaatgag ccctggcagt gcctctgtga gaccaactgg | 1380 |
| ggcggccagc tctgtgacaa agatctcaat tactgtggga ctcatcagcc gtgtctcaac | 1440 |

-continued

```
gggggaactt gtagcaacac aggccctgac aaatatcagt gttcctgccc tgagggtat     1500 tcaggaccca actgtgaaat tgctgagcac gcctgcctct ctgatccctg tcacaacaga    1560
ggcagctgta aggagacctc cctgggcttt gagtgtgagt gttccccagg ctggaccggc    1620
cccacatgct ctacaaacat tgatgactgt tctcctaata actgttccca cgggggcacc    1680
tgccaggacc tggttaacgg atttaagtgt gtgtgccccc cacagtggac tgggaaaacg    1740
tgccagttag atgcaaatga atgtgaggcc aaaccttgtg taaacgccaa atcctgtaag    1800
aatctcattg ccagctacta ctgcgactgt cttcccggct ggatgggtca gaattgtgac    1860
ataaatatta atgactgcct tggccagtgt cagaatgacg cctcctgtcg ggatttggtt    1920
aatggttatc gctgtatctg tccacctggc tatgcaggcg atcactgtga gagagacatc    1980
gatgaatgtg ccagcaaccc ctgtttgaat ggggggtcact gtcagaatga aatcaacaga    2040
ttccagtgtc tgtgtcccac tggtttctct ggaaacctct gtcagctgga catcgattat    2100
tgtgagccta atccctgcca gaacggtgcc cagtgctaca accgtgccag tgactatttc    2160
tgcaagtgcc ccgaggacta tgagggcaag aactgctcac acctgaaaga ccactgccgc    2220
acgaccccct gtgaagtgat tgacagctgc acagtggcca tggcttccaa cgacacacct    2280
gaaggggtgc ggtatatttc ctccaacgtc tgtggtcctc acgggaagtg caagagtcag    2340
tcgggaggca aattcacctg tgactgtaac aaaggcttca cgggaacata ctgccatgaa    2400
aatattaatg actgtgagag caaccttgt agaaacggtg gcacttgcat cgatggtgtc    2460
aactcctaca gtgcatctg tagtgacggc tgggaggggg cctactgtga aaccaatatt    2520
aatgactgca gccagaaccc ctgccacaat gggggcacgt gtcgcgacct ggtcaatgac    2580
ttctactgtg actgtaaaaa tgggtggaaa ggaaagacct gccactcacg tgacagtcag    2640
tgtgatgagg ccacgtgcaa caacggtggc acctgctatg atgaggggga tgcttttaag    2700
tgcatgtgtc ctggcggctg ggaaggaaca acctgtaaca tagcccgaaa cagtagctgc    2760
ctgcccaacc cctgccataa tgggggcaca tgtgtggtca acggcgagtc ctttacgtgc    2820
gtctgcaagg aaggctggga ggggcccatc tgtgctcaga ataccaatga ctgcagccct    2880
catccctgtt acaacagcgg cacctgtgtg gatggagaca actggtaccg gtgcgaatgt    2940
gccccgggtt ttgctgggcc cgactgcaga ataaacatca atgaatgcca gtcttcacct    3000
tgtgcctttg gagcgacctg tgtggatgag atcaatggct accggtgtgt ctgccctcca    3060 ggcacagtg gtgccaagtg ccaggaagtt tcagggagac cttgcatcac catggggagt    3120
gtgataccag atggggccaa atgggatgat gactgtaata cctgccagtg cctgaatgga    3180
cggatcgcct gctcaaaggt ctggtgtggc cctcgacctt gcctgctcca caaagggcac    3240
agcgagtgcc ccagcgggca gagctgcatc cccatcctgg acgaccagtg cttcgtccac    3300
ccctgcactg gtgtgggcga gtgtcggtct tccagtctcc agccggtgaa gacaaagtgc    3360
acctctgact cctattacca ggataactgt gcgaacatca catttacctt taacaaggag    3420
atgatgtcac aggtcttac tacggagcac atttgcagtg aattgaggaa tttgaatatt    3480
ttgaagaatg tttccgctga atattcaatc tacatcgctt gcgagccttc cccttcagcg    3540
aacaatgaaa tacatgtggc catttctgct gaagatatac gggatgatgg gaacccgatc    3600
aaggaaatca ctgacaaaat aatcgatctt gttagtaaac gtgatggaaa cagctcgctg    3660
attgctgccg ttcagaagt aagagttcag aggcggcctc tgaagaacag aacagatttc    3720
cttgttccct tgctgagctc tgtcttaact gtggcttgga tctgttgctt ggtgacggcc    3780
```

-continued

```
ttctactggt gcctgcggaa gcggcggaag ccgggcagcc acacacactc agcctctgag    3840
gacaacacca ccaacaacgt gcgggagcag ctgaaccaga tcaaaaaccc cattgagaaa    3900
catggggcca acacggtccc catcaaggat tatgagaaca agaactccaa aatgtctaaa    3960
ataaggacac acaattctga agtagaagag gacgacatgg acaaacacca gcagaaagcc    4020
cggtttgcca agcagccggc gtacacgctg gtagacagag aagagaagcc ccccaacggc    4080
acgccgacaa acaccccaaa ctggacaaac aaacaggaca acagagactt ggaaagtgcc    4140
cagagcttaa accgaatgga gtacatcgta tagcagaccg cgggcactgc cgccgctagg    4200
tagagtctga gggcttgtag ttctttaaac tgtcgtgtca tactcgagtc tgaggccgtt    4260
gctgacttag aatccctgtg ttaatttaag ttttgacaag ctggcttaca ctggcaatgg    4320
tagtttctgt ggttggctgg gaaatcgagt gccgcatctc acagctatgc aaaaagctag    4380
tcaacagtac cctggttgtg tgtccccttg cagccgacac ggtctcggat caggctccca    4440
ggagcctgcc cagcccctg gtctttgagc tcccacttct gccagatgtc ctaatggtga    4500
tgcagtctta gatcatagtt ttatttatat ttattgactc ttgagttgtt tttgtatatt    4560
ggttttatga tgacgtacaa gtagttctgt atttgaaagt gcctttgcag ctcagaacca    4620
cagcaacgat cacaaatgac tttattattt atttttttta attgtatttt tgttgttggg    4680
ggaggggaga ctttgatgtc agcagttgct ggtaaaatga agaatttaaa gaaaaaaatg    4740
tcaaaagtag aactttgtat agttatgtaa ataattcttt tttattaatc actgtgtata    4800
tttgatttat taacttaata atcaagagcc ttaaaacatc attccttttt atttatatgt    4860
atgtgtttag aattgaaggt ttttgatagc attgtaagcg tatggcttta ttttttttgaa    4920 ctcttctcat tacttgttgc ctataagcca aaattaaggt gtttgaaaat agtttatttt    4980
aaaacaatag gatgggcttc tgtgcccaga atactgatgg aattttttg tacgacgtca    5040 gatgtttaaa acaccttcta tagcatcact taaaacacgt tttaaggact gactgaggca    5100
gtttgaggat tagtttagaa caggtttttt tgtttgtttg tttttttgttt ttctgcttta    5160 gacttgaaaa gagacaggca ggtgatctgc tgcagagcag taagggaaca agttgagcta    5220
tgacttaaca tagccaaaat gtgagtggtt gaatatgatt aaaaatatca aattaattgt    5280
gtgaacttgg aagcacacca atcttacttt gtaaattctg atttcttttc accattcgta    5340
cataatactg aaccacttgt agatttgatt ttttttttta atctactgca tttagggagt    5400
attctaataa gctagttgaa tacttgaacc ataaaatgtc cagtaagatc actgtttaga    5460
tttgccatag agtacactgc ctgccttaag tgaggaaatc aaagtgctat tacgaagttc    5520
aagatcaaaa aggcttataa aacagagtaa tcttgttggt tcaccattga gaccgtgaag    5580
atactttgta ttgtcctatt agtgttatat gaacatacaa atgcatcttt gatgtgttgt    5640
tcttggcaat aaattttgaa aagtaatatt tattaaattt ttttgtatga aaacatggaa    5700
cagtgtggcc tcttctgagc ttacgtagtt ctaccggctt tgccatgtgc ttctgccacc    5760
ctgctgagtc tgttctggta atcggggtat aataggctct gcctgacaga gggatggagg    5820
aagaactgaa aggcttttca accacaaaac tcatctggag ttctcaaaga cctggggctg    5880
ctgtgaagct ggaactgcgg gagccccatc taggggagcc ttgattccct tgttattcaa    5940
cagcaagtgt gaatactgct tgaataaaca ccactggatt aatggcca                 5988
```

<210> SEQ ID NO 21
<211> LENGTH: 1603
<212> TYPE: DNA
<213> ORGANISM: Homo sapiens

<400> SEQUENCE: 21

| | | | | | |
|---|---|---|---|---|---|
| aaggcactct | ggcacccagt | tttggaactg | cagttttaaa | agtcataaat | tgaatgaaaa | 60 |
| tgatagcaaa | ggtggaggtt | tttaaagagc | tatttatagg | tccctggaca | gcatcttttt | 120 |
| tcaattaggc | agcaaccttt | tgccctatg | ccgtaacctg | tgtctgcaac | ttcctctaat | 180 |
| tgggaaatag | ttaagcagat | tcatagagct | gaatgataaa | attgtactac | gagatgcact | 240 |
| gggactcaac | gtgaccttat | caagtgagca | ggcttggtgc | atttgacact | tcatgatatc | 300 |
| agccaaagtg | gaactaaaaa | cagctcctgg | aagaggacta | tgacatcatc | aggttgggag | 360 |
| tctccaggga | cagcggaccc | tttggaaaag | gactagaaag | tgtgaaatct | attagtcttc | 420 |
| gatatgaaat | tctctgtctc | tgtaaaagca | tttcatattt | acaagacaca | ggcctactcc | 480 |
| tagggcagca | aaaagtggca | acaggcaagc | agagggaaaa | gagatcatga | ggcatttcag | 540 |
| agtgcactgt | cttttcatat | atttctcaat | gccgtatgtt | tggttttatt | ttggccaagc | 600 |
| ataacaatct | gctcaagaaa | aaaaaatctg | gagaaaacaa | aggtgccttt | gccaatgtta | 660 |
| tgtttctttt | tgacaagccc | tgagatttct | gaggggaatt | cacataaatg | ggatcaggtc | 720 |
| attcatttac | gttgtgtgca | aatatgattt | aaagatacaa | cctttgcaga | gagcatgctt | 780 |
| tcctaagggt | aggcacgtgg | aggactaagg | gtaaagcatt | cttcaagatc | agttaatcaa | 840 |
| gaaaggtgct | ctttgcattc | tgaaatgccc | ttgttcaaa | tattggttat | attgattaaa | 900 |
| tttacactta | atggaaacaa | cctttaactt | acagatgaac | aaacccacaa | aagcaaaaaa | 960 |
| tcaaaagccc | tacctatgat | ttcatatttt | ctgtgtaact | ggattaaagg | attcctgctt | 1020 |
| gcttttgggc | ataaatgata | atggaatatt | tccaggtatt | gtttaaaatg | agggcccatc | 1080 |
| tacaaattct | tagcaatact | ttggataatt | ctaaaattca | gctggacatt | gtctaattgt | 1140 |
| tttttatata | catctttgct | agaatttcaa | attttaagta | tgtgaattta | gttaattagc | 1200 |
| tgtgctgatc | aattcaaaaa | cattactttc | ctaaattta | gactatgaag | gtcataaatt | 1260 |
| caacaaatat | atctacacat | acaattatag | attgttttc | attataatgt | cttcatctta | 1320 |
| acagaattgt | ctttgtgatt | gttttagaa | aactgagagt | tttaattcat | aattacttga | 1380 |
| tcaaaaaatt | gtgggaacaa | tccagcatta | attgtatgtg | attgttttta | tgtacataag | 1440 |
| gagtcttaag | cttggtgcct | tgaagtcttt | tgtacttagt | cccatgttta | aaattactac | 1500 |
| tttatatcta | aagcatttat | gtttttcaat | tcaatttaca | tgatgctaat | tatggcaatt | 1560 |
| ataacaaata | ttaaagattt | cgaaatagaa | aaaaaaaaa | aaa | | 1603 |

<210> SEQ ID NO 22
<211> LENGTH: 4934
<212> TYPE: DNA
<213> ORGANISM: Homo sapiens

<400> SEQUENCE: 22

| | | | | | |
|---|---|---|---|---|---|
| aaacccgatc | tccttggact | tgaatgagga | ggaggaggcg | gcggcggcgg | cggcggcgga | 60 |
| ggcgctcggc | tggggaaagc | tagcggcaga | ggctcagccc | cggcggcagc | gcgcgccccg | 120 |
| ctgccagccc | attttccgga | cgccacccgc | gggcactgcc | gacgccccg | gggctgccga | 180 |
| ggggaggccg | ggggggcgca | gcggagcgcg | gtcccgcgca | ctgagccccg | cggcgccccg | 240 |
| ggaacttggc | ggcgacccga | gcccggcgag | ccggggcgcg | cctccccgc | cgcgcgcctc | 300 |
| ctgcatgcgg | ggccccagct | ccgggcgccg | gccggagccc | ccccggccg | ccccgagcc | 360 |
| ccccgcgccc | cgcgccgcgc | cgccgcgccg | tccatgcacc | gcttgatggg | ggtcaacagc | 420 |

-continued

```
accgccgccg ccgccgccgg gcagcccaat gtctcctgca cgtgcaactg caaacgctct    480
ttgttccaga gcatggagat cacggagctg gagtttgttc agatcatcat catcgtggtg    540
gtgatgatgg tgatggtggt ggtgatcacg tgcctgctga gccactacaa gctgtctgca    600
cggtccttca tcagccggca cagccagggg cggaggagag aagatgccct gtcctcagaa    660
ggatgcctgt ggccctcgga gagcacagtg tcaggcaacg gaatcccaga gccgcaggtc    720
tacgccccgc ctcggcccac cgaccgcctg gccgtgccgc ccttcgccca gcgggagcgc    780
ttccaccgct tccagcccac ctatccgtac ctgcagcacg agatcgacct gccacccacc    840
atctcgctgt cagacgggga ggagccccca ccctaccagg gcccctgcac cctccagctt    900
cgggaccccg agcagcagct ggaactgaac cgggagtcgg tgcgcgcacc cccaaacaga    960
accatcttcg acagtgacct gatggatagt gccaggctgg gcggcccctg ccccccccagc   1020
agtaactcgg gcatcagcgc cacgtgctac ggcagcggcg ggcgcatgga ggggccgccg   1080
cccacctaca gcgaggtcat cggccactac ccggggtcct ccttccagca ccagcagagc   1140
agtgggccgc cctccttgct ggaggggacc cggctccacc acacacacat cgcgcccctc   1200
gagagcgcag ccatctggag caaagagaag gataaacaga aaggacaccc tctctagggt   1260
ccccaggggg gccgggctgg ggctgcgtag gtgaaaaggc agaacactcc gcgcttctta   1320
gaagaggagt gagaggaagg cgggggggcgc agcaacgcat cgtgtggccc tcccctccca   1380
cctccctgtg tataaatatt tacatgtgat gtctggtctg aatgcacaag ctaagagagc   1440
ttgcaaaaaa aaaagaaaa aagaaaaaaa aaaaccacgt ttctttgttg agctgtgtct   1500
tgaaggcaaa agaaaaaaaa tttctacagt agtctttctt gtttctagtt gagctgcgtg   1560
cgtgaatgct tattttcttt tgtttatgat aatttcactt aactttaaag acatatttgc   1620
acaaaacctt tgtttaaaga tctgcaatat tatatatata aatatatata agataagaga   1680
aactgtatgt gcgagggcag gagtattttt gtattagaag aggcctatta aaaaaaaag   1740
ttgttttctg aactagaaga ggaaaaaaat ggcaattttt gagtgccaag tcagaaagtg   1800
tgtattacct tgtaaagaaa aaattacaa agcagggtt tagagttatt tatataaatg   1860
ttgagatttt gcactatttt ttaatataaa tatgtcagtg cttgcttgat ggaaacttct   1920
cttgtgtctg ttgagacttt aagggagaaa tgtcggaatt tcagagtcgc ctgacggcag   1980
agggtgagcc cccgtggagt ctgcagagag gccttggcca ggagcggcgg gctttcccga   2040
ggggccactg tccctgcaga gtggatgctt ctgcctagtg acaggttatc accacgttat   2100
atattcccta ccgaaggaga cacctttttcc ccctgaccc agaacagcct ttaaatcaca   2160
agcaaaatag gaaagttaac cacggaggca ccgagttcca ggtagtggtt tgcctttcc   2220
caaaaatgaa aataaactgt taccgaagga attagttttt cctcttcttt tttccaactg   2280
tgaaggtccc cgtggggtgg agcatggtgc ccctcacaag ccgcagcggc tggtgcccgg   2340
gctaccaggg acatgccaga gggctcgatg acttgtctct gcagggcgct ttggtggttg   2400
ttcagctggc taaaggttca ccggtgaagg caggtgcggt aactgccgca ctggacccta   2460
ggaagcccca ggtattcgca atctgacctc ctcctgtctg tttcccttca cggatcaatt   2520
ctcacttaag aggccaataa acaacccaac atgaaaaggt gacaagcctg gtttctccc   2580
aggataggtg aaagggttaa aatgagtaaa gcagttgagc aaacaccaac ccgagcttcg   2640
ggcgcagaat tcttcacctt ctcttcccct ttccatctcc tttccccgcg gaaacaacgc   2700
ttccccttctg tgtgtctgt tgatctgtgt tttcatttac atctctctta gactccgctc   2760
ttgttctcca ggttttcacc agatagattt gggttggcg ggacctgctg gtgacgtgca   2820
```

```
ggtgaaggac aggaaggggc atgtgagcgt aaatagaggt gaccagagga gagcatgagg   2880
ggtggggctt tgggacccac cggggccagt ggctggagct tgacgtcttt cctccccatg   2940
ggggtgggag ggccccccagc tggaagagca gactcccagc tgctacccc tcccttccca   3000 tgggagtggc tttccatttt gggcagaatg ctgactagta gactaacata aaagatataa   3060
aaggcaataa ctattgtttg tgagcaactt ttttataact tccaaaacaa aaacctgagc   3120
acagttttga agttctagcc actcgagctc atgcatgtga acgtgtgct ttacgaaggt    3180 ggcagctgac agacgtgggc tctgcatgcc gccagcctag tagaaagttc tcgttcattg   3240
gcaacagcag aacctgcctc tccgtgaagt cgtcagccta aaatttgttt ctctcttgaa   3300
gaggattctt tgaaaaggtc ctgcagagaa atcagtacag gttatcccga aaggtacaag   3360
gacgcacttg taaagatgat taaaacgtat ctttccttta tgtgacgcgt ctctagtgcc   3420
ttactgaaga agcagtgaca ctcccgtcgc tcggtgagga cgttcccgga cagtgcctca   3480
ctcacctggg actggtatcc cctcccaggg tccaccaagg gctcctgctt ttcagacacc   3540
ccatcatcct cgcgcgtcct caccctgtct ctaccaggga ggtgcctagc ttggtgaggt   3600
tactcctgct cctccaacct tttttttgcca aggtttgtac acgactccca tctaggctga   3660
aaacctagaa gtggaccttg tgtgtgtgca tggtgtcagc ccaaagccag gctgagacag   3720
tcctcatatc ctcttgagcc aaactgtttg ggtctcgttg cttcatggta tggtctggat   3780
ttgtgggaat ggctttgcgt gagaaagggg aggagagtgg ttgctgccct cagccggctt   3840
gaggacagag cctgtccctc tcatgacaac tcagtgttga agcccagtgt cctcagcttc   3900
atgtccagtg gatggcagaa gttcatgggg tagtggcctc tcaaaggctg ggcgcatccc   3960
aagacagcca gcaggttgtc tctggaaacg accagagtta agctctcggc ttctctgctg   4020
agggtgcacc ctttcctcta gatggtagtt gtcacgttat ctttgaaaac tcttggactg   4080
ctcctgagga ggccctcttt tccagtagga agttagatgg gggttctcag aagtggctga   4140
ttggaagggg acaagcttcg tttcagggt ctgccgttcc atcctggttc agagaaggcc    4200
gagcgtggct ttctctagcc ttgtcactgt ctccctgcct gtcaatcacc acctttcctc   4260
cagaggagga aaattatctc ccctgcaaag cccggttcta cacagatttc acaaattgtg   4320
ctaagaaccg tccgtgttct cagaaagccc agtgttttg caaagaatga aaagggaccc    4380
catatgtagc aaaaatcagg gctggggag agccgggttc attccctgtc ctcattggtc    4440
gtccctatga attgtacgtt tcagagaaat ttttttttcct atgtgcaaca cgaagcttcc   4500
agaaccataa aatatcccgt cgataaggaa agaaaatgtc gttgttgttg ttttttctgga   4560 aactgcttga atcttgctg tactatagag ctcagaagga cacagcccgt cctcccctgc    4620
ctgcctgatt ccatggctgt tgtgctgatt ccaatgcttt cacgttggtt cctggcgtgg   4680
gaactgctct cctttgcagc cccatttccc aagctctgtt caagttaaac ttatgtaagc   4740
tttccgtggc atgcggggcg cgcacccacg tccccgctgc gtaagactct gtatttggat   4800
gccaatccac aggcctgaag aaactgcttg ttgtgtatca gtaatcatta gtggcaatga   4860
tgacattctg aaaagctgca atacttatac aataaatttt acaattcttt ggaatgagaa   4920
aaaaaaaaaa aaaa                                                     4934

<210> SEQ ID NO 23
<211> LENGTH: 2593
<212> TYPE: DNA
<213> ORGANISM: Homo sapiens
```

<400> SEQUENCE: 23

```
agaaccagga caggtgaggt gcaggctggc tttcctctcg cagcgcggtg tggagtcctg    60
tcctgcctca gggcttttcg gagcctggat cctcaaggaa caagtagacc tggccgcggg   120
gagtggggag ggaaggggtg tctattgggc aacagggcgg ggcaaagccc tgaataaagg   180
ggcgcagggc aggcgcaagt ggcagagcct tcgtttgcca agtcgcctcc agaccgcaga   240
catgaaactt gtcttcctcg tcctgctgtt cctcggggcc ctcggactgt gtctggctgg   300
ccgtaggagg agtgttcagt ggtgcgccgt atcccaaccc gaggccacaa aatgcttcca   360
atggcaaagg aatatgagaa aagtgcgtgg ccctcctgtc agctgcataa agagagactc   420
ccccatccag tgtatccagg ccattgcgga aaacagggcc gatgctgtga cccttgatgg   480
tggtttcata tacgaggcag gcctggcccc ctacaaactg cgacctgtag cggcggaagt   540
ctacgggacc gaaagacagc cacgaactca ctattatgcc gtggctgtgg tgaagaaggg   600
cggcagcttt cagctgaacg aactgcaagg tctgaagtcc tgccacacag gccttcgcag   660
gaccgctgga tggaatgtcc ctataggac acttcgtcca ttcttgaatt ggacgggtcc   720
acctgagccc attgaggcag ctgtggccag gttcttctca gccagctgtg ttcccggtgc   780
agataaagga cagttcccca acctgtgtcg cctgtgtgcg gggacagggg aaaacaaatg   840
tgccttctcc tcccaggaac cgtacttcag ctactctggt gccttcaagt gtctgagaga   900
cggggctgga gacgtggctt ttatcagaga gagcacagtg tttgaggacc tgtcagacga   960
ggctgaaagg gacgagtatg agttactctg cccagacaac actcggaagc cagtggacaa  1020
gttcaaagac tgccatctgg cccgggtccc ttctcatgcc gttgtggcac gaagtgtgaa  1080
tggcaaggag gatgccatct ggaatcttct ccgccaggca caggaaaagt ttggaaagga  1140
caagtcaccg aaattccagc tctttggctc ccctagtggg cagaaagatc tgctgttcaa  1200
ggactctgcc attgggtttt cgagggtgcc cccgaggata gattctgggc tgtaccttgg  1260
ctccggctac ttcactgcca tcagaactt gaggaaaagt gaggaggaag tggctgcccg  1320
gcgtgcgcgg gtcgtgtggt gtgcggtggg cgagcaggag ctgcgcaagt gtaaccagtg  1380
gagtggcttg agcgaaggca gcgtgacctg ctcctcggcc tccaccacag aggactgcat  1440
cgccctggtg ctgaaaggag aagctgatgc catgagtttg gatggaggat atgtgtacac  1500
tgcaggcaaa tgtggtttgg tgcctgtcct ggcagagaac tacaaatccc aacaaagcag  1560
tgaccctgat cctaactgtg tggatagacc tgtggaagga tatcttgctg tggcggtggt  1620
taggagatca gacactagcc ttacctggaa ctctgtgaaa ggcaagaagt cctgccacac  1680
cgccgtggac aggactgcag gctggaatat ccccatgggc ctgctcttca ccagacgggg  1740
ctcctgcaaa tttgatgaat atttcagtca aagctgtgcc cctgggtctg acccgagatc  1800
taatctctgt gctctgtgta ttggcgacga gcagggtgag aataagtgcg tgcccaacag  1860
caacgagaga tactacggct acactgaggc tttccggtgc ctggctgaga atgctggaga  1920
cgttgcattt gtgaaagatg tcactgtctt gcagaacact gatggaaata caatgaggc  1980
atgggctaag gatttgaagc tggcagactt tgcgctgctg tgcctcgatg gcaaacggaa  2040
gcctgtgact gaggctagaa gctgccatct tgccatggcc cgaatcatg ccgtggtgtc  2100
tcggatggat aaggtggaac gcctgaaaca ggtgttgctc caccaacagg ctaaatttgg  2160
gagaaatgga tctgactgcc cggacaagtt ttgcttattc cagtctgaaa ccaaaaacct  2220
tctgttcaat gacaacactg agtgtctggc cagactccat ggcaaacaa catatgaaaa  2280
atatttggga ccacagtatg tcgcaggcat tactaatctg aaaaagtgct caacctcccc  2340
```

```
cctcctggaa gcctgtgaat tcctcaggaa gtaaaaccga agaagatggc ccagctcccc    2400
aagaaagcct cagccattca ctgccccag ctcttctccc caggtgtgtt ggggccttgg    2460
cctcccctgc tgaaggtggg gattgcccat ccatctgctt acaattccct gctgtcgtct    2520
tagcaagaag taaaatgaga aattttgttg atattctctc cttaaaaaaa aaaaaaaaaa    2580
aaaaaaaaaa aaa                                                      2593

<210> SEQ ID NO 24
<211> LENGTH: 2371
<212> TYPE: DNA
<213> ORGANISM: Homo sapiens

<400> SEQUENCE: 24
gcctcgcctc ggcgccgcgg ccggcatttc tcctcgcagc tcgctgcctc ctctatccct     60
gcctccctct cccccctctg tttttctccc ttccttccct ctccgaccct cttcctctcc    120
ctcccgatcc tttccctcct cctctcatct ttccctgtc tctccgttct agctcgtccc    180
ccaccccacc ttttcttctt tctcctcctc tccttcctct cccctctcc tctgtctcct    240 tccaccgtct ccctgcctc cctgtctttc agtccctgtt tttcagcccc gtctccctct    300
cggtttctct ccccaccct ccctccgggt ttcctcccg gtgccctccc tcctctctcc    360
ctcccctccc cctccgcccc tcgcagcccc gccgctcgca gctcccagtc tgcctccccg    420
aaccggcgcc gccgcccgca ctcgccgcag gaccggcccg cccggctccc ggggtgcgcc    480
ctcctcggtc ccgcgccctc cgggctcgca gggacgtctc ctccctcccg gctcgcggcc    540
ccgcccggcc cggcccccgc ccagagcccc agcgcgccga ggatgtgagt cctgctcgcc    600
tctggcggag cagcagccac tcgcgcgcgg agcggagcg cagcgcagcg cagccgcggg    660
cgctctccgg gccgctcgcg cgagtgccgc gctcttgccc tagcggcgtc ccccggcctc    720
tcgccggcgc caccgccgca gcagcccgcg ggccgtcccc ggccggccgc ccccggcccc    780
agcgccgctg accctgtccg ccgcggcgg ggacgcgggc ggaggaggcg ccgcggcgga    840
gcccccggac gcgaccatgt cggaggtgct gccctacggc gacgagaagc tgagccccta    900
cggcgacggc ggcgacgtgg gccagatctt ctcctgccgc ctgcaggaca ccaacaactt    960
cttcggcgcc gggcagaaca gcggccgcc caagctgggc cagatcggcc ggagcaagcg   1020
ggttgttatt gaagatgata ggattgatga cgtgctgaaa aatatgaccg acaaggcacc   1080
tcctggtgtc taactccccc aaagacaatg agttaaggga gagaataaga acggcggtaa   1140
cagttattgg caaaaagcat gaaaagagaa agcactttga aatttattac tagcttgcta   1200
cccacgatga aatcaacaac ctgtatctgg tatcaggccg ggagacagat gaggcgagag   1260
gaggaggagg aggaggagaa ggctctgggc tcctctgcaa aatataaaat aaaaaaataa   1320
ataaaatttt aaaaataata aaaattcact atatacacat ataagaaat aaaagaagt    1380 ctcagttgca gctatttgtc aaaattaata tccatttctt tttatatacg gtgaatattg   1440
cgcaattata gatctggatt ttgaaccact taatgaagcg gcaacaccag gtgttttgag   1500
gtgttggcat tcttcgctga tttggctgtt cccaatgttt acattattta atcttgcaaa   1560
aatggttctg tgcacttgga tgtgaaatgc tgtccagttt tatttttttt atgttgttat   1620
ccttggatgt acaaaaaatt cagaaaatga tctctgtaga tattctgttt tattttggtc   1680
atctttagaa gttatcagga atgtgtttaa aacaagaaga gaacttttct aaggaatgat   1740
acatagaaaa gattttatt taaaatgagt tgtaaagctt gtgtttcttt gttgctgcaa   1800
```

-continued

| | |
|---|---|
| gctatctgcc caagttaatg caaatggaca cattttttat gtcagaaaaa cacacacaca | 1860 |
| cacacacaca cacacacaca cacacgaaaa acaaagaaaa aaatgcttga gcttttcta | 1920 |
| acttccccct gcagtctgtt gtgtgagcag cctgtttatt tctctaatat tatgtcagtt | 1980 |
| tattctcttt aatggactgt aaaaaaatgt aatcacaaga gtgccaaata tcttgaaatg | 2040 |
| ccaaaaggca ttttagtttc ttttctctgt gctctgagtc cacgtacagg aatgcttgga | 2100 |
| gtgtcttttc tgttatttat agggattctc ttaaggcaca ccagctgcct gttttgcatg | 2160 |
| gtatttgcaa aaatgcctct tgcgtgagga aatctttac cattttttgt ttgcaacttt | 2220 |
| ggacctcaag aggtttccct tcccttcccc gttccctctt ttcttaattc aatattctgt | 2280 |
| atgttgcacc ttgaaccagc acacagggct atttctccaa tgtacaataa aagaattgtt | 2340 |
| cctgtgtctc aaaaaaaaaa aaaaaaaaaa a | 2371 |

<210> SEQ ID NO 25
<211> LENGTH: 5330
<212> TYPE: DNA
<213> ORGANISM: Homo sapiens

<400> SEQUENCE: 25

| | |
|---|---|
| ggcggagcca ggccggccta gagtcacttc tccccgcccc tgactgggcc gggagcccgg | 60 |
| ggctggtctc taagagtggg taccgagaac agcctgaccg tggagaaggg ctgcgggaag | 120 |
| cagaacaccg cccccagcgc ccagcgtgct ccagaaacat gagcacaaac gcctcagcct | 180 |
| ccttccccgg cggcaccggc accggcacca gtacccgcac cagtaccggc accggcacca | 240 |
| gtacccgcac cagtaccggc accggcacca gtacccgcac cagtaccggc accggcaccg | 300 |
| agcgcaaggc ggagggcccg cccgaagccg ggggcacaac tgcccaggtc ccgaacccgg | 360 |
| actccagctt ggacgacacc tcctacagcc tgtccgaatg gagcgtccgt tctgagtggc | 420 |
| ggtccgtctc ggatccgcta gccagttccc agtggagcac gtcctcaact gccgaggccg | 480 |
| cctcctggag ctccagcata cactcccaa tcagcactac cggtcttagc gagagtactg | 540 |
| actccgactc caagagtggc ctccggggtt tcagcgctta caacccgagc agtcggatcc | 600 |
| ccaagtctac caccagctcg aactcctccg atggggccgt cacagcctcc aatcaggaca | 660 |
| ccggcattcc ctgggtatta gtaacaggac ctaccccgcc cgtaaactcc cccgtagagt | 720 |
| cattgcaagg gtctgccttc tcctcagggt tcagcacccc acggggtttg gtaaaaggac | 780 |
| cgaccctgcc cccggattcc aacctgacct cagtgtccga ctacacttgg atatttgtac | 840 |
| ggggacctcc tatcccaat gacctttcgc aagtgtcaat acaagcacct cctacaccca | 900 |
| gtaacacccc cgagtgtcag tacaagggtc tgccgcatcc tcagtgtcca gcttcccctg | 960 |
| gggtttggta ccaggaccac ctctacccaa taacatttcc ccagtgtcgc cacaagcacc | 1020 |
| tcctgcaccc cataacatcc ccccagtgtc aaggcaggcg tctaccccca cctcagtgcc | 1080 |
| tgacactccg cggggttcaa tacaagaacc tcctgcaccc agtaatcctt tccagctgcc | 1140 |
| gacacaagga cattctaaac ctaataactc tcgccgagtg tcagtacaag ggtccgcccc | 1200 |
| gctctcagtg cccagctccc cccgggtatc agctgaaaca tcagctccgc ccctgggcgc | 1260 |
| tcccggagta tcagcaaaag ggttcgcccc gcccacagtg cccggctccc ccgggtatc | 1320 |
| aaagaagga tcggctccgc cccgggctc ccggggggag ttgatagaag gtccttccc | 1380 |
| acccttgcc gtccccactc ctgtgcctac gacccaggag cgtgtcagcc aaagcatgga | 1440 |
| gaatcaagag aaggcgagta tcgcgggcca catgttcgac gtagtcgtga tcggaggtgg | 1500 |
| catttcagga ctatctgctg ccaaactctt gactgaatat ggcgttagtg ttttggtttt | 1560 |

```
agaagctcgg gacagggttg gaggaagaac atatactata aggaatgagc atgttgatta    1620
cgtagatgtt ggtggagctt atgtgggacc aacccaaaac agaatcttac gcttgtctaa    1680
ggagctgggc atagagactt acaaagtgaa tgtcagtgag cgtctcgttc aatatgtcaa    1740
ggggaaaaca tatccatttc ggggcgcctt tccaccagta tggaatccca ttgcatattt    1800
ggattacaat aatctgtgga ggacaataga taacatgggg aaggagattc caactgatgc    1860
accctgggag gctcaacatg ctgacaaatg gacaaaatg accatgaaag agctcattga     1920
caaaatctgc tggacaaaga ctgctaggcg gtttgcttat cttttttgtga atatcaatgt   1980 gacctctgag cctcacgaag tgtctgccct gtggttcttg tggtatgtga agcagtgcgg    2040
gggcaccact cggatattct ctgtcaccaa tggtggccag gaacggaagt tgtaggtgg     2100 atctggtcaa gtgagcgaac ggataatgga cctcctcgga gaccaagtga agctgaacca    2160
tcctgtcact cacgttgacc agtcaagtga caacatcatc atagagacgc tgaaccatga    2220
acattatgag tgcaaatacg taattaatgc gatccctccg accttgactg ccaagattca    2280
cttcagacca gagcttccag cagagagaaa ccagttaatt cagcggcttc caatgggagc    2340
tgtcattaag tgcatgatgt attacaagga ggccttctgg aagaagaagg attactgtgg    2400
ctgcatgatc attgaagatg aagatgctcc aatttcaata accttggatg acaccaagcc    2460
agatgggtca ctgcctgcca tcatgggctt cattcttgcc cggaaagctg atcgacttgc    2520
taagctacat aaggaaataa ggaagaagaa aatctgtgag ctctatgcca aagtgctggg    2580
atcccaagaa gctttacatc cagtgcatta tgaagagaag aactggtgtg aggagcagta    2640 ctctggggc tgctacacgg cctacttccc tcctgggatc atgactcaat atggaagggt     2700
gattcgtcaa cccgtgggca ggattttctt tgcgggcaca gagactgcca caaagtggag    2760
cggctacatg gaagggcag ttgaggctgg agaacgagca gctagggagg tcttaaatgg     2820
tctcgggaag gtgaccgaga agatatctg ggtacaagaa cctgaatcaa aggacgttcc     2880
agcggtagaa atcaccccaca ccttctggga aaggaacctg ccctctgttt ctggcctgct   2940
gaagatcatt ggatttccca catcagtaac tgccctgggg tttgtgctgt acaaatacaa    3000
gctcctgcca cggtcttgaa gttctgttct tatgctctct gctcactggt tttcaatacc    3060
accaagagga aaatattgac aagtttaaag gctgtgtcat tgggccatgt ttaagtgtac    3120
tggatttaac taccttggc ttaattccaa tcattgttaa agtaaaaaca attcaaagaa      3180
tcacctaatt aatttcagta agatcaagct ccatcttatt tgtcagtgta gatcaactca    3240
tgttaattga tagaataaag ccttgtgatc actttctgaa attcacaaag ttaaacgtga    3300
tgtgctcatc agaaacaatt tctgtgtcct gttttattc ccttcaatgc aaaatacatg     3360
atgatttcag aaacaaagca tttgactttc tgtctgtgga ggtggagtag gtgaaggccc    3420
agcctgtaac tgtcctttttt cttcccttag gcaatggtga actgtcatta cagagcctag   3480
aggctcacag cctcctggag gaagcagcct ccactttgga tcaggaaata gtaaggaaa    3540 gcagtgttgg gggtagcggc atgcagaccc tcagaccaga atggggacat cttgtggtct    3600
gctgcctcag gaatctcctg accacttgta gtccctccga cttctctaga catctagtct    3660
cagtgctagc ttatttgtat ttttcctctt tcacttctta tggaggagag tgtttaactg    3720
agttagaatg ttgaaactga cttgctgtga cttatgtgca gctttccagt tgagcagagg    3780
aaaatagtgg caggactgtc ccccaggagg actccctgct tagctctgtg ggagaccaac    3840
tacgactggc atcttctctt cccctggaa ggcagctaga caccaatgga tccttgtcag     3900
```

```
ttgtaacatt ctatttcaac ttcaggaaag cagcagtttt cttttaattt ttcctatgac    3960
cataaaatta gacatacctc tcaacttaca tatgtcttca acatggttac ctctgcataa    4020
atattagcaa agcatgccaa tttctcttaa gtactgaaat acatatgata aatttgactg    4080
ttatttgttg agactatcaa acagaaaaga aattagggct ctaatttcct taaagcaagc    4140
tcacttgctt tagttgttaa gttttataaa agacatgaaa ttgagtcatt ttatatatga    4200
aaactaagtt ctctatctta ggagtaatgt cggcccacaa gggtgcccac ctcttgtttt    4260 cccctttttaa aaactcagat ttttaaaagc cctttccaaa ggtttcaact gtaaaatact    4320 tcttttttaca atgtatcaac atattttttat ttaaggggaa ttaacaattg ccagggaaac    4380
cagccaaccc aagtttatta tatcattaac cttatcataa attcaaacct aagttgctgg    4440
accctggtgt gaggacataa atcttccaaa gttttgccta tcctaagagc tgcattttc    4500 tactgctctt taccttgcat tttagctaat ttaggagttt tgagaatgta ttggatacgc    4560
tccagtacat aaggagttgc cgcatattat atcagactgc tttgagaaat ctcatccta    4620 gtctattgca gttgtttcta ttagcttact gattaactca gtcctgacac accttttggg    4680
aaatgctgat ttaaacttct taactggcaa cagttggaac agtaatcagt ttgctaacat    4740
atttaaagtc ttgaatgttg aagaactcat gtgatttacc cttttcaact ttttggaaaa    4800
cgatttaatt tattctaatt agattaaccc tattaatcta tggattgggt atcaaaatga    4860
atgccagtcc agatgtgcct agacacgaaa ttggagctga ggactctcac gatatgcaag    4920
ttcatccaac gtgaagatac cataagcttt ttctctgaac cagagaaatg aaagtcagtt    4980
taagaggctg atagatcttg gccctgttaa ggcatccact tcacagttct gaaggctgag    5040
tcagccccac tccacagtta ggccaagaat tagattttaa aacttcatct gtctgtccca    5100
gttaactgtt aaataaggcc tcatcctcca ctgaagagta tggattgaag gattgtgaac    5160
tatgtttagt gtgattgtga acttggtgcc taatgttcca tgtctgaagt ttgccccagt    5220
gctacacgtt ggagtatacc tatgtgtgtg ctttgccact gaagtaagat tttgcctgta    5280
tggtactgtt ttgtttgtta ataaagtgca ctgccacccc caatgcagac                5330
```

<210> SEQ ID NO 26
<211> LENGTH: 5490
<212> TYPE: DNA
<213> ORGANISM: Homo sapiens

<400> SEQUENCE: 26

```
ggctgagttt tatgacgggc ccggtgctga agggcaggga acaacttgat ggtgctactt      60
tgaactgctt ttcttttctc cttttttgcac aaagagtctc atgtctgata tttagacatg     120
atgagctttg tgcaaaaggg gagctggcta cttctcgctc tgcttcatcc cactattatt     180
ttggcacaac aggaagctgt tgaaggagga tgttcccatc ttggtcagtc ctatgcggat     240
agagatgtct ggaagccaga accatgccaa atatgtgtct gtgactcagg atccgttctc     300
tgcgatgaca taatatgtga cgatcaagaa ttagactgcc ccaacccaga aattccattt     360
ggagaatgtt gtgcagtttg cccacagcct ccaactgctc ctactcgccc tcctaatggt     420
caaggacctc aaggccccaa gggagatcca ggccctcctg gtattcctgg agaaatggt     480 gaccctggta ttccaggaca accagggtcc cctggttctc ctggccccc tggaatctgt     540 gaatcatgcc ctactggtcc tcagaactat tctccccagt atgattcata tgatgtcaag     600
tctggagtag cagtaggagg actcgcaggc tatcctggac cagctggccc ccaggcct     660 cccggtcccc ctggtacatc tggtcatcct ggttcccctg gatctccagg ataccaagga     720
```

| | |
|---|---|
| cccccctggtg aacctgggca agctggtcct tcaggccctc caggacctcc tggtgctata | 780 |
| ggtccatctg gtcctgctgg aaaagatgga gaatcaggta gacccggacg acctggagag | 840 |
| cgaggattgc ctggacctcc aggtatcaaa ggtccagctg gatacctgg attccctggt | 900 |
| atgaaaggac acagaggctt cgatggacga aatggagaaa agggtgaaac aggtgctcct | 960 |
| ggattaaagg gtgaaaatgg tcttccaggc gaaaatggag ctcctggacc catgggtcca | 1020 |
| agagggctc ctggtgagcg aggacggcca ggacttcctg gggctgcagg tgctcggggt | 1080 |
| aatgacggtg ctcgaggcag tgatggtcaa ccaggccctc ctggtcctcc tggaactgcc | 1140 |
| ggattccctg gatccctgg tgctaagggt gaagttggac ctgcagggtc tcctggttca | 1200 |
| aatggtgccc ctggacaaag aggagaacct ggacctcagg acacgctgg tgctcaaggt | 1260 |
| cctcctggcc ctcctgggat taatggtagt cctggtggta aaggcgaaat gggtcccgct | 1320 |
| ggcattcctg gagctcctgg actgatggga gcccgggtc ctccaggacc agccggtgct | 1380 |
| aatggtgctc ctggactgcg agtggtgca gtgagcctg taagaatgg tgccaaagga | 1440 |
| gagcccggac cacgtggtga acgcggtgag gctggtattc caggtgttcc aggagctaaa | 1500 |
| ggcgaagatg gcaaggatgg atcacctgga gaacctggtg caaatgggct tccaggagct | 1560 |
| gcaggagaaa ggggtgcccc tgggttccga ggacctgctg gaccaaatgg catcccagga | 1620 |
| gaaaagggtc ctgctggaga gcgtggtgct ccaggccctg cagggcccag aggagctgct | 1680 |
| ggagaacctg gcagagatgg cgtccctgga ggtccaggaa tgaggggcat gcccggaagt | 1740 |
| ccaggaggac caggaagtga tgggaaacca gggcctcccg gaagtcaagg agaaagtggt | 1800 |
| cgaccaggtc ctcctgggcc atctggtccc cgaggtcagc ctggtgtcat gggcttcccc | 1860 |
| ggtcctaaag gaaatgatgg tgctcctggt aagaatggag aacgaggtgg ccctggagga | 1920 |
| cctggccctc agggtcctcc tggaaagaat ggtgaaactg gacctcaggg accccagggg | 1980 |
| cctactgggc tggtggtga caaaggagac acaggacccc ctggtccaca aggattacaa | 2040 |
| ggcttgcctg gtacaggtgg tcctccagga gaaaatggaa aacctgggga accaggtcca | 2100 |
| aagggtgatg ccggtgcacc tggagctcca ggaggcaagg gtgatgctgg tgcccctggt | 2160 |
| gaacgtggac ctcctggatt ggcaggggcc ccaggactta gaggtggagc tggtcccct | 2220 |
| ggtcccgaag gaggaaaggg tgctgctggt cctcctgggc cacctggtgc tgctggtact | 2280 |
| cctggtctgc aaggaatgcc tggagaaaga ggaggtcttg gaagtcctgg tccaaagggt | 2340 |
| gacaagggtg aaccaggcgg tccaggtgct gatggtgtcc cagggaaaga tggcccaagg | 2400 |
| ggtcctactg tcctattgg tcctcctggc ccagctggcc agcctggaga taagggtgaa | 2460 |
| ggtggtgccc ccggacttcc aggtatagct ggacctcgtg gtagccctgg tgagagaggt | 2520 |
| gaaactggcc ctcaggacc tgctggttc cctggtgctc ctggacagaa tggtgaacct | 2580 |
| ggtggtaaag gagaaagagg ggctccgggt gagaaaggtg aaggaggccc tcctggagtt | 2640 |
| gcaggacccc ctggaggttc tggacctgct ggtcctcctg gtccccaagg tgtcaaaggt | 2700 |
| gaacgtggca gtcctggtgg acctggtgct gctggcttcc ctggtgctcg tggtcttcct | 2760 |
| ggtcctcctg gtagtaatgg taaccccagga ccccaggtc ccagcggttc tccaggcaag | 2820 |
| gatgggcccc aggtcctgc gggtaacact ggtgctcctg gcagccctgg agtgtctgga | 2880 |
| ccaaaaggtg atgctggcca accaggagag aagggatcgc ctggtgccca gggcccacca | 2940 |
| ggagctccag gccacttgg gattgctggg atcactggag cacggggtct tgcaggacca | 3000 |
| ccaggcatgc caggtcctag gggaagccct ggccctcagg gtgtcaaggg tgaaagtggg | 3060 |

```
aaaccaggag ctaacggtct cagtggagaa cgtggtcccc ctggacccca gggtcttcct   3120
ggtctggctg gtacagctgg tgaacctgga agagatggaa accctggatc agatggtctt   3180
ccaggccgag atggatctcc tggtggcaag ggtgatcgtg gtgaaaatgg ctctcctggt   3240 gccccctggcg ctcctggtca tccaggccca cctggtcctg tcggtccagc tggaaagagt   3300
ggtgacagag gagaaagtgg ccctgctggc cctgctggtg ctcccggtcc tgctggttcc   3360
cgaggtgctc ctggtcctca aggcccacgt ggtgacaaag gtgaaacagg tgaacgtgga   3420
gctgctggca tcaaaggaca tcgaggattc cctggtaatc caggtgcccc aggttctcca   3480
ggccctgctg gtcagcaggg tgcaatcggc agtccaggac ctgcaggccc agaggacct   3540 gttggaccca gtggacctcc tggcaaagat ggaaccagtg gacatccagg tcccattgga   3600
ccaccagggc ctcgaggtaa cagaggtgaa agaggatctg agggctcccc aggccaccca   3660
gggcaaccag gccctcctgg acctcctggt gcccctggtc cttgctgtgg tggtgttgga   3720
gccgctgcca ttgctgggat tggaggtgaa aaagctggcg ttttgccccc gtattatgga   3780
gatgaaccaa tggatttcaa aatcaacacc gatgagatta tgacttcact caagtctgtt   3840
aatggacaaa tagaaagcct cattagtcct gatggttctc gtaaaaaccc cgctagaaac   3900
tgcagagacc tgaaattctg ccatcctgaa ctcaagagtg gagaatactg ggttgaccct   3960
aaccaaggat gcaaattgga tgctatcaag gtattctgta atatggaaac tgggaaaca   4020 tgcataagtg ccaatccttt gaatgttcca cggaaacact ggtggacaga ttctagtgct   4080
gagaagaaac acgtttggtt tggagagtcc atggatggtg gttttcagtt tagctacggc   4140
aatcctgaac ttcctgaaga tgtccttgat gtgcagctgg cattccttcg acttctctcc   4200
agccgagctt cccagaacat cacatatcac tgcaaaaata gcattgcata catggatcag   4260
gccagtggaa atgtaaagaa ggccctgaag ctgatggggt caaatgaagg tgaattcaag   4320
gctgaaggaa atagcaaatt cacctacaca gttctggagg atggttgcac gaaacacact   4380
ggggaatgga gcaaaacagt ctttgaatat cgaacacgca aggctgtgag actacctatt   4440
gtagatattg caccctatga cattggtggt cctgatcaag aatttggtgt ggacgttggc   4500
cctgtttgct ttttataaac caaactctat ctgaaatccc aacaaaaaa atttaactcc   4560 atatgtgttc ctcttgttct aatcttgtca accagtgcaa gtgaccgaca aaattccagt   4620
tatttatttc caaaatgttt ggaaacagta aatttgaca agaaaaatg atacttctct   4680 ttttttgctg ttccaccaaa tacaattcaa atgcttttg tttattttt ttaccaattc   4740 caatttcaaa atgtctcaat ggtgctataa taaataaact tcaacactct ttatgataac   4800
aacactgtgt tatattcttt gaatcctagc ccatctgcag agcaatgact gtgctcacca   4860
gtaaaagata acctttcttt ctgaaatagt caaatacgaa attagaaaag ccctcccat   4920 tttaactacc tcaactggtc agaaacacag attgtattct atgagtccca gaagatgaaa   4980
aaaattttat acgttgataa aacttataaa tttcattgat taatctcctg gaagattggt   5040 ttaaaagaa aagtgtaatg caagaattta agaaatatt tttaaagcca caattatttt   5100
aatattggat atcaactgct tgtaaaggtg ctcctctttt ttcttgtcat tgctggtcaa   5160
gattactaat atttgggaag ctttaaaga cgcatgttat ggtgctaatg tactttcact   5220
tttaaactct agatcagaat tgttgacttg cattcagaac ataaatgcac aaaatctgta   5280
catgtctccc atcagaaaga ttcattggca tgccacaggg gattctcctc cttcatcctg   5340
taaaggtcaa caataaaaac caaattatgg ggctgctttt gtcacactag catagagaat   5400
gtgttgaaat ttaactttgt aagcttgtat gtggttgttg atctttttt tccttacaga   5460
```

```
cacccataat aaaatatcat attaaaattc                                      5490
```

<210> SEQ ID NO 27
<211> LENGTH: 382
<212> TYPE: PRT
<213> ORGANISM: Homo sapiens

<400> SEQUENCE: 27

| Met | Ala | Leu | Gln | Gly | Ile | Ser | Val | Val | Glu | Leu | Ser | Gly | Leu | Ala | Pro |
|---|---|---|---|---|---|---|---|---|---|---|---|---|---|---|---|
| 1 | | | | 5 | | | | | 10 | | | | | 15 | |

Gly Pro Phe Cys Ala Met Val Leu Ala Asp Phe Gly Ala Arg Val Val
            20                  25                  30

Arg Val Asp Arg Pro Gly Ser Arg Tyr Asp Val Ser Arg Leu Gly Arg
        35                  40                  45

Gly Lys Arg Ser Leu Val Leu Asp Leu Lys Gln Pro Arg Gly Ala Ala
    50                  55                  60

Val Leu Arg Arg Leu Cys Lys Arg Ser Asp Val Leu Leu Glu Pro Phe
65                  70                  75                  80

Arg Arg Gly Val Met Glu Lys Leu Gln Leu Gly Pro Glu Ile Leu Gln
                85                  90                  95

Arg Glu Asn Pro Arg Leu Ile Tyr Ala Arg Leu Ser Gly Phe Gly Gln
            100                 105                 110

Ser Gly Ser Phe Cys Arg Leu Ala Gly His Asp Ile Asn Tyr Leu Ala
        115                 120                 125

Leu Ser Gly Val Leu Ser Lys Ile Gly Arg Ser Gly Glu Asn Pro Tyr
    130                 135                 140

Ala Pro Leu Asn Leu Leu Ala Asp Phe Ala Gly Gly Leu Met Cys
145                 150                 155                 160

Ala Leu Gly Ile Ile Met Ala Leu Phe Asp Arg Thr Arg Thr Gly Lys
                165                 170                 175

Gly Gln Val Ile Asp Ala Asn Met Val Glu Gly Thr Ala Tyr Leu Ser
            180                 185                 190

Ser Phe Leu Trp Lys Thr Gln Lys Leu Ser Leu Trp Glu Ala Pro Arg
        195                 200                 205

Gly Gln Asn Met Leu Asp Gly Gly Ala Pro Phe Tyr Thr Thr Tyr Arg
    210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
                245                 250                 255

Asn Gln Met Ser Met Asp Asp Trp Pro Glu Met Lys Lys Lys Phe Ala
            260                 265                 270

Asp Val Phe Ala Glu Lys Thr Lys Ala Glu Trp Cys Gln Ile Phe Asp
        275                 280                 285

Gly Thr Asp Ala Cys Val Thr Pro Val Leu Thr Phe Glu Glu Val Val
    290                 295                 300

His His Asp His Asn Lys Glu Arg Gly Ser Phe Ile Thr Ser Glu Glu
305                 310                 315                 320

Gln Asp Val Ser Pro Arg Pro Ala Pro Leu Leu Leu Asn Thr Pro Ala
                325                 330                 335

Ile Pro Ser Phe Lys Arg Asp Pro Phe Ile Gly Glu His Thr Glu Glu
            340                 345                 350

Ile Leu Glu Glu Phe Gly Phe Ser Arg Glu Glu Ile Tyr Gln Leu Asn
        355                 360                 365

```
Ser Asp Lys Ile Ile Glu Ser Asn Lys Val Lys Ala Ser Leu
    370                 375                 380
```

<210> SEQ ID NO 28
<211> LENGTH: 479
<212> TYPE: PRT
<213> ORGANISM: Homo sapiens

<400> SEQUENCE: 28

```
Met Ala Ser Thr Ile Lys Glu Ala Leu Ser Val Val Ser Glu Asp Gln
1               5                   10                  15

Ser Leu Phe Glu Cys Ala Tyr Gly Thr Pro His Leu Ala Lys Thr Glu
            20                  25                  30

Met Thr Ala Ser Ser Ser Ser Asp Tyr Gly Gln Thr Ser Lys Met Ser
        35                  40                  45

Pro Arg Val Pro Gln Gln Asp Trp Leu Ser Gln Pro Pro Ala Arg Val
    50                  55                  60

Thr Ile Lys Met Glu Cys Asn Pro Ser Gln Val Asn Gly Ser Arg Asn
65                  70                  75                  80

Ser Pro Asp Glu Cys Ser Val Ala Lys Gly Gly Lys Met Val Gly Ser
                85                  90                  95

Pro Asp Thr Val Gly Met Asn Tyr Gly Ser Tyr Met Glu Glu Lys His
            100                 105                 110

Met Pro Pro Pro Asn Met Thr Thr Asn Glu Arg Arg Val Ile Val Pro
        115                 120                 125

Ala Asp Pro Thr Leu Trp Ser Thr Asp His Val Arg Gln Trp Leu Glu
    130                 135                 140

Trp Ala Val Lys Glu Tyr Gly Leu Pro Asp Val Asn Ile Leu Leu Phe
145                 150                 155                 160

Gln Asn Ile Asp Gly Lys Glu Leu Cys Lys Met Thr Lys Asp Asp Phe
                165                 170                 175

Gln Arg Leu Thr Pro Ser Tyr Asn Ala Asp Ile Leu Leu Ser His Leu
            180                 185                 190

His Tyr Leu Arg Glu Thr Pro Leu Pro His Leu Thr Ser Asp Asp Val
        195                 200                 205

Asp Lys Ala Leu Gln Asn Ser Pro Arg Leu Met His Ala Arg Asn Thr
    210                 215                 220

Gly Gly Ala Ala Phe Ile Phe Pro Asn Thr Ser Val Tyr Pro Glu Ala
225                 230                 235                 240

Thr Gln Arg Ile Thr Thr Arg Pro Asp Leu Pro Tyr Glu Pro Pro Arg
                245                 250                 255

Arg Ser Ala Trp Thr Gly His Gly His Pro Thr Pro Gln Ser Lys Ala
            260                 265                 270

Ala Gln Pro Ser Pro Ser Thr Val Pro Lys Thr Glu Asp Gln Arg Pro
        275                 280                 285

Gln Leu Asp Pro Tyr Gln Ile Leu Gly Pro Thr Ser Ser Arg Leu Ala
    290                 295                 300

Asn Pro Gly Ser Gly Gln Ile Gln Leu Trp Gln Phe Leu Leu Glu Leu
305                 310                 315                 320

Leu Ser Asp Ser Ser Asn Ser Ser Cys Ile Thr Trp Glu Gly Thr Asn
                325                 330                 335

Gly Glu Phe Lys Met Thr Asp Pro Asp Glu Val Ala Arg Arg Trp Gly
            340                 345                 350

Glu Arg Lys Ser Lys Pro Asn Met Asn Tyr Asp Lys Leu Ser Arg Ala
```

```
                355                 360                 365
Leu Arg Tyr Tyr Tyr Asp Lys Asn Ile Met Thr Lys Val His Gly Lys
    370                 375                 380

Arg Tyr Ala Tyr Lys Phe Asp Phe His Gly Ile Ala Gln Ala Leu Gln
385                 390                 395                 400

Pro His Pro Pro Glu Ser Ser Leu Tyr Lys Tyr Pro Ser Asp Leu Pro
                405                 410                 415

Tyr Met Gly Ser Tyr His Ala His Pro Gln Lys Met Asn Phe Val Ala
            420                 425                 430

Pro His Pro Pro Ala Leu Pro Val Thr Ser Ser Ser Phe Phe Ala Ala
        435                 440                 445

Pro Asn Pro Tyr Trp Asn Ser Pro Thr Gly Gly Ile Tyr Pro Asn Thr
    450                 455                 460

Arg Leu Pro Thr Ser His Met Pro Ser His Leu Gly Thr Tyr Tyr
465                 470                 475

<210> SEQ ID NO 29
<211> LENGTH: 462
<212> TYPE: PRT
<213> ORGANISM: Homo sapiens

<400> SEQUENCE: 29

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Asn Met Thr Thr Asn
        115                 120                 125

Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
    210                 215                 220

Leu Met His Ala Arg Asn Thr Asp Leu Pro Tyr Glu Pro Pro Arg Arg
225                 230                 235                 240

Ser Ala Trp Thr Gly His Gly His Pro Thr Pro Gln Ser Lys Ala Ala
                245                 250                 255
```

```
Gln Pro Ser Pro Ser Thr Val Pro Lys Thr Glu Asp Gln Arg Pro Gln
                260                 265                 270

Leu Asp Pro Tyr Gln Ile Leu Gly Pro Thr Ser Ser Arg Leu Ala Asn
            275                 280                 285

Pro Gly Ser Gly Gln Ile Gln Leu Trp Gln Phe Leu Leu Glu Leu Leu
        290                 295                 300

Ser Asp Ser Ser Asn Ser Ser Cys Ile Thr Trp Glu Gly Thr Asn Gly
305                 310                 315                 320

Glu Phe Lys Met Thr Asp Pro Asp Glu Val Ala Arg Arg Trp Gly Glu
                325                 330                 335

Arg Lys Ser Lys Pro Asn Met Asn Tyr Asp Lys Leu Ser Arg Ala Leu
            340                 345                 350

Arg Tyr Tyr Tyr Asp Lys Asn Ile Met Thr Lys Val His Gly Lys Arg
        355                 360                 365

Tyr Ala Tyr Lys Phe Asp Phe His Gly Ile Ala Gln Ala Leu Gln Pro
370                 375                 380

His Pro Pro Glu Ser Ser Leu Tyr Lys Tyr Pro Ser Asp Leu Pro Tyr
385                 390                 395                 400

Met Gly Ser Tyr His Ala His Pro Gln Lys Met Asn Phe Val Ala Pro
                405                 410                 415

His Pro Pro Ala Leu Pro Val Thr Ser Ser Phe Phe Ala Ala Pro
            420                 425                 430

Asn Pro Tyr Trp Asn Ser Pro Thr Gly Gly Ile Tyr Pro Asn Thr Arg
        435                 440                 445

Leu Pro Thr Ser His Met Pro Ser His Leu Gly Thr Tyr Tyr
450                 455                 460

<210> SEQ ID NO 30
<211> LENGTH: 325
<212> TYPE: PRT
<213> ORGANISM: Homo sapiens

<400> SEQUENCE: 30

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
                20                  25                  30

Pro His Leu Ala Lys Thr Glu Met Thr Ala Ser Ser Ser Ser Asp Tyr
            35                  40                  45

Gly Gln Thr Ser Lys Met Ser Pro Arg Val Pro Gln Gln Asp Trp Leu
        50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Asn Met Thr Thr Asn
        115                 120                 125

Glu Arg Arg Val Ile Val Pro Ala Asp Pro Thr Leu Trp Ser Thr Asp
        130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175
```

```
Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
    210                 215                 220

Leu Met His Ala Arg Asn Thr Gly Gly Ala Ala Phe Ile Phe Pro Asn
225                 230                 235                 240

Thr Ser Val Tyr Pro Glu Ala Thr Gln Arg Ile Thr Thr Arg Pro Gly
                245                 250                 255

Thr Lys Thr Pro Leu Cys Asp Leu Phe Ile Glu Arg His Pro Arg Cys
                260                 265                 270

Pro Ala Glu Ile Arg Ala Leu Ser His Val Ile Gln Arg Glu Leu Ile
            275                 280                 285

Pro Glu Leu Lys Pro Val Pro Asp Ser Leu Ile Leu Pro Leu Leu Ile
        290                 295                 300

Trp Arg Leu Asn Pro Leu Lys Pro Phe His Ser Lys Thr Thr Leu Lys
305                 310                 315                 320

Glu Leu Arg Ala Asp
                325

<210> SEQ ID NO 31
<211> LENGTH: 225
<212> TYPE: PRT
<213> ORGANISM: Homo sapiens

<400> SEQUENCE: 31

Met Ala Thr His Ala Leu Glu Ile Ala Gly Leu Phe Leu Gly Gly Val
1               5                   10                  15

Gly Met Val Gly Thr Val Ala Val Thr Val Met Pro Gln Trp Arg Val
            20                  25                  30

Ser Ala Phe Ile Glu Asn Asn Ile Val Val Phe Glu Asn Phe Trp Glu
        35                  40                  45

Gly Leu Trp Met Asn Cys Val Arg Gln Ala Asn Ile Arg Met Gln Cys
    50                  55                  60

Lys Ile Tyr Asp Ser Leu Leu Ala Leu Ser Pro Asp Leu Gln Ala Ala
65                  70                  75                  80

Arg Gly Leu Met Cys Ala Ala Ser Val Met Ser Phe Leu Ala Phe Met
                85                  90                  95

Met Ala Ile Leu Gly Met Lys Cys Thr Arg Cys Thr Gly Asp Asn Glu
            100                 105                 110

Lys Val Lys Ala His Ile Leu Leu Thr Ala Gly Ile Ile Phe Ile Ile
        115                 120                 125

Thr Gly Met Val Val Leu Ile Pro Val Ser Trp Val Ala Asn Ala Ile
    130                 135                 140

Ile Arg Asp Phe Tyr Asn Ser Ile Val Asn Val Ala Gln Lys Arg Glu
145                 150                 155                 160

Leu Gly Glu Ala Leu Tyr Leu Gly Trp Thr Thr Ala Leu Val Leu Ile
                165                 170                 175

Val Gly Gly Ala Leu Phe Cys Cys Val Phe Cys Cys Asn Glu Lys Ser
            180                 185                 190

Ser Ser Tyr Arg Tyr Ser Ile Pro Ser His Arg Thr Thr Gln Lys Ser
        195                 200                 205

Tyr His Thr Gly Lys Lys Ser Pro Ser Val Tyr Ser Arg Ser Gln Tyr
```

```
                    210                 215                 220

Val
225

<210> SEQ ID NO 32
<211> LENGTH: 2181
<212> TYPE: PRT
<213> ORGANISM: Homo sapiens

<400> SEQUENCE: 32

Met Met Met Met Met Met Met Lys Lys Met Gln His Gln Arg Gln Gln
1               5                   10                  15

Gln Ala Asp His Ala Asn Glu Ala Asn Tyr Ala Arg Gly Thr Arg Leu
            20                  25                  30

Pro Leu Ser Gly Glu Gly Pro Thr Ser Gln Pro Asn Ser Ser Lys Gln
        35                  40                  45

Thr Val Leu Ser Trp Gln Ala Ile Asp Ala Ala Arg Gln Ala Lys
    50                  55                  60

Ala Ala Gln Thr Met Ser Thr Ser Ala Pro Pro Val Gly Ser Leu
65                  70                  75                  80

Ser Gln Arg Lys Arg Gln Gln Tyr Ala Lys Ser Lys Lys Gln Gly Asn
                85                  90                  95

Ser Ser Asn Ser Arg Pro Ala Arg Ala Leu Phe Cys Leu Ser Leu Asn
            100                 105                 110

Asn Pro Ile Arg Arg Ala Cys Ile Ser Ile Val Glu Trp Lys Pro Phe
        115                 120                 125

Asp Ile Phe Ile Leu Leu Ala Ile Phe Ala Asn Cys Val Ala Leu Ala
    130                 135                 140

Ile Tyr Ile Pro Phe Pro Glu Asp Asp Ser Asn Ser Thr Asn His Asn
145                 150                 155                 160

Leu Glu Lys Val Glu Tyr Ala Phe Leu Ile Ile Phe Thr Val Glu Thr
                165                 170                 175

Phe Leu Lys Ile Ile Ala Tyr Gly Leu Leu Leu His Pro Asn Ala Tyr
            180                 185                 190

Val Arg Asn Gly Trp Asn Leu Leu Asp Phe Val Ile Val Ile Val Gly
        195                 200                 205

Leu Phe Ser Val Ile Leu Glu Gln Leu Thr Lys Glu Thr Glu Gly Gly
    210                 215                 220

Asn His Ser Ser Gly Lys Ser Gly Gly Phe Asp Val Lys Ala Leu Arg
225                 230                 235                 240

Ala Phe Arg Val Leu Arg Pro Leu Arg Leu Val Ser Gly Val Pro Ser
                245                 250                 255

Leu Gln Val Val Leu Asn Ser Ile Ile Lys Ala Met Val Pro Leu Leu
            260                 265                 270

His Ile Ala Leu Leu Val Leu Phe Val Ile Ile Tyr Ala Ile Ile
        275                 280                 285

Gly Leu Glu Leu Phe Ile Gly Lys Met His Lys Thr Cys Phe Phe Ala
    290                 295                 300

Asp Ser Asp Ile Val Ala Glu Glu Asp Pro Ala Pro Cys Ala Phe Ser
305                 310                 315                 320

Gly Asn Gly Arg Gln Cys Thr Ala Asn Gly Thr Glu Cys Arg Ser Gly
                325                 330                 335

Trp Val Gly Pro Asn Gly Gly Ile Thr Asn Phe Asp Asn Phe Ala Phe
            340                 345                 350
```

```
Ala Met Leu Thr Val Phe Gln Cys Ile Thr Met Glu Gly Trp Thr Asp
            355                 360                 365

Val Leu Tyr Trp Val Asn Asp Ala Ile Gly Trp Glu Trp Pro Trp Val
370                 375                 380

Tyr Phe Val Ser Leu Ile Ile Leu Gly Ser Phe Phe Val Leu Asn Leu
385                 390                 395                 400

Val Leu Gly Val Leu Ser Gly Glu Phe Ser Lys Glu Arg Glu Lys Ala
                405                 410                 415

Lys Ala Arg Gly Asp Phe Gln Lys Leu Arg Glu Lys Gln Gln Leu Glu
            420                 425                 430

Glu Asp Leu Lys Gly Tyr Leu Asp Trp Ile Thr Gln Ala Glu Asp Ile
            435                 440                 445

Asp Pro Glu Asn Glu Glu Gly Glu Glu Gly Lys Arg Asn Thr
            450                 455                 460

Ser Met Pro Thr Ser Glu Thr Glu Ser Val Asn Thr Glu Asn Val Ser
465                 470                 475                 480

Gly Glu Gly Glu Asn Arg Gly Cys Cys Gly Ser Leu Trp Cys Trp Trp
                485                 490                 495

Arg Arg Arg Gly Ala Ala Lys Ala Gly Pro Ser Gly Cys Arg Arg Trp
            500                 505                 510

Gly Gln Ala Ile Ser Lys Ser Lys Leu Ser Arg Arg Trp Arg Arg Trp
            515                 520                 525

Asn Arg Phe Asn Arg Arg Cys Arg Ala Ala Val Lys Ser Val Thr
            530                 535                 540

Phe Tyr Trp Leu Val Ile Val Leu Val Phe Leu Asn Thr Leu Thr Ile
545                 550                 555                 560

Ser Ser Glu His Tyr Asn Gln Pro Asp Trp Leu Thr Gln Ile Gln Asp
                565                 570                 575

Ile Ala Asn Lys Val Leu Leu Ala Leu Phe Thr Cys Glu Met Leu Val
            580                 585                 590

Lys Met Tyr Ser Leu Gly Leu Gln Ala Tyr Phe Val Ser Leu Phe Asn
            595                 600                 605

Arg Phe Asp Cys Phe Val Val Cys Gly Gly Ile Thr Glu Thr Ile Leu
610                 615                 620

Val Glu Leu Glu Ile Met Ser Pro Leu Gly Ile Ser Val Phe Arg Cys
625                 630                 635                 640

Val Arg Leu Leu Arg Ile Phe Lys Val Thr Arg His Trp Thr Ser Leu
            645                 650                 655

Ser Asn Leu Val Ala Ser Leu Leu Asn Ser Met Lys Ser Ile Ala Ser
            660                 665                 670

Leu Leu Leu Leu Leu Phe Leu Phe Ile Ile Phe Ser Leu Leu Gly
            675                 680                 685

Met Gln Leu Phe Gly Gly Lys Phe Asn Phe Asp Glu Thr Gln Thr Lys
690                 695                 700

Arg Ser Thr Phe Asp Asn Phe Pro Gln Ala Leu Leu Thr Val Phe Gln
705                 710                 715                 720

Ile Leu Thr Gly Glu Asp Trp Asn Ala Val Met Tyr Asp Gly Ile Met
                725                 730                 735

Ala Tyr Gly Gly Pro Ser Ser Ser Gly Met Ile Val Cys Ile Tyr Phe
            740                 745                 750

Ile Ile Leu Phe Ile Cys Gly Asn Tyr Ile Leu Leu Asn Val Phe Leu
            755                 760                 765

Ala Ile Ala Val Asp Asn Leu Ala Asp Ala Glu Ser Leu Asn Thr Ala
```

```
                770             775             780
Gln Lys Glu Ala Glu Glu Lys Glu Arg Lys Lys Ile Ala Arg Lys
785             790             795             800

Glu Ser Leu Glu Asn Lys Lys Asn Asn Lys Pro Glu Val Asn Gln Ile
            805             810             815

Ala Asn Ser Asp Asn Lys Val Thr Ile Asp Asp Tyr Arg Glu Glu Asp
            820             825             830

Glu Asp Lys Asp Pro Tyr Pro Pro Cys Asp Val Pro Val Gly Glu Glu
            835             840             845

Glu Glu Glu Glu Glu Glu Asp Glu Pro Glu Val Pro Ala Gly Pro Arg
            850             855             860

Pro Arg Arg Ile Ser Glu Leu Asn Met Lys Glu Lys Ile Ala Pro Ile
865             870             875             880

Pro Glu Gly Ser Ala Phe Phe Ile Leu Ser Lys Thr Asn Pro Ile Arg
            885             890             895

Val Gly Cys His Lys Leu Ile Asn His His Ile Phe Thr Asn Leu Ile
            900             905             910

Leu Val Phe Ile Met Leu Ser Ser Ala Ala Leu Ala Ala Glu Asp Pro
            915             920             925

Ile Arg Ser His Ser Phe Arg Asn Thr Ile Leu Gly Tyr Phe Asp Tyr
            930             935             940

Ala Phe Thr Ala Ile Phe Thr Val Glu Ile Leu Leu Lys Met Thr Thr
945             950             955             960

Phe Gly Ala Phe Leu His Lys Gly Ala Phe Cys Arg Asn Tyr Phe Asn
            965             970             975

Leu Leu Asp Met Leu Val Val Gly Val Ser Leu Val Ser Phe Gly Ile
            980             985             990

Gln Ser Ser Ala Ile Ser Val Val Lys Ile Leu Arg Val Leu Arg Val
            995             1000            1005

Leu Arg Pro Leu Arg Ala Ile Asn Arg Ala Lys Gly Leu Lys His
       1010            1015            1020

Val Val Gln Cys Val Phe Val Ala Ile Arg Thr Ile Gly Asn Ile
       1025            1030            1035

Met Ile Val Thr Thr Leu Leu Gln Phe Met Phe Ala Cys Ile Gly
       1040            1045            1050

Val Gln Leu Phe Lys Gly Lys Phe Tyr Arg Cys Thr Asp Glu Ala
       1055            1060            1065

Lys Ser Asn Pro Glu Glu Cys Arg Gly Leu Phe Ile Leu Tyr Lys
       1070            1075            1080

Asp Gly Asp Val Asp Ser Pro Val Val Arg Glu Arg Ile Trp Gln
       1085            1090            1095

Asn Ser Asp Phe Asn Phe Asp Asn Val Leu Ser Ala Met Met Ala
       1100            1105            1110

Leu Phe Thr Val Ser Thr Phe Glu Gly Trp Pro Ala Leu Leu Tyr
       1115            1120            1125

Lys Ala Ile Asp Ser Asn Gly Glu Asn Ile Gly Pro Ile Tyr Asn
       1130            1135            1140

His Arg Val Glu Ile Ser Ile Phe Phe Ile Ile Tyr Ile Ile Ile
       1145            1150            1155

Val Ala Phe Phe Met Met Asn Ile Phe Val Gly Phe Val Ile Val
       1160            1165            1170

Thr Phe Gln Glu Gln Gly Glu Lys Glu Tyr Lys Asn Cys Glu Leu
       1175            1180            1185
```

-continued

```
Asp Lys Asn Gln Arg Gln Cys Val Glu Tyr Ala Leu Lys Ala Arg
    1190            1195                1200

Pro Leu Arg Arg Tyr Ile Pro Lys Asn Pro Tyr Gln Tyr Lys Phe
    1205            1210                1215

Trp Tyr Val Val Asn Ser Ser Pro Phe Glu Tyr Met Met Phe Val
    1220            1225                1230

Leu Ile Met Leu Asn Thr Leu Cys Leu Ala Met Gln His Tyr Glu
    1235            1240                1245

Gln Ser Lys Met Phe Asn Asp Ala Met Asp Ile Leu Asn Met Val
    1250            1255                1260

Phe Thr Gly Val Phe Thr Val Glu Met Val Leu Lys Val Ile Ala
    1265            1270                1275

Phe Lys Pro Lys Gly Tyr Phe Ser Asp Ala Trp Asn Thr Phe Asp
    1280            1285                1290

Ser Leu Ile Val Ile Gly Ser Ile Ile Asp Val Ala Leu Ser Glu
    1295            1300                1305

Ala Asp Pro Thr Glu Ser Glu Asn Val Pro Val Pro Thr Ala Thr
    1310            1315                1320

Pro Gly Asn Ser Glu Glu Ser Asn Arg Ile Ser Ile Thr Phe Phe
    1325            1330                1335

Arg Leu Phe Arg Val Met Arg Leu Val Lys Leu Leu Ser Arg Gly
    1340            1345                1350

Glu Gly Ile Arg Thr Leu Leu Trp Thr Phe Ile Lys Ser Phe Gln
    1355            1360                1365

Ala Leu Pro Tyr Val Ala Leu Leu Ile Ala Met Leu Phe Phe Ile
    1370            1375                1380

Tyr Ala Val Ile Gly Met Gln Met Phe Gly Lys Val Ala Met Arg
    1385            1390                1395

Asp Asn Asn Gln Ile Asn Arg Asn Asn Asn Phe Gln Thr Phe Pro
    1400            1405                1410

Gln Ala Val Leu Leu Leu Phe Arg Cys Ala Thr Gly Glu Ala Trp
    1415            1420                1425

Gln Glu Ile Met Leu Ala Cys Leu Pro Gly Lys Leu Cys Asp Pro
    1430            1435                1440

Glu Ser Asp Tyr Asn Pro Gly Glu Glu Tyr Thr Cys Gly Ser Asn
    1445            1450                1455

Phe Ala Ile Val Tyr Phe Ile Ser Phe Tyr Met Leu Cys Ala Phe
    1460            1465                1470

Leu Ile Ile Asn Leu Phe Val Ala Val Ile Met Asp Asn Phe Asp
    1475            1480                1485

Tyr Leu Thr Arg Asp Trp Ser Ile Leu Gly Pro His His Leu Asp
    1490            1495                1500

Glu Phe Lys Arg Ile Trp Ser Glu Tyr Asp Pro Glu Ala Lys Gly
    1505            1510                1515

Arg Ile Lys His Leu Asp Val Val Thr Leu Leu Arg Arg Ile Gln
    1520            1525                1530

Pro Pro Leu Gly Phe Gly Lys Leu Cys Pro His Arg Val Ala Cys
    1535            1540                1545

Lys Arg Leu Val Ala Met Asn Met Pro Leu Asn Ser Asp Gly Thr
    1550            1555                1560

Val Met Phe Asn Ala Thr Leu Phe Ala Leu Val Arg Thr Ala Leu
    1565            1570                1575
```

-continued

Lys Ile Lys Thr Glu Gly Asn Leu Glu Gln Ala Asn Glu Glu Leu
1580            1585                1590

Arg Ala Val Ile Lys Lys Ile Trp Lys Lys Thr Ser Met Lys Leu
1595            1600                1605

Leu Asp Gln Val Val Pro Pro Ala Gly Asp Glu Val Thr Val
1610            1615                1620

Gly Lys Phe Tyr Ala Thr Phe Leu Ile Gln Asp Tyr Phe Arg Lys
1625            1630                1635

Phe Lys Lys Arg Lys Glu Gln Gly Leu Val Gly Lys Tyr Pro Ala
1640            1645                1650

Lys Asn Thr Thr Ile Ala Leu Gln Ala Gly Leu Arg Thr Leu His
1655            1660                1665

Asp Ile Gly Pro Glu Ile Arg Arg Ala Ile Ser Cys Asp Leu Gln
1670            1675                1680

Asp Asp Glu Pro Glu Glu Thr Lys Arg Glu Glu Glu Asp Asp Val
1685            1690                1695

Phe Lys Arg Asn Gly Ala Leu Leu Gly Asn His Val Asn His Val
1700            1705                1710

Asn Ser Asp Arg Arg Asp Ser Leu Gln Gln Thr Asn Thr Thr His
1715            1720                1725

Arg Pro Leu His Val Gln Arg Pro Ser Ile Pro Pro Ala Ser Asp
1730            1735                1740

Thr Glu Lys Pro Leu Phe Pro Pro Ala Gly Asn Ser Val Cys His
1745            1750                1755

Asn His His Asn His Asn Ser Ile Gly Lys Gln Val Pro Thr Ser
1760            1765                1770

Thr Asn Ala Asn Leu Asn Asn Ala Asn Met Ser Lys Ala Ala His
1775            1780                1785

Gly Lys Arg Pro Ser Ile Gly Asn Leu Glu His Val Ser Glu Asn
1790            1795                1800

Gly His His Ser Ser His Lys His Asp Arg Glu Pro Gln Arg Arg
1805            1810                1815

Ser Ser Val Lys Arg Thr Arg Tyr Tyr Glu Thr Tyr Ile Arg Ser
1820            1825                1830

Asp Ser Gly Asp Glu Gln Leu Pro Thr Ile Cys Arg Glu Asp Pro
1835            1840                1845

Glu Ile His Gly Tyr Phe Arg Asp Pro His Cys Leu Gly Glu Gln
1850            1855                1860

Glu Tyr Phe Ser Ser Glu Glu Cys Tyr Glu Asp Asp Ser Ser Pro
1865            1870                1875

Thr Trp Ser Arg Gln Asn Tyr Gly Tyr Tyr Ser Arg Tyr Pro Gly
1880            1885                1890

Arg Asn Ile Asp Ser Glu Arg Pro Arg Gly Tyr His His Pro Gln
1895            1900                1905

Gly Phe Leu Glu Asp Asp Asp Ser Pro Val Cys Tyr Asp Ser Arg
1910            1915                1920

Arg Ser Pro Arg Arg Arg Leu Leu Pro Pro Thr Pro Ala Ser His
1925            1930                1935

Arg Arg Ser Ser Phe Asn Phe Glu Cys Leu Arg Arg Gln Ser Ser
1940            1945                1950

Gln Glu Glu Val Pro Ser Ser Pro Ile Phe Pro His Arg Thr Ala
1955            1960                1965

Leu Pro Leu His Leu Met Gln Gln Gln Ile Met Ala Val Ala Gly

```
                    1970                1975                1980

Leu Asp Ser Ser Lys Ala Gln Lys Tyr Ser Pro Ser His Ser Thr
    1985                1990                1995

Arg Ser Trp Ala Thr Pro Pro Ala Thr Pro Pro Tyr Arg Asp Trp
    2000                2005                2010

Thr Pro Cys Tyr Thr Pro Leu Ile Gln Val Glu Gln Ser Glu Ala
    2015                2020                2025

Leu Asp Gln Val Asn Gly Ser Leu Pro Ser Leu His Arg Ser Ser
    2030                2035                2040

Trp Tyr Thr Asp Glu Pro Asp Ile Ser Tyr Arg Thr Phe Thr Pro
    2045                2050                2055

Ala Ser Leu Thr Val Pro Ser Ser Phe Arg Asn Lys Asn Ser Asp
    2060                2065                2070

Lys Gln Arg Ser Ala Asp Ser Leu Val Glu Ala Val Leu Ile Ser
    2075                2080                2085

Glu Gly Leu Gly Arg Tyr Ala Arg Asp Pro Lys Phe Val Ser Ala
    2090                2095                2100

Thr Lys His Glu Ile Ala Asp Ala Cys Asp Leu Thr Ile Asp Glu
    2105                2110                2115

Met Glu Ser Ala Ala Ser Thr Leu Leu Asn Gly Asn Val Arg Pro
    2120                2125                2130

Arg Ala Asn Gly Asp Val Gly Pro Leu Ser His Arg Gln Asp Tyr
    2135                2140                2145

Glu Leu Gln Asp Phe Gly Pro Gly Tyr Ser Asp Glu Glu Pro Asp
    2150                2155                2160

Pro Gly Arg Asp Glu Glu Asp Leu Ala Asp Glu Met Ile Cys Ile
    2165                2170                2175

Thr Thr Leu
    2180

<210> SEQ ID NO 33
<211> LENGTH: 153
<212> TYPE: PRT
<213> ORGANISM: Homo sapiens

<400> SEQUENCE: 33

Met Leu Ser Asn Cys Arg Gln Asn Thr Leu Gly His Asn Thr Gln Thr
1               5                   10                  15

Ser Ile Ala Gln Asp Phe Ser Ser Glu Gln Gly Arg Thr Ala Pro Gln
            20                  25                  30

Asp Gln Lys Ala Ser Ile Gln Ile Tyr Pro Trp Met Gln Arg Met Asn
        35                  40                  45

Ser His Ser Gly Val Gly Tyr Gly Ala Asp Arg Arg Gly Arg Gln
    50                  55                  60

Ile Tyr Ser Arg Tyr Gln Thr Leu Glu Leu Glu Lys Glu Phe His Phe
65                  70                  75                  80

Asn Arg Tyr Leu Thr Arg Arg Arg Ile Glu Ile Ala Asn Ala Leu
                85                  90                  95

Cys Leu Thr Glu Arg Gln Ile Lys Ile Trp Phe Gln Asn Arg Arg Met
            100                 105                 110

Lys Trp Lys Lys Glu Ser Asn Leu Thr Ser Thr Leu Ser Gly Gly Gly
        115                 120                 125

Gly Gly Ala Thr Ala Asp Ser Leu Gly Gly Lys Glu Glu Lys Arg Glu
    130                 135                 140
```

Glu Thr Glu Glu Glu Lys Gln Lys Glu
145             150

<210> SEQ ID NO 34
<211> LENGTH: 374
<212> TYPE: PRT
<213> ORGANISM: Homo sapiens

<400> SEQUENCE: 34

Met Val Leu Trp Glu Ser Pro Arg Gln Cys Ser Ser Trp Thr Leu Cys
1               5                   10                  15

Glu Gly Phe Cys Trp Leu Leu Leu Pro Val Met Leu Leu Ile Val
                20                  25                  30

Ala Arg Pro Val Lys Leu Ala Ala Phe Pro Thr Ser Leu Ser Asp Cys
            35                  40                  45

Gln Thr Pro Thr Gly Trp Asn Cys Ser Gly Tyr Asp Asp Arg Glu Asn
    50                  55                  60

Asp Leu Phe Leu Cys Asp Thr Asn Thr Cys Lys Phe Asp Gly Glu Cys
65                  70                  75                  80

Leu Arg Ile Gly Asp Thr Val Thr Cys Val Cys Gln Phe Lys Cys Asn
                85                  90                  95

Asn Asp Tyr Val Pro Val Cys Gly Ser Asn Gly Glu Ser Tyr Gln Asn
            100                 105                 110

Glu Cys Tyr Leu Arg Gln Ala Ala Cys Lys Gln Gln Ser Glu Ile Leu
    115                 120                 125

Val Val Ser Glu Gly Ser Cys Ala Thr Asp Ala Gly Ser Gly Ser Gly
130                 135                 140

Asp Gly Val His Glu Gly Ser Gly Glu Thr Ser Gln Lys Glu Thr Ser
145                 150                 155                 160

Thr Cys Asp Ile Cys Gln Phe Gly Ala Glu Cys Asp Glu Asp Ala Glu
                165                 170                 175

Asp Val Trp Cys Val Cys Asn Ile Asp Cys Ser Gln Thr Asn Phe Asn
            180                 185                 190

Pro Leu Cys Ala Ser Asp Gly Lys Ser Tyr Asp Asn Ala Cys Gln Ile
    195                 200                 205

Lys Glu Ala Ser Cys Gln Lys Gln Glu Lys Ile Glu Val Met Ser Leu
210                 215                 220

Gly Arg Cys Gln Asp Asn Thr Thr Thr Thr Lys Ser Glu Asp Gly
225                 230                 235                 240

His Tyr Ala Arg Thr Asp Tyr Ala Glu Asn Ala Asn Lys Leu Glu Glu
                245                 250                 255

Ser Ala Arg Glu His His Ile Pro Cys Pro Glu His Tyr Asn Gly Phe
            260                 265                 270

Cys Met His Gly Lys Cys Glu His Ser Ile Asn Met Gln Glu Pro Ser
    275                 280                 285

Cys Arg Cys Asp Ala Gly Tyr Thr Gly Gln His Cys Glu Lys Lys Asp
    290                 295                 300

Tyr Ser Val Leu Tyr Val Pro Gly Pro Val Arg Phe Gln Tyr Val
305                 310                 315                 320

Leu Ile Ala Ala Val Ile Gly Thr Ile Gln Ile Ala Val Ile Cys Val
                325                 330                 335

Val Val Leu Cys Ile Thr Arg Lys Cys Pro Arg Ser Asn Arg Ile His
            340                 345                 350

Arg Gln Lys Gln Asn Thr Gly His Tyr Ser Ser Asp Asn Thr Thr Arg
    355                 360                 365

Ala Ser Thr Arg Leu Ile
        370

<210> SEQ ID NO 35
<211> LENGTH: 97
<212> TYPE: PRT
<213> ORGANISM: Homo sapiens

<400> SEQUENCE: 35

Met Leu Gly Asn Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
            20                  25                  30

Pro Asp Asn Pro Gly Glu Asp Ala Pro Ala Glu Asp Met Ala Arg Tyr
        35                  40                  45

Tyr Ser Ala Leu Arg His Tyr Ile Asn Leu Ile Thr Arg Gln Arg Tyr
    50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ala Met
                85                  90                  95

Trp

<210> SEQ ID NO 36
<211> LENGTH: 145
<212> TYPE: PRT
<213> ORGANISM: Homo sapiens

<400> SEQUENCE: 36

Met Ser Lys Gln Asn Gly Gly Glu Gly Ile Ile Ile Asn Met Ser
1               5                   10                  15

Ser Leu Ala Gly Leu Met Pro Val Ala Gln Gln Pro Val Tyr Cys Ala
            20                  25                  30

Ser Lys His Gly Ile Val Gly Phe Thr Arg Ser Ala Ala Leu Ala Ala
        35                  40                  45

Asn Leu Met Asn Ser Gly Val Arg Leu Asn Ala Ile Cys Pro Gly Phe
    50                  55                  60

Val Asn Thr Ala Ile Leu Glu Ser Ile Glu Lys Glu Asn Met Gly
65                  70                  75                  80

Gln Tyr Ile Glu Tyr Lys Asp His Ile Lys Asp Met Ile Lys Tyr Tyr
                85                  90                  95

Gly Ile Leu Asp Pro Pro Leu Ile Ala Asn Gly Leu Ile Thr Leu Ile
            100                 105                 110

Glu Asp Asp Ala Leu Asn Gly Ala Ile Met Lys Ile Thr Thr Ser Lys
        115                 120                 125

Gly Ile His Phe Gln Asp Tyr Asp Thr Thr Pro Phe Gln Ala Lys Thr
    130                 135                 140

Gln
145

<210> SEQ ID NO 37
<211> LENGTH: 975
<212> TYPE: PRT
<213> ORGANISM: Homo sapiens

<400> SEQUENCE: 37

Met Ala Ala Glu Glu Val Leu Gln Thr Val Asp His Tyr Lys Thr Glu

-continued

```
1               5                   10                  15

Ile Glu Arg Leu Thr Lys Glu Leu Thr Glu Thr Thr His Glu Lys Ile
                20                  25                  30
Gln Ala Ala Glu Tyr Gly Leu Val Val Leu Glu Glu Lys Leu Thr Leu
                35                  40                  45
Lys Gln Gln Tyr Asp Glu Leu Glu Ala Glu Tyr Asp Ser Leu Lys Gln
                50                  55                  60
Glu Leu Glu Gln Leu Lys Glu Ala Phe Gly Gln Ser Phe Ser Ile His
 65                 70                  75                  80
Arg Lys Val Ala Glu Asp Gly Glu Thr Arg Glu Glu Thr Leu Leu Gln
                85                  90                  95
Glu Ser Ala Ser Lys Glu Ala Tyr Tyr Leu Gly Lys Ile Leu Glu Met
                100                 105                 110
Gln Asn Glu Leu Lys Gln Ser Arg Ala Val Val Thr Asn Val Gln Ala
                115                 120                 125
Glu Asn Glu Arg Leu Thr Ala Val Val Gln Asp Leu Lys Glu Asn Asn
                130                 135                 140
Glu Met Val Glu Leu Gln Arg Ile Arg Met Lys Asp Glu Ile Arg Glu
145                 150                 155                 160
Tyr Lys Phe Arg Glu Ala Arg Leu Leu Gln Asp Tyr Thr Glu Leu Glu
                165                 170                 175
Glu Glu Asn Ile Thr Leu Gln Lys Leu Val Ser Thr Leu Lys Gln Asn
                180                 185                 190
Gln Val Glu Tyr Glu Gly Leu Lys His Glu Ile Lys Arg Phe Glu Glu
                195                 200                 205
Glu Thr Val Leu Leu Asn Ser Gln Leu Glu Asp Ala Ile Arg Leu Lys
                210                 215                 220
Glu Ile Ala Glu His Gln Leu Glu Glu Ala Leu Glu Thr Leu Lys Asn
225                 230                 235                 240
Glu Arg Glu Gln Lys Asn Asn Leu Arg Lys Glu Leu Ser Gln Tyr Ile
                245                 250                 255
Ser Leu Asn Asp Asn His Ile Ser Ile Ser Val Asp Gly Leu Lys Phe
                260                 265                 270
Ala Glu Asp Gly Ser Glu Pro Asn Asn Asp Asp Lys Met Asn Gly His
                275                 280                 285
Ile His Gly Pro Leu Val Lys Leu Asn Gly Asp Tyr Arg Thr Pro Thr
                290                 295                 300
Leu Arg Lys Gly Glu Ser Leu Asn Pro Val Ser Asp Leu Phe Ser Glu
305                 310                 315                 320
Leu Asn Ile Ser Glu Ile Gln Lys Leu Lys Gln Gln Leu Met Gln Val
                325                 330                 335
Glu Arg Glu Lys Ala Ile Leu Leu Ala Asn Leu Gln Glu Ser Gln Thr
                340                 345                 350
Gln Leu Glu His Thr Lys Gly Ala Leu Thr Glu Gln His Glu Arg Val
                355                 360                 365
His Arg Leu Thr Glu His Val Asn Ala Met Arg Gly Leu Gln Ser Ser
                370                 375                 380
Lys Glu Leu Lys Ala Glu Leu Asp Gly Glu Lys Gly Arg Asp Ser Gly
385                 390                 395                 400
Glu Glu Ala His Asp Tyr Glu Val Asp Ile Asn Gly Leu Glu Ile Leu
                405                 410                 415
Glu Cys Lys Tyr Arg Val Ala Val Thr Glu Val Ile Asp Leu Lys Ala
                420                 425                 430
```

```
Glu Ile Lys Ala Leu Lys Glu Lys Tyr Asn Lys Ser Val Glu Asn Tyr
            435                 440                 445

Thr Asp Glu Lys Ala Lys Tyr Glu Ser Lys Ile Gln Met Tyr Asp Glu
    450                 455                 460

Gln Val Thr Ser Leu Glu Lys Thr Thr Lys Glu Ser Gly Glu Lys Met
465                 470                 475                 480

Ala His Met Glu Lys Glu Leu Gln Lys Met Thr Ser Ile Ala Asn Glu
                485                 490                 495

Asn His Ser Thr Leu Asn Thr Ala Gln Asp Glu Leu Val Thr Phe Ser
            500                 505                 510

Glu Glu Leu Ala Gln Leu Tyr His His Val Cys Leu Cys Asn Asn Glu
            515                 520                 525

Thr Pro Asn Arg Val Met Leu Asp Tyr Tyr Arg Gln Ser Arg Val Thr
    530                 535                 540

Arg Ser Gly Ser Leu Lys Gly Pro Asp Pro Arg Gly Leu Leu Ser
545                 550                 555                 560

Pro Arg Leu Ala Arg Arg Gly Val Ser Ser Pro Val Glu Thr Arg Thr
                565                 570                 575

Ser Ser Glu Pro Val Ala Lys Glu Ser Thr Glu Ala Ser Lys Glu Pro
            580                 585                 590

Ser Pro Thr Lys Thr Pro Thr Ile Ser Pro Val Ile Thr Ala Pro Pro
            595                 600                 605

Ser Ser Pro Val Leu Asp Thr Ser Asp Ile Arg Lys Glu Pro Met Asn
610                 615                 620

Ile Tyr Asn Leu Asn Ala Ile Ile Arg Asp Gln Ile Lys His Leu Gln
625                 630                 635                 640

Lys Ala Val Asp Arg Ser Leu Gln Leu Ser Arg Gln Arg Ala Ala Ala
                645                 650                 655

Arg Glu Leu Ala Pro Met Ile Asp Lys Asp Lys Glu Ala Leu Met Glu
                660                 665                 670

Glu Ile Leu Lys Leu Lys Ser Leu Leu Ser Thr Lys Arg Glu Gln Ile
            675                 680                 685

Ala Thr Leu Arg Ala Val Leu Lys Ala Asn Lys Gln Thr Ala Glu Val
            690                 695                 700

Ala Leu Ala Asn Leu Lys Asn Lys Tyr Glu Asn Glu Lys Ala Met Val
705                 710                 715                 720

Thr Glu Thr Met Thr Lys Leu Arg Asn Glu Leu Lys Ala Leu Lys Glu
                725                 730                 735

Asp Ala Ala Thr Phe Ser Ser Leu Arg Ala Met Phe Ala Thr Arg Cys
            740                 745                 750

Asp Glu Tyr Val Thr Gln Leu Asp Glu Met Gln Arg Gln Leu Ala Ala
            755                 760                 765

Ala Glu Asp Glu Lys Lys Thr Leu Asn Thr Leu Leu Arg Met Ala Ile
770                 775                 780

Gln Gln Lys Leu Ala Leu Thr Gln Arg Leu Glu Asp Leu Glu Phe Asp
785                 790                 795                 800

His Glu Gln Ser Arg Arg Ser Lys Gly Lys Leu Gly Lys Ser Lys Ile
                805                 810                 815

Gly Ser Pro Lys Val Ser Gly Glu Ala Ser Val Thr Val Pro Thr Ile
            820                 825                 830

Asp Thr Tyr Leu Leu His Ser Gln Gly Pro Gln Thr Pro Asn Ile Arg
            835                 840                 845
```

```
Val Ser Ser Gly Thr Gln Arg Lys Arg Gln Phe Ser Pro Ser Leu Cys
    850                 855                 860

Asp Gln Ser Arg Pro Arg Thr Ser Gly Ala Ser Tyr Leu Gln Asn Leu
865                 870                 875                 880

Leu Arg Val Pro Pro Asp Pro Thr Ser Thr Glu Ser Phe Leu Leu Lys
                885                 890                 895

Gly Pro Pro Ser Met Ser Glu Phe Ile Gln Gly His Arg Leu Ser Lys
                900                 905                 910

Glu Lys Arg Leu Thr Val Ala Pro Pro Asp Cys Gln Gln Pro Ala Ala
            915                 920                 925

Ser Val Pro Pro Gln Cys Ser Gln Leu Ala Gly Arg Gln Asp Cys Pro
930                 935                 940

Thr Val Ser Pro Asp Thr Ala Leu Pro Glu Glu Gln Pro His Ser Ser
945                 950                 955                 960

Ser Gln Cys Ala Pro Leu His Cys Leu Ser Lys Pro Pro His Pro
                965                 970                 975

<210> SEQ ID NO 38
<211> LENGTH: 318
<212> TYPE: PRT
<213> ORGANISM: Homo sapiens

<400> SEQUENCE: 38

Met Met Val Asp Pro Asn Gly Asn Glu Ser Ser Ala Thr Tyr Phe Ile
1               5                   10                  15

Leu Ile Gly Leu Pro Gly Leu Glu Glu Ala Gln Phe Trp Leu Ala Phe
            20                  25                  30

Pro Leu Cys Ser Leu Tyr Leu Ile Ala Val Leu Gly Asn Leu Thr Ile
        35                  40                  45

Ile Tyr Ile Val Arg Thr Glu His Ser Leu His Glu Pro Met Tyr Ile
    50                  55                  60

Phe Leu Cys Met Leu Ser Gly Ile Asp Ile Leu Ile Ser Thr Ser Ser
65                  70                  75                  80

Met Pro Lys Met Leu Ala Ile Phe Trp Phe Asn Ser Thr Thr Ile Gln
                85                  90                  95

Phe Asp Ala Cys Leu Leu Gln Met Phe Ala Ile His Ser Leu Ser Gly
                100                 105                 110

Met Glu Ser Thr Val Leu Leu Ala Met Ala Phe Asp Arg Tyr Val Ala
            115                 120                 125

Ile Cys His Pro Leu Arg His Ala Thr Val Leu Thr Leu Pro Arg Val
    130                 135                 140

Thr Lys Ile Gly Val Ala Ala Val Val Arg Gly Ala Ala Leu Met Ala
145                 150                 155                 160

Pro Leu Pro Val Phe Ile Lys Gln Leu Pro Phe Cys Arg Ser Asn Ile
                165                 170                 175

Leu Ser His Ser Tyr Cys Leu His Gln Asp Val Met Lys Leu Ala Cys
                180                 185                 190

Asp Asp Ile Arg Val Asn Val Val Tyr Gly Leu Ile Val Ile Ile Ser
            195                 200                 205

Ala Ile Gly Leu Asp Ser Leu Leu Ile Ser Phe Ser Tyr Leu Leu Ile
    210                 215                 220

Leu Lys Thr Val Leu Gly Leu Thr Arg Glu Ala Gln Ala Lys Ala Phe
225                 230                 235                 240

Gly Thr Cys Val Ser His Val Cys Ala Val Phe Ile Phe Tyr Val Pro
                245                 250                 255
```

```
Phe Ile Gly Leu Ser Met Val His Arg Phe Ser Lys Arg Arg Asp Ser
                260                 265                 270

Pro Leu Pro Val Ile Leu Ala Asn Ile Tyr Leu Leu Val Pro Pro Val
            275                 280                 285

Leu Asn Pro Ile Val Tyr Gly Val Lys Thr Lys Glu Ile Arg Gln Arg
        290                 295                 300

Ile Leu Arg Leu Phe His Val Ala Thr His Ala Ser Glu Pro
305                 310                 315

<210> SEQ ID NO 39
<211> LENGTH: 320
<212> TYPE: PRT
<213> ORGANISM: Homo sapiens

<400> SEQUENCE: 39

Met Ser Ser Cys Asn Phe Thr His Ala Thr Phe Val Leu Ile Gly Ile
1               5                   10                  15

Pro Gly Leu Glu Lys Ala His Phe Trp Val Gly Phe Pro Leu Leu Ser
                20                  25                  30

Met Tyr Val Val Ala Met Phe Gly Asn Cys Ile Val Val Phe Ile Val
                35                  40                  45

Arg Thr Glu Arg Ser Leu His Ala Pro Met Tyr Leu Phe Leu Cys Met
        50                  55                  60

Leu Ala Ala Ile Asp Leu Ala Leu Ser Thr Ser Thr Met Pro Lys Ile
65                  70                  75                  80

Leu Ala Leu Phe Trp Phe Asp Ser Arg Glu Ile Ser Phe Glu Ala Cys
                85                  90                  95

Leu Thr Gln Met Phe Phe Ile His Ala Leu Ser Ala Ile Glu Ser Thr
                100                 105                 110

Ile Leu Leu Ala Met Ala Phe Asp Arg Tyr Val Ala Ile Cys His Pro
            115                 120                 125

Leu Arg His Ala Ala Val Leu Asn Asn Thr Val Thr Ala Gln Ile Gly
        130                 135                 140

Ile Val Ala Val Val Arg Gly Ser Leu Phe Phe Phe Pro Leu Pro Leu
145                 150                 155                 160

Leu Ile Lys Arg Leu Ala Phe Cys His Ser Asn Val Leu Ser His Ser
                165                 170                 175

Tyr Cys Val His Gln Asp Val Met Lys Leu Ala Tyr Ala Asp Thr Leu
                180                 185                 190

Pro Asn Val Val Tyr Gly Leu Thr Ala Ile Leu Leu Val Met Gly Val
            195                 200                 205

Asp Val Met Phe Ile Ser Leu Ser Tyr Phe Leu Ile Ile Arg Thr Val
        210                 215                 220

Leu Gln Leu Pro Ser Lys Ser Glu Arg Ala Lys Ala Phe Gly Thr Cys
225                 230                 235                 240

Val Ser His Ile Gly Val Val Leu Ala Phe Tyr Val Pro Leu Ile Gly
                245                 250                 255

Leu Ser Val Val His Arg Phe Gly Asn Ser Leu His Pro Ile Val Arg
                260                 265                 270

Val Val Met Gly Asp Ile Tyr Leu Leu Leu Pro Pro Val Ile Asn Pro
            275                 280                 285

Ile Ile Tyr Gly Ala Lys Thr Lys Gln Ile Arg Thr Arg Val Leu Ala
        290                 295                 300

Met Phe Lys Ile Ser Cys Asp Lys Asp Leu Gln Ala Val Gly Gly Lys
```

<210> SEQ ID NO 40
<211> LENGTH: 750
<212> TYPE: PRT
<213> ORGANISM: Homo sapiens

<400> SEQUENCE: 40

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
            85                  90                  95

Gln Ser Gln Trp Lys Glu Phe Gly Leu Asp Ser Val Glu Leu Ala His
        100                 105                 110

Tyr Asp Val Leu Leu Ser Tyr Pro Asn Lys Thr His Pro Asn Tyr Ile
    115                 120                 125

Ser Ile Ile Asn Glu Asp Gly Asn Glu Ile Phe Asn Thr Ser Leu Phe
130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
            165                 170                 175

Val Asn Tyr Ala Arg Thr Glu Asp Phe Phe Lys Leu Glu Arg Asp Met
        180                 185                 190

Lys Ile Asn Cys Ser Gly Lys Ile Val Ile Ala Arg Tyr Gly Lys Val
    195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
            245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
            325                 330                 335

Phe Ser Thr Gln Lys Val Lys Met His Ile His Ser Thr Asn Glu Val
        340                 345                 350

Thr Arg Ile Tyr Asn Val Ile Gly Thr Leu Arg Gly Ala Val Glu Pro
    355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
                435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
                515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
                595                 600                 605

Asp Lys Ile Tyr Ser Ile Ser Met Lys His Pro Gln Glu Met Lys Thr
                610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
                675                 680                 685

His Val Ile Tyr Ala Pro Ser Ser His Asn Lys Tyr Ala Gly Glu Ser
                690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
                740                 745                 750

<210> SEQ ID NO 41
<211> LENGTH: 303
<212> TYPE: PRT
<213> ORGANISM: Homo sapiens

<400> SEQUENCE: 41

```
Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Glu Phe Asp Asp Gly Ala Glu Glu Thr Glu Glu
    50                  55                  60

Glu Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
    130                 135                 140

Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
                165                 170                 175

Thr Leu Tyr Glu Arg Asp Glu Asp Asn Asn Leu Leu Thr Glu Lys Gln
            180                 185                 190

Lys Leu Arg Val Lys Lys Ile His Glu Asn Glu Lys Arg Leu Glu Ala
        195                 200                 205

Gly Asp His Pro Val Glu Leu Leu Ala Arg Asp Phe Glu Lys Asn Tyr
    210                 215                 220

Asn Met Tyr Ile Phe Pro Val His Trp Gln Phe Gly Gln Leu Asp Gln
225                 230                 235                 240

His Pro Ile Asp Gly Tyr Leu Ser His Thr Glu Leu Ala Pro Leu Arg
                245                 250                 255

Ala Pro Leu Ile Pro Met Glu His Cys Thr Thr Arg Phe Phe Glu Thr
            260                 265                 270

Cys Asp Leu Asp Asn Asp Lys Tyr Ile Ala Leu Asp Glu Trp Ala Gly
        275                 280                 285

Cys Phe Gly Ile Lys Gln Lys Asp Ile Asp Lys Asp Leu Val Ile
    290                 295                 300

<210> SEQ ID NO 42
<211> LENGTH: 441
<212> TYPE: PRT
<213> ORGANISM: Homo sapiens

<400> SEQUENCE: 42

Met Val Pro Pro Lys Leu His Val Leu Phe Cys Leu Cys Gly Cys Leu
1               5                   10                  15

Ala Val Val Tyr Pro Phe Asp Trp Gln Tyr Ile Asn Pro Val Ala His
            20                  25                  30

Met Lys Ser Ser Ala Trp Val Asn Lys Ile Gln Val Leu Met Ala Ala
        35                  40                  45

Ala Ser Phe Gly Gln Thr Lys Ile Pro Arg Gly Asn Gly Pro Tyr Ser
    50                  55                  60

Val Gly Cys Thr Asp Leu Met Phe Asp His Thr Asn Lys Gly Thr Phe
```

```
                65                  70                  75                  80
Leu Arg Leu Tyr Tyr Pro Ser Gln Asp Asn Arg Leu Asp Thr Leu
                    85                  90                  95
Trp Ile Pro Asn Lys Glu Tyr Phe Trp Gly Leu Ser Lys Phe Leu Gly
                    100                 105                 110
Thr His Trp Leu Met Gly Asn Ile Leu Arg Leu Leu Phe Gly Ser Met
                    115                 120                 125
Thr Thr Pro Ala Asn Trp Asn Ser Pro Leu Arg Pro Gly Glu Lys Tyr
                130                 135                 140
Pro Leu Val Val Phe Ser His Gly Leu Gly Ala Phe Arg Thr Leu Tyr
145                 150                 155                 160
Ser Ala Ile Gly Ile Asp Leu Ala Ser His Gly Phe Ile Val Ala Ala
                    165                 170                 175
Val Glu His Arg Asp Arg Ser Ala Ser Ala Thr Tyr Tyr Phe Lys Asp
                    180                 185                 190
Gln Ser Ala Ala Glu Ile Gly Asp Lys Ser Trp Leu Tyr Leu Arg Thr
                    195                 200                 205
Leu Lys Gln Glu Glu Glu Thr His Ile Arg Asn Glu Gln Val Arg Gln
                210                 215                 220
Arg Ala Lys Glu Cys Ser Gln Ala Leu Ser Leu Ile Leu Asp Ile Asp
225                 230                 235                 240
His Gly Lys Pro Val Lys Asn Ala Leu Asp Leu Lys Phe Asp Met Glu
                    245                 250                 255
Gln Leu Lys Asp Ser Ile Asp Arg Glu Lys Ile Ala Val Ile Gly His
                    260                 265                 270
Ser Phe Gly Gly Ala Thr Val Ile Gln Thr Leu Ser Glu Asp Gln Arg
                    275                 280                 285
Phe Arg Cys Gly Ile Ala Leu Asp Ala Trp Met Phe Pro Leu Gly Asp
                290                 295                 300
Glu Val Tyr Ser Arg Ile Pro Gln Pro Leu Phe Phe Ile Asn Ser Glu
305                 310                 315                 320
Tyr Phe Gln Tyr Pro Ala Asn Ile Ile Lys Met Lys Lys Cys Tyr Ser
                    325                 330                 335
Pro Asp Lys Glu Arg Lys Met Ile Thr Ile Arg Gly Ser Val His Gln
                    340                 345                 350
Asn Phe Ala Asp Phe Thr Phe Ala Thr Gly Lys Ile Ile Gly His Met
                    355                 360                 365
Leu Lys Leu Lys Gly Asp Ile Asp Ser Asn Val Ala Ile Asp Leu Ser
                370                 375                 380
Asn Lys Ala Ser Leu Ala Phe Leu Gln Lys His Leu Gly Leu His Lys
385                 390                 395                 400
Asp Phe Asp Gln Trp Asp Cys Leu Ile Glu Gly Asp Asp Glu Asn Leu
                    405                 410                 415
Ile Pro Gly Thr Asn Ile Asn Thr Thr Asn Gln His Ile Met Leu Gln
                    420                 425                 430
Asn Ser Ser Gly Ile Glu Lys Tyr Asn
                435                 440

<210> SEQ ID NO 43
<211> LENGTH: 1285
<212> TYPE: PRT
<213> ORGANISM: Homo sapiens

<400> SEQUENCE: 43
```

```
Met Glu Asp Gly Lys Pro Val Trp Ala Pro His Pro Thr Asp Gly Phe
1               5                   10                  15
Gln Met Gly Asn Ile Val Asp Ile Gly Pro Asp Ser Leu Thr Ile Glu
                20                  25                  30
Pro Leu Asn Gln Lys Gly Lys Thr Phe Leu Ala Leu Ile Asn Gln Val
            35                  40                  45
Phe Pro Ala Glu Glu Asp Ser Lys Lys Asp Val Glu Asp Asn Cys Ser
50                  55                  60
Leu Met Tyr Leu Asn Glu Ala Thr Leu Leu His Asn Ile Lys Val Arg
65                  70                  75                  80
Tyr Ser Lys Asp Arg Ile Tyr Thr Tyr Val Ala Asn Ile Leu Ile Ala
                85                  90                  95
Val Asn Pro Tyr Phe Asp Ile Pro Lys Ile Tyr Ser Ser Glu Ala Ile
                100                 105                 110
Lys Ser Tyr Gln Gly Lys Ser Leu Gly Thr Arg Pro Pro His Val Phe
                115                 120                 125
Ala Ile Ala Asp Lys Ala Phe Arg Asp Met Lys Val Leu Lys Met Ser
            130                 135                 140
Gln Ser Ile Ile Val Ser Gly Glu Ser Gly Ala Gly Lys Thr Glu Asn
145                 150                 155                 160
Thr Lys Phe Val Leu Arg Tyr Leu Thr Glu Ser Tyr Gly Thr Gly Gln
                165                 170                 175
Asp Ile Asp Asp Arg Ile Val Glu Ala Asn Pro Leu Leu Glu Ala Phe
                180                 185                 190
Gly Asn Ala Lys Thr Val Arg Asn Asn Asn Ser Ser Arg Phe Gly Lys
            195                 200                 205
Phe Val Glu Ile His Phe Asn Glu Lys Ser Ser Val Val Gly Gly Phe
210                 215                 220
Val Ser His Tyr Leu Leu Glu Lys Ser Arg Ile Cys Val Gln Gly Lys
225                 230                 235                 240
Glu Glu Arg Asn Tyr His Ile Phe Tyr Arg Leu Cys Ala Gly Ala Ser
                245                 250                 255
Glu Asp Ile Arg Glu Lys Leu His Leu Ser Ser Pro Asp Asn Phe Arg
                260                 265                 270
Tyr Leu Asn Arg Gly Cys Thr Arg Tyr Phe Ala Asn Lys Glu Thr Asp
                275                 280                 285
Lys Gln Ile Leu Gln Asn Arg Lys Ser Pro Glu Tyr Leu Lys Ala Gly
            290                 295                 300
Ser Met Lys Asp Pro Leu Leu Asp Asp His Gly Asp Phe Ile Arg Met
305                 310                 315                 320
Cys Thr Ala Met Lys Lys Ile Gly Leu Asp Asp Glu Glu Lys Leu Asp
                325                 330                 335
Leu Phe Arg Val Val Ala Gly Val Leu His Leu Gly Asn Ile Asp Phe
                340                 345                 350
Glu Glu Ala Gly Ser Thr Ser Gly Gly Cys Asn Leu Lys Asn Lys Ser
                355                 360                 365
Ala Gln Ser Leu Glu Tyr Cys Ala Glu Leu Leu Gly Leu Asp Gln Asp
            370                 375                 380
Asp Leu Arg Val Ser Leu Thr Thr Arg Val Met Leu Thr Thr Ala Gly
385                 390                 395                 400
Gly Thr Lys Gly Thr Val Ile Lys Val Pro Leu Lys Val Glu Gln Ala
                405                 410                 415
Asn Asn Ala Arg Asp Ala Leu Ala Lys Thr Val Tyr Ser His Leu Phe
```

-continued

```
            420                 425                 430
Asp His Val Val Asn Arg Val Asn Gln Cys Phe Pro Phe Glu Thr Ser
                435                 440                 445

Ser Tyr Phe Ile Gly Val Leu Asp Ile Ala Gly Phe Glu Tyr Phe Glu
450                 455                 460

His Asn Ser Phe Glu Gln Phe Cys Ile Asn Tyr Cys Asn Glu Lys Leu
465                 470                 475                 480

Gln Gln Phe Phe Asn Glu Arg Ile Leu Lys Glu Gln Glu Leu Tyr
                485                 490                 495

Gln Lys Glu Gly Leu Gly Val Asn Glu Val His Tyr Val Asp Asn Gln
                500                 505                 510

Asp Cys Ile Asp Leu Ile Glu Ala Lys Leu Val Gly Ile Leu Asp Ile
                515                 520                 525

Leu Asp Glu Glu Asn Arg Leu Pro Gln Pro Ser Asp Gln His Phe Thr
                530                 535                 540

Ser Ala Val His Gln Lys His Lys Asp His Phe Arg Leu Thr Ile Pro
545                 550                 555                 560

Arg Lys Ser Lys Leu Ala Val His Arg Asn Ile Arg Asp Asp Glu Gly
                565                 570                 575

Phe Ile Ile Arg His Phe Ala Gly Ala Val Cys Tyr Glu Thr Thr Gln
                580                 585                 590

Phe Val Glu Lys Asn Asn Asp Ala Leu His Met Ser Leu Glu Ser Leu
                595                 600                 605

Ile Cys Glu Ser Arg Asp Lys Phe Ile Arg Glu Leu Phe Glu Ser Ser
                610                 615                 620

Thr Asn Asn Asn Lys Asp Thr Lys Gln Lys Ala Gly Lys Leu Ser Phe
625                 630                 635                 640

Ile Ser Val Gly Asn Lys Phe Lys Thr Gln Leu Asn Leu Leu Leu Asp
                645                 650                 655

Lys Leu Arg Ser Thr Gly Ala Ser Phe Ile Arg Cys Ile Lys Pro Asn
                660                 665                 670

Leu Lys Met Thr Ser His His Phe Glu Gly Ala Gln Ile Leu Ser Gln
                675                 680                 685

Leu Gln Cys Ser Gly Met Val Ser Val Leu Asp Leu Met Gln Gly Gly
                690                 695                 700

Tyr Pro Ser Arg Ala Ser Phe His Glu Leu Tyr Asn Met Tyr Lys Lys
705                 710                 715                 720

Tyr Met Pro Asp Lys Leu Ala Arg Leu Asp Pro Arg Leu Phe Cys Lys
                725                 730                 735

Ala Leu Phe Lys Ala Leu Gly Leu Asn Glu Asn Asp Tyr Lys Phe Gly
                740                 745                 750

Leu Thr Lys Val Phe Phe Arg Pro Gly Lys Phe Ala Glu Phe Asp Gln
                755                 760                 765

Ile Met Lys Ser Asp Pro Asp His Leu Ala Glu Leu Val Lys Arg Val
                770                 775                 780

Asn His Trp Leu Thr Cys Ser Arg Trp Lys Lys Val Gln Trp Cys Ser
785                 790                 795                 800

Leu Ser Val Ile Lys Leu Lys Asn Lys Ile Lys Tyr Arg Ala Glu Ala
                805                 810                 815

Cys Ile Lys Met Gln Lys Thr Ile Arg Met Trp Leu Cys Lys Arg Arg
                820                 825                 830

His Lys Pro Arg Ile Asp Gly Leu Val Lys Val Gly Thr Leu Lys Lys
                835                 840                 845
```

```
Arg Leu Asp Lys Phe Asn Glu Val Val Ser Val Leu Lys Asp Gly Lys
    850                 855                 860

Pro Glu Met Asn Lys Gln Ile Lys Asn Leu Glu Ile Ser Ile Asp Thr
865                 870                 875                 880

Leu Met Ala Lys Ile Lys Ser Thr Met Met Thr Gln Glu Gln Ile Gln
                885                 890                 895

Lys Glu Tyr Asp Ala Leu Val Lys Ser Ser Glu Glu Leu Leu Ser Ala
                900                 905                 910

Leu Gln Lys Lys Lys Gln Gln Glu Glu Ala Glu Arg Leu Arg Arg
            915                 920                 925

Ile Gln Glu Glu Met Glu Lys Glu Arg Lys Arg Glu Glu Asp Glu
    930                 935                 940

Lys Arg Arg Arg Lys Glu Glu Glu Arg Arg Met Lys Leu Glu Met
945                 950                 955                 960

Glu Ala Lys Arg Lys Gln Glu Glu Glu Arg Lys Lys Arg Glu Asp
                965                 970                 975

Asp Glu Lys Arg Ile Gln Ala Glu Val Glu Ala Gln Leu Ala Arg Gln
                980                 985                 990

Lys Glu Glu Glu Ser Gln Gln Gln Ala Val Leu Glu Gln Glu Arg Arg
            995                1000                1005

Asp Arg Glu Leu Ala Leu Arg Ile Ala Gln Ser Glu Ala Glu Leu
    1010                1015                1020

Ile Ser Asp Glu Ala Gln Ala Asp Leu Ala Leu Arg Arg Asn Asp
    1025                1030                1035

Gly Thr Arg Pro Lys Met Thr Pro Glu Gln Met Ala Lys Glu Met
    1040                1045                1050

Ser Glu Phe Leu Ser Arg Gly Pro Ala Val Leu Ala Thr Lys Ala
    1055                1060                1065

Ala Ala Gly Thr Lys Lys Tyr Asp Leu Ser Lys Trp Lys Tyr Ala
    1070                1075                1080

Glu Leu Arg Asp Thr Ile Asn Thr Ser Cys Asp Ile Glu Leu Leu
    1085                1090                1095

Ala Ala Cys Arg Glu Glu Phe His Arg Arg Leu Lys Val Tyr His
    1100                1105                1110

Ala Trp Lys Ser Lys Asn Lys Lys Arg Asn Thr Glu Thr Glu Gln
    1115                1120                1125

Arg Ala Pro Lys Ser Val Thr Asp Tyr Asp Phe Ala Pro Phe Leu
    1130                1135                1140

Asn Asn Ser Pro Gln Gln Asn Pro Ala Ala Gln Ile Pro Ala Arg
    1145                1150                1155

Gln Arg Glu Ile Glu Met Asn Arg Gln Gln Arg Phe Phe Arg Ile
    1160                1165                1170

Pro Phe Ile Arg Pro Ala Asp Gln Tyr Lys Asp Pro Gln Ser Lys
    1175                1180                1185

Lys Lys Gly Trp Trp Tyr Ala His Phe Asp Gly Pro Trp Ile Ala
    1190                1195                1200

Arg Gln Met Glu Leu His Pro Asp Lys Pro Pro Ile Leu Leu Val
    1205                1210                1215

Ala Gly Lys Asp Asp Met Glu Met Cys Glu Leu Asn Leu Glu Glu
    1220                1225                1230

Thr Gly Leu Thr Arg Lys Arg Gly Ala Glu Ile Leu Pro Arg Gln
    1235                1240                1245
```

```
Phe Glu Glu Ile Trp Glu Arg Cys Gly Gly Ile Gln Tyr Leu Gln
    1250                1255                1260

Asn Ala Ile Glu Ser Arg Gln Ala Arg Pro Thr Tyr Ala Thr Ala
    1265                1270                1275

Met Leu Gln Ser Leu Leu Lys
    1280                1285

<210> SEQ ID NO 44
<211> LENGTH: 258
<212> TYPE: PRT
<213> ORGANISM: Homo sapiens

<400> SEQUENCE: 44

Met Lys Gln Ile Leu His Pro Ala Leu Glu Thr Thr Ala Met Thr Leu
1               5                   10                  15

Phe Pro Val Leu Leu Phe Leu Val Ala Gly Leu Leu Pro Ser Phe Pro
            20                  25                  30

Ala Asn Glu Asp Lys Asp Pro Ala Phe Thr Ala Leu Leu Thr Thr Gln
        35                  40                  45

Thr Gln Val Gln Arg Glu Ile Val Asn Lys His Asn Glu Leu Arg Arg
    50                  55                  60

Ala Val Ser Pro Pro Ala Arg Asn Met Leu Lys Met Glu Trp Asn Lys
65                  70                  75                  80

Glu Ala Ala Ala Asn Ala Gln Lys Trp Ala Asn Gln Cys Asn Tyr Arg
                85                  90                  95

His Ser Asn Pro Lys Asp Arg Met Thr Ser Leu Lys Cys Gly Glu Asn
            100                 105                 110

Leu Tyr Met Ser Ser Ala Ser Ser Trp Ser Gln Ala Ile Gln Ser
        115                 120                 125

Trp Phe Asp Glu Tyr Asn Asp Phe Asp Phe Gly Val Gly Pro Lys Thr
    130                 135                 140

Pro Asn Ala Val Val Gly His Tyr Thr Gln Val Val Trp Tyr Ser Ser
145                 150                 155                 160

Tyr Leu Val Gly Cys Gly Asn Ala Tyr Cys Pro Asn Gln Lys Val Leu
                165                 170                 175

Lys Tyr Tyr Tyr Val Cys Gln Tyr Cys Pro Ala Gly Asn Trp Ala Asn
            180                 185                 190

Arg Leu Tyr Val Pro Tyr Glu Gln Gly Ala Pro Cys Ala Ser Cys Pro
        195                 200                 205

Asp Asn Cys Asp Asp Gly Leu Cys Thr Asn Gly Cys Lys Tyr Glu Asp
    210                 215                 220

Leu Tyr Ser Asn Cys Lys Ser Leu Lys Leu Thr Leu Thr Cys Lys His
225                 230                 235                 240

Gln Leu Val Arg Asp Ser Cys Lys Ala Ser Cys Asn Cys Ser Asn Ser
                245                 250                 255

Ile Tyr

<210> SEQ ID NO 45
<211> LENGTH: 202
<212> TYPE: PRT
<213> ORGANISM: Homo sapiens

<400> SEQUENCE: 45

Met Met Gln Asp Val Ser Ser Ser Pro Val Ser Pro Ala Asp Asp Ser
1               5                   10                  15

Leu Ser Asn Ser Glu Glu Glu Pro Asp Arg Gln Gln Pro Pro Ser Gly
```

```
            20                  25                  30
Lys Arg Gly Gly Arg Lys Arg Arg Ser Ser Arg Ser Ala Gly Gly
         35                  40                  45
Gly Ala Gly Pro Gly Gly Ala Ala Gly Gly Val Gly Gly Gly Asp
     50                  55                  60
Glu Pro Gly Ser Pro Ala Gln Gly Lys Arg Gly Lys Lys Ser Ala Gly
 65                  70                  75                  80
Cys Gly Gly Gly Gly Ala Gly Gly Gly Gly Ser Ser Ser Gly
                 85                  90                  95
Gly Gly Ser Pro Gln Ser Tyr Glu Glu Leu Gln Thr Gln Arg Val Met
             100                 105                 110
Ala Asn Val Arg Glu Arg Gln Arg Thr Gln Ser Leu Asn Glu Ala Phe
             115                 120                 125
Ala Ala Leu Arg Lys Ile Ile Pro Thr Leu Pro Ser Asp Lys Leu Ser
         130                 135                 140
Lys Ile Gln Thr Leu Lys Leu Ala Ala Arg Tyr Ile Asp Phe Leu Tyr
145                 150                 155                 160
Gln Val Leu Gln Ser Asp Glu Leu Asp Ser Lys Met Ala Ser Cys Ser
                 165                 170                 175
Tyr Val Ala His Glu Arg Leu Ser Tyr Ala Phe Ser Val Trp Arg Met
             180                 185                 190
Glu Gly Ala Trp Ser Met Ser Ala Ser His
         195                 200

<210> SEQ ID NO 46
<211> LENGTH: 1218
<212> TYPE: PRT
<213> ORGANISM: Homo sapiens

<400> SEQUENCE: 46

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
             20                  25                  30

Gly Gln Phe Glu Leu Glu Ile Leu Ser Met Gln Asn Val Asn Gly Glu
         35                  40                  45

Leu Gln Asn Gly Asn Cys Cys Gly Gly Ala Arg Asn Pro Gly Asp Arg
     50                  55                  60

Lys Cys Thr Arg Asp Glu Cys Asp Thr Tyr Phe Lys Val Cys Leu Lys
 65                  70                  75                  80

Glu Tyr Gln Ser Arg Val Thr Ala Gly Gly Pro Cys Ser Phe Gly Ser
                 85                  90                  95

Gly Ser Thr Pro Val Ile Gly Gly Asn Thr Phe Asn Leu Lys Ala Ser
             100                 105                 110

Arg Gly Asn Asp Arg Asn Arg Ile Val Leu Pro Phe Ser Phe Ala Trp
         115                 120                 125

Pro Arg Ser Tyr Thr Leu Leu Val Glu Ala Trp Asp Ser Ser Asn Asp
     130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                 165                 170                 175

Ala His Phe Glu Tyr Gln Ile Arg Val Thr Cys Asp Asp Tyr Tyr Tyr
             180                 185                 190
```

```
Gly Phe Gly Cys Asn Lys Phe Cys Arg Pro Arg Asp Phe Phe Gly
        195                 200                 205
His Tyr Ala Cys Asp Gln Asn Gly Asn Lys Thr Cys Met Glu Gly Trp
        210                 215                 220
Met Gly Pro Glu Cys Asn Arg Ala Ile Cys Arg Gln Gly Cys Ser Pro
225                 230                 235                 240
Lys His Gly Ser Cys Lys Leu Pro Gly Asp Cys Arg Cys Gln Tyr Gly
                245                 250                 255
Trp Gln Gly Leu Tyr Cys Asp Lys Cys Ile Pro His Pro Gly Cys Val
            260                 265                 270
His Gly Ile Cys Asn Glu Pro Trp Gln Cys Leu Cys Glu Thr Asn Trp
        275                 280                 285
Gly Gly Gln Leu Cys Asp Lys Asp Leu Asn Tyr Cys Gly Thr His Gln
        290                 295                 300
Pro Cys Leu Asn Gly Gly Thr Cys Ser Asn Thr Gly Pro Asp Lys Tyr
305                 310                 315                 320
Gln Cys Ser Cys Pro Glu Gly Tyr Ser Gly Pro Asn Cys Glu Ile Ala
                325                 330                 335
Glu His Ala Cys Leu Ser Asp Pro Cys His Asn Arg Gly Ser Cys Lys
            340                 345                 350
Glu Thr Ser Leu Gly Phe Glu Cys Glu Cys Ser Pro Gly Trp Thr Gly
        355                 360                 365
Pro Thr Cys Ser Thr Asn Ile Asp Asp Cys Ser Pro Asn Asn Cys Ser
        370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
                405                 410                 415
Glu Ala Lys Pro Cys Val Asn Ala Lys Ser Cys Lys Asn Leu Ile Ala
            420                 425                 430
Ser Tyr Tyr Cys Asp Cys Leu Pro Gly Trp Met Gly Gln Asn Cys Asp
        435                 440                 445
Ile Asn Ile Asn Asp Cys Leu Gly Gln Cys Gln Asn Asp Ala Ser Cys
        450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
                485                 490                 495
Leu Asn Gly Gly His Cys Gln Asn Glu Ile Asn Arg Phe Gln Cys Leu
            500                 505                 510
Cys Pro Thr Gly Phe Ser Gly Asn Leu Cys Gln Leu Asp Ile Asp Tyr
        515                 520                 525
Cys Glu Pro Asn Pro Cys Gln Asn Gly Ala Gln Cys Tyr Asn Arg Ala
        530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
                565                 570                 575
Ser Cys Thr Val Ala Met Ala Ser Asn Asp Thr Pro Glu Gly Val Arg
            580                 585                 590
Tyr Ile Ser Ser Asn Val Cys Gly Pro His Gly Lys Cys Lys Ser Gln
        595                 600                 605
Ser Gly Gly Lys Phe Thr Cys Asp Cys Asn Lys Gly Phe Thr Gly Thr
```

```
                610             615             620
Tyr Cys His Glu Asn Ile Asn Asp Cys Glu Ser Asn Pro Cys Arg Asn
625             630             635             640

Gly Gly Thr Cys Ile Asp Gly Val Asn Ser Tyr Lys Cys Ile Cys Ser
            645             650             655

Asp Gly Trp Glu Gly Ala Tyr Cys Glu Thr Asn Ile Asn Asp Cys Ser
        660             665             670

Gln Asn Pro Cys His Asn Gly Thr Cys Arg Asp Leu Val Asn Asp
        675             680             685

Phe Tyr Cys Asp Cys Lys Asn Gly Trp Lys Gly Lys Thr Cys His Ser
690             695             700

Arg Asp Ser Gln Cys Asp Glu Ala Thr Cys Asn Asn Gly Gly Thr Cys
705             710             715             720

Tyr Asp Glu Gly Asp Ala Phe Lys Cys Met Cys Pro Gly Gly Trp Glu
            725             730             735

Gly Thr Thr Cys Asn Ile Ala Arg Asn Ser Ser Cys Leu Pro Asn Pro
            740             745             750

Cys His Asn Gly Gly Thr Cys Val Val Asn Gly Glu Ser Phe Thr Cys
        755             760             765

Val Cys Lys Glu Gly Trp Glu Gly Pro Ile Cys Ala Gln Asn Thr Asn
770             775             780

Asp Cys Ser Pro His Pro Cys Tyr Asn Ser Gly Thr Cys Val Asp Gly
785             790             795             800

Asp Asn Trp Tyr Arg Cys Glu Cys Ala Pro Gly Phe Ala Gly Pro Asp
            805             810             815

Cys Arg Ile Asn Ile Asn Glu Cys Gln Ser Ser Pro Cys Ala Phe Gly
            820             825             830

Ala Thr Cys Val Asp Glu Ile Asn Gly Tyr Arg Cys Val Cys Pro Pro
        835             840             845

Gly His Ser Gly Ala Lys Cys Gln Glu Val Ser Gly Arg Pro Cys Ile
    850             855             860

Thr Met Gly Ser Val Ile Pro Asp Gly Ala Lys Trp Asp Asp Cys
865             870             875             880

Asn Thr Cys Gln Cys Leu Asn Gly Arg Ile Ala Cys Ser Lys Val Trp
            885             890             895

Cys Gly Pro Arg Pro Cys Leu Leu His Lys Gly His Ser Glu Cys Pro
        900             905             910

Ser Gly Gln Ser Cys Ile Pro Ile Leu Asp Asp Gln Cys Phe Val His
        915             920             925

Pro Cys Thr Gly Val Gly Glu Cys Arg Ser Ser Leu Gln Pro Val
    930             935             940

Lys Thr Lys Cys Thr Ser Asp Ser Tyr Tyr Gln Asp Asn Cys Ala Asn
945             950             955             960

Ile Thr Phe Thr Phe Asn Lys Glu Met Met Ser Pro Gly Leu Thr Thr
            965             970             975

Glu His Ile Cys Ser Glu Leu Arg Asn Leu Asn Ile Leu Lys Asn Val
        980             985             990

Ser Ala Glu Tyr Ser Ile Tyr Ile Ala Cys Glu Pro Ser  Pro Ser Ala
        995             1000             1005

Asn Asn  Glu Ile His Val Ala  Ile Ser Ala Glu Asp  Ile Arg Asp
        1010             1015             1020

Asp Gly  Asn Pro Ile Lys Glu  Ile Thr Asp Lys Ile  Ile Asp Leu
        1025             1030             1035
```

```
Val Ser Lys Arg Asp Gly Asn Ser Ser Leu Ile Ala Ala Val Ala
    1040            1045                1050

Glu Val Arg Val Gln Arg Arg Pro Leu Lys Asn Arg Thr Asp Phe
    1055            1060                1065

Leu Val Pro Leu Leu Ser Ser Val Leu Thr Val Ala Trp Ile Cys
    1070            1075                1080

Cys Leu Val Thr Ala Phe Tyr Trp Cys Leu Arg Lys Arg Arg Lys
    1085            1090                1095

Pro Gly Ser His Thr His Ser Ala Ser Glu Asp Asn Thr Thr Asn
    1100            1105                1110

Asn Val Arg Glu Gln Leu Asn Gln Ile Lys Asn Pro Ile Glu Lys
    1115            1120                1125

His Gly Ala Asn Thr Val Pro Ile Lys Asp Tyr Glu Asn Lys Asn
    1130            1135                1140

Ser Lys Met Ser Lys Ile Arg Thr His Asn Ser Glu Val Glu Glu
    1145            1150                1155

Asp Asp Met Asp Lys His Gln Gln Lys Ala Arg Phe Ala Lys Gln
    1160            1165                1170

Pro Ala Tyr Thr Leu Val Asp Arg Glu Glu Lys Pro Pro Asn Gly
    1175            1180                1185

Thr Pro Thr Lys His Pro Asn Trp Thr Asn Lys Gln Asp Asn Arg
    1190            1195                1200

Asp Leu Glu Ser Ala Gln Ser Leu Asn Arg Met Glu Tyr Ile Val
    1205            1210                1215

<210> SEQ ID NO 47
<211> LENGTH: 287
<212> TYPE: PRT
<213> ORGANISM: Homo sapiens

<400> SEQUENCE: 47

Met His Arg Leu Met Gly Val Asn Ser Thr Ala Ala Ala Ala Gly
1               5                   10                  15

Gln Pro Asn Val Ser Cys Thr Cys Asn Cys Lys Arg Ser Leu Phe Gln
            20                  25                  30

Ser Met Glu Ile Thr Glu Leu Glu Phe Val Gln Ile Ile Ile Val
            35                  40                  45

Val Val Met Met Val Met Val Val Ile Thr Cys Leu Leu Ser His
        50                  55                  60

Tyr Lys Leu Ser Ala Arg Ser Phe Ile Ser Arg His Ser Gln Gly Arg
65                  70                  75                  80

Arg Arg Glu Asp Ala Leu Ser Ser Glu Gly Cys Leu Trp Pro Ser Glu
                85                  90                  95

Ser Thr Val Ser Gly Asn Gly Ile Pro Glu Pro Gln Val Tyr Ala Pro
                100                 105                 110

Pro Arg Pro Thr Asp Arg Leu Ala Val Pro Pro Phe Ala Gln Arg Glu
            115                 120                 125

Arg Phe His Arg Phe Gln Pro Thr Tyr Pro Tyr Leu Gln His Glu Ile
            130                 135                 140

Asp Leu Pro Pro Thr Ile Ser Leu Ser Asp Gly Glu Glu Pro Pro Pro
145                 150                 155                 160

Tyr Gln Gly Pro Cys Thr Leu Gln Leu Arg Asp Pro Glu Gln Gln Leu
                165                 170                 175

Glu Leu Asn Arg Glu Ser Val Arg Ala Pro Pro Asn Arg Thr Ile Phe
```

```
                    180                 185                 190
Asp Ser Asp Leu Met Asp Ser Ala Arg Leu Gly Gly Pro Cys Pro Pro
                195                 200                 205

Ser Ser Asn Ser Gly Ile Ser Ala Thr Cys Tyr Gly Ser Gly Gly Arg
            210                 215                 220

Met Glu Gly Pro Pro Thr Tyr Ser Glu Val Ile Gly His Tyr Pro
225                 230                 235                 240

Gly Ser Ser Phe Gln His Gln Gln Ser Ser Gly Pro Pro Ser Leu Leu
                245                 250                 255

Glu Gly Thr Arg Leu His His Thr His Ile Ala Pro Leu Glu Ser Ala
            260                 265                 270

Ala Ile Trp Ser Lys Glu Lys Asp Lys Gln Lys Gly His Pro Leu
            275                 280                 285

<210> SEQ ID NO 48
<211> LENGTH: 710
<212> TYPE: PRT
<213> ORGANISM: Homo sapiens

<400> SEQUENCE: 48

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser Gln
            20                  25                  30

Pro Glu Ala Thr Lys Cys Phe Gln Trp Gln Arg Asn Met Arg Lys Val
            35                  40                  45

Arg Gly Pro Pro Val Ser Cys Ile Lys Arg Asp Ser Pro Ile Gln Cys
        50                  55                  60

Ile Gln Ala Ile Ala Glu Asn Arg Ala Asp Ala Val Thr Leu Asp Gly
65                  70                  75                  80

Gly Phe Ile Tyr Glu Ala Gly Leu Ala Pro Tyr Lys Leu Arg Pro Val
                85                  90                  95

Ala Ala Glu Val Tyr Gly Thr Glu Arg Gln Pro Arg Thr His Tyr Tyr
            100                 105                 110

Ala Val Ala Val Val Lys Lys Gly Gly Ser Phe Gln Leu Asn Glu Leu
            115                 120                 125

Gln Gly Leu Lys Ser Cys His Thr Gly Leu Arg Arg Thr Ala Gly Trp
        130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
            195                 200                 205

Phe Ser Tyr Ser Gly Ala Phe Lys Cys Leu Arg Asp Gly Ala Gly Asp
        210                 215                 220

Val Ala Phe Ile Arg Glu Ser Thr Val Phe Glu Asp Leu Ser Asp Glu
225                 230                 235                 240

Ala Glu Arg Asp Glu Tyr Glu Leu Leu Cys Pro Asp Asn Thr Arg Lys
                245                 250                 255

Pro Val Asp Lys Phe Lys Asp Cys His Leu Ala Arg Val Pro Ser His
            260                 265                 270
```

```
Ala Val Val Ala Arg Ser Val Asn Gly Lys Glu Asp Ala Ile Trp Asn
            275                 280                 285

Leu Leu Arg Gln Ala Gln Glu Lys Phe Gly Lys Asp Lys Ser Pro Lys
        290                 295                 300

Phe Gln Leu Phe Gly Ser Pro Ser Gly Gln Lys Asp Leu Leu Phe Lys
305                 310                 315                 320

Asp Ser Ala Ile Gly Phe Ser Arg Val Pro Pro Arg Ile Asp Ser Gly
                325                 330                 335

Leu Tyr Leu Gly Ser Gly Tyr Phe Thr Ala Ile Gln Asn Leu Arg Lys
            340                 345                 350

Ser Glu Glu Glu Val Ala Ala Arg Arg Ala Arg Val Val Trp Cys Ala
        355                 360                 365

Val Gly Glu Gln Glu Leu Arg Lys Cys Asn Gln Trp Ser Gly Leu Ser
370                 375                 380

Glu Gly Ser Val Thr Cys Ser Ser Ala Ser Thr Thr Glu Asp Cys Ile
385                 390                 395                 400

Ala Leu Val Leu Lys Gly Glu Ala Asp Ala Met Ser Leu Asp Gly Gly
                405                 410                 415

Tyr Val Tyr Thr Ala Gly Lys Cys Gly Leu Val Pro Val Leu Ala Glu
            420                 425                 430

Asn Tyr Lys Ser Gln Gln Ser Ser Asp Pro Asp Pro Asn Cys Val Asp
        435                 440                 445

Arg Pro Val Glu Gly Tyr Leu Ala Val Ala Val Val Arg Arg Ser Asp
        450                 455                 460

Thr Ser Leu Thr Trp Asn Ser Val Lys Gly Lys Lys Ser Cys His Thr
465                 470                 475                 480

Ala Val Asp Arg Thr Ala Gly Trp Asn Ile Pro Met Gly Leu Leu Phe
                485                 490                 495

Asn Gln Thr Gly Ser Cys Lys Phe Asp Glu Tyr Phe Ser Gln Ser Cys
            500                 505                 510

Ala Pro Gly Ser Asp Pro Arg Ser Asn Leu Cys Ala Leu Cys Ile Gly
        515                 520                 525

Asp Glu Gln Gly Glu Asn Lys Cys Val Pro Asn Ser Asn Glu Arg Tyr
        530                 535                 540

Tyr Gly Tyr Thr Gly Ala Phe Arg Cys Leu Ala Glu Asn Ala Gly Asp
545                 550                 555                 560

Val Ala Phe Val Lys Asp Val Thr Val Leu Gln Asn Thr Asp Gly Asn
                565                 570                 575

Asn Asn Glu Ala Trp Ala Lys Asp Leu Lys Leu Ala Asp Phe Ala Leu
            580                 585                 590

Leu Cys Leu Asp Gly Lys Arg Lys Pro Val Thr Glu Ala Arg Ser Cys
        595                 600                 605

His Leu Ala Met Ala Pro Asn His Ala Val Val Ser Arg Met Asp Lys
        610                 615                 620

Val Glu Arg Leu Lys Gln Val Leu Leu His Gln Gln Ala Lys Phe Gly
625                 630                 635                 640

Arg Asn Gly Ser Asp Cys Pro Asp Lys Phe Cys Leu Phe Gln Ser Glu
                645                 650                 655

Thr Lys Asn Leu Leu Phe Asn Asp Asn Thr Glu Cys Leu Ala Arg Leu
            660                 665                 670

His Gly Lys Thr Thr Tyr Glu Lys Tyr Leu Gly Pro Gln Tyr Val Ala
        675                 680                 685

Gly Ile Thr Asn Leu Lys Lys Cys Ser Thr Ser Pro Leu Leu Glu Ala
```

```
                690                 695                 700

Cys Glu Phe Leu Arg Lys
705                 710

<210> SEQ ID NO 49
<211> LENGTH: 78
<212> TYPE: PRT
<213> ORGANISM: Homo sapiens

<400> SEQUENCE: 49

Met Ser Glu Val Leu Pro Tyr Gly Asp Glu Lys Leu Ser Pro Tyr Gly
1               5                   10                  15

Asp Gly Asp Val Gly Gln Ile Phe Ser Cys Arg Leu Gln Asp Thr
            20                  25                  30

Asn Asn Phe Phe Gly Ala Gly Gln Asn Lys Arg Pro Pro Lys Leu Gly
        35                  40                  45

Gln Ile Gly Arg Ser Lys Arg Val Val Ile Glu Asp Asp Arg Ile Asp
    50                  55                  60

Asp Val Leu Lys Asn Met Thr Asp Lys Ala Pro Pro Gly Val
65                  70                  75

<210> SEQ ID NO 50
<211> LENGTH: 527
<212> TYPE: PRT
<213> ORGANISM: Homo sapiens

<400> SEQUENCE: 50

Met Glu Asn Gln Glu Lys Ala Ser Ile Ala Gly His Met Phe Asp Val
1               5                   10                  15

Val Val Ile Gly Gly Gly Ile Ser Gly Leu Ser Ala Ala Lys Leu Leu
            20                  25                  30

Thr Glu Tyr Gly Val Ser Val Leu Val Leu Glu Ala Arg Asp Arg Val
        35                  40                  45

Gly Gly Arg Thr Tyr Thr Ile Arg Asn Glu His Val Asp Tyr Val Asp
    50                  55                  60

Val Gly Gly Ala Tyr Val Gly Pro Thr Gln Asn Arg Ile Leu Arg Leu
65                  70                  75                  80

Ser Lys Glu Leu Gly Ile Glu Thr Tyr Lys Val Asn Val Ser Glu Arg
            85                  90                  95

Leu Val Gln Tyr Val Lys Gly Lys Thr Tyr Pro Phe Arg Gly Ala Phe
        100                 105                 110

Pro Pro Val Trp Asn Pro Ile Ala Tyr Leu Asp Tyr Asn Asn Leu Trp
    115                 120                 125

Arg Thr Ile Asp Asn Met Gly Lys Glu Ile Pro Thr Asp Ala Pro Trp
130                 135                 140

Glu Ala Gln His Ala Asp Lys Trp Asp Lys Met Thr Met Lys Glu Leu
145                 150                 155                 160

Ile Asp Lys Ile Cys Trp Thr Lys Thr Ala Arg Arg Phe Ala Tyr Leu
            165                 170                 175

Phe Val Asn Ile Asn Val Thr Ser Glu Pro His Glu Val Ser Ala Leu
        180                 185                 190

Trp Phe Leu Trp Tyr Val Lys Gln Cys Gly Gly Thr Thr Arg Ile Phe
    195                 200                 205

Ser Val Thr Asn Gly Gly Gln Glu Arg Lys Phe Val Gly Gly Ser Gly
210                 215                 220

Gln Val Ser Glu Arg Ile Met Asp Leu Leu Gly Asp Gln Val Lys Leu
```

```
                    225                 230                 235                 240

Asn His Pro Val Thr His Val Asp Gln Ser Ser Asp Asn Ile Ile Ile
                245                 250                 255

Glu Thr Leu Asn His Glu His Tyr Glu Cys Lys Tyr Val Ile Asn Ala
            260                 265                 270

Ile Pro Pro Thr Leu Thr Ala Lys Ile His Phe Arg Pro Glu Leu Pro
        275                 280                 285

Ala Glu Arg Asn Gln Leu Ile Gln Arg Leu Pro Met Gly Ala Val Ile
    290                 295                 300

Lys Cys Met Met Tyr Tyr Lys Glu Ala Phe Trp Lys Lys Asp Tyr
305                 310                 315                 320

Cys Gly Cys Met Ile Ile Glu Asp Glu Asp Ala Pro Ile Ser Ile Thr
                325                 330                 335

Leu Asp Asp Thr Lys Pro Asp Gly Ser Leu Pro Ala Ile Met Gly Phe
            340                 345                 350

Ile Leu Ala Arg Lys Ala Asp Arg Leu Ala Lys Leu His Lys Glu Ile
        355                 360                 365

Arg Lys Lys Lys Ile Cys Glu Leu Tyr Ala Lys Val Leu Gly Ser Gln
    370                 375                 380

Glu Ala Leu His Pro Val His Tyr Glu Glu Lys Asn Trp Cys Glu
385                 390                 395                 400

Gln Tyr Ser Gly Gly Cys Tyr Thr Ala Tyr Phe Pro Pro Gly Ile Met
                405                 410                 415

Thr Gln Tyr Gly Arg Val Ile Arg Gln Pro Val Gly Arg Ile Phe Phe
            420                 425                 430

Ala Gly Thr Glu Thr Ala Thr Lys Trp Ser Gly Tyr Met Glu Gly Ala
        435                 440                 445

Val Glu Ala Gly Glu Arg Ala Ala Arg Glu Val Leu Asn Gly Leu Gly
    450                 455                 460

Lys Val Thr Glu Lys Asp Ile Trp Val Gln Glu Pro Glu Ser Lys Asp
465                 470                 475                 480

Val Pro Ala Val Glu Ile Thr His Thr Phe Trp Glu Arg Asn Leu Pro
                485                 490                 495

Ser Val Ser Gly Leu Leu Lys Ile Ile Gly Phe Ser Thr Ser Val Thr
            500                 505                 510

Ala Leu Gly Phe Val Leu Tyr Lys Tyr Lys Leu Leu Pro Arg Ser
        515                 520                 525

<210> SEQ ID NO 51
<211> LENGTH: 1466
<212> TYPE: PRT
<213> ORGANISM: Homo sapiens

<400> SEQUENCE: 51

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
                20                  25                  30

Ser His Leu Gly Gln Ser Tyr Ala Asp Arg Asp Val Trp Lys Pro Glu
            35                  40                  45

Pro Cys Gln Ile Cys Val Cys Asp Ser Gly Ser Val Leu Cys Asp Asp
        50                  55                  60

Ile Ile Cys Asp Asp Gln Glu Leu Asp Cys Pro Asn Pro Glu Ile Pro
65                  70                  75                  80
```

-continued

```
Phe Gly Glu Cys Cys Ala Val Cys Pro Gln Pro Thr Ala Pro Thr
                 85                  90                  95
Arg Pro Pro Asn Gly Gln Gly Pro Gln Gly Pro Lys Gly Asp Pro Gly
             100                 105                 110
Pro Pro Gly Ile Pro Gly Arg Asn Gly Asp Pro Gly Ile Pro Gly Gln
             115                 120                 125
Pro Gly Ser Pro Gly Ser Pro Gly Pro Pro Gly Ile Cys Glu Ser Cys
             130                 135                 140
Pro Thr Gly Pro Gln Asn Tyr Ser Pro Gln Tyr Asp Ser Tyr Asp Val
145                 150                 155                 160
Lys Ser Gly Val Ala Val Gly Gly Leu Ala Gly Tyr Pro Gly Pro Ala
                 165                 170                 175
Gly Pro Pro Gly Pro Pro Gly Pro Pro Gly Thr Ser Gly His Pro Gly
             180                 185                 190
Ser Pro Gly Ser Pro Gly Tyr Gln Gly Pro Pro Gly Glu Pro Gly Gln
             195                 200                 205
Ala Gly Pro Ser Gly Pro Pro Gly Pro Pro Gly Ala Ile Gly Pro Ser
             210                 215                 220
Gly Pro Ala Gly Lys Asp Gly Glu Ser Gly Arg Pro Gly Arg Pro Gly
225                 230                 235                 240
Glu Arg Gly Leu Pro Gly Pro Pro Gly Ile Lys Gly Pro Ala Gly Ile
                 245                 250                 255
Pro Gly Phe Pro Gly Met Lys Gly His Arg Gly Phe Asp Gly Arg Asn
             260                 265                 270
Gly Glu Lys Gly Glu Thr Gly Ala Pro Gly Leu Lys Gly Glu Asn Gly
             275                 280                 285
Leu Pro Gly Glu Asn Gly Ala Pro Gly Pro Met Gly Pro Arg Gly Ala
290                 295                 300
Pro Gly Glu Arg Gly Arg Pro Gly Leu Pro Gly Ala Ala Gly Ala Arg
305                 310                 315                 320
Gly Asn Asp Gly Ala Arg Gly Ser Asp Gly Gln Pro Gly Pro Pro Gly
                 325                 330                 335
Pro Pro Gly Thr Ala Gly Phe Pro Gly Ser Pro Gly Ala Lys Gly Glu
             340                 345                 350
Val Gly Pro Ala Gly Ser Pro Gly Ser Asn Gly Ala Pro Gly Gln Arg
             355                 360                 365
Gly Glu Pro Gly Pro Gln Gly His Ala Gly Ala Gln Gly Pro Pro Gly
             370                 375                 380
Pro Pro Gly Ile Asn Gly Ser Pro Gly Gly Lys Gly Glu Met Gly Pro
385                 390                 395                 400
Ala Gly Ile Pro Gly Ala Pro Gly Leu Met Gly Ala Arg Gly Pro Pro
                 405                 410                 415
Gly Pro Ala Gly Ala Asn Gly Ala Pro Gly Leu Arg Gly Gly Ala Gly
             420                 425                 430
Glu Pro Gly Lys Asn Gly Ala Lys Gly Glu Pro Gly Pro Arg Gly Glu
             435                 440                 445
Arg Gly Glu Ala Gly Ile Pro Gly Val Pro Gly Ala Lys Gly Glu Asp
             450                 455                 460
Gly Lys Asp Gly Ser Pro Gly Glu Pro Gly Ala Asn Gly Leu Pro Gly
465                 470                 475                 480
Ala Ala Gly Glu Arg Gly Ala Pro Gly Phe Arg Gly Pro Ala Gly Pro
                 485                 490                 495
Asn Gly Ile Pro Gly Glu Lys Gly Pro Ala Gly Glu Arg Gly Ala Pro
```

```
            500                 505                 510
Gly Pro Ala Gly Pro Arg Gly Ala Gly Glu Pro Gly Arg Asp Gly
            515                 520                 525
Val Pro Gly Gly Pro Gly Met Arg Gly Met Pro Gly Ser Pro Gly
            530                 535                 540
Pro Gly Ser Asp Gly Lys Pro Gly Pro Gly Ser Gln Gly Glu Ser
545                 550                 555                 560
Gly Arg Pro Gly Pro Pro Gly Ser Gly Pro Arg Gly Gln Pro Gly
                    565                 570                 575
Val Met Gly Phe Pro Gly Pro Lys Gly Asn Asp Gly Ala Pro Gly Lys
            580                 585                 590
Asn Gly Glu Arg Gly Gly Pro Gly Gly Pro Gly Pro Gln Gly Pro Pro
            595                 600                 605
Gly Lys Asn Gly Glu Thr Gly Pro Gln Gly Pro Pro Gly Pro Thr Gly
            610                 615                 620
Pro Gly Gly Asp Lys Gly Asp Thr Gly Pro Pro Gly Pro Gln Gly Leu
625                 630                 635                 640
Gln Gly Leu Pro Gly Thr Gly Gly Pro Pro Gly Glu Asn Gly Lys Pro
                    645                 650                 655
Gly Glu Pro Gly Pro Lys Gly Asp Ala Gly Ala Pro Gly Ala Pro Gly
                    660                 665                 670
Gly Lys Gly Asp Ala Gly Ala Pro Gly Glu Arg Gly Pro Pro Gly Leu
            675                 680                 685
Ala Gly Ala Pro Gly Leu Arg Gly Gly Ala Gly Pro Pro Gly Pro Glu
            690                 695                 700
Gly Gly Lys Gly Ala Ala Gly Pro Pro Gly Pro Pro Gly Ala Ala Gly
705                 710                 715                 720
Thr Pro Gly Leu Gln Gly Met Pro Gly Glu Arg Gly Gly Leu Gly Ser
                    725                 730                 735
Pro Gly Pro Lys Gly Asp Lys Gly Glu Pro Gly Gly Pro Gly Ala Asp
                    740                 745                 750
Gly Val Pro Gly Lys Asp Gly Pro Arg Gly Pro Thr Gly Pro Ile Gly
            755                 760                 765
Pro Pro Gly Pro Ala Gly Gln Pro Gly Asp Lys Gly Glu Gly Gly Ala
            770                 775                 780
Pro Gly Leu Pro Gly Ile Ala Gly Pro Arg Gly Ser Pro Gly Glu Arg
785                 790                 795                 800
Gly Glu Thr Gly Pro Pro Gly Pro Ala Gly Phe Pro Gly Ala Pro Gly
                    805                 810                 815
Gln Asn Gly Glu Pro Gly Gly Lys Gly Glu Arg Gly Ala Pro Gly Glu
                    820                 825                 830
Lys Gly Glu Gly Gly Pro Pro Gly Val Ala Gly Pro Pro Gly Gly Ser
            835                 840                 845
Gly Pro Ala Gly Pro Pro Gly Pro Gln Gly Val Lys Gly Glu Arg Gly
            850                 855                 860
Ser Pro Gly Gly Pro Gly Ala Ala Gly Phe Pro Gly Ala Arg Gly Leu
865                 870                 875                 880
Pro Gly Pro Pro Gly Ser Asn Gly Asn Pro Gly Pro Pro Gly Pro Ser
                    885                 890                 895
Gly Ser Pro Gly Lys Asp Gly Pro Pro Gly Pro Ala Gly Asn Thr Gly
                    900                 905                 910
Ala Pro Gly Ser Pro Gly Val Ser Gly Pro Lys Gly Asp Ala Gly Gln
            915                 920                 925
```

```
Pro Gly Glu Lys Gly Ser Pro Gly Ala Gln Gly Pro Pro Gly Ala Pro
    930                 935                 940
Gly Pro Leu Gly Ile Ala Gly Ile Thr Gly Ala Arg Gly Leu Ala Gly
945                 950                 955                 960
Pro Pro Gly Met Pro Gly Pro Arg Gly Ser Pro Gly Pro Gln Gly Val
            965                 970                 975
Lys Gly Glu Ser Gly Lys Pro Gly Ala Asn Gly Leu Ser Gly Glu Arg
            980                 985                 990
Gly Pro Pro Gly Pro Gln Gly Leu Pro Gly Leu Ala Gly Thr Ala Gly
        995                 1000                1005
Glu Pro Gly Arg Asp Gly Asn Pro Gly Ser Asp Gly Leu Pro Gly
    1010                1015                1020
Arg Asp Gly Ser Pro Gly Gly Lys Gly Asp Arg Gly Glu Asn Gly
    1025                1030                1035
Ser Pro Gly Ala Pro Gly Ala Pro Gly His Pro Gly Pro Pro Gly
    1040                1045                1050
Pro Val Gly Pro Ala Gly Lys Ser Gly Asp Arg Gly Glu Ser Gly
    1055                1060                1065
Pro Ala Gly Pro Ala Gly Ala Pro Gly Pro Ala Gly Ser Arg Gly
    1070                1075                1080
Ala Pro Gly Pro Gln Gly Pro Arg Gly Asp Lys Gly Glu Thr Gly
    1085                1090                1095
Glu Arg Gly Ala Ala Gly Ile Lys Gly His Arg Gly Phe Pro Gly
    1100                1105                1110
Asn Pro Gly Ala Pro Gly Ser Pro Gly Pro Ala Gly Gln Gln Gly
    1115                1120                1125
Ala Ile Gly Ser Pro Gly Pro Ala Gly Pro Arg Gly Pro Val Gly
    1130                1135                1140
Pro Ser Gly Pro Pro Gly Lys Asp Gly Thr Ser Gly His Pro Gly
    1145                1150                1155
Pro Ile Gly Pro Pro Gly Pro Arg Gly Asn Arg Gly Glu Arg Gly
    1160                1165                1170
Ser Glu Gly Ser Pro Gly His Pro Gly Gln Pro Gly Pro Pro Gly
    1175                1180                1185
Pro Pro Gly Ala Pro Gly Pro Cys Cys Gly Gly Val Gly Ala Ala
    1190                1195                1200
Ala Ile Ala Gly Ile Gly Gly Glu Lys Ala Gly Gly Phe Ala Pro
    1205                1210                1215
Tyr Tyr Gly Asp Glu Pro Met Asp Phe Lys Ile Asn Thr Asp Glu
    1220                1225                1230
Ile Met Thr Ser Leu Lys Ser Val Asn Gly Gln Ile Glu Ser Leu
    1235                1240                1245
Ile Ser Pro Asp Gly Ser Arg Lys Asn Pro Ala Arg Asn Cys Arg
    1250                1255                1260
Asp Leu Lys Phe Cys His Pro Glu Leu Lys Ser Gly Glu Tyr Trp
    1265                1270                1275
Val Asp Pro Asn Gln Gly Cys Lys Leu Asp Ala Ile Lys Val Phe
    1280                1285                1290
Cys Asn Met Glu Thr Gly Glu Thr Cys Ile Ser Ala Asn Pro Leu
    1295                1300                1305
Asn Val Pro Arg Lys His Trp Trp Thr Asp Ser Ser Ala Glu Lys
    1310                1315                1320
```

-continued

```
Lys His Val Trp Phe Gly Glu Ser Met Asp Gly Gly Phe Gln Phe
    1325                1330            1335

Ser Tyr Gly Asn Pro Glu Leu Pro Glu Asp Val Leu Asp Val Gln
    1340                1345            1350

Leu Ala Phe Leu Arg Leu Leu Ser Ser Arg Ala Ser Gln Asn Ile
    1355                1360            1365

Thr Tyr His Cys Lys Asn Ser Ile Ala Tyr Met Asp Gln Ala Ser
    1370                1375            1380

Gly Asn Val Lys Lys Ala Leu Lys Leu Met Gly Ser Asn Glu Gly
    1385                1390            1395

Glu Phe Lys Ala Glu Gly Asn Ser Lys Phe Thr Tyr Thr Val Leu
    1400                1405            1410

Glu Asp Gly Cys Thr Lys His Thr Gly Glu Trp Ser Lys Thr Val
    1415                1420            1425

Phe Glu Tyr Arg Thr Arg Lys Ala Val Arg Leu Pro Ile Val Asp
    1430                1435            1440

Ile Ala Pro Tyr Asp Ile Gly Gly Pro Asp Gln Glu Phe Gly Val
    1445                1450            1455

Asp Val Gly Pro Val Cys Phe Leu
    1460                1465
```

PROSTATE CANCER GENE EXPRESSION PROFILES

CROSS REFERENCE TO RELATED APPLICATIONS

This patent application is a U.S. National Stage Application of PCT/US2013/053836 filed 6 Aug. 2013, which claims priority to U.S. Provisional Application Ser. No. 61/680,633 filed 7 Aug. 2012, which provisional application is herein incorporated by reference in its entirety.

GOVERNMENT INTEREST

This invention was made with government support under contract number HU0001-10-2-0002 awarded by the Uniformed Services University. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 5, 2013, is named HMJ-136-PCT-_SL.txt and is 241,807 bytes in size.

BACKGROUND

Prostate cancer (CaP) is the most common malignancy and the second leading cause of cancer deaths in American men. The current clinical methods used for the detection of CaP are the serum prostate specific antigen (PSA) test, and the digital rectal examination (DRE) followed by biopsy, which is the gold standard for prostate cancer diagnosis. The PSA test was introduced into clinical practice two decades ago and has led to the detection of CaP at a potentially curable stage. Despite the high sensitivity of the PSA test (about 94%), a significant limitation is the very low specificity (about 20%), which is due to the fact that PSA is not a cancer-specific marker [1]. As a result, the clinical use of the PSA test has sparked controversy over the increased incidence in CaP observed in the U.S., which has led to the "over-diagnosis" and "overtreatment" of CaP [2]. A PSA level greater than/or equal to 4.0 ng/ml represents a clinical decision limit that prompts diagnostic biopsy testing [2]. However, a subset of patients with PSA levels below 4.0 ng/ml may have or will develop CaP, and a large portion (65-75%) with greater than 4.0 ng/ml may have a noncancerous prostate-related disorder [3,4]. To increase the detection sensitivity of CaP, the PSA test is used along with the DRE; however, even when used together, the specificity of the screening procedure remains low, leading to unnecessary diagnostic biopsies (65-75% of all biopsies). The prostate biopsy, which can be painful, stressful and lead to infection, is the primary method used for the diagnostic confirmation of CaP [5]. Recently a urine based PCA3 gene expression assay entered clinical practice, which displays specificity higher than serum PSA, but suffers from low sensitivity.

Therefore, developing better biomarkers will be useful in the clinical practice and reduce the number of unnecessary biopsies. New and improved diagnostic tools and methods are needed to enhance the sensitivity and specificity of current methods for the non-invasive detection of cancers in biological samples.

SUMMARY

The present disclosure provides gene expression profiles that are associated with prostate cancer. The gene expression profiles can be used to detect prostate cancer cells in a sample or to prognose the severity or stage of prostate cancer in a subject, such as distinguishing between well differentiated (WD) prostate cancer and poorly differentiated (PD) prostate cancer. The gene expression profiles can be measured at either the nucleic acid or protein level.

In a related aspect, the disclosure provides an array comprising oligonucleotide probes for detecting the gene expression profile associated with WD and/or PD prostate cancer. In one embodiment, the array comprises (a) a substrate and (b) a plurality of polynucleotide probes immobilized on the substrate for detecting the expression of at least 3 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1. The polynucleotide probes are preferably arranged on the substrate within addressable elements to facilitate detection. Preferably, the array comprises a limited number of addressable elements so as to distinguish the array from a more comprehensive array, such as a genomic array or the like. Thus, in one embodiment, the array comprises 500 or fewer addressable elements. In another embodiment, the array comprises no more than 250, 100, 50, or 25 addressable elements. In another embodiment, no more than 1000 polynucleotide probes are immobilized on the array. In another aspect, the disclosure provides methods of using the arrays described herein to detect or prognose prostate cancer in a biological sample.

In one embodiment, the array comprises a plurality of polynucleotide probes for detecting the expression of at least the following human genes: ERG, CLDN8, CACNA1D, HOXC6, TMEFF2, NPY, and HPGD. In another embodiment, the array comprises a plurality of polynucleotide probes for detecting the expression of at least the following human genes: ERG, CLDN8, CACNA1D, HOXC6, TMEFF2, NPY, and HPGD and at least one of the following human genes: BICD1, OR51E1, OR51E2, FOLH1, and SPARC. In another embodiment, the array comprises a plurality of polynucleotide probes for detecting the expression of at least the following human genes: ERG, CLDN8, CACNA1D, HOXC6, TMEFF2, NPY, HPGD, BICD1, OR51E1, OR51E2, FOLH1, and SPARC. In yet another embodiment, the array comprises a plurality of polynucleotide probes for detecting the expression of at least the following human genes: ERG, CLDN8, CACNA1D, HOXC6, TMEFF2, NPY, HPGD, BICD1, OR51E1, OR51E2, FOLH1, SPARC, and at least one of the following human genes: PLA2G7, MYO6, CRISP3, TWIST1, and JAG1. In yet another embodiment, the array comprises a plurality of polynucleotide probes for detecting the expression of at least the following human genes: ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, and JAG1. Alternatively, the array comprises a plurality of ligands (e.g., antibodies) that specifically bind to the proteins encoded by the genes noted in this paragraph.

In one embodiment, the array comprises a plurality of polynucleotide probes for detecting the expression of at least the following human genes: ERG, AMACR, CLDN8, TMEFF2, NPY, and HPGD. In another embodiment, the array comprises a plurality of polynucleotide probes for detecting the expression of at least the following human genes: ERG, OR51E1, PCGEM1, PMEPA1, and LTF. In yet another embodiment, the array comprises a plurality of polynucleotide probes for detecting the expression of at least the following human genes: CAMK2N1, MAOA, COL3A1, HPGD, and SPARC. Alternatively, the array comprises a plurality of ligands (e.g., antibodies) that specifically bind to the proteins encoded by the genes noted in this paragraph.

Also provided is a method of detecting prostate cancer in a biological sample obtained from a subject, wherein the biological sample comprises prostate cells or prostate tissue, the method comprising (a) measuring the expression level of at least 3, 5, 7, or 12 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1 in the biological sample to obtain a gene expression profile; and (b) comparing the gene expression profile in the biological sample to a control sample, where increased (for all genes except PMEPA1 or LTF) or decreased (for PMEPA1 and LTF) expression of at least one of the genes in the biological sample as compared to the control sample indicates the presence of prostate cancer in the subject. The preferred gene expression profiles are discussed throughout the application. In one embodiment, the increased or decreased expression of at least one of the genes in the biological sample comprises at least a 2.5 fold increase or decrease (for PMEPA1 or LTF) in expression relative to a control sample. In another embodiment, the control sample comprises normal prostate tissue or normal prostate cells obtained from the subject. In yet another embodiment, the biological sample comprises prostate tissue, blood, serum, plasma, urine, saliva, or prostatic fluid. In one embodiment, the method comprises a further step of obtaining the biological sample from a subject. The gene expression profiles can be measured at either the nucleic acid or protein level.

The gene expression profiles can also be used to evaluate the severity or stage of prostate cancer or to assess the effectiveness of a therapy or monitor the progression or regression of prostate cancer following therapy (e.g., disease-free recurrence following surgery). Thus, in a related aspect, the disclosure provides a method of prognosing prostate cancer in a subject, the method comprising (a) measuring the expression level of at least 3, 5, 7, or 12 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1 in a biological sample obtained from the subject to obtain a gene expression profile, wherein the biological sample comprises prostate cells or prostate tissue; and (b) comparing the gene expression profile in the biological sample to a control sample, where increased (for all genes except PMEPA1 or LTF) or decreased (for PMEPA1 or LTF) expression of at least one of the genes in the biological sample as compared to the control sample indicates the presence of either well differentiated (WD) or poorly differentiated (PD) prostate cancer in the subject. For example, a minimum gene expression profile to detect WD prostate cancer comprises 1) ERG, CLDN8, and CACNA1D, or 2) ERG, CLDN8, and AMACR, whereas a minimum gene expression profile to detect PD prostate cancer comprises 1) CLDN8, HOXC6, TMEFF2, NPY, and HPGD or 2) AMACR, CLDN8, TMEFF2, NPY, and HPGD. In one embodiment, the increased or decreased expression of at least one of the genes in the biological sample comprises at least a 2.5 fold increase or decrease (for PMEPA1 or LTF) in expression relative to a control sample. In another embodiment, the control sample comprises normal prostate tissue or normal prostate cells obtained from the subject. In yet another embodiment, the biological sample comprises prostate tissue, blood, serum, plasma, urine, saliva, or prostatic fluid. In one embodiment, the method comprises a further step of obtaining the biological sample from a subject. The gene expression profiles can be measured at either the nucleic acid or protein level.

In another embodiment, the disclosure provides a method of detecting the expression of a combination of genes that are associated with prostate cancer, the method comprising (a) measuring the expression level of at least 3, 5, 7, or 12 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1 in a biological sample to obtain a gene expression profile. The preferred gene expression profiles are discussed throughout the application. Such methods typically comprise a further step of comparing the gene expression profile in the biological sample to a control sample. In one embodiment, the control sample comprises normal prostate tissue or normal prostate cells obtained from a subject. In yet another embodiment, the biological sample comprises prostate tissue, blood, serum, plasma, urine, saliva, or prostatic fluid. In one embodiment, the method comprises a further step of obtaining the biological sample from a subject. The gene expression profiles can be measured at either the nucleic acid or protein level.

The disclosure further provides kits for detecting the expression of a plurality of nucleic acids or proteins that serve as prostate cancer markers. In some embodiments, the kit comprises a plurality of polynucleotide probes, such as the probes described elsewhere in the disclosure, for detecting the expression of at least 3-15 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1. In other embodiments, the kit comprises a plurality of polynucleotide primer pairs for amplifying a portion of the mRNA transcripts of at least 3-15 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1. Alternatively, the kit comprises a plurality of antibodies for detecting the expression of at least 3-15 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1. The preferred gene expression profiles are discussed throughout the application.

Additional objects will be set forth in part in practice of the embodiments described in this application. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate certain embodiments, and together with the written description, serve to explain certain principles of the constructs and methods disclosed herein.

Figure 1:
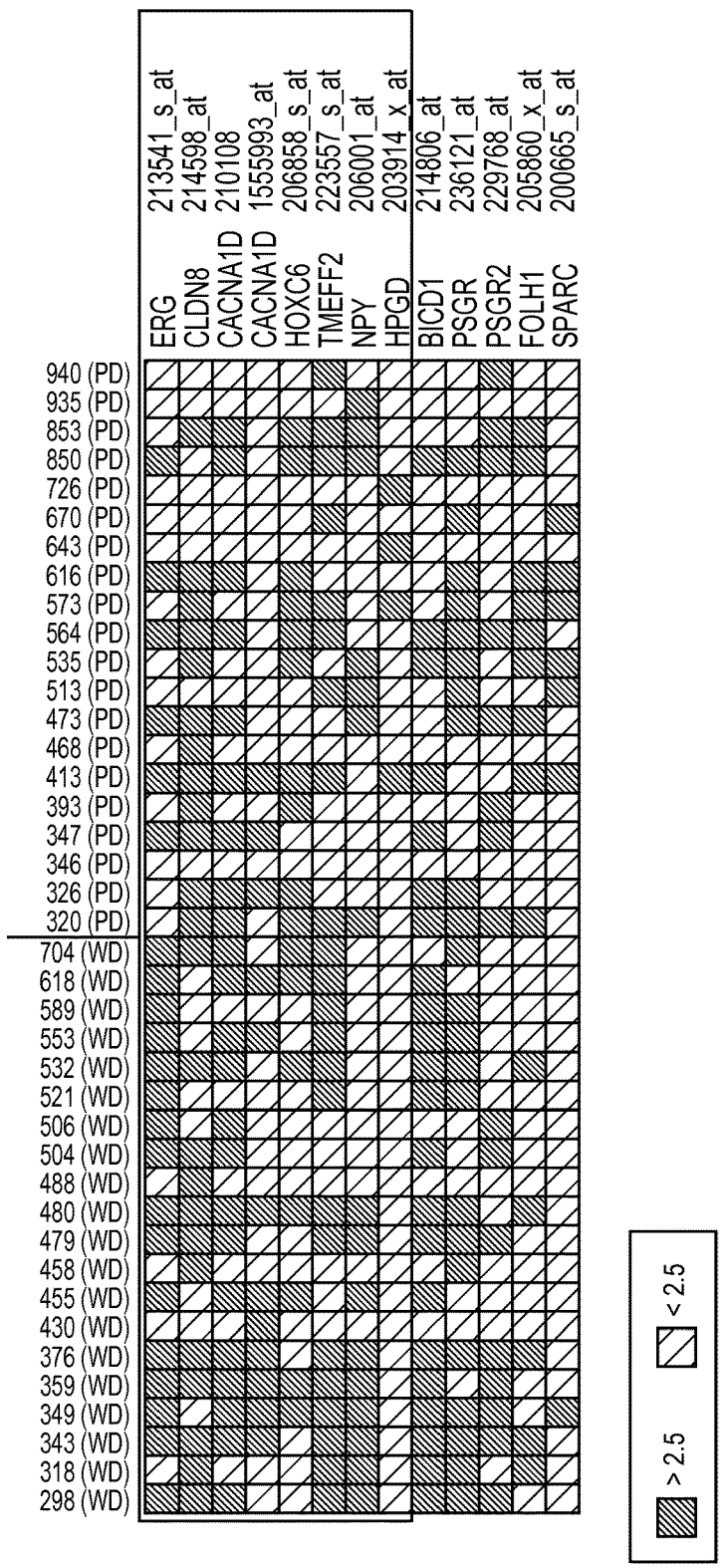
FIG. 1 shows a heatmap of a 12-gene panel in the 40-patient cohort. The first seven genes listed represent a minimum 7-gene panel (ERG, CLDN8, CACNA1D, HOXC6, TMEFF2, NPY, and HPGD). Shaded boxes indicate an increased expression of at least 2.5 fold relative to a control sample.

Processor(s) 110 may further communicate via a network interface 108, which in turn may communicate via the one or more networks 104, such as the Internet or other public or private networks, such that a query or other request may be received from client 102, or other device or service. Additionally, processor(s) 110 may utilize network interface 108 to send information, instructions, workflows query partial workflows, or other data to a user via the one or more networks 104. Network interface 104 may include or be communicatively coupled to one or more servers. Client 102 may be, e.g., a personal computer coupled to the internet.

Processor(s) 110 may, in general, be programmed or configured to execute control logic and control operations to implement methods disclosed herein. Processors 110 may be further communicatively coupled (i.e., coupled by way of a communication channel) to co-processors 114. Co-processors 114 can be dedicated hardware and/or firmware components configured to execute the methods disclosed herein. Thus, the methods disclosed herein can be executed by processor 110 and/or co-processors 114.

Other configurations of computer system 106, associated network connections, and other hardware, software, and service resources are possible.

DETAILED DESCRIPTION

It is to be understood that the following detailed description is provided to give the reader a fuller understanding of certain embodiments, features, and details of aspects of the invention, and should not be interpreted as a limitation of the scope of the invention.

Definitions

In order that the present invention may be more readily understood, certain terms are first defined. Additional definitions are set forth throughout the detailed description.

The term "gene expression profile" refers to the expression levels of a plurality of genes in a sample. As is understood in the art, the expression level of a gene can be analyzed by measuring the expression of a nucleic acid (e.g., mRNA) or a polypeptide that is encoded by the nucleic acid.

The term "isolated," when used in the context of a polypeptide or nucleic acid refers to a polypeptide or nucleic acid that is substantially free of its natural environment and is thus distinguishable from a polypeptide or nucleic acid that might happen to occur naturally. For instance, an isolated polypeptide or nucleic acid is substantially free of cellular material or other polypeptides or nucleic acids from the cell or tissue source from which it was derived.

The terms "polypeptide," "peptide," and "protein" are used interchangeably herein to refer to polymers of amino acids.

The term "primer" means a polynucleotide capable of binding to a region of a target nucleic acid, or its complement, and promoting nucleic acid amplification of the target nucleic acid. Generally, a primer will have a free 3' end that can be extended by a nucleic acid polymerase. Primers also generally include a base sequence capable of hybridizing via complementary base interactions either directly with at least one strand of the target nucleic acid or with a strand that is complementary to the target sequence. A primer may comprise target-specific sequences and optionally other sequences that are non-complementary to the target sequence. These non-complementary sequences may comprise, for example, a promoter sequence or a restriction endonuclease recognition site.

The term "detecting" or "detection" means any of a variety of methods known in the art for determining the presence or amount of a nucleic acid or a protein. As used throughout the specification, the term "detecting" or "detection" includes either qualitative or quantitative detection.

The term "antibody" refers to an immunoglobulin or fragment thereof, and encompasses any polypeptide comprising an antigen-binding fragment or an antigen-binding domain. The term includes but is not limited to polyclonal, monoclonal, monospecific, polyspecific, humanized, human, single-chain, chimeric, synthetic, recombinant, hybrid, mutated, grafted, and in vitro generated antibodies. Unless preceded by the word "intact", the term "antibody" includes antibody fragments such as Fab, F(ab')$_2$, Fv, scFv, Fd, dAb, and other antibody fragments that retain antigen-binding function. Unless otherwise specified, an antibody is not necessarily from any particular source, nor is it produced by any particular method.

The present disclosure provides gene expression profiles and methods of obtaining the same, as well as methods of using those gene expression profiles for detecting prostate cancer or analyzing the severity of prostate cancer in a subject (e.g., distinguishing between a well differentiated prostate tumor (WD) or a poorly differentiated prostate tumor (PD)), where the gene expression profile represents the expression of a combination of two or more of the following human genes: AMACR, ERG, CLDN8, CACNA1D, HOXC6, TMEFF2, NPY, HPGD, BICD1, OR51E1 (PSGR), OR51E2 (PSGR2), FOLH1, SPARC, PLA2G7, MYO6, CRISP3, TWIST1, JAG1, PCGEM1, PMEPA1, LTF, CAMK2N1, MAOA, and COL3A1. As used herein, the expression of a gene refers to the expression of a nucleic acid (e.g., mRNA) or a protein encoded by the nucleic acid.

The methods of detecting the expression of certain combinations of specific genes can also be used for other purposes, such as to assess the effectiveness of treatment or to monitor the progression or regression of prostate cancer, including, for example, monitoring disease-free recurrence following prostatectomy. In the context of such uses, the method can be applied to different samples (e.g., a first and second sample) taken from the same patient at different points in time and the results compared, wherein a change in the gene expression profile can be used to determine whether the cancer has progressed or regressed or to assess the effectiveness of a given treatment.

The gene expression profiles were selected on the basis of the complementary power of the member genes for prostate cancer detection in a wide range of subjects, covering both WD and PD tumor types. In one embodiment, the gene expression profile is associated with WD prostate cancer and includes the following 3 human genes: ERG, CLDN8, and CACNA1D or ERG, CLDN8, and AMACR. In another embodiment, the gene expression profile is specific for PD prostate cancer and includes the following 5 human genes: CLDN8, HOXC6, TMEFF2, NPY, and HPGD or AMACR, CLDN8, TMEFF2, NPY, and HPGD. In another embodiment, the gene expression profile is specific for PD prostate cancer and includes the following human genes: MAOA, COL3A1, CAMK2N1, SPARC, and HPGD. In another embodiment, the gene expression profile includes the following 6 human genes, AMACR, ERG, CLDN8, TMEFF2, NPY and HPGD. In another embodiment, the gene expression profile includes the following 5 human genes: ERG, OR51E1 (PSGR), PCGEM1, PMEPA1, and LTF. In another embodiment, the gene expression profile includes the following 7 human genes: ERG, CACNA1D, CLDN8, HOXC6, TMEFF2, NPY and HPGD with or without one of the following human genes: BICD1, OR51E1 (PSGR), OR51E2 (PSGR2), FOLH1 and SPARC. In yet another embodiment, the gene expression profile includes the following 12 human genes: ERG, CACNA1D, CLDN8, HOXC6, TMEFF2, NPY, HPGD, BICD1, OR51E1 (PSGR), OR51E2 (PSGR2), FOLH1 and SPARC. The gene expression profiles listed above can also include one or more of the following human genes: PLA2G7, MYO6, CRISP3, TWIST1, and JAG1, which are preferentially overexpressed in PD prostate cancer.

AMACR.

One of the genes that can be analyzed in the gene expression profile is alpha-methylacyl-CoA racemase (AMACR). The Hugo Gene Nomenclature Committee (HGNC) has assigned AMACR the unique identifier code: HGNC:451. The AMACR gene encodes a racemase. The encoded enzyme interconverts pristanoyl-CoA and C27-bile acylCoAs between their (R)- and (S)-stereoisomers. The conversion to the (S)-stereoisomers is necessary for degradation of these substrates by peroxisomal beta-oxidation. Significant overexpression of AMACR has been identified in prostate cancer [6]. As reported herein, AMACR is one of the top genes overexpressed in prostate cancer in both WD and PD tumors. The NCBI Reference Sequence for AMACR is NM_014324 (version NM 014324.5), GI:266456114, represented by SEQ ID NO:1 (mRNA) and SEQ ID NO:27 (protein), which sequences are hereby incorporated by reference.

ERG.

Another gene that can be analyzed in the gene expression profile is Ets-related gene (ERG). The HGNC has assigned ERG the unique identifier code: HGNC:3446. The ERG gene encodes a member of the erythroblast transformation-specific (ETS) family of transcriptions factors. All members of this family are key regulators of embryonic development, cell proliferation, differentiation, angiogenesis, inflammation, and apoptosis. The protein encoded by this gene is mainly expressed in the nucleus. It contains an ETS DNA-binding domain and a PNT (pointed) domain which is implicated in the self-association of chimeric oncoproteins. ERG is involved in chromosomal translocations, resulting in different fusion gene products, such as TMPRSS2-ERG, SLC45A3-ERG, NDRG1-ERG, etc. in prostate cancer, EWS-ERG in Ewing's sarcoma and FUS-ERG in acute myeloid leukemia. Multiple alternatively spliced transcript variants encoding different isoforms have been identified. As reported herein, ERG is one of the top genes overexpressed in prostate cancer, particularly in WD tumors. The NCBI Reference Sequences for two isoforms of ERG are transcript variant 1) NM_182918 (version NM_182918.3), GI:209954798, represented by SEQ ID NO:2 (mRNA) and SEQ ID NO:28 (protein); and transcript variant 2) NM_004449 (version NM_004449.4), GI:209954801, represented by SEQ ID NO:3 (mRNA) and SEQ ID NO:29 (protein). The GenBank reference for a third ERG isoform, transcript variant 8 is AY204742 (version AY204742.1), GI:37781336, represented by SEQ ID NO:4 (mRNA) and SEQ ID NO:30 (protein), which sequences are hereby incorporated by reference. Analyzing the expression of ERG includes analyzing the gene fusion products that are associated with prostate cancer, such as TMPRSS2-ERG. As the gene fusion occurs at the 5' end of the ERG nucleic acid sequence and at the N-terminal end of the ERG protein, one of skill in the art can use existing probes or antibodies, or design their own, to detect the ERG gene fusion products.

CLDN8.

Another gene that can be analyzed in the gene expression profile is claudin 8 (CLDN8). The HGNC has assigned CLDN8 the unique identifier code: HGNC:2050. This gene encodes a member of the claudin family. Claudins are integral membrane proteins and components of tight junction strands. Tight junction strands serve as a physical barrier to prevent solutes and water from passing freely through the paracellular space between epithelial or endothelial cell sheets, and also play critical roles in maintaining cell polarity and signal transductions. This protein plays important roles in the paracellular cation barrier of the distal renal tubule, and in the paracellular barrier to prevent sodium back-leakage in distal colon. Differential expression of this gene has been observed in colorectal carcinoma and renal cell tumors, and along with claudin-7, is an immunohistochemical marker for the differential diagnosis of chromophobe renal cell carcinoma and renal oncocytoma. As reported herein, CLDN8 is one of the top genes overexpressed in prostate cancer, particularly in WD tumors. The NCBI Reference Sequence for CLDN8 is NM_199328 (version NM_199328.2), GI:297206863, represented by SEQ ID NO:5 (mRNA) and SEQ ID NO:31 (protein), which sequences are hereby incorporated by reference.

CACNA1D.

CACNA1D is another gene that can be analyzed in the gene expression profile. The HGNC has assigned CACANA1D the unique identifier code: HGNC:1391. The CACNA1D gene encodes a calcium channel, voltage dependent, L-type, alpha 1D subunit. Multiple alternatively spliced transcript variants encoding different isoforms have been identified. This variant represents the longest transcript and encodes the longest isoform (a). As reported herein, CACNA1D is one of the top genes overexpressed in prostate cancer, particularly in WD tumors. The NCBI Reference Sequence for CACNA1D is NM_000720 (version NM_000720.2), GI:192807296, represented by SEQ ID NO:6 (mRNA) and SEQ ID NO:32 (protein), which sequences are hereby incorporated by reference.

HOXC6.

Another gene that can be analyzed in the gene expression profile is Homeobox C6 (HOXC6). The HGNC has assigned HOXC6 the unique identifier code: HGNC:5128. This gene belongs to the homeobox family, members of which encode a highly conserved family of transcription factors that play an important role in morphogenesis in all multicellular organisms. Mammals possess four similar homeobox gene clusters, HOXA, HOXB, HOXC and HOXD, which are located on different chromosomes and consist of 9 to 11 genes arranged in tandem. HOXC6 is one of several HOXC genes located in a cluster on chromosome 12. Alternatively spliced transcript variants encoding different isoforms have been identified for HOXC6. Transcript variant two includes the shared exon, and transcript variant one includes only gene-specific exons. This variant (2) contains a distinct 5' UTR and lacks an in-frame portion of the 5' coding region, compared to variant 1. The resulting isoform (2) has a shorter N-terminus when compared to isoform 1. As reported herein, HOXC6 is one of the top genes overexpressed in prostate cancer, particularly in PD tumors. The NCBI Reference Sequence for HOXC6 is NM_153693 (version NM_153693.3), GI:100349242, represented by SEQ ID NO:7 (mRNA) and SEQ ID NO:33 (protein), which sequences are hereby incorporated by reference.

TMEFF2.

Another gene that can be analyzed in the gene expression profile is TMEFF2. The HGNC has assigned TMEFF2 the unique identifier code: HGNC:11867. The TMEFF2 gene encodes a transmembrane protein with a single EGF-like domain and two follistatin-like domains. Suppressed expression of TMEFF2 is associated with its hypermethylation in several human tumor types, including glioblastoma and cancers of ovarian, rectal, colon and lung origins. As reported herein, TMEFF2 is one of the top genes overexpressed in prostate cancer, particularly in PD tumors. The NCBI Reference Sequence for TMEFF2 is NM_016192 (version NM_016192.2), GI:12383050, represented by SEQ ID NO:8 (mRNA) and SEQ ID NO:34 (protein), which sequences are hereby incorporated by reference.

NPY.

Another gene that can be analyzed in the gene expression profile is neuropeptide Y (NPY). The HGNC has assigned NPY the unique identifier code: HGNC:7955. NPY encodes a neuropeptide that is widely expressed in the central nervous system and influences many physiological processes, including cortical excitability, stress response, food intake, circadian rhythms, and cardiovascular function. The neuropeptide functions through G protein-coupled receptors to inhibit adenylyl cyclase, activate mitogen-activated protein kinase (MAPK), regulate intracellular calcium levels, and activate potassium channels. A polymorphism in this gene resulting in a change of leucine 7 to proline in the signal peptide is associated with elevated cholesterol levels, higher alcohol consumption, and may be a risk factor for various metabolic and cardiovascular diseases. As reported herein, NPY is one of the top genes overexpressed in prostate cancer, particularly in PD tumors. The NCBI Reference Sequence for NPY is NM_000905 (version NM_000905.3), GI:268834883, represented by SEQ ID NO:9 (mRNA) and SEQ ID NO:35 (protein), which sequences are hereby incorporated by reference.

HPGD.

Another gene that can be analyzed in the gene expression profile is hydroxyprostaglandin dehydrogenase 15-(NAD) (HPGD). The HGNC has assigned HPGD the unique identifier code: HGNC:5154. This gene encodes a member of the short-chain nonmetalloenzyme alcohol dehydrogenase protein family. The encoded enzyme is responsible for the metabolism of prostaglandins, which function in a variety of physiologic and cellular processes such as inflammation. Multiple transcript variants encoding different isoforms have been found for this gene. This variant (3) differs in the 5' UTR and lacks a portion of the 5' coding region, compared to variant 1. These differences result in translation at a downstream start codon and an isoform (3) with a shorter N-terminus, compared to isoform 1. Variants 3 and 6 encode the same protein (isoform 3). As reported herein, HPGD is one of the top genes overexpressed in prostate cancer, particularly in PD tumors. The NCBI Reference Sequence for HPGD is NM_001256301 (version NM_001256301.1), GI:372626409, represented by SEQ ID NO:10 (mRNA) and SEQ ID NO:36 (protein), which sequences are hereby incorporated by reference.

BICD1.

Another gene that can be analyzed in the gene expression profile is bicaudal D homolog 1 (BICD1). The HGNC has assigned BICD1 the unique identifier code: HGNC:1049. This gene is one of two human homologs of *Drosophila* bicaudal-D. It has been implicated in COPI-independent membrane transport from the Golgi apparatus to the endoplasmic reticulum. Two alternative splice variants have been described. Other alternative splice variants that encode different protein isoforms have been described but their full-length nature has not been determined. This variant (1) encodes the longer isoform (1). As reported herein, BICD1 is one of the top genes overexpressed in prostate cancer. The NCBI Reference Sequence for BICD1 is NM_001714 (version NM_001714.2), GI:51039801, represented by SEQ ID NO:11 (mRNA) and SEQ ID NO:37 (protein), which sequences are hereby incorporated by reference.

OR51E1.

Another gene that can be analyzed in the gene expression profile is the olfactory receptor, family 51, subfamily E, member 1 (OR51E1), also known as the prostate specific G-protein coupled receptor (PSGR). The HGNC has assigned OR51E1 the unique identifier code: HGNC:15194. The olfactory receptor proteins are members of a large family of G-protein-coupled receptors (GPCR) arising from single coding-exon genes. Olfactory receptors share a 7-transmembrane domain structure with many neurotransmitter and hormone receptors and are responsible for the recognition and G protein-mediated transduction of odorant signals. The olfactory receptor gene family is the largest in the genome. OR51E1 encodes a prostate specific G-protein coupled receptor that is overexpressed in prostate cancer. As reported herein, OR51E1 is one of the top genes overexpressed in prostate cancer. The NCBI Reference Sequence for OR51E1 is NM_152430 (version NM_152430.3), GI:205277377, represented by SEQ ID NO:12 (mRNA) and SEQ ID NO:38 (protein), which sequences are hereby incorporated by reference.

OR51E2.

Another gene that can be analyzed in the gene expression profile is the olfactory receptor, family 51, subfamily E, member 2 (OR51E2), also known as the prostate specific G-protein coupled receptor 2 (PSGR2). The HGNC has assigned OR51E2 the unique identifier code: HGNC:15195. The olfactory receptor proteins are members of a large family of G-protein-coupled receptors (GPCR) arising from single coding-exon genes. Olfactory receptors share a 7-transmembrane domain structure with many neurotransmitter and hormone receptors and are responsible for the recognition and G protein-mediated transduction of odorant signals. The olfactory receptor gene family is the largest in the genome. OR51E2 encodes a prostate specific G-protein coupled receptor that is overexpressed in prostate cancer. As reported herein, OR51E2 is one of the top genes overexpressed in prostate cancer. The NCBI Reference Sequence for OR51E2 is NM_030774 (version NM_030774.3), GI:218563727, represented by SEQ ID NO:13 (mRNA) and SEQ ID NO:39 (protein), which sequences are hereby incorporated by reference.

FOLH1.

Another gene that can be analyzed in the gene expression profile is the folate hydrolase 1 (FOLH1), also known as the prostate specific membrane antigen (PSMA). The HGNC has assigned FOLH1 the unique identifier code: HGNC:3788. This gene encodes a type II transmembrane glycoprotein belonging to the M28 peptidase family. The protein acts as a glutamate carboxypeptidase on different alternative substrates, including the nutrient folate and the neuropeptide N-acetyl-1-aspartyl-1-glutamate and is expressed in a number of tissues such as prostate, central and peripheral nervous system and kidney. In the prostate the protein is up-regulated in cancerous cells and is used as an effective diagnostic and prognostic indicator of prostate cancer. Alternative splicing gives rise to multiple transcript variants encoding several different isoforms. This variant (1) encodes the longest isoform (1). As reported herein, FOLH1 is one of the top genes overexpressed in prostate cancer. The NCBI Reference Sequence for FOLH1 is NM_004476 (version NM_004476.1), GI:4758397, represented by SEQ ID NO:14 (mRNA) and SEQ ID NO:40 (protein), which sequences are hereby incorporated by reference.

SPARC.

Another gene that can be analyzed in the gene expression profile is the secreted protein, acidic, cysteine rich (SPARC). The HGNC has assigned SPARC the unique identifier code: HGNC:11219. This gene encodes a cysteine-rich acidic matrix-associated protein. The encoded protein is required for the collagen in bone to become calcified but is also involved in extracellular matrix synthesis and promotion of changes to cell shape. The gene product has been associated with tumor suppression but has also been correlated with metastasis based on changes to cell shape which can promote tumor cell invasion. As reported herein, SPARC is one of the top genes overexpressed in prostate cancer. The NCBI Reference Sequence for SPARC is NM_003118 (version NM_003118.3), GI:365777426, represented by SEQ ID NO:15 (mRNA) and SEQ ID NO:41 (protein), which sequences are hereby incorporated by reference.

PLA2G7.

Another gene that can be analyzed in the gene expression profile is the phospholipase A2, group VII (platelet-activating factor acetylhydrolase, plasma) (PLA2G7). The HGNC has assigned PLA2G7 the unique identifier code: HGNC:9040. PLA2G7 encodes a secreted enzyme that catalyzes the degradation of platelet-activating factor to biologically inactive products. Defects in this gene are a cause of platelet-activating factor acetylhydrolase deficiency. Two transcript variants encoding the same protein have been found for this gene. This variant (2) differs in the 5' UTR compared to variant 1. Variants 1 and 2 both encode the same protein. As reported herein, PLA2G7 is one of the top genes overexpressed in prostate cancer, particularly in PD tumors. The NCBI Reference Sequence for PLA2G7 is NM_001168357 (version NM_ 001168357.1), GI:270133070, represented by SEQ ID NO:16 (mRNA) and SEQ ID NO:42 (protein), which sequences are hereby incorporated by reference.

MYO6.

Another gene that can be analyzed in the gene expression profile is the myosin VI (MYO6). The HGNC has assigned MYO6 the unique identifier code: HGNC:7605. MYO6 encodes a protein involved intracellular vesicle and organelle transport, especially in the hair cell of the inner ear. As reported herein, MYO6 is one of the top genes overexpressed in prostate cancer, particularly in PD tumors. The NCBI Reference Sequence for MYO6 is NM_004999 (version NM_004999.3), GI:92859700, represented by SEQ ID NO:17 (mRNA) and SEQ ID NO:43 (protein), which sequences are hereby incorporated by reference.

CRISP3.

Another gene that can be analyzed in the gene expression profile is the cysteine-rich secretory protein 3 (CRISP3). The HGNC has assigned CRISP3 the unique identifier code: HGNC:16904. CRISP3 is an extracellular matrix protein mainly found in human plasma, saliva, seminal plasma and sweat, which can be stored intracellularly in specific compartments or granules or appear associated with membrane proteins in a glycosylated state. Its exact function, however, remains unclear. Based on sequence similarities to pathogenesis-related proteins in plants, cellular localization, and expression profile in neutrophils and thymus, a role as an immune response molecule has been proposed. Specifically, the presence of CRISP3 in secretory granules of neutrophils, which are rich in matrix-degradation enzymes, suggests a proteolytic role and an involvement in cellular matrix remodeling. CRISP3 is a direct target of the ERG transcription factor and is strongly overexpressed in prostate cancer cells harboring a TMPRSS2/ERG fusion. As reported herein, CRISP3 is one of the top genes overexpressed in prostate cancer, particularly in PD tumors. The NCBI Reference Sequence for CRISP3 is NM_006061 (version NM_00661.2), GI:300244559, represented by SEQ ID NO:18 (mRNA) and SEQ ID NO:44 (protein), which sequences are hereby incorporated by reference.

TWIST1.

Another gene that can be analyzed in the gene expression profile is the twist 1 homolog (TWIST1). The HGNC has assigned TWIST1 the unique identifier code: HGNC:12428. The protein encoded by this gene is a beta helix-loop-helix (bHLH) transcription factor and shares similarity with another bHLH transcription factor, Dermot. The strongest expression of this mRNA is in placental tissue; in adults, mesodermally derived tissues express this mRNA preferentially. Mutations in this gene have been found in patients with Saethre-Chotzen syndrome. As reported herein, TWIST1 is one of the top genes overexpressed in prostate cancer, particularly in PD tumors. The NCBI Reference Sequence for TWIST1 is NM_000474 (version NM_000474.3), GI:68160957, represented by SEQ ID NO:19 (mRNA) and SEQ ID NO:45 (protein), which sequences are hereby incorporated by reference.

JAG1.

Another gene that can be analyzed in the gene expression profile is jagged 1 (JAG1). The HGNC has assigned JAG1 the unique identifier code: HGNC:6188. The jagged 1 protein encoded by JAG1 is the human homolog of the Drosophilia jagged protein. Human jagged 1 is the ligand for the receptor notch 1, the latter a human homolog of the Drosophilia jagged receptor notch. Mutations that alter the jagged 1 protein cause Alagille syndrome. Jagged 1 signalling through notch 1 has also been shown to play a role in hematopoiesis. As reported herein, JAG1 is one of the top genes overexpressed in prostate cancer, particularly in PD tumors. The NCBI Reference Sequence for JAG1 is NM_000214 (version NM_000214.2), GI:168480146, represented by SEQ ID NO:20 (mRNA) and SEQ ID NO:46 (protein), which sequences are hereby incorporated by reference.

PCGEM1.

Another gene that can be analyzed in the gene expression profile is prostate-specific transcript 1 (PCGEM1). The HGNC has assigned PCGEM1 the unique identifier code: HGNC:30145. PCGEM1 is a non-coding mRNA sequence that is overexpressed in prostate cancer. As measured by quantitative RT-PCR in laser microdissected prostate tissue, PCGEM1 is frequently overexpressed in prostate cancer. The NCBI Reference Sequence for PCGEM1 is NR_002769 (version NR_002769.1), GI:84872058, represented by SEQ ID NO:21 (mRNA), which sequence is hereby incorporated by reference.

PMEPA1.

Another gene that can be analyzed in the gene expression profile is prostate transmembrane protein, androgen induced 1 (PMEPA1). The HGNC has assigned PMEPA1 the unique identifier code: HGNC:14107. This gene encodes a transmembrane protein that contains a Smad interacting motif (SIM). Expression of this gene is induced by androgens and transforming growth factor beta, and the encoded protein suppresses the androgen receptor and transforming growth factor beta signaling pathways though interactions with Smad proteins. Overexpression of this gene may play a role in multiple types of cancer. Alternatively spliced transcript variants encoding multiple isoforms have been observed for this gene. This variant (1) represents the longest transcript and encodes the longest isoform (a). As measured by quantitative RT-PCR in laser microdissected prostate tissue, PMEPA1 is frequently reduced or absent in prostate cancer. The NCBI Reference Sequence for PMEPA1 is NMO20182 (version NMO20182.4), GI:364023807, represented by SEQ ID NO:22 (mRNA) and SEQ ID NO:47 (protein), which sequences are hereby incorporated by reference.

LTF.

Another gene that can be analyzed in the gene expression profile is lactotransferrin (LTF). The HGNC has assigned LTF the unique identifier code: HGNC:6720. This gene is a member of the transferrin family of genes and its protein product is found in the secondary granules of neutrophils. The protein is a major iron-binding protein in milk and body secretions with an antimicrobial activity, making it an important component of the non-specific immune system. The protein demonstrates a broad spectrum of properties, including regulation of iron homeostasis, host defense against a broad range of microbial infections, anti-inflammatory activity, regulation of cellular growth and differentiation and protection against cancer development and metastasis. Alternatively spliced transcript variants encoding different isoforms have been found for this gene. This variant (1) encodes the longer isoform (1). As measured by quantitative RT-PCR in laser microdissected prostate tissue, LTF expression is frequently reduced or absent in prostate cancer. The NCBI Reference Sequence for LTF is NM_002343 (version NM_002343.3), GI:312434005, represented by SEQ ID NO:23 (mRNA) and SEQ ID NO:48 (protein), which sequences are hereby incorporated by reference.

CAMK2N1.

Another gene that can be analyzed in the gene expression profile is calcium/calmodulin-dependent protein kinase II (CAMK2N1). The HGNC has assigned CAMK2N1 the unique identifier code: HGNC:24190. This gene encodes a calcium/calmodulin-dependent protein kinase capable of autophosphorylation. As reported herein, CAMK2N1 is overexpressed in prostate cancer, particularly in PD tumors. The NCBI Reference Sequence for CAMK2N1 is NM_018584 (version NM_018584.5), GI:115387115, represented by SEQ ID NO:24 (mRNA) and SEQ ID NO:49 (protein), which sequences are hereby incorporated by reference.

MAOA.

Another gene that can be analyzed in the gene expression profile is monoamine oxidase A (MAOA). The HGNC has assigned MAOA the unique identifier code: HGNC:6833. This gene is one of two neighboring gene family members that encode mitochondrial enzymes which catalyze the oxidative deamination of amines, such as dopamine, norepinephrine, and serotonin. Mutation of this gene results in Brunner syndrome. This gene has also been associated with a variety of other psychiatric disorders, including antisocial behavior. Alternatively spliced transcript variants encoding multiple isoforms have been observed. This variant (1) encodes the longer isoform (1). As reported herein, MAOA is overexpressed in prostate cancer, particularly in PD tumors. The NCBI Reference Sequence for MAOA is NM_000240 (version NM_000240.3), GI:395132502, represented by SEQ ID NO:25 (mRNA) and SEQ ID NO:50 (protein), which sequences are hereby incorporated by reference.

COL3A1.

Another gene that can be analyzed in the gene expression profile is collagen type III, alpha 1 (COL3A1). The HGNC has assigned COL3A1 the unique identifier code: HGNC:2201. This gene encodes the pro-alpha1 chains of type III collagen, a fibrillar collagen that is found in extensible connective tissues such as skin, lung, uterus, intestine and the vascular system, frequently in association with type I collagen. Two transcripts, resulting from the use of alternate polyadenylation signals, have been identified for this gene.

As reported herein, COL3A1 is overexpressed in prostate cancer, particularly in PD tumors. The NCBI Reference Sequence for COL3A1 is NM_000090 (version NM_000090.3), GI:110224482, represented by SEQ ID NO:26 (mRNA) and SEQ ID NO:51 (protein), which sequences are hereby incorporated by reference.

Detecting Gene Expression

Measuring or detecting the expression of any of the foregoing genes or nucleic acids comprises measuring or detecting any nucleic acid transcript (e.g., mRNA) thereof or protein encoded thereby. If a gene is associated with more than one mRNA transcript, the expression of the gene can be measured or detected by measuring or detecting any one or more of the mRNA transcripts of the gene, or all of the mRNA transcripts associated with the gene.

Typically, the gene expression can be detected or measured on the basis of mRNA or cDNA levels, although protein levels also can be used when appropriate. Any quantitative or qualitative method for measuring mRNA levels, cDNA, or protein levels can be used. Suitable methods of detecting or measuring mRNA or cDNA levels include, for example, Northern Blotting, microarray analysis, or a nucleic acid amplification procedure, such as reverse-transcription PCR (RT-PCR) or real-time RT-PCR, also known as quantitative RT-PCR (qRT-PCR). Such methods are well known in the art. See e.g., Sambrook et al., Molecular Cloning: A Laboratory Manual, 4$^{th}$ Ed., Cold Spring Harbor Press, Cold Spring Harbor, N.Y., 2012. Other techniques include digital, multiplexed analysis of gene expression, such as the nCounter® (NanoString Technologies, Seattle, Wash.) gene expression assays, which are further described in [9], [10], US20100112710 and US20100047924, all of which are hereby incorporated by reference in their entirety.

Detecting a nucleic acid of interest generally involves hybridization between a target (e.g. mRNA or cDNA) and a probe. Sequences of the genes used in the prostate cancer gene expression profile are known (see above). Therefore, one of skill in the art can readily design hybridization probes for detecting those genes. See e.g., Sambrook et al., Molecular Cloning: A Laboratory Manual, 4$^{th}$ Ed., Cold Spring Harbor Press, Cold Spring Harbor, N.Y., 2012. Each probe should be substantially specific for its target, to avoid any cross-hybridization and false positives. An alternative to using specific probes is to use specific reagents when deriving materials from transcripts (e.g., during cDNA production, or using target-specific primers during amplification). In both cases specificity can be achieved by hybridization to portions of the targets that are substantially unique within the group of genes being analyzed, e.g. hybridization to the polyA tail would not provide specificity. If a target has multiple splice variants, it is possible to design a hybridization reagent that recognizes a region common to each variant and/or to use more than one reagent, each of which may recognize one or more variants.

Preferably, microarray analysis or a PCR-based method is used. In this respect, measuring the expression of the foregoing nucleic acids in prostate cancer tissue can comprise, for instance, contacting a sample containing or suspected of containing prostate cancer cells with polynucleotide probes specific to the genes of interest, or with primers designed to amplify a portion of the genes of interest, and detecting binding of the probes to the nucleic acid targets or amplification of the nucleic acids, respectively. Detailed protocols for designing PCR probes are known in the art. See e.g., Sambrook et al., Molecular Cloning: A Laboratory Manual, 4$^{th}$ Ed., Cold Spring Harbor Press, Cold Spring Harbor, N.Y., 2012. Similarly, detailed protocols for preparing and using microarrays to analyze gene expression are known in the art and described herein.

Alternatively or additionally, expression levels of genes can be determined at the protein level, meaning that levels of proteins encoded by the genes discussed above are measured. Several methods and devices are well known for determining levels of proteins including immunoassays such as described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; 5,458,852; and 5,480,792, each of which is hereby incorporated by reference in its entirety. These assays include various sandwich, competitive, or non-competitive assay formats, to generate a signal that is related to the presence or amount of a protein of interest. Any suitable immunoassay may be utilized, for example, lateral flow, enzyme-linked immunoassays (ELISA), radioimmunoassays (RIAs), competitive binding assays, and the like. Numerous formats for antibody arrays have been described proposed employing antibodies. Such arrays typically include different antibodies having specificity for different proteins intended to be detected. For example, at least 100 different antibodies are used to detect 100 different protein targets, each antibody being specific for one target. Other ligands having specificity for a particular protein target can also be used, such as the synthetic antibodies disclosed in WO/2008/048970, which is hereby incorporated by reference in its entirety. Other compounds with a desired binding specificity can be selected from random libraries of peptides or small molecules. U.S. Pat. No. 5,922,615, which is hereby incorporated by reference in its entirety, describes a device that utilizes multiple discrete zones of immobilized antibodies on membranes to detect multiple target antigens in an array. Microtiter plates or automation can be used to facilitate detection of large numbers of different proteins.

One type of immunoassay, called nucleic acid detection immunoassay (NADIA), combines the specificity of protein antigen detection by immunoassay with the sensitivity and precision of the polymerase chain reaction (PCR). This amplified DNA-immunoassay approach is similar to that of an enzyme immunoassay, involving antibody binding reactions and intermediate washing steps, except the enzyme label is replaced by a strand of DNA and detected by an amplification reaction using an amplification technique, such as PCR. Exemplary NADIA techniques are described in U.S. Pat. No. 5,665,539 and published U.S. Application 2008/0131883, both of which are hereby incorporated by reference in their entirety. Briefly, NADIA uses a first (reporter) antibody that is specific for the protein of interest and labelled with an assay-specific nucleic acid. The presence of the nucleic acid does not interfere with the binding of the antibody, nor does the antibody interfere with the nucleic acid amplification and detection. Typically, a second (capturing) antibody that is specific for a different epitope on the protein of interest is coated onto a solid phase (e.g., paramagnetic particles). The reporter antibody/nucleic acid conjugate is reacted with sample in a microtiter plate to form a first immune complex with the target antigen. The immune complex is then captured onto the solid phase particles coated with the capture antibody, forming an insoluble sandwich immune complex. The microparticles are washed to remove excess, unbound reporter antibody/nucleic acid conjugate. The bound nucleic acid label is then detected by subjecting the suspended particles to an amplification reaction (e.g. PCR) and monitoring the amplified nucleic acid product.

Samples

The methods described in this application involve analysis of gene expression profiles in prostate cells. These prostate cells are found in a biological sample, such as prostate tissue, blood, serum, plasma, urine, saliva, or prostatic fluid. In one embodiment, the biological sample comprises prostate tissue and is obtained through a biopsy, such as a transrectal or transperineal biopsy. In another embodiment, the biological sample is urine. Urine samples may be collected following a digital rectal examination (DRE) or a prostate biopsy. In another embodiment, the sample is blood, serum, or plasma, and contains circulating tumor cells that have detached from a primary tumor. The sample may also contain tumor-derived exosomes. Exosomes are small (typically 30 to 100 nm) membrane-bound particles that are released from normal, diseased, and neoplastic cells and are present in blood and other bodily fluids. The methods disclosed in this application can be used with samples collected from a variety of mammals, but preferably with samples obtained from a human subject.

Controls

The control can be any suitable reference that allows evaluation of the expression level of the genes in the prostate cancer cells as compared to the expression of the same genes in a sample comprising non-cancerous prostate cells, such as normal prostate epithelial cells from a matched subject, or a pool of such samples. Thus, for instance, the control can be a sample from the same subject that is analyzed simultaneously or sequentially with the test sample, or the control can be the average expression level of the genes of interest, as described above, in a pool of prostate samples known to be non-cancerous. Alternatively, the control can be defined by mRNA copy numbers of other genes in the sample, such as housekeeping genes (e.g., PBGD or GAPDH) that can be used to normalize gene expression levels. Thus, the control can be embodied, for example, in a pre-prepared microarray used as a standard or reference, or in data that reflects the expression profile of relevant genes in a sample or pool of non-cancerous samples, such as might be part of an electronic database or computer program.

Over expression and decreased expression of a gene can be determined by any suitable method, such as by comparing the expression of the genes in a test sample with a control (e.g., a positive or negative control), or by using a predetermined "cut-off" of absolute expression. A control can be provided as previously discussed. Regardless of the method used, over expression and decreased expression can be defined as any level of expression greater than or less than, respectively, the level of expression of the same genes in non-cancerous prostate cells or tissue. By way of further illustration, over expression can be defined as expression that is at least about 1.2-fold, 1.5-fold, 2-fold, 2.5-fold, 5-fold, 10-fold, 20-fold, 50-fold, 100-fold higher or even greater expression as compared to non-cancerous prostate cells or tissue, and decreased expression can similarly be defined as expression that is at least about 1.2-fold, 1.5-fold, 2-fold, 2.5-fold, 5-fold, 10-fold, 20-fold, 50-fold, 100-fold lower or even lower expression as compared to non-cancerous prostate cells or tissue. In one embodiment, over expression or descreased expression is defined as expression that is at least about 2.5-fold higher or lower, respectively, as compared to non-cancerous prostate cells or tissue Prostate Cancer This disclosure provides gene expression profiles that are associated with prostate cancer. The gene expression profiles can be used to detect prostate cancer cells in a sample or to measure the severity or aggressiveness of the prostate cancer, for example, distinguishing between well differentiated prostate (WD) cancer and poorly differentiated (PD) prostate cancer.

When prostate cancer is found in a biopsy, it is typically graded to estimate how quickly it is likely to grow and spread. The most commonly used prostate cancer grading system, called Gleason grading, evaluates prostate cancer cells on a scale of 1 to 5, based on their pattern when viewed under a microscope.

Cancer cells that still resemble healthy prostate cells have uniform patterns with well-defined boundaries and are considered well differentiated (Gleason grades 1 and 2). The more closely the cancer cells resemble prostate tissue, the more the cells will behave like normal prostate tissue and the less aggressive the cancer. Gleason grade 3, the most common grade, shows cells that are moderately differentiated, that is, still somewhat well-differentiated, but with boundaries that are not as well-defined. Poorly-differentiated cancer cells have random patterns with poorly defined boundaries and no longer resemble prostate tissue (Gleason grades 4 and 5), indicating a more aggressive cancer.

Prostate cancers often have areas with different grades. A combined Gleason score is determined by adding the grades from the two most common cancer cell patterns within the tumor. For example, if the most common pattern is grade 4 and the second most common pattern is grade 3, then the combined Gleason score is 4+3=7. If there is only one pattern within the tumor, the combined Gleason score can be as low as 1+1=2 or as high as 5+5=10. Combined scores of 2 to 4 are considered well-differentiated, scores of 5 to 6 are considered moderately-differentiated and scores of 7 to 10 are considered poorly-differentiated. Cancers with a high Gleason score are more likely to have already spread beyond the prostate gland at the time they were found.

In general, the lower the Gleason score, the less aggressive the cancer and the better the prognosis (outlook for cure or long-term survival). The higher the Gleason score, the more aggressive the cancer and the poorer the prognosis for long-term, metastasis-free survival.

Array

A convenient way of measuring RNA transcript levels for multiple genes in parallel is to use an array (also referred to as microarrays in the art). Techniques for using arrays to assess and compare gene expression levels are well known in the art and include appropriate hybridization, detection and data processing protocols. A useful array includes multiple polynucleotide probes (typically DNA) that are immobilized on a solid substrate (e.g. a glass support such as a microscope slide, or a membrane) in separate locations (e.g., addressable elements) such that detectable hybridization can occur between the probes and the transcripts to indicate the amount of each transcript that is present. The arrays disclosed in this application can be used in methods of measure the expression level of a desired combination of genes, which combinations are discussed throughout this application.

In one embodiment, the array comprises (a) a substrate and (b) five or more different addressable elements that each comprise at least one polynucleotide probe for detecting the expression of an mRNA transcript of one of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1, or cDNA synthesized from the mRNA transcript. As used herein, the term "addressable element" means an element that is attached to the substrate at a predetermined position and specifically binds a known target molecule, such that when target-binding is detected (e.g., by fluorescent labeling), information regarding the identity of the bound molecule is provided on the basis of the location of the element on the substrate. Addressable elements are "different" for the purposes of the present disclosure if they do not bind to the same target gene. The addressable element comprises one or more polynucleotide probes specific for an mRNA transcript of a given gene, or a cDNA synthesized from the mRNA transcript. The addressable element can comprise more than one copy of a polynucleotide, can comprise more than one different polynucleotide, provided that all of the polynucleotides bind the same target molecule. Where a gene is known to express more than one mRNA transcript, the addressable element for the gene can comprise different probes for different transcripts, or probes designed to detect a nucleic acid sequence common to two or more (or all) of the transcripts. Alternatively, the array can comprise an addressable element for the different transcripts. The addressable element also can comprise a detectable label, suitable examples of which are well known in the art.

The array can comprise addressable elements that bind to mRNA or cDNA other than that of AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1. However, an array capable of detecting a vast number of targets (e.g., mRNA or polypeptide targets), such as arrays designed for comprehensive expression profiling of a cell line, chromosome, genome, or the like, are not economical or convenient for use as a diagnostic tool or screen for prostate cancer. Thus, to facilitate the convenient use of the array as a diagnostic tool or screen, for example, in conjunction with the methods described herein, the array preferably comprises a limited number of addressable elements. In this regard, in one embodiment, the array comprises no more than about 1000 different addressable elements, more preferably no more than about 500 different addressable elements, no more than about 250 different addressable elements, or even no more than about 100 different addressable elements, such as about 75 or fewer different addressable elements, or even about 50 or fewer different addressable elements. Of course, even smaller arrays can comprise about 25 or fewer different addressable elements, such as about 15 or fewer different addressable elements or about 12 or fewer different addressable elements. The array can even be limited to about 7 different addressable elements without interfering with its functionality. It is also possible to distinguish these diagnostic arrays from the more comprehensive genomic arrays and the like by limiting the number of polynucleotide probes on the array. Thus, in one embodiment, the array has no more than 1000 polynucleotide probes immobilized on the substrate. In other embodiments, the array has no more than 500, no more than 250, no more than 100, no more than 50, no more than 25, or no more than 15 polynucleotide probes immobilized on the substrate.

The substrate can be any rigid or semi-rigid support to which polynucleotides can be covalently or non-covalently attached. Suitable substrates include membranes, filters, chips, slides, wafers, fibers, beads, gels, capillaries, plates, polymers, microparticles, and the like. Materials that are suitable for substrates include, for example, nylon, glass, ceramic, plastic, silica, aluminosilicates, borosilicates, metal oxides such as alumina and nickel oxide, various clays, nitrocellulose, and the like.

The polynucleotides of the addressable elements (also referred to as "probes") can be attached to the substrate in a pre-determined 1- or 2-dimensional arrangement, such that the pattern of hybridization or binding to a probe is easily correlated with the expression of a particular gene. Because the probes are located at specified locations on the substrate (i.e., the elements are "addressable"), the hybridization or binding patterns and intensities create a unique expression profile, which can be interpreted in terms of expression levels of particular genes and can be correlated with prostate cancer in accordance with the methods described herein.

Polynucleotide and polypeptide probes can be generated by any suitable method known in the art (see e.g., Sambrook et al., Molecular Cloning: A Laboratory Manual, $4^{th}$ Ed., Cold Spring Harbor Press, Cold Spring Harbor, N.Y., 2012). For example, polynucleotide probes that specifically bind to the mRNA transcripts of the genes described herein (or cDNA synthesized therefrom) can be created using the nucleic acid sequences of the mRNA or cDNA targets themselves (e.g., SEQ ID NOs: 1-26 or fragments thereof) by routine techniques (e.g., PCR or synthesis). As used herein, the term "fragment" means a contiguous part or portion of a polynucleotide sequence comprising about 10 or more nucleotides, about 15 or more nucleotides, about 20 or more nucleotides, about 30 or more, or even about 50 or more nucleotides. By way of further illustration, a polynucleotide probe that binds to an mRNA transcript of AMACR (or cDNA corresponding thereto) can be provided by a polynucleotide comprising a nucleic acid sequence that is complementary to the mRNA transcript (e.g., SEQ ID NO: 1) or a fragment thereof, or sufficiently complementary to SEQ ID NO: 1 or fragment thereof that it selectively binds to SEQ ID NO: 1. The same is true with respect to the other genes described herein. The exact nature of the polynucleotide probe is not critical to the invention; any probe that will selectively bind the mRNA or cDNA target can be used. Typically, the polynucleotide probes will comprise 10 or more nucleic acids, 20 or more, 50 or more, or 100 or more nucleic acids. In order to confer sufficient specificity, the probe will have a sequence identity to a complement of the target sequence (e.g., SEQ ID NOs: 1-26 or corresponding fragment thereof) of about 90% or more, preferably about 95% or more (e.g., about 98% or more or about 99% or more) as determined, for example, using the well-known Basic Local Alignment Search Tool (BLAST) algorithm (available through the National Center for Biotechnology Information (NCBI), Bethesda, Md.).

The array can comprise other elements common to polynucleotide arrays. For instance, the array also can include one or more elements that serve as a control, standard, or reference molecule, such as a housekeeping gene or portion thereof (e.g., PBGD or GAPDH), to assist in the normalization of expression levels or the determination of nucleic acid quality and binding characteristics, reagent quality and effectiveness, hybridization success, analysis thresholds and success, etc. These other common aspects of the arrays or the addressable elements, as well as methods for constructing and using arrays, including generating, labeling, and attaching suitable probes to the substrate, consistent with the invention are well-known in the art. Other aspects of the array are as previously described herein with respect to the methods of the invention.

In one embodiment, the array comprises (a) a substrate and (b) three or more different addressable elements that each comprise at least one polynucleotide probe for detecting the expression of an mRNA transcript of one of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1, wherein the array comprises no more than 500, no more than 250, no more than 100, no more than 50, no more than 25, or no more than 15 addressable elements. In one embodiment, the array comprises at least 5, 7, 12, or 15 different addressable elements.

In one embodiment, the array comprises at least three different addressable elements each of which comprises at least one polynucleotide probe for detecting the expression of an mRNA transcript of one of the following human genes: 1) ERG, CLDN8, and CACNA1D or 2) ERG, CLDN8, and AMACR. In another embodiment, the array comprises at least five different addressable elements each of which comprises at least one polynucleotide probe for detecting the expression of an mRNA transcript of one of the following human genes: 1) CLDN8, HOXC6, TMEFF2, NPY, and HPGD or 2) AMACR, CLDN8, TMEFF2, NPY, and HPGD. In one embodiment, the array comprises at least seven different addressable elements each of which comprises at least one polynucleotide probe for detecting the expression of an mRNA transcript of one of the following human genes: ERG, CLDN8, CACNA1D, HOXC6, TMEFF2, NPY, and HPGD. In another embodiment, the array comprises at least eight different addressable elements each of which comprises at least one polynucleotide probe for detecting the expression of an mRNA transcript of one of the following human genes: ERG, CLDN8, CACNA1D, HOXC6, TMEFF2, NPY, and HPGD and at least one of the following human genes: BICD1, OR51E1, OR51E2, FOLH1, and SPARC. In yet another embodiment, the array comprises at least 12 different addressable elements each of which comprises at least one polynucleotide probe for detecting the expression of an mRNA transcript of one of the following human genes: ERG, CLDN8, CACNA1D, HOXC6, TMEFF2, NPY, HPGD, BICD1, OR51E1, OR51E2, FOLH1, and SPARC. In yet another embodiment, the array comprises at least 13 different addressable elements each of which comprises at least one polynucleotide probe for detecting the expression of an mRNA transcript of one of the following human genes: ERG, CLDN8, CACNA1D, HOXC6, TMEFF2, NPY, HPGD, BICD1, OR51E1, OR51E2, FOLH1, and SPARC and at least one of the following human genes: PLA2G7, MYO6, CRISP3, TWIST1, and JAG1. In yet another embodiment, the array comprises at least 17 different addressable elements each of which comprises at least one polynucleotide probe for detecting the expression of an mRNA transcript of one of the following human genes: ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, and JAG1.

In another embodiment, the array comprises at least six different addressable elements each of which comprises at least one polynucleotide probe for detecting the expression of an mRNA transcript of one the following human genes: ERG, AMACR, CLDN8, TMEFF2, NPY, and HPGD.

In another embodiment, the array comprises at least five different addressable elements each of which comprises at least one polynucleotide probe for detecting the expression of an mRNA transcript of one of the following human genes: ERG, OR51E1, PCGEM1, PMEPA1, and LTF.

In another embodiment, the array comprises at least five different addressable elements each of which comprises at least one polynucleotide probe for detecting the expression of an mRNA transcript of one of the following human genes: CAMK2N1, MAOA, COL3A1, HPGD, and SPARC.

An array can also be used to measure protein levels of multiple proteins in parallel. Such an array comprises one or more supports bearing a plurality of ligands that specifically bind to a plurality of proteins, wherein the plurality of proteins comprises no more than 500, no more than 250, no more than 100, no more than 50, no more than 25, or no more than 15 different proteins. The ligands are optionally attached to a planar support or beads. In one embodiment, the ligands are antibodies. The proteins that are to be detected using the array correspond to the proteins encoded by the nucleic acids of interest, as described above, including the specific gene expression profiles disclosed. Thus, each ligand (e.g. antibody) is designed to bind to one of the target proteins (e.g., one of SEQ ID NOs. 27-51). As with the nucleic acid arrays, each ligand is preferably associated with a different addressable element to facilitate detection of the different proteins in a sample.

Patient Treatment

This application describes methods of detecting and prognosing prostate cancer in a sample obtained from a subject, in which gene expression in prostate cells and/or tissues are analyzed. If a sample shows over expression of certain genes, then there is a strong likelihood that the subject has prostate cancer or a less or more advanced stage (e.g., WD or PD prostate cancer) of prostate cancer. In the event of such a result, the methods of detecting or prognosing prostate cancer may include one or more of the following steps: informing the patient that they are likely to have prostate cancer, WD prostate cancer or PD prostate cancer; confirmatory histological examination of prostate tissue; and/or treating the patient by a prostate cancer therapy. Thus, in certain aspects, if the detection step indicates that the subject has prostate cancer, the methods further comprise a step of taking a prostate biopsy from the subject and examining the prostate tissue in the biopsy (e.g., histological examination) to confirm whether the patient has prostate cancer. Alternatively, the methods of detecting or prognosing prostate cancer may be used to assess the effectiveness of a treatment or to monitor a response to a therapy (e.g., disease-free recurrence following surgery or other therapy), and, thus may include an additional step of treating a subject having prostate cancer prior to analyzing the gene expression profile in a biological sample obtained from the patient.

Prostate cancer treatment options include surgery, radiation therapy, hormone therapy, chemotherapy, biological therapy, or high intensity focused ultrasound. Drugs approved for prostate cancer include: Abiraterone Acetate, Cabazitaxel, Degarelix, Jevtana (Cabazitaxel), Prednisone, Provenge (Sipuleucel-T), Sipuleucel-T, or Docetaxel. Thus a method as described in this application may, after a positive result, include a further step of surgery, radiation therapy, hormone therapy, chemotherapy, biological therapy, or high intensity focused ultrasound.

Drug Screening

The gene expression profiles associated with prostate cancer or lack thereof provided by the methods described in this application can also be useful in screening drugs, either in clinical trials or in animal models of prostate cancer. A clinical trial can be performed on a drug in similar fashion to the monitoring of an individual patient, except that the drug is administered in parallel to a population of prostate cancer patients, usually in comparison with a control population administered a placebo.

The changes in expression levels of genes can be analyzed in individual patients and across a treated or control population. Analysis at the level of an individual patient provides an indication of the overall status of the patient at the end of the trial (i.e., whether gene expression profile indicates the presence or severity (e.g., WD or PD) of prostate cancer) and/or an indication whether that profile has changed toward or away from such indication in the course of the trial. Results for individual patients can be aggregated for a population allowing comparison between treated and control population.

Similar trials can be performed in non-human animal models of prostate cancer. In this case, the expression levels of genes detected are the species variants or homologs of the human genes referenced above in whatever species of non-human animal on which tests are being conducted. Although the average expression levels of human genes determined in human prostate cancer patients are not necessarily directly comparable to those of homolog genes in an animal model, the human values can nevertheless be used to provide an indication whether a change in expression level of a non-human homolog is in a direction toward or away from the diagnosis of prostate cancer or prognosis of WD or PD prostate cancer. The expression profile of individual animals in a trial can provide an indication of the status of the animal at the end of the trial (i.e., whether gene expression profile indicates the presence or severity (e.g., WD or PD) of prostate cancer) and/or change in such status during the trial. Results from individual animals can be aggregated across a population and treated and control populations compared. Average changes in the expression levels of genes can then be compared between the two populations.

Computer Implemented Models

In accordance with all aspects and embodiments of the invention, the methods provided may be computer-implemented.

Gene expression levels can be analyzed and associated with status of a subject (e.g., presence of prostate cancer or severity of disease (e.g., WD or PD prostate cancer) in a digital computer. Optionally, such a computer is directly linked to a scanner or the like receiving experimentally determined signals related to gene expression levels. Alternatively, expression levels can be input by other means. The computer can be programmed to convert raw signals into expression levels (absolute or relative), compare measured expression levels with one or more reference expression levels, or a scale of such values. The computer can also be programmed to assign values or other designations to expression levels based on the comparison with one or more reference expression levels, and to aggregate such values or designations for multiple genes in an expression profile. The computer can also be programmed to output a value or other designation providing an indication of the presence or severity of prostate cancer as well as any of the raw or intermediate data used in determining such a value or designation.

Figure 4:
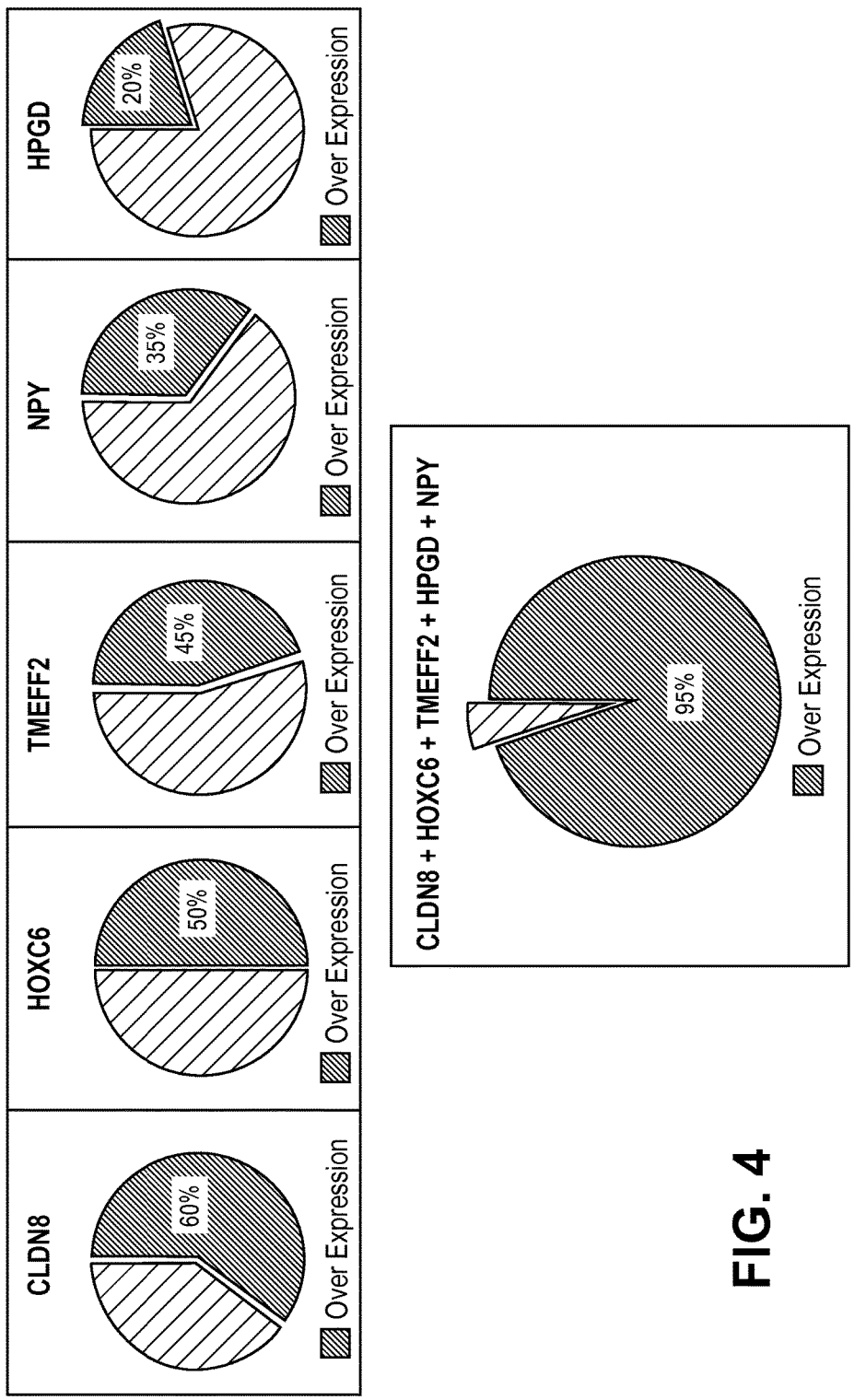
FIG. 4 shows the performance of a 5-gene panel (CLDN8, HOXC6, TMEFF2, NPY, and HPGD) in patients with PD tumor (N=20). 95% of the patients over expressed at least one of the five genes.
Figure 5:
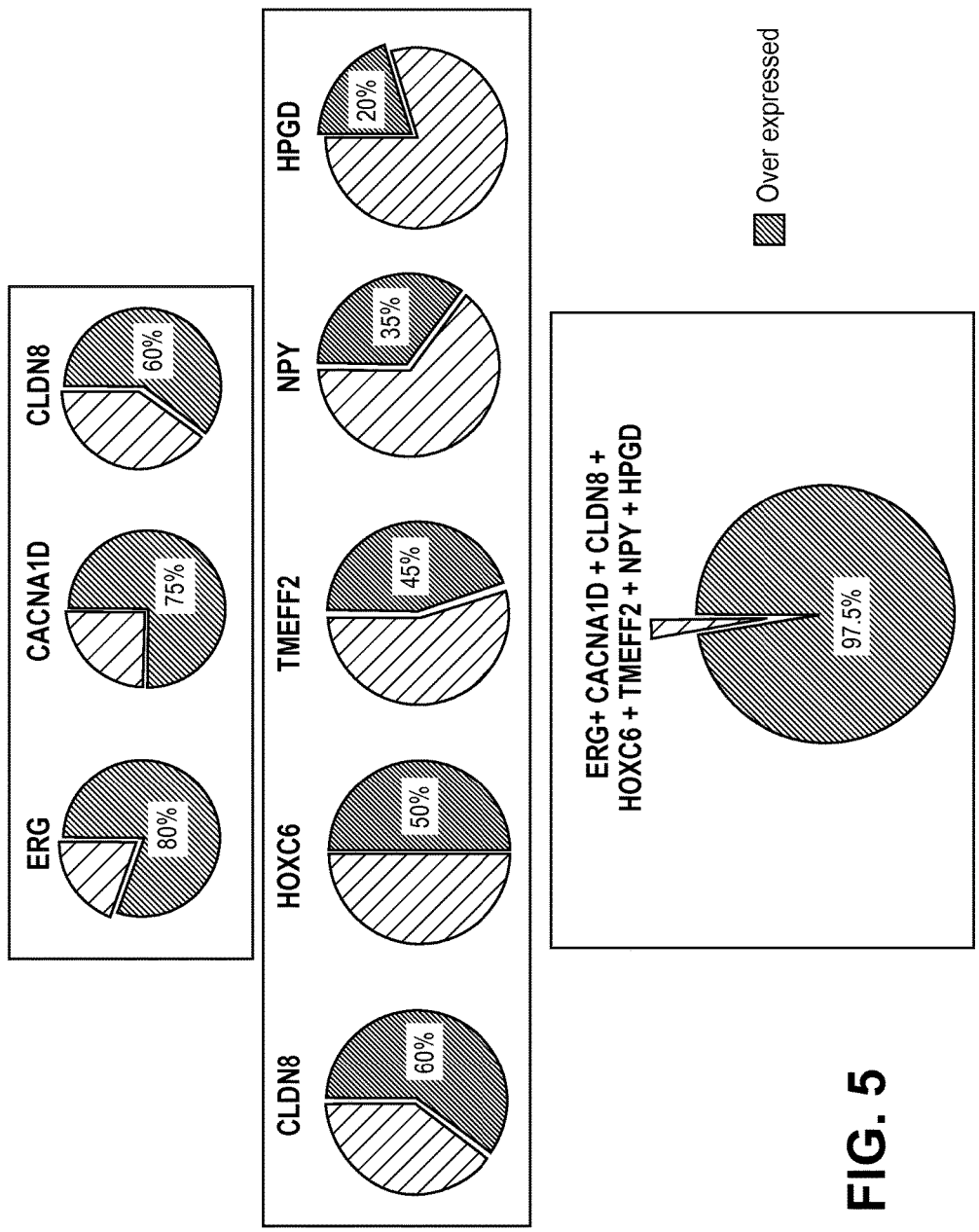
FIG. 5 shows the performance of a 7-gene panel (ERG, CACNA1D, CLDN8, HOXC6, TMEFF2, NPY, and HPGD) in 40-patient cohort (20 WD+20 PD). 97.5% of the patients over expressed at least one of the seven genes.

A typical computer (see U.S. Pat. No. 6,785,613; FIGS. 4 and 5) includes a bus which interconnects major subsystems such as a central processor, a system memory, an input/output controller, an external device such as a printer via a parallel port, a display screen via a display adapter, a serial port, a keyboard, a fixed disk drive and a port (e.g., USB port) operative to receive an external memory storage device. Many other devices can be connected such as a scanner via I/O controller, a mouse connected to serial port or a network interface. The computer contains computer readable media holding codes to allow the computer to perform a variety of functions. These functions include controlling automated apparatus, receiving input and delivering output as described above. The automated apparatus can include a robotic arm for delivering reagents for determining expression levels, as well as small vessels, e.g., microtiter wells for performing the expression analysis.

Figure 13:
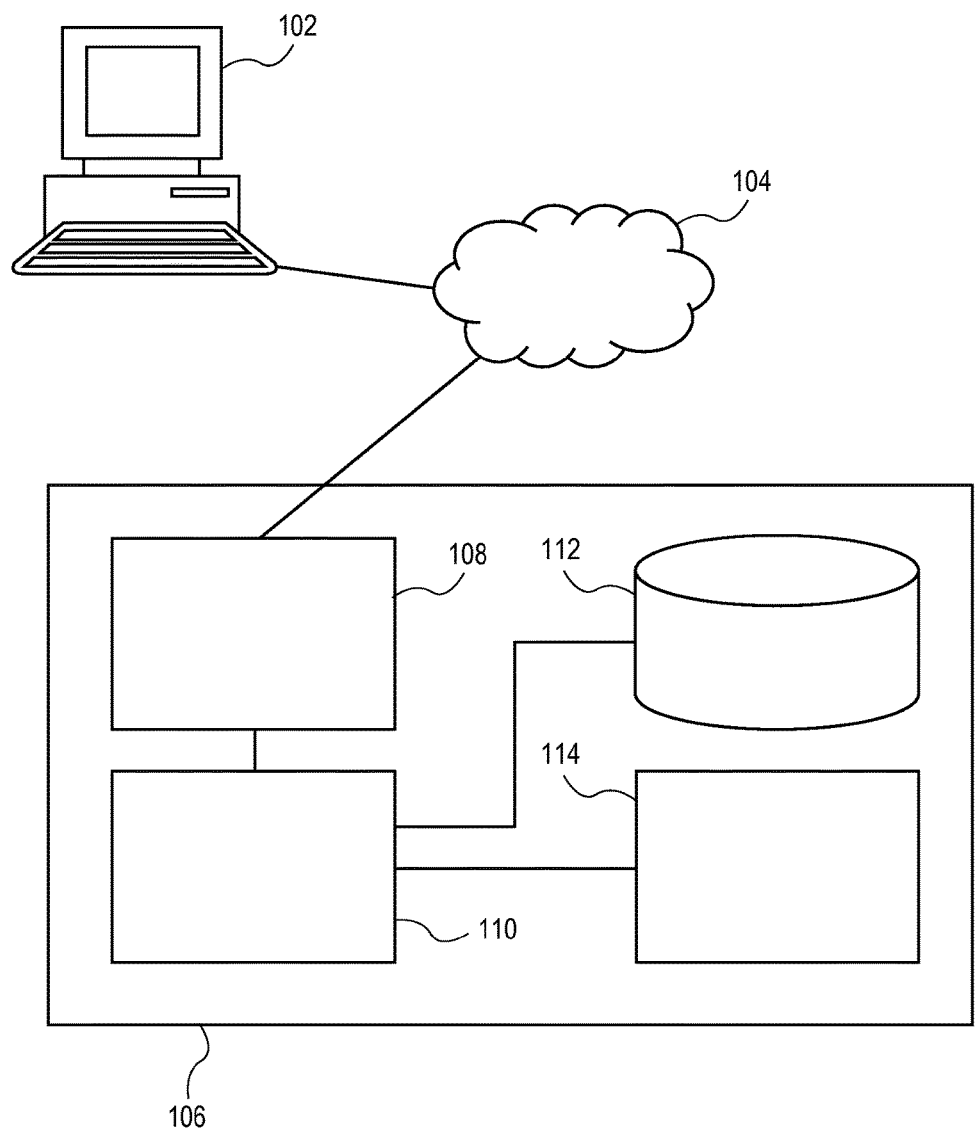
FIG. 13 shows a schematic diagram of a system according to some embodiments of the invention. In particular, this figure illustrates various hardware, software, and other resources that may be used in implementations of computer system 106 according to disclosed systems and methods. In embodiments as shown, computer system 106 may include one or more processors 110 coupled to random access memory operating under control of or in conjunction with an operating system. The processor(s) 110 in embodiments may be included in one or more servers, clusters, or other computers or hardware resources, or may be implemented using cloud-based resources. The operating system may be, for example, a distribution of the Linux™ operating system, the Unix™ operating system, or other open-source or proprietary operating system or platform. Processor(s) 110 may communicate with data store 112, such as a database stored on a hard drive or drive array, to access or store program instructions other data.

A typical computer system 106 may also include one or more processors 110 coupled to random access memory operating under control of or in conjunction with an operating system as set forth in FIG. 13 and discussed above.

In one embodiment, any of the computer-implemented methods of the invention may comprise a step of obtaining by at least one processor information reflecting the expression level of 1) at least five of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1 in a biological sample; 2) at least three of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1 in a biological sample; 3) the following human genes: ERG, CLDN8, CACNA1D, HOXC6, TMEFF2, NPY, and HPGD in a biological sample; 4) the following human genes: ERG, CLDN8, CACNA1D, HOXC6, TMEFF2, NPY in a biological sample, and HPGD and at least one of the following human genes: BICD1, OR51E1, OR51E2, FOLH1, and SPARC in the biological sample; 5) the following human genes: ERG, CLDN8, CACNA1D, HOXC6, TMEFF2, NPY, HPGD, BICD1, OR51E1, OR51E2, FOLH1, and SPARC in a biological sample; 6) the following human genes: ERG, CLDN8, CACNA1D, HOXC6, TMEFF2, NPY, HPGD, BICD1, OR51E1, OR51E2, FOLH1, SPARC in a biological sample, and at least one of the following human genes: PLA2G7, MYO6, CRISP3, TWIST1, and JAG1 in the biological sample; 7) the following human genes: ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, and JAG1 in a biological sample; 8) the following human genes: ERG, AMACR, CLDN8, TMEFF2, NPY, and HPGD in a biological sample; 9) the following human genes: ERG, OR51E1, PCGEM1, PMEPA1, and LTF; or 10) the following human genes: CAMK2N1, MAOA, COL3A1, HPGD, and SPARC.

In another embodiment of the computer-implemented methods of the invention, the methods may additionally comprise the steps of i) determining by at least one processor a difference between the expression level of one or more control genes and the expression level of 1) at least five of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1 in a biological sample; 2) at least three of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1 in a biological sample; 3) the following human genes: ERG, CLDN8, CACNA1D, HOXC6, TMEFF2, NPY, and HPGD in a biological sample; 4) the following human genes: ERG, CLDN8, CACNA1D, HOXC6, TMEFF2, NPY in a biological sample, and HPGD and at least one of the following human genes: BICD1, OR51E1, OR51E2, FOLH1, and SPARC in the biological sample; 5) the following human genes: ERG, CLDN8, CACNA1D, HOXC6, TMEFF2, NPY, HPGD, BICD1, OR51E1, OR51E2, FOLH1, and SPARC in a biological sample; 6) the following human genes: ERG, CLDN8, CACNA1D, HOXC6, TMEFF2, NPY, HPGD, BICD1, OR51E1, OR51E2, FOLH1, SPARC in a biological sample, and at least one of the following human genes: PLA2G7, MYO6, CRISP3, TWIST1, and JAG1 in the biological sample; 7) the following human genes: ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, and JAG1 in a biological sample; 8) the following human genes: ERG, AMACR, CLDN8, TMEFF2, NPY, and HPGD in a biological sample; 9) the following human genes: ERG, OR51E1, PCGEM1, PMEPA1, and LTF; or 10) the following human genes: CAMK2N1, MAOA, COL3A1, HPGD, and SPARC; and (ii) outputting in user readable format the difference obtained in the determining step.

In another embodiment of the computer-implemented methods of the invention, the methods may further comprise outputting in user readable format a determination that the subject has prostate cancer, well differentiated prostate cancer, or poorly differentiated prostate cancer based on the difference obtained in the outputting step.

Kits

The polynucleotide probes and/or primers or antibodies that are used in the methods described in this application can be arranged in a kit. Thus, one embodiment is directed to a kit comprising polynucleotide probes for detecting the expression of at least 3, 4, 5, 6, 7, 8, 9, 10, 11, 12, 13, 14, 15 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1. The polynucleotide probes may be optionally labeled. The kit may optionally include polynucleotide primers for amplifying a portion of the mRNA transcripts from at least 3, 4, 5, 6, 7, 8, 9, 10, 11, 12, 13, 14, 15 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1.

In another embodiment, the kit comprises antibodies for detecting the polypeptides encoded by at least 3, 4, 5, 6, 7, 8, 9, 10, 11, 12, 13, 14, 15 of the following human genes: AMACR, ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, JAG1, PCGEM1, PMEPA1, LTF, CAMK2N1, MAOA, and COL3A1. The antibodies are optionally labeled.

In one embodiment, the kit is designed for detecting the expression of at least the following human genes: 1) ERG, CLDN8, and CACNA1D or 2) ERG, CLDN8, and AMACR. In another embodiment, the kit is designed for detecting the expression of at least the following human genes: 1) CLDN8, HOXC6, TMEFF2, NPY, and HPGD or 2) AMACR, CLDN8, TMEFF2, NPY, and HPGD.

In one embodiment, the kit is designed for detecting the expression of at least the following human genes: ERG, CLDN8, CACNA1D, HOXC6, TMEFF2, NPY, and HPGD. In another embodiment, the kit is designed for detecting the expression of the following human genes: ERG, CLDN8, CACNA1D, HOXC6, TMEFF2, NPY, and HPGD and at least one of the following human genes: BICD1, OR51E1, OR51E2, FOLH1, and SPARC. In yet another embodiment, the kit is designed for detecting the expression of at least the following human genes: ERG, CLDN8, CACNA1D, HOXC6, TMEFF2, NPY, HPGD, BICD1, OR51E1, OR51E2, FOLH1, and SPARC. In yet another embodiment, the kit is designed for detecting the expression of at least the following human genes: ERG, CLDN8, CACNA1D, HOXC6, TMEFF2, NPY, HPGD, BICD1, OR51E1, OR51E2, FOLH1, and SPARC and at least one of the following human genes: PLA2G7, MYO6, CRISP3, TWIST1, and JAG1. In yet another embodiment, the kit is designed for detecting the expression of at least the following human genes: ERG, CLDN8, CACNA1D, HOXC6, TMEFF2, NPY, HPGD, BICD1, OR51E1, OR51E2, FOLH1, SPARC, PLA2G7, MYO6, CRISP3, TWIST1, and JAG1.

In another embodiment, the kit is designed for detecting the expression of at least the following human genes: ERG, AMACR, CLDN8, TMEFF2, NPY, and HPGD. In another embodiment, the kit is designed for detecting the expression of at least the following human genes: ERG, OR51E1, PCGEM1, PMEPA1, and LTF. In yet another embodiment, the kit is designed for detecting the expression of at least the following human genes: CAMK2N1, MAOA, COL3A1, HPGD, and SPARC.

Other components that can be included in these kits, include, but are not limited to, buffers, enzymes, labeling compounds, and the like. The kit can also include a reference or control sample. The reference or control sample can be a biological sample or a data base.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

To identify and optimize a gene expression profile for prostate cancer, initial candidate genes were identified by selecting the genes with the highest level of over expression (tumor over normal) in 20 patients with well differentiated (WD) tumor and 20 patients with poorly differentiated (PD) tumor. To identify the genes of interest, gene expression levels were measured using human genome (HG) U133A arrays (Affymetric, Santa Clara, Calif.) and/or QRT-PCR TaqMan® (Life Technologies, Carlsbad, Calif.) assays. SPARC and HPGD were included based on recent publications [7] and [8]. The initial candidate genes are listed in Table 1, which shows the average levels of over expression of each of the initial candidate genes in prostate cancer samples.

TABLE 1

Initial Candidate Genes

| Serial number | Probe-sets | Gene Symbol | Average T vs N (WD) | Average T vs N (PD) | Average T vs N |
|---|---|---|---|---|---|
| 1 | 209426_s_at | AMACR | 33.08 | 10.12 | 12.74 |
| 2 | 213541_s_at | ERG | 15.16 | 5.7 | 6.62 |
| 3 | 242488_at | CHRM3 | 8.32 | -1.65 | 5.36 |
| 4 | 210108_at | CACNA1D | 6.99 | -3.64 | 4.97 |
| 5 | 229768_at | PSGR2 | 6.23 | 11.04 | 7.49 |
| 6 | 214806_at | BICD1 | 5.68 | -3.12 | 3.89 |
| 7 | 206214_at | PLA2G7 | 5.38 | -3.12 | 3.66 |
| 8 | 217771_at | GOLPH2 | 4.62 | -2.03 | 3.01 |
| 9 | 203216_s_at | MYO6 | 4.55 | 5.3 | 4.56 |
| 10 | 214598_at | CLDN8 | 4.55 | -2.21 | 2.6 |
| 11 | 236121_at | PSGR | 4.44 | -1.81 | 3.2 |
| 12 | 1555993_at | CACNA1D | 3.94 | -2.48 | 3.19 |
| 13 | 207802_at | CRISP3 | 3.36 | -5.49 | 4.26 |
| 14 | 225987_at | STEAP4 | 3.25 | -1.65 | 2.41 |
| 15 | 223557_s_at | TMEFF2 | 3.21 | -2.45 | 2.6 |
| 16 | 206858_s_at | HOXC6 | 2.82 | -5.01 | 3.58 |
| 17 | 206001_at | NPY | 2.82 | -2.32 | 2.65 |
| 18 | 213943_at | TWIST1 | 2.34 | -5.34 | 3.27 |
| 19 | 212445_s_at | NEDD4L | 1.96 | -2.07 | 1.99 |
| 20 | 231183_s_at | JAG1 | 1.42 | 3.8 | 2.51 |
| 21 | 205860_x_at | FOLH1 | 1.32 | -4.06 | 2.36 |
| 22 | 203914_x_at | HPGD | 0.98 | -2.01 | 1.65 |
| 23 | 200665_s_at | SPARC | 0.67 | -1.66 | 1.12 |

The tumor over normal data for each candidate gene in each of the 20 WD prostate cancer patients is set forth in Table 2.

TABLE 2

Tumor vs. Normal Ratios in Patients with WD Prostate Cancer

| Gene Symbol | AMACR | FRG | CACNA1D | CACNA1D | BCD1 | TMEFF2 | CHRM3 | CLDN8 | MYO6 | GOLPH2 | PLA2G7 | TWIST1 |
|---|---|---|---|---|---|---|---|---|---|---|---|---|
| Probe ID | 20946_s_at | 213541_s_at | 210108_at | 1555993_at | 214806_at | 223557_s_at | 242488_at | 214598_at | 203216_s_at | 217771_at | 206214_at | 213943_at |
| 298 | 68.32 | 39.94 | 6.35 | 1.95 | 34.48 | 3.23 | 46.27 | 6.98 | 9.08 | 27.15 | 6.97 | 1.73 |
| 318 | 4.02 | 0.82 | 2.16 | 1.75 | 8.6 | 44.24 | 1.18 | 13.65 | 0.36 | 11.56 | 0.67 | 0.89 |
| 343 | 26.19 | 35.13 | 5.23 | 2.55 | 6.49 | 97.73 | 17.14 | 68.64 | 17.03 | 37.5 | 35.11 | 4.45 |
| 349 | 46.88 | 17.21 | 18.52 | 8.07 | 5.07 | 31.46 | 2.39 | 1.77 | 2.75 | 1.79 | 0.91 | 2.92 |
| 359 | 18.66 | 15.9 | 55.69 | 32.54 | 3.03 | 9.6 | 12.43 | 8.58 | 17.35 | 8.19 | 4.8 | 3.05 |
| 376 | 31.29 | 9.18 | 26.82 | 15.84 | 11.18 | 114.62 | 30.31 | 6.14 | 2.34 | 6.29 | 7.11 | 1.44 |
| 430 | 10.99 | 1.33 | 1.78 | 4.55 | 0.89 | 0.6 | 1.5 | 0.6 | 0.97 | 1.15 | 1.16 | 1.13 |
| 455 | 20.56 | 27.62 | 10.1 | 3.3 | 2.91 | 2.33 | 7.07 | 1.02 | 1.05 | 3.01 | 5.3 | 4.79 |
| 458 | 3.56 | 1.18 | 0.65 | 0.76 | 0.67 | 1.27 | 1.42 | 7.88 | 0.65 | 0.13 | 1.1 | 0.91 |
| 479 | 7 | 6.93 | 2.54 | 2.15 | 5.61 | 9.38 | 6.34 | 6.22 | 7.94 | 10.87 | 2.05 | 2.69 |
| 480 | 17.84 | 6.82 | 6.6 | 2.7 | 6.99 | 37.05 | 2.08 | 6.72 | 9.62 | 17.99 | 1.54 | 1.31 |
| 488 | 1.07 | 0.84 | 0.95 | 0.64 | 0.31 | 0.01 | 1.02 | 3.27 | 1.1 | 0.12 | 1.08 | 0.4 |
| 504 | 44.22 | 17.83 | 4.6 | 1.39 | 5.49 | 1.04 | 19.65 | 4.68 | 4.16 | 1.04 | 2.37 | 2.25 |
| 506 | 49.31 | 5.26 | 4.05 | 1.54 | 1.51 | 0.17 | 1.96 | 1.05 | 3.56 | 0.67 | 5.46 | 2.18 |
| 521 | 95.23 | 12.86 | 0.94 | 1.51 | 3.07 | 10.15 | 1.02 | 2.32 | 1.12 | 7.28 | 1.65 | 2.71 |
| 532 | 107.7 | 21.37 | 3.54 | 1.42 | 4.59 | 17.76 | 5.89 | 11.44 | 12.65 | 9.85 | 18.4 | 2.35 |
| 553 | 25.83 | 33.34 | 13.29 | 4.5 | 8 | 3.87 | 12.38 | 2.03 | 43.15 | 10.75 | 8.4 | 3.57 |
| 589 | 3.41 | 4.78 | 2.44 | 0.66 | 3.59 | 6.34 | 11.43 | 0.87 | 0.89 | 0.3 | 1.35 | 2.99 |
| 618 | 24.69 | 23.69 | 8.76 | 3.37 | 5.44 | 8.48 | 12.21 | 1.62 | 7.05 | 3.64 | 5.79 | 1.57 |
| 704 | 41.26 | 21.15 | 4.16 | 1.45 | 1.15 | 15.94 | 3.2 | 6.82 | 6.55 | 13.55 | 13.5 | 6.85 |
| | 19 | 16 | 16 | 10 | 15 | 15 | 14 | 14 | 13 | 13 | 12 | 12 |

| Gene Symbol | PSGR | STEAP4 | HOXC6 | NPY | PSGR2 | CRISP3 | IAG1 | NEDD4L | FOLH1 | SPARC | HPGD | |
|---|---|---|---|---|---|---|---|---|---|---|---|---|
| Probe ID | 236121_at | 225987_at | 206858_s_at | 206001_at | 229768_at | 207802_at | 231183_s_at | 212445_s_at | 205860_x_at | 200665_s_at | 203914_x_at | |
| 298 | 121.51 | 5.22 | 1.29 | 22.05 | 42.19 | 7.39 | 0.77 | 4.57 | 1.32 | 0.08 | 1 | 16 |
| 318 | 209.74 | 0.38 | 2.46 | 3.69 | 0.29 | 1.01 | 4.75 | 3.27 | 9.55 | 0.71 | 1.69 | 12 |
| 343 | 296.76 | 74.86 | 1.46 | 180.35 | 4.14 | 9.1 | 4.33 | 5.8 | 3.57 | 0.74 | 1.02 | 20 |
| 349 | 58.87 | 1.27 | 4.34 | 59.22 | 18.61 | 1.1 | 2.39 | 1.68 | 1.72 | 2.56 | 1.12 | 15 |
| 359 | 0.47 | 3.94 | 6.03 | 2.92 | 3.83 | 8.68 | 2.54 | 1.25 | 1.75 | 0.19 | 1.04 | 18 |
| 376 | 2.99 | 2.81 | 1.12 | 11.66 | 148.45 | 2.99 | 2.28 | 5.06 | 6.07 | 0.58 | 0.85 | 19 |
| 430 | 1. | 1.36 | 1.49 | 1.7 | 0.7 | 1.15 | 1.06 | 1.17 | 0.2 | 1.34 | 1.05 | 2 |
| 455 | 1.37 | 1.58 | 2.89 | 4.8 | 0.84 | 1.02 | 0.6 | 1.05 | 1.28 | 0.37 | 1.05 | 12 |
| 458 | 18.67 | 0.44 | 1.62 | 0.63 | 1.51 | 0.34 | 1.08 | 0.7 | 0.04 | 0.54 | 1.25 | 3 |
| 479 | 29.22 | 3.89 | 0.98 | 5.57 | 31.16 | 1.82 | 1.52 | 0.89 | 1.97 | 0.93 | 1.06 | 16 |
| 480 | 83.45 | 1.59 | 7.8 | 28.13 | 1.15 | 1.44 | 1.87 | 1.06 | 4.61 | 0.77 | 1 | 14 |
| 488 | 0.07 | 1.54 | 0.99 | 1.77 | 0.04 | 1 | 1.19 | 0.51 | 0.83 | 1.15 | 1.01 | 1 |
| 504 | 0.49 | 2.35 | 1.4 | 1.6 | 57.51 | 26.01 | 0.68 | 1.21 | 0.78 | 0.11 | 1.08 | 12 |
| 506 | 0.5 | 1.81 | 0.51 | 0.84 | 67.95 | 2.65 | 0.5 | 1.29 | 0.32 | 0.51 | 1.07 | 8 |
| 521 | 31124 | 2.47 | 1.25 | 2.15 | 1.43 | 1.05 | 6.37 | 2.39 | 0.04 | 0.7 | 0.96 | 12 |
| 532 | 9.41 | 11.19 | 17.6 | 1.69 | 0.22 | 1.08 | 3.4 | 2.73 | 4.23 | 1.52 | 1.03 | 17 |
| 553 | 8.48 | 6.25 | 2.14 | 0.87 | 0.8 | 4.81 | 1.53 | 6.48 | 1.35 | 0.7 | 1.01 | 17 |
| 589 | 45.56 | 1.1 | 2.21 | 0.28 | 0.68 | 0.79 | 0.25 | 0.88 | 0.54 | 0.39 | 1.21 | 9 |
| 618 | 1.46 | 4.98 | 3.34 | 0.84 | 1.09 | 1.7 | 0.78 | 0.94 | 0.21 | 0.77 | 1.08 | 12 |
| 704 | 10.41 | 3.69 | 7.71 | 0.05 | 2.25 | 1.4 | 0.75 | 1.81 | 0.76 | 0.43 | 0.98 | 14 |
| | 13 | 11 | 10 | 10 | 9 | 7 | 7 | 7 | 5 | 1 | 0 | |

The tumor over normal data for each candidate gene in each of the 20 PD prostate cancer patients is set forth in Table 3.

TABLE 3

Tumor vs. Normal Ratios in Patients with PD Prostate Cancer

| Gene Symbol | AMACR | CLDN8 | HOXC6 | COLPH2 | CACNA1D | CACNA1D | FOLH1 | PSGR | MYO6 | TMEFF2 | PSGR2 | PLA2G7 |
|---|---|---|---|---|---|---|---|---|---|---|---|---|
| Probe ID | 209426_s_at | 214598_at | 206858_s_at | 217771_at | 210108_at | 1555993_at | 205860_x_at | 236121_at | 203216_s_at | 223557_s_at | 229768_at | 206214_at |
| 320 | 168.06 | 43.19 | 13.24 | 23.9 | 5.96 | 1.79 | 57.82 | 27.34 | 17.17 | 3.8 | 4.69 | 2 |
| 326 | 29.12 | 24.95 | 32.63 | 2.63 | 5.33 | 5.34 | 1.11 | 6.43 | 15.12 | 1.55 | 0.11 | 0.95 |
| 346 | 4.1 | 0.1 | 1 | 0.7 | 1.63 | 1.23 | 1.49 | 0.06 | 0.99 | 0.79 | 0.91 | 1.3 |
| 347 | 2.77 | 3.1 | 0.93 | 3.94 | 51.54 | 11.18 | 1.64 | 0.89 | 9.38 | 0.95 | 12.21 | 3.47 |
| 393 | 43.92 | 4.03 | 6.15 | 1.5 | 1.19 | 0.8 | 2.31 | 0.38 | 5.89 | 0.79 | 32.59 | 4.29 |
| 413 | 14.43 | 126.11 | 3.62 | 2.8 | 17.59 | 9.95 | 13.3 | 0.28 | 39.15 | 4.76 | 0.32 | 3.41 |
| 468 | 0.91 | 3.59 | 0.92 | 1.07 | 0.73 | 1.46 | 1.01 | 0.65 | 0.89 | 0.27 | 0.81 | 0.76 |
| 473 | 80.64 | 56.26 | 0.93 | 11.83 | 11.89 | 2.13 | 28.14 | 32.46 | 10.37 | 0.23 | 80 | 13.55 |
| 513 | 28.28 | 0.78 | 2.13 | 0.73 | 1.09 | 1.47 | 0.82 | 6.68 | 0.15 | 84.88 | 0.98 | 1.33 |
| 535 | 12.52 | 2.95 | 23.56 | 2.64 | 2.08 | 1.47 | 5.51 | 14.1 | 0.77 | 0.01 | 1.28 | 1.21 |
| 564 | 6.78 | 9.46 | 17.56 | 10.92 | 7.95 | 2.22 | 20.21 | 12.25 | 40.98 | 367.89 | 19.82 | 3.3 |
| 573 | 0.6 | 4.02 | 8.75 | 8.57 | 1.32 | 1.58 | 3.51 | 3.27 | 1.09 | 17.19 | 1.02 | 1.25 |
| 616 | 20.6 | 132.78 | 10.08 | 2.07 | 12.29 | 1.81 | 70.01 | 9.97 | 22.34 | 0.58 | 1.31 | 22.35 |
| 643 | 1.07 | 1.19 | 0.45 | 0.84 | 0.51 | 1.2 | 1.2 | 0.85 | 0.55 | 0.97 | 1.05 | 1.26 |
| 670 | 1.11 | 1.02 | 1.08 | 2.52 | 0.98 | 1.14 | 1.6 | 10.74 | 0.75 | 4.58 | 0.34 | 1.2 |
| 726 | 0.48 | 0.23 | 2.2 | 0.17 | 0.99 | 1.11 | 0.16 | 0.42 | 0.49 | 0.48 | 0.87 | 1.12 |
| 850 | 33.1 | 1.03 | 16.77 | 9.93 | 7.7 | 1.81 | 12.39 | 85.07 | 6.71 | 369.17 | 78.53 | 8.48 |
| 853 | 22.88 | 2.93 | 13.23 | 0.99 | 4.21 | 1.49 | 2.54 | 0.91 | 0.58 | 145.11 | 10.43 | 0.96 |
| 935 | 0.46 | 2.48 | 1.09 | 0.39 | 0.83 | 0.82 | 1.72 | 0.41 | 1.05 | 1.99 | 1.09 | 2.74 |
| 940 | 26.17 | 0.46 | 1.01 | 0.5 | 0.74 | 1.41 | 0.98 | 0.97 | 0.53 | 4.01 | 13.74 | 1.17 |
|  | 14 | 13 | 12 | 11 | 10 | 5 | 10 | 10 | 9 | 9 | 8 | 8 |

| Gene Symbol | IAG1 | BICD1 | TWIST1 | NPY | ERG | CRISP3 | STEAP4 | NEDD4L | SPARC | CHRM3 | HPGD | |
|---|---|---|---|---|---|---|---|---|---|---|---|---|
| Probe ID | 231183_s_at | 214806_at | 213943_at | 206001_at | 213541_s_at | 207802_at | 225987_at | 212445_s_at | 200665_s_at | 242488_at | 203914_x_at | |
| 320 | 1.73 | 14.58 | 14.25 | 2.67 | 0.96 | 1.46 | 0.84 | 8 | 0.53 | 1.63 | 0.66 | 14 |
| 326 | 3.54 | 5.37 | 26.76 | 0.32 | 0.58 | 11.1 | 4.14 | 5.87 | 0.24 | 0.96 | 0.2 | 14 |
| 346 | 0.95 | 1.26 | 1.34 | 0.98 | 0.79 | 1.06 | 1.73 | 0.97 | 0.86 | 1.18 | 1 | 1 |
| 347 | 6.67 | 4.56 | 13.02 | 1.57 | 29.57 | 8.08 | 1.03 | 2.77 | 1.31 | 2.91 | 0.98 | 15 |
| 393 | 1.61 | 0.95 | 1.2 | 0.04 | 1.02 | 24.06 | 1.29 | 1.1 | 1.86 | 1.32 | 1.33 | 8 |
| 413 | 6.07 | 7.63 | 3.51 | 0.03 | 23.28 | 0.98 | 1.16 | 3.46 | 7.22 | 0.87 | 7.49 | 17 |
| 468 | 0.95 | 0.79 | 1 | 1.76 | 0.85 | 0.94 | 0.49 | 1.05 | 1.98 | 1.01 | 1.05 | 1 |
| 473 | 27.1 | 1.99 | 15.19 | 81.17 | 21.07 | 1.09 | 7.45 | 1.24 | 0.97 | 1.74 | 0.81 | 15 |
| 513 | 0.16 | 0.92 | 0.95 | 4.21 | 1.01 | 3.53 | 2.96 | 1.08 | 2.61 | 0.69 | 0.74 | 8 |
| 535 | 5.4 | 2.64 | 2.73 | 19.79 | 0.89 | 40.19 | 1.55 | 0.72 | 10.52 | 2.42 | 0.97 | 14 |

TABLE 3-continued

| 564 | 46.19 | 9.04 | 1.26 | 1.14 | 25.27 | 8.8 | 4.22 | 4.3 | 1.24 | 6.42 | 1.19 | 19 |
|---|---|---|---|---|---|---|---|---|---|---|---|---|
| 573 | 1.08 | 1.91 | 1.15 | 0.07 | 1.07 | 1.01 | 0.19 | 1.35 | 5.94 | 1.04 | 3.17 | 8 |
| 616 | 1.12 | 1.08 | 1.32 | 1.69 | 3.38 | 1.87 | 3.82 | 8.42 | 11.94 | 0.92 | 0.94 | 13 |
| 643 | 0.44 | 1.1 | 1.03 | 0.97 | 1 | 1.18 | 0.94 | 0.66 | 0.46 | 1.06 | 2.89 | 1 |
| 670 | 0.61 | 1.17 | 1.09 | 0.58 | 1.15 | 1.06 | 0.73 | 0.96 | 2.84 | 1.15 | 1.45 | 4 |
| 726 | 0.64 | 0.59 | 0.86 | 0.05 | 0.97 | 1.02 | 0.26 | 0.91 | 1.19 | 0.95 | 3.4 | 2 |
| 850 | 1.91 | 3.48 | 9.38 | 33.49 | 11.36 | 1.01 | 3.9 | 1.62 | 0.72 | 1.3 | 1.01 | 16 |
| 853 | 3.58 | 0.99 | 1.84 | 9.52 | 1.03 | 1.17 | 1.44 | 0.77 | 1 | 1.15 | 0.35 | 9 |
| 935 | 5.09 | 1.39 | 1.1 | 3.94 | 0.77 | 1.02 | 0.28 | 1.57 | 0.62 | 0.89 | 0.93 | 4 |
| 940 | 0.22 | 1.72 | 1.01 | 0.41 | 1.41 | 1.61 | 0.56 | 0.62 | 0.62 | 3.54 | 0.79 | 4 |
|  | 8 | 7 | 7 | 7 | 6 | 6 | 6 | 6 | 6 | 4 | 4 |  |

Next, the genes that were over expressed in tumor (at least 2.5-fold) in the largest number of patients were selected. Other genes that were over expressed in tumor (at least 2.5-fold) in the remaining patients were selected to complement already selected genes, until each patient had at least one over expressed gene in the panel. Table 4 shows the genes most frequently over expressed in patients with WD prostate cancer.

TABLE 4

Genes Most Frequently Over Expressed in WD Prostate Cancer

| Gene Symbol | ERG | BICD1 | CACNA1D | CACNA1D | TMEFF2 | PSGR | CLDN8 | NPY | PSGR2 | HOXC6 | FOLH1 | SPARC | HPGD | |
|---|---|---|---|---|---|---|---|---|---|---|---|---|---|---|
| Probe ID | 213541_s_at | 214806_at | 210108_at | 1555993_at | 223557_s_at | 236121_at | 214598_at | 206001_at | 229768_at | 206858_s_at | 205860_x_at | 200665_s_at | 203914_x_at | |
| 298 | 39.34 | 34.48 | 6.35 | 1.95 | 3.23 | 121.51 | 6.98 | 22.05 | 42.19 | 1.29 | 1.32 | 0.08 | 1 | 8 |
| 318 | 0.82 | 8.6 | 2.16 | 1.75 | 44.24 | 209.74 | 13.65 | 3.69 | 0.29 | 2.46 | 9.55 | 0.71 | 1.69 | 6 |
| 343 | 35.13 | 6.49 | 5.23 | 2.55 | 97.73 | 296.76 | 68.64 | 180.35 | 4.14 | 1.46 | 3.57 | 0.74 | 1.02 | 10 |
| 349 | 17.21 | 5.07 | 18.52 | 8.07 | 31.46 | 58.87 | 1.77 | 59.22 | 18.61 | 4.34 | 1.72 | 2.56 | 1.12 | 10 |
| 359 | 15.9 | 3.03 | 55.69 | 32.54 | 9.6 | 0.47 | 8.58 | 2.92 | 3.83 | 6.03 | 1.75 | 0.19 | 1.04 | 9 |
| 376 | 9.18 | 11.18 | 26.82 | 15.84 | 114.62 | 2.99 | 6.14 | 11.66 | 148.45 | 1.12 | 6.07 | 0.58 | 0.85 | 10 |
| 430 | 1.33 | 0.89 | 1.78 | 4.55 | 0.6 | 1 | 0.6 | 1.7 | 0.7 | 1.49 | 0.2 | 1.34 | 1.05 | 1 |
| 455 | 27.62 | 2.91 | 10.1* | 3.3 | 2.33 | 1.37 | 1.02 | 4.8 | 0.84 | 2.89 | 1.28 | 0.37 | 1.05 | 6 |
| 458 | 1.18 | 0.67 | 0.65 | 0.76 | 1.27 | 18.67 | 7.88 | 0.63 | 1.51 | 1.62 | 0.04 | 0.54 | 1.25 | 2 |
| 479 | 6.93 | 5.61 | 2.54 | 2.15 | 9.38 | 29.22 | 6.22 | 5.57 | 31.16 | 0.98 | 1.97 | 0.93 | 1.06 | 8 |
| 480 | 6.82 | 6.99 | 6.6 | 2.7 | 37.05 | 83.45 | 6.72 | 28.13 | 1.15 | 7.8 | 4.61 | 0.77 | 1 | 10 |
| 488 | 0.84 | 0.31 | 0.95 | 0.64 | 0.01 | 0.07 | 3.27 | 1.77 | 0.04 | 0.99 | 0.83 | 1.15 | 1.01 | 1 |
| 504 | 17.83 | 5.49 | 4.6 | 1.39 | 1.04 | 0.49 | 4.68 | 1.6 | 57.51 | 1.4 | 0.78 | 0.11 | 1.08 | 5 |
| 506 | 5.26 | 1.51 | 4.05 | 1.54 | 0.17 | 0.5 | 1.05 | 0.84 | 67.95 | 0.51 | 0.32 | 0.51 | 1.07 | 3 |
| 521 | 12.86 | 3.07 | 0.94 | 1.51 | 10.15 | 311.24 | 2.32 | 2.15 | 1.43 | 1.25 | 0.04 | 0.7 | 0.96 | 4 |
| 532 | 21.37 | 4.59 | 3.54 | 1.42 | 17.76 | 9.41 | 11.44 | 1.69 | 0.22 | 17.6* | 4.23 | 1.52 | 1.03 | 8 |
| 553 | 33.34 | 8 | 13.29 | 4.5 | 3.87 | 8.48 | 2.03 | 0.87 | 0.8 | 2.14 | 1.35 | 0.7 | 1.01 | 6 |
| 589 | 4.78 | 3.59 | 2.44 | 0.66 | 6.34 | 45.56 | 0.87 | 0.28 | 0.68 | 2.21 | 0.54 | 0.39 | 1.21 | 4 |
| 618 | 23.69 | 5.44 | 8.76 | 3.37 | 8.48 | 1.46 | 1.62 | 0.84 | 1.09 | 3.34 | 0.21 | 0.77 | 1.08 | 6 |
| 704 | 21.15 | 1.15 | 4.16 | 1.45 | 15.94 | 10.41 | 6.82 | 0.05 | 2.25 | 7.71 | 0.76 | 0.43 | 0.98 | 6 |
|  | 16 | 15 | 14.** | 9 | 14 | 13 | 12 | 9 | 8 | 7 | 5 | 1 | 0 |  |
| Percentage | 80 | 75 | 70.** | 45 | 70 | 65 | 60 | 45 | 40 | 35 | 25 | 5 | 0 | 0 |

Table 5 shows the genes most frequently over expressed in patients with PD prostate cancer.

TABLE 5

Genes Most Frequently Over Expressed in PD Prostate Cancer

| Gene Symbol | CLDN8 | HOXC6 | PSGR | CACNA1D | CACNA1D | FOLH1 | TMEFF2 | PSGR2 | BICD1 | NPY | ERG | SPARC | HPGD | |
|---|---|---|---|---|---|---|---|---|---|---|---|---|---|---|
| Probe ID | 214598_at | 206858_s_at | 236121_at | 210108_at | 1555993_at | 205860_x_at | 223557_s_at | 229768_at | 214806_at | 206001_at | 213541_s_at | 200665_s_at | 203914_x_at | |
| 320 | 43.19 | 13.24 | 27.34 | 5.96 | 1.79 | 57.82 | 3.8 | 4.69 | 14.58 | 2.67 | 0.96 | 0.53 | 0.66 | 9 |
| 326 | 24.95 | 32.63 | 6.43 | 5.33 | 5.34 | 1.11 | 1.55 | 0.11 | 5.37 | 0.32 | 0.58 | 0.24 | 0.2 | 6 |
| 346 | 0.1 | 1 | 0.06 | 1.63 | 1.23 | 1.49 | 0.79 | 0.91 | 1.26 | 0.98 | 0.79 | 0.86 | 1 | 0 |
| 347 | 3.1 | 0.93 | 0.89 | 51.54 | 11.18 | 1.64 | 0.95 | 12.21 | 4.56 | 1.57 | 29.57 | 1.31 | 0.98 | 6 |
| 393 | 4.03 | 6.15 | 0.38 | 1.19 | 0.8 | 2.31 | 0.79 | 32.59 | 0.95 | 0.04 | 1.02 | 1.86 | 1.33 | 3 |
| 413 | 126.11 | 3.62 | 0.28 | 17.59 | 9.95 | 13.3 | 4.76 | 0.32 | 7.63 | 0.03 | 23.28 | 7.22 | 7.49 | 10 |
| 468 | 3.59 | 0.92 | 0.65 | 0.73 | 1.46 | 1.01 | 0.27 | 0.81 | 0.79 | 1.76 | 0.85 | 1.98 | 1.05 | 1 |
| 473 | 56.26 | 0.93 | 32.46 | 11.89 | 2.13 | 28.14 | 0.23 | 80 | 1.99 | 81.17 | 21.07 | 0.97 | 0.81 | 7 |
| 513 | 0.78 | 2.13 | 6.68 | 1.09 | 1.47 | 0.82 | 84.88 | 0.98 | 0.92 | 4.21 | 1.01 | 2.61 | 0.74 | 6 |
| 535 | 2.95 | 23.56 | 14.1 | 2.08 | 1.47 | 5.51 | 0.01 | 1.28 | 2.64 | 19.79 | 0.89 | 10.52 | 0.97 | 7 |
| 564 | 9.46 | 17.56 | 12.25 | 7.95 | 2.22 | 20.21 | 367.89 | 19.82 | 9.04 | 1.14 | 25.27 | 1.24 | 1.19 | 9 |
| 573 | 4.02 | 8.75 | 3.27 | 1.32 | 1.58 | 3.51 | 17.19 | 1.02 | 1.91 | 0.07 | 1.07 | 5.94 | 3.17 | 7 |
| 616 | 132.78 | 10.08 | 9.97 | 12.29 | 1.81 | 70.01 | 0.58 | 1.31 | 1.08 | 1.69 | 3.38 | 11.94 | 0.94 | 7 |
| 643 | 1.19 | 0.45 | 0.85 | 0.51 | 1.2 | 1.2 | 0.97 | 1.05 | 1.1 | 0.97 | 1 | 0.46 | 2.89 | 1 |
| 670 | 1.02 | 1.08 | 10.74 | 0.98 | 1.14 | 1.6 | 4.58 | 0.34 | 1.17 | 0.58 | 1.15 | 2.84 | 1.45 | 3 |
| 726 | 0.23 | 2.2 | 0.42 | 0.99 | 1.11 | 0.16 | 0.48 | 0.87 | 0.59 | 0.05 | 0.97 | 1.19 | 3.4 | 1 |
| 850 | 1.03 | 16.77 | 85.07 | 7.7 | 1.81 | 12.39 | 369.17 | 78.53 | 3.48 | 33.49 | 11.36 | 0.72 | 1.04 | 9 |
| 853 | 2.98 | 13.23 | 0.91 | 4.21 | 1.49 | 2.54 | 145.11 | 10.43 | 0.99 | 9.52 | 1.03 | 1 | 0.35 | 7 |
| 935 | 2.48 | 1.09 | 0.41 | 0.83 | 0.82 | 1.72 | 1.99 | 1.09 | 1.39 | 3.94 | 0.77 | 0.62 | 0.93 | 1 |
| 940 | 0.46 | 1.01 | 0.97 | 0.74 | 1.41 | 0.98 | 4.01 | 13.74 | 1.72 | 0.41 | 1.41 | 0.62 | 0.79 | 2 |
|  | 12 | 10 | 10 | 9 | 3 | 9 | 9 | 8 | 7 | 7 | 6 | 6 | 4 | |
| Percentage | 60 | 50 | 50 | 45 | 15 | 45 | 45 | 40 | 35 | 35 | 30 | 30 | 20 | |

Two main types of patients were discovered in the patient-by-patient gene expression table. Type A patients over expressed many (8 to 20) candidate genes in their tumor. A total of 30 patients were Type A: 17 of 20 (85%) with WD tumor and 13 of 20 (65%) with PD tumor. Type B patients over expressed only a few (1 to 4) candidate genes in their tumor. A total of 10 patients were Type B: 3 of 20 (15%) with WD tumor and 7 of 20 (35%) with PD tumor (Tables 2-3).

Figure 2:
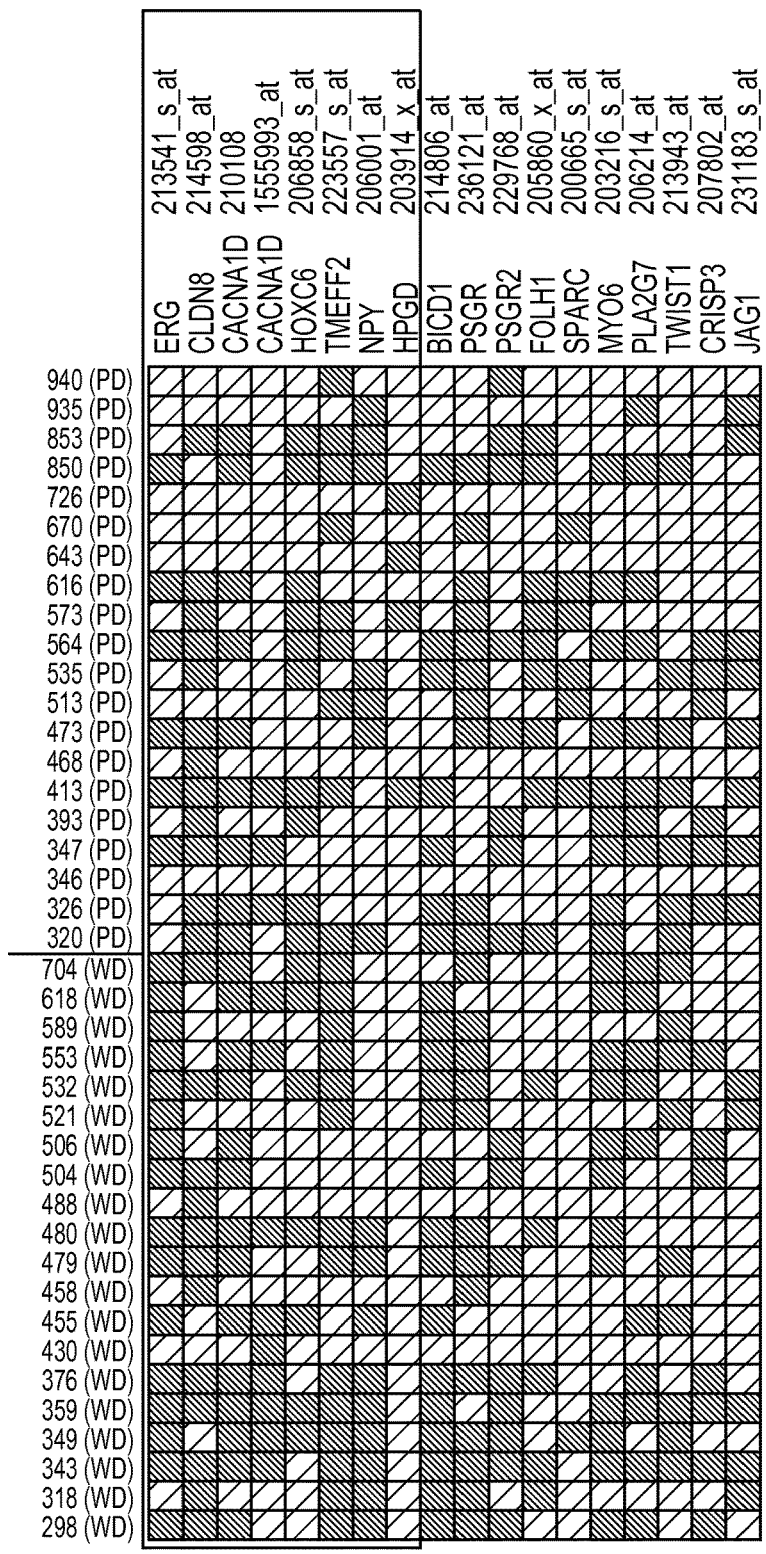
FIG. 2 shows a heatmap of an extended gene panel (17 genes) in the 40-patient cohort. Shaded boxes indicate an increased expression of at least 2.5 fold relative to a control sample.
Figure 3:
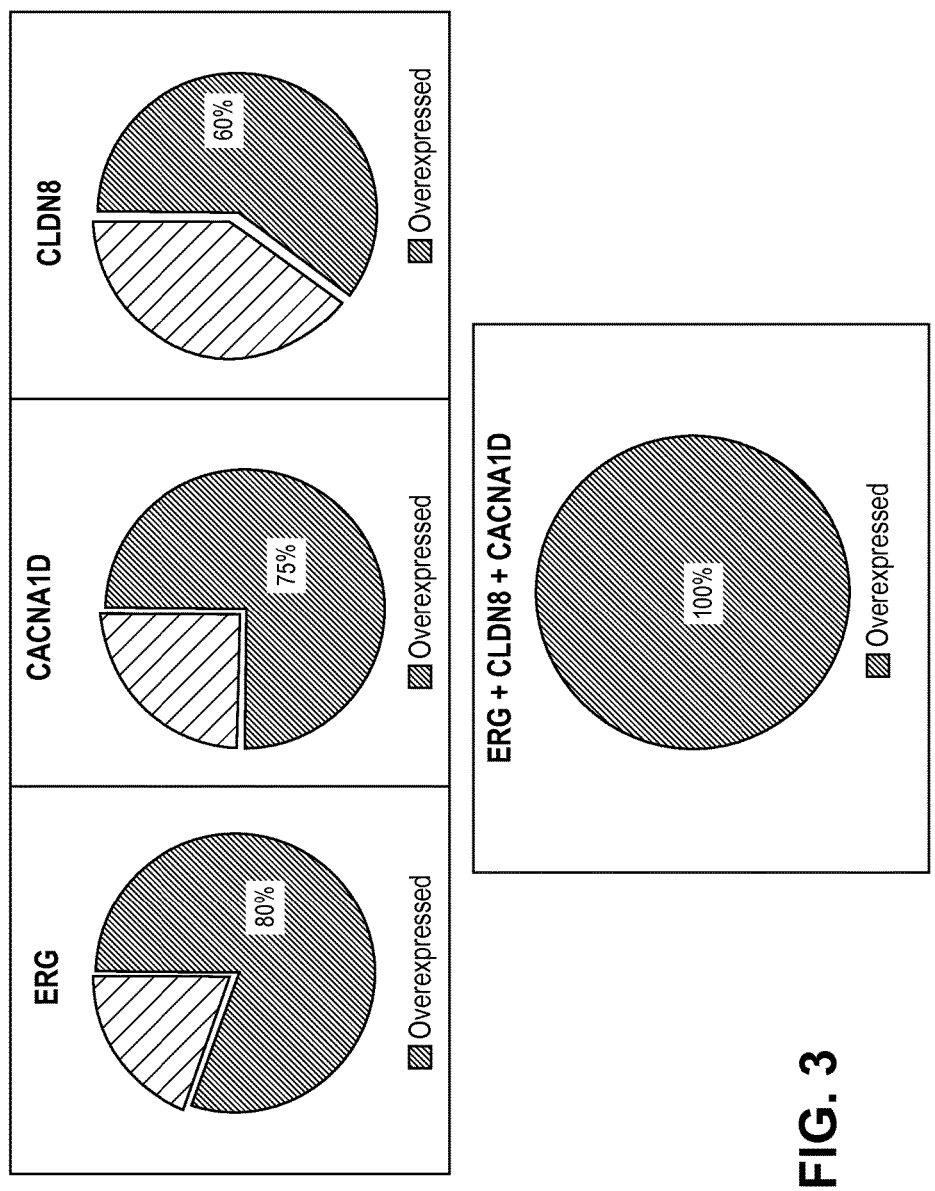
FIG. 3 shows the performance of a 3-gene panel (ERG, CACNA1D, and CLDN8) in patients with WD tumor (N=20). 100% of the patients over expressed at least one of the three genes.

The performance of the prostate cancer gene expression profile panel is presented in a heat-map format to demonstrate the complementary nature of the genes in the panel across different patients (FIGS. 1-2). A minimum gene panel to detect WD prostate cancer comprises three genes: ERG, CLDN8 and CACNA1D (FIG. 3). A minimum gene panel to detect PD prostate cancer comprises five genes: CLDN8, HOXC6, TMEFF2, NPY and HPGD (FIG. 4). Combining these two minimum panels results in a minimum gene panel to detect WD and/or PD prostate cancer that comprises seven genes: c) (FIG. 5). Five secondary genes were added (BICD1, PSGR, PSGR2, FOLH1 and SPARC) to the 7-gene panel to generate a 12-gene panel and provide multiple gene coverage for the majority of patients, as shown in Table 6.

TABLE 6

12-Gene Panel in WD and PD Prostate Cancer

| Gene | In WD tumors | In PD tumors |
|---|---|---|
| ERG | 80% | 30% |
| CLDN8 | 60% | 60% |
| CACNA1D * | 75% | 45% |
| TMEFF2 | 70% | 45% |
| BICD1 | 65% | 50% |
| PSGR | 65% | 50% |
| NPY | 45% | 35% |
| HOXC6 | 35% | 50% |
| PSGR2 | 40% | 40% |
| FOLH1 | 25% | 45% |
| SPARC | 5% | 30% |
| HPGD | 0% | 20% |
| 12-gene panel | 100% | 95% |

*: two probes combined.

The potential performance of this prostate cancer gene panel is best in patients with WD tumor (the majority of prostate cancer patients in PSA-screened populations). In patient cohorts with more PD tumor (more Type B patients), additional genes (PLA2G7, MYO6, CRISP3, TWIST1 and JAG1) could be beneficial to consider for expanding the panel, due to the good performance of these genes in PD tumor (Table 1). In most PSA-screened populations only about 10-15% of unselected patients have PD tumors (the 20 PD patients in our GeneChip cohort were selected from over 300 patients).

Figure 6:
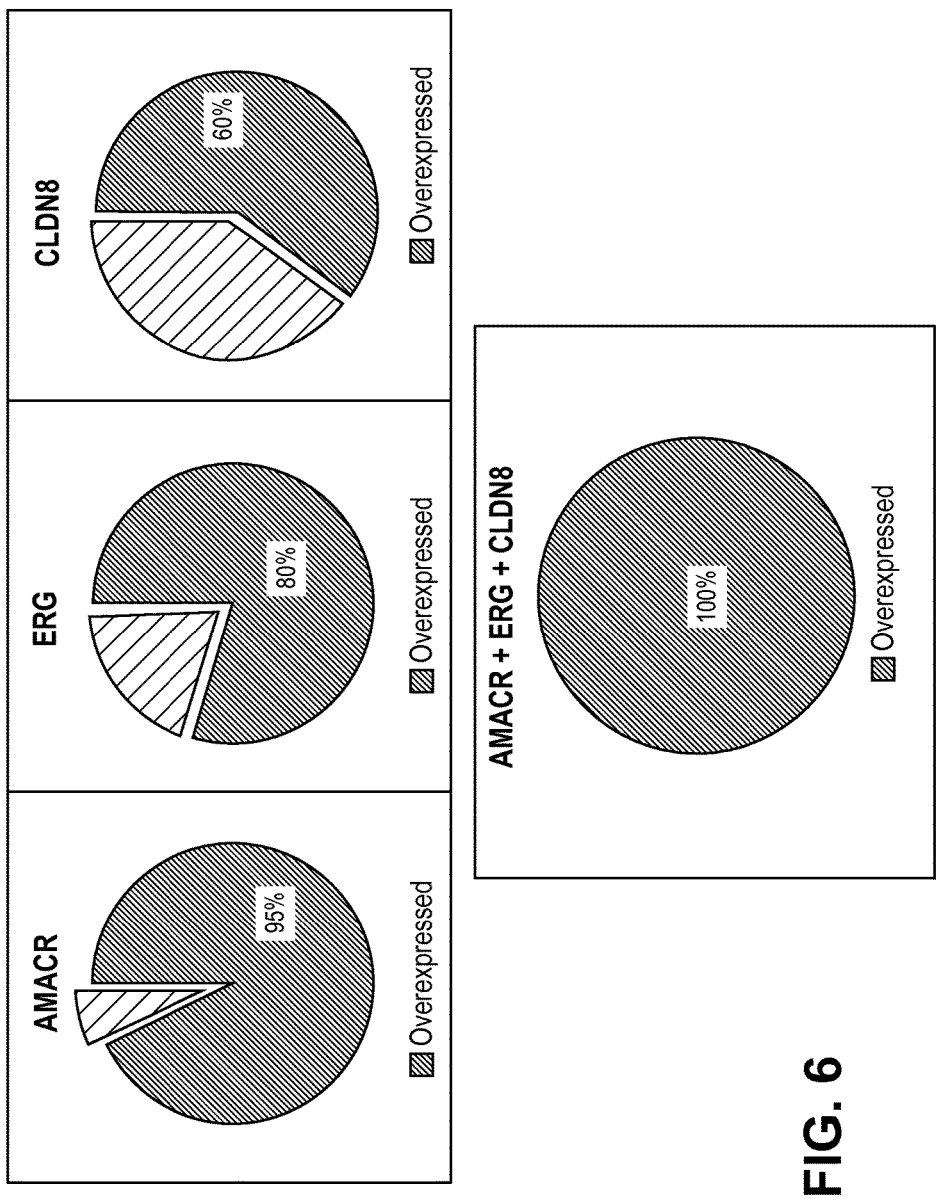
FIG. 6 shows the performance of a 3-gene panel (AMACR, ERG, and CLDN8) in patients with WD tumor (N=20). 100% of the patients over expressed at least one of the three genes.
Figure 7:
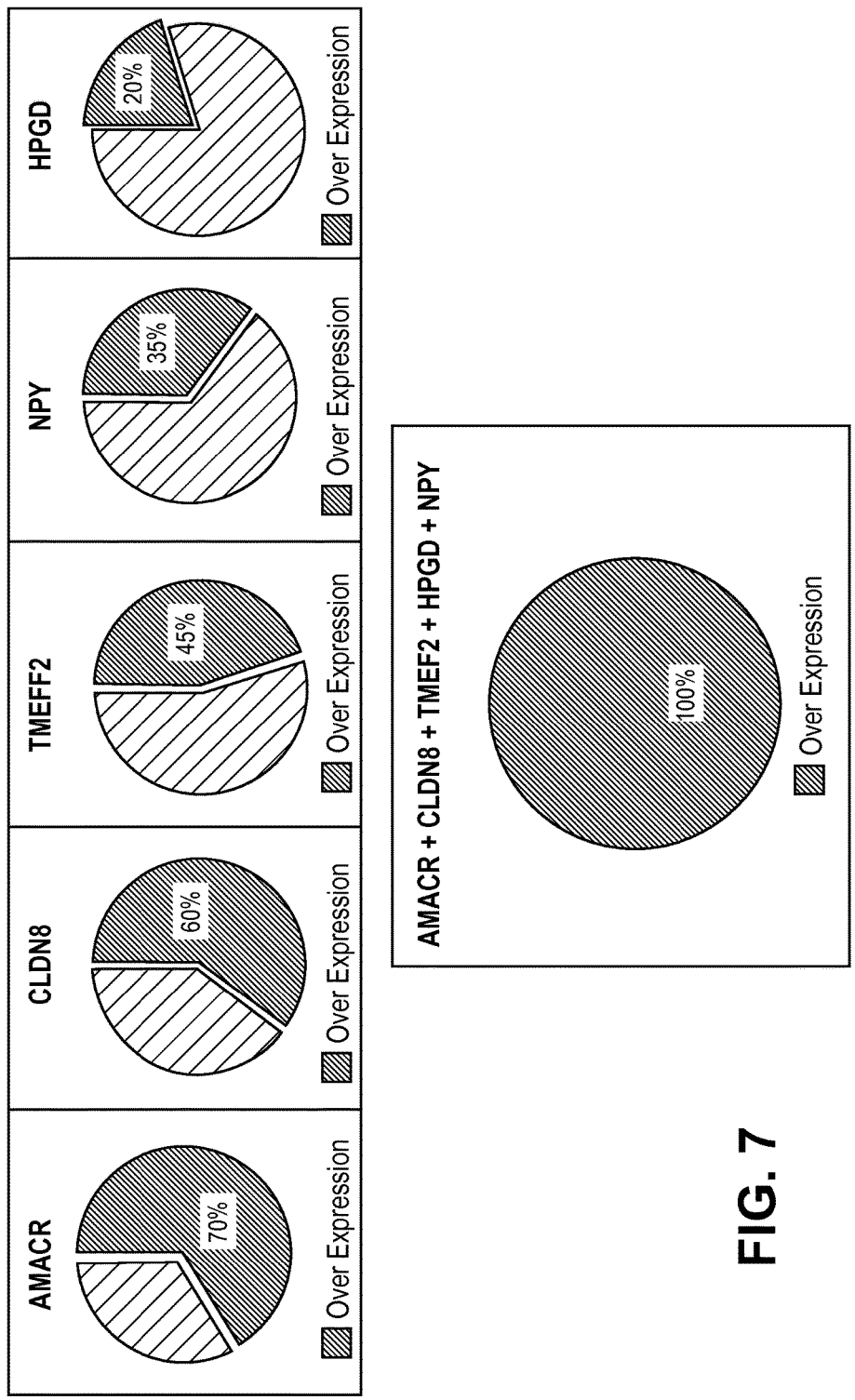
FIG. 7 shows the performance of a 5-gene panel (AMACR, CLDN8, TMEFF2, NPY, and HPGD) in patients with PD tumor (N=20). 100% of the patients over expressed at least one of the five genes.
Figure 8:
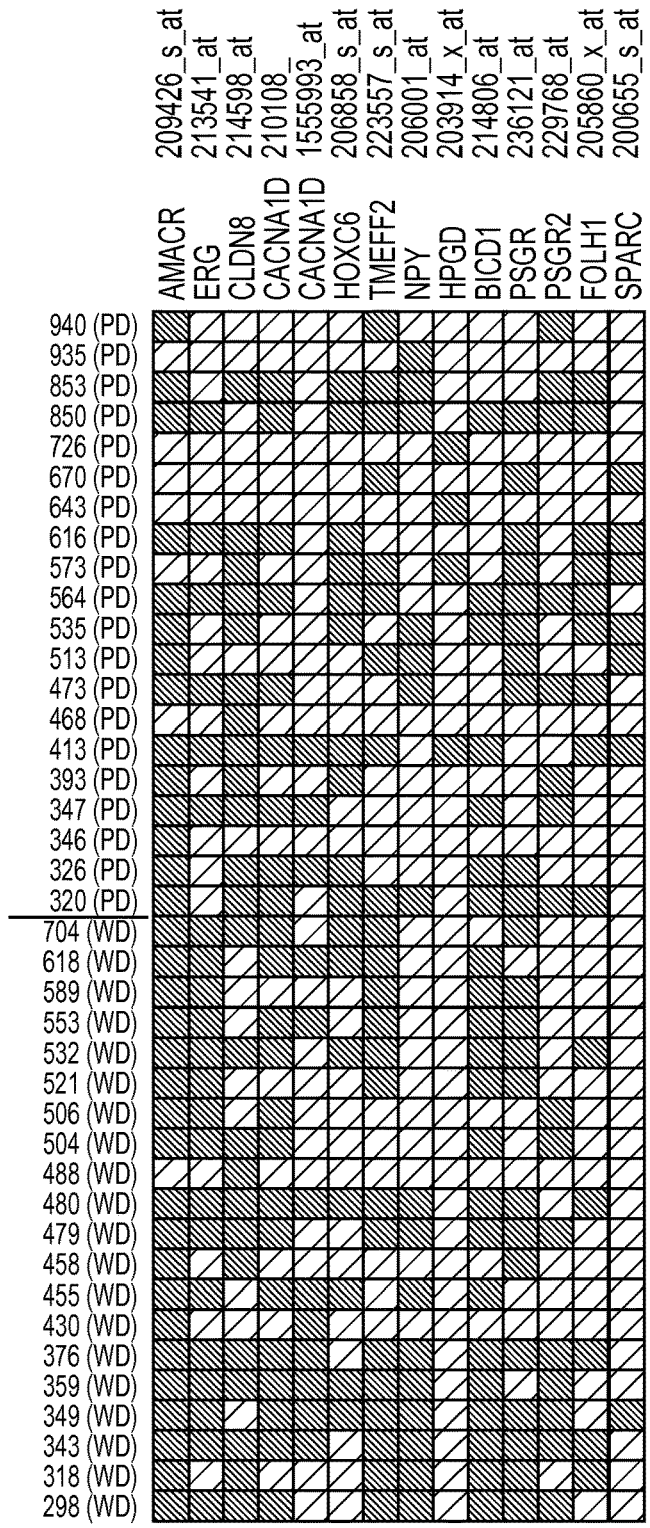
FIG. 8 shows a heatmap of an extended gene panel (13 genes) in the 40-patient cohort. Shaded boxes indicate an increased expression of at least 2.5 fold relative to a control sample.

We also used the AMACR gene, which is highly over expressed in prostate cancer (see Table 1) to improve the diagnostic gene panel. AMACR was used to replace CACNA1D in a 3-gene panel for detecting WD prostate cancer. Using this 3-gene panel, we detected over expression of at least one of the three genes in 100% of the patients with WD prostate cancer (FIG. 6). AMACR was also used in an alternative minimum gene panel to detect PD prostate cancer comprising the following five genes: AMACR, CLDN8, TMEFF2, NPY and HPGD. Over expression of at least one of these five genes was detected in 100% of the patients with PD prostate cancer (FIG. 7). By adding AMACR, the 7-gene panel was reduced to 6 genes, with the AMACR gene replacing the HOXC6 and CACNA1D. The 6-gene panel comprises the following genes: AMACR, ERG, CLDN8, TMEFF2, NPY and HPGD. The performance of the prostate cancer gene expression profile panel is presented in a heat-map format to demonstrate the complementary nature of the genes in the panel across different patients (FIG. 8).

An alternative gene panel to detect prostate cancer comprises the following genes: ERG, PSGR, PCGEM1, PMEPA1, and LTF. As measured by QRT-PCR in laser microdissected prostate tissue (N=78 samples), the expression of the ERG, PSGR and PCGEM1 genes are frequently up-regulated, while the expression of the PMEPA1 and LTF genes are frequently down-regulated in prostate cancer cells as shown in Table 7.

TABLE 7

Average Levels of Over Expression or Decreased Expression in Tumor

| FP | ERG | PSGR | PCGEM1 | PMEPA1 | LTF |
|---|---|---|---|---|---|
| 320 | 1 | 1.55 | 0.1 | 0.55 | 0.01 |
| 326 | 0.02 | 8.51 | 4.56 | 3.85 | 0.13 |
| 346 | 1 | 0.08 | 1 | 2.52 | 0.02 |
| 393 | 6.86 | 0.19 | 1 | 0.11 | 0.22 |
| 413 | 3182.57 | 0.15 | 0 | 0.18 | 0.02 |
| 468 | 22.15 | 0.88 | 0.27 | 0.07 | 0 |
| 473 | 638.59 | 10.78 | 1 | 0.38 | 0.04 |
| 513 | 494.09 | 11.2 | 18053.61 | 5.7 | 0 |
| 564 | 1.55 | 2.55 | 1 | 0.12 | 3728076 |
| 298 | 9.23 | 4.81 | 0.12 | 0.23 | 0.3 |
| 318 | 1 | 179.77 | 729.11 | 0.46 | 0.04 |
| 343 | 779.03 | 3.53 | 0.01 | 0.17 | 0 |
| 349 | 821.8 | 1.03 | 1251.98 | 0.37 | 0 |
| 359 | 707.87 | 0.26 | 0 | 0.1 | 1.22 |
| 376 | 0.06 | 1.78 | 1 | 0.55 | 0 |
| 430 | 2361.06 | 3588 | 5042.77 | 0.57 | 0 |
| 455 | 70.59 | 0.41 | 0.1 | 0.29 | 0.87 |
| 458 | 3009.69 | 72 | 1 | 0.46 | 0.1 |
| 480 | 238.08 | 41.07 | 67847.12 | 0.77 | 0.01 |
| 488 | 0.78 | 1.29 | 0.52 | 0.37 | 4.26 |
| 504 | 3469.21 | 0.01 | 1 | 0.18 | 0.87 |
| 506 | 20.54 | 2.58 | 0 | 0.24 | 0.55 |
| 521 | 19064.25 | 113.77 | 1 | 0.08 | 0 |
| 532 | 6586.34 | 28.64 | 0.02 | 1.19 | 0 |
| 203 | 1.15 | 1.77 | 7.26 | 5.15 | 1.49 |
| 232 | 101.34 | 0.15 | 0 | 0.07 | 0 |
| 238 | 2.33 | 74.54 | 1509.65 | 0.37 | 0 |
| 247 | 1 | 7.11 | 3.18 | 0.69 | 402882.6 |
| 251 | 40.25 | 31.02 | 0.79 | 0.34 | 0.98 |
| 253 | 1 | 34.42 | 0.89 | 1.1 | 0.65 |
| 257 | 0.02 | 24.93 | 8.11 | 6.96 | 0 |
| 261 | 209.23 | 253.35 | 4.69 | 0.64 | 0 |
| 278 | 617.11 | 21.41 | 989.12 | 0.46 | 17.39 |
| 291 | 298.97 | 4.01 | 1 | 0.03 | 0 |
| 302 | 15.26 | 0.05 | 16.34 | 0 | 0.22 |
| 310 | 1 | 1.66 | 0 | 0.19 | 0.6 |

TABLE 7-continued

Average Levels of Over Expression or Decreased Expression in Tumor

| FP | ERG | PSGR | PCGEM1 | PMEPA1 | LTF |
|---|---|---|---|---|---|
| 331 | 2712.99 | 0.53 | 0 | 0.33 | 7.65 |
| 337 | 443.8 | 6.52 | 1.47 | 0.93 | 0.01 |
| 355 | 3629.8 | 10.13 | 1 | 1.2 | 0 |
| 363 | 85.18 | 749.61 | 719.08 | 1.31 | 0.05 |
| 369 | 2347.4 | 2.24 | 0.07 | 0.18 | 0 |
| 370 | 1.85 | 60.97 | 2721.15 | 0.13 | 0 |
| 385 | 1 | 1.2 | 0 | 0.05 | 0.02 |
| 387 | 1 | 41.21 | 8.06 | 1.31 | 0 |
| 391 | 1.4 | 0.18 | 0 | 0.08 | 0 |
| 394 | 118.13 | 5.54 | 0 | 0.67 | 0.83 |
| 402 | 172.09 | 35.51 | 7.89 | 2.01 | 2.77 |
| 414 | 0.55 | 0.69 | 0.07 | 0.06 | 5.52 |
| 424 | 0.23 | 398.93 | 0.58 | 0.08 | 2.69 |
| 441 | 36327.39 | 8.2 | 0 | 1.3 | 0.11 |
| 446 | 112.12 | 0.38 | 6.68 | 0.26 | 3.32 |
| 448 | 1754.8 | 25.11 | 5220.6 | 1.48 | 0.18 |
| 449 | 43.16 | 2.01 | 8.57 | 0.6 | 1.02 |
| 457 | 54.31 | 173.65 | 4837.35 | 0.63 | 0 |
| 472 | 1 | 10.27 | 292.04 | 0.45 | 0.54 |
| 483 | 1 | 1.99 | 8.69 | 0.03 | 417090.2 |
| 484 | 3674.2 | 3.63 | 249 | 0.39 | 0 |
| 485 | 2605.74 | 88.65 | 1629.26 | 0.23 | 1883520 |
| 489 | 4.87 | 34.42 | 188.71 | 0.82 | 0.02 |
| 490 | 0.02 | 0.54 | 1.02 | 0.87 | 0 |
| 493 | 0.01 | 5.64 | 0 | 0.04 | 0 |
| 495 | 1 | 8.43 | 108700.57 | 18.93 | 0 |
| 507 | 0.02 | 5.46 | 1.15 | 0 | 0 |
| 510 | 11.44 | 1.89 | 0.14 | 2.62 | 0.84 |
| 519 | 1380.23 | 0.53 | 0 | 0.17 | 0 |
| 523 | 798.73 | 1234.75 | 186.11 | 1.85 | 0 |
| 526 | 0.45 | 0.42 | 0 | 0.2 | 0.55 |
| 527 | 0.37 | 0.12 | 508.46 | 0.21 | 0 |
| 528 | 4.76 | 2.68 | 1 | 2.07 | 0.05 |
| 534 | 7320.38 | 4.58 | 1332.57 | 0.45 | 59681.66 |
| 538 | 66.2 | 1.99 | 1128.35 | 0.37 | 0.01 |
| 541 | 1 | 2.55 | 6.54 | 1.05 | 121.52 |
| 545 | 1 | 0.02 | 0.01 | 0.21 | 8.57 |
| 548 | 112 | 0.38 | 5.7 | 0.19 | 0 |
| 554 | 0.82 | 1.48 | 13.93 | 0.15 | 0 |
| 594 | 2029.93 | 0.5 | 0 | 0.06 | 0.93 |
| 605 | 23839.77 | 0.23 | 0.05 | 0.77 | 0.08 |

Figure 9:
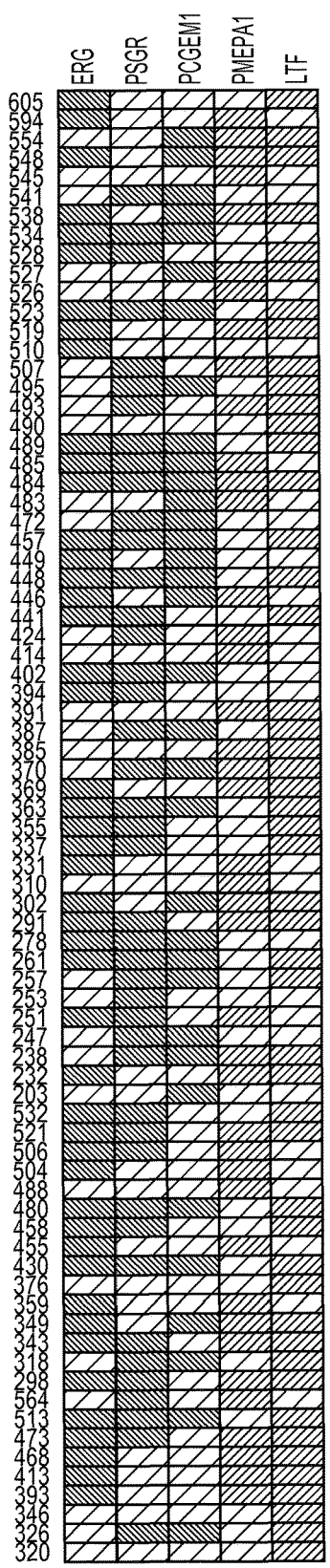
FIG. 9 shows a heatmap of an alternative gene panel (ERG, PSGR, PCGEM1, PMEPA1, and LTF) analyzed by QRT-PCR TaqMan® (Life Technologies, Carlsbad, Calif.) assay in a 78-patient cohort. The darker shaded boxes for ERG, PSGR, and PCGEM1 indicate an increased expression of at least 2.5 fold relative to a control sample, while the lighter shaded boxes for PMEPA1 and LTF indicate a decreased or reduced expression by at least 2.5 fold relative to a control sample.
Figure 10:
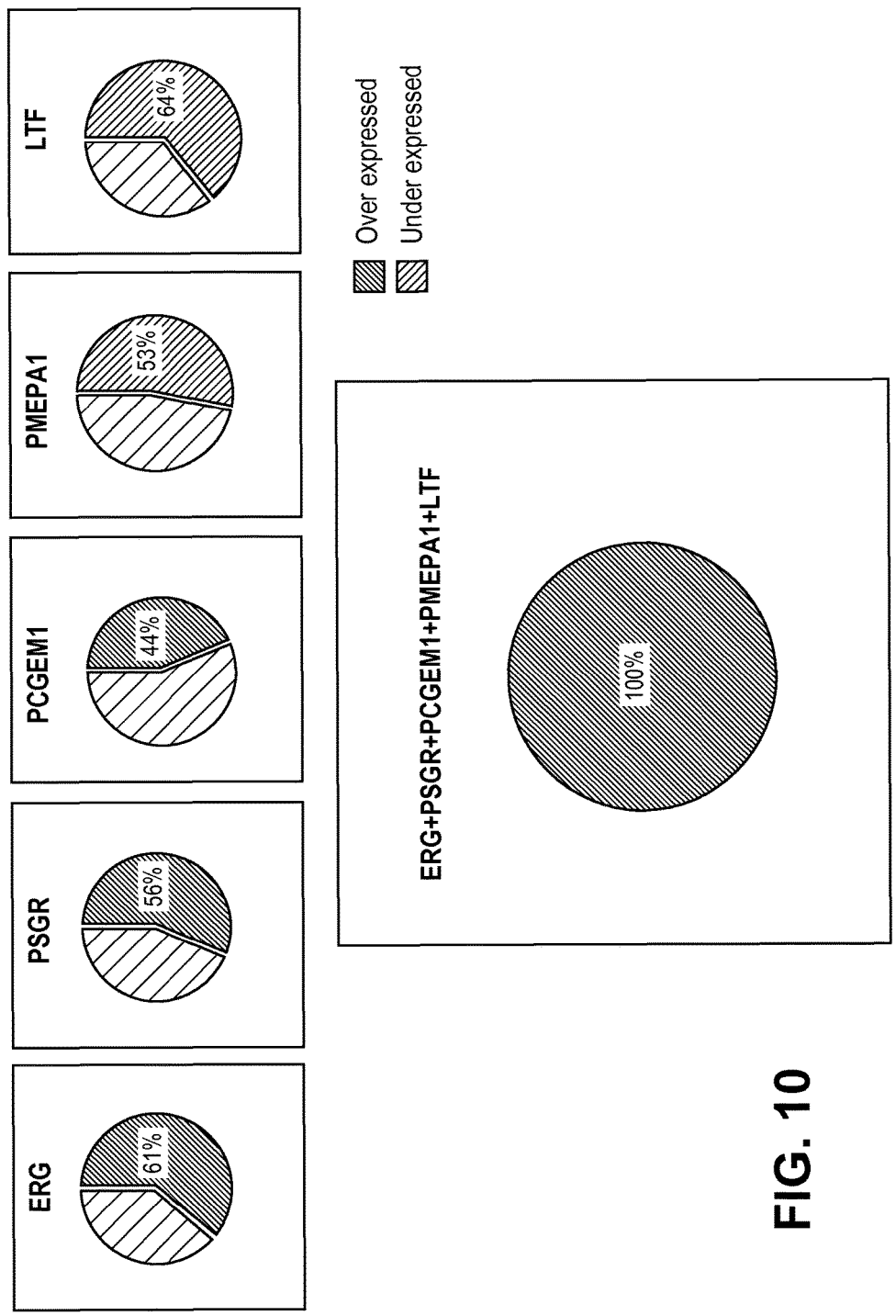
FIG. 10 shows the performance of 5-gene panel (ERG, PSGR, PCGEM1, PMEPA1, and LTF) in a 78-patient cohort. 100% of the patients over expressed at least one of the five genes.

Over expression of at least one of ERG, PSGR, or PCGEM1 or decreased expression of at least one of PMEPA1 or LTF was detected in 100% of the samples in the 78-patient cohort (FIG. 10). The performance of the prostate cancer gene expression profile panel is presented in a heat-map format to demonstrate the complementary nature of the genes in the panel across different patients (FIG. 9).

A gene panel to distinguish between WD (better prognosis) and PD (worse prognosis) tumors was also developed. The eight candidate genes, which have stronger average up-regulation in PD than in WD tumors compared to normal prostate epithelial cells in the same prostate, are listed in Table 8.

TABLE 8

Candidate Prognostic Prostate Cancer Markers

| Serial number | Probe-sets | Gene Symbol | Average T vs N (PD) | Average T vs N (WD) |
|---|---|---|---|---|
| 1 | 218309_at | CAMK2N1 | 6.21 | 3.3 |
| 2 | 204388_s_at | MAOA | 5.37 | 2.27 |
| 3 | 205860_x_at | FOLH1 | 4.06 | 2.36 |
| 4 | 215076_s_at | COL3A1 | 3.06 | 1.71 |
| 5 | 1556499_s_at | COL1A1 | 2.4 | 1.15 |
| 6 | 203914_x_at | HPGD | 2.01 | 1.65 |
| 7 | 209022_at | STAG2 | 1.84 | 1.37 |
| 8 | 200665_s_at | SPARC | 1.66 | 1.12 |

The tumor over normal data for each of the eight candidate genes in each of the 20 PD prostate cancer patients is set forth in Table 9.

TABLE 9

Tumor vs. Normal Ratios in Patients with PD Prostate Cancer

| Gene Symbol | MAOA | COL3A1 | FOLH3 | STAG2 | COL1A1 | CAMK2N3 | SPARC | HRGD | |
|---|---|---|---|---|---|---|---|---|---|
| Probe ID | 204388_s_at | 215076_s_at | 205860_x_at | 209022_at | 1556499_s_at | 218309_at | 200665_s_at | 203914_x_at | |
| 320 | 3.15 | 0.88 | 57.82 | 9.01 | 0.14 | 2.76 | 0.53 | 0.66 | 4 |
| 326 | 5.41 | 0.55 | 1.11 | 1.75 | 0.6 | 0.71 | 0.24 | 0.2 | 1 |
| 346 | 0.93 | 0.71 | 1.49 | 1.06 | 0.14 | 1.02 | 0.86 | 1 | 0 |
| 347 | 4.16 | 2.38 | 1.64 | 11.44 | 4.12 | 4.05 | 1.31 | 0.98 | 4 |
| 393 | 3.25 | 22.71 | 2.31 | 2.82 | 3.11 | 3.88 | 1.86 | 1.33 | 5 |
| 413 | 5.81 | 6.97 | 13.3 | 2.53 | 1.09 | 63.91 | 7.22 | 7.49 | 7 |
| 468 | 1.11 | 3.35 | 1.01 | 2 | 18.77 | 1.19 | 1.98 | 1.05 | 2 |
| 473 | 1.34 | 2.57 | 28.14 | 9.41 | 1.13 | 1.34 | 0.97 | 0.81 | 3 |
| 513 | 0.41 | 6.56 | 0.82 | 0.19 | 4.43 | 0.56 | 2.61 | 0.74 | 3 |
| 535 | 25.15 | 106.01 | 5.51 | 3.17 | 13.13 | 2.58 | 10.52 | 0.97 | 7 |
| 564 | 5.4 | 3.99 | 20.21 | 3.16 | 0.93 | 1.72 | 1.24 | 1.19 | 4 |
| 573 | 1.02 | 3.24 | 3.51 | 9.19 | 0.52 | 1.14 | 5.94 | 3.17 | 5 |
| 616 | 8.43 | 85.78 | 70.01 | 2.54 | 58.23 | 2.43 | 11.94 | 0.94 | 6 |
| 643 | 1.68 | 0.54 | 1.2 | 0.81 | 0.11 | 0.55 | 0.46 | 2.89 | 1 |
| 670 | 0.89 | 2.19 | 1.6 | 0.42 | 16.27 | 0.38 | 2.84 | 1.45 | 2 |
| 726 | 0.47 | 3.13 | 0.16 | 0.63 | 1.95 | 1.28 | 1.19 | 3.4 | 2 |
| 850 | 1.51 | 0.5 | 12.39 | 2.45 | 0.68 | 13.68 | 0.72 | 1.04 | 2 |
| 853 | 5.58 | 0.61 | 2.54 | 0.24 | 1.55 | 0.88 | 1 | 0.35 | 2 |
| 935 | 4.5 | 0.7 | 1.72 | 1.36 | 0.4 | 1.24 | 0.62 | 0.93 | 1 |
| 940 | 0.23 | 0.23 | 0.98 | 0.26 | 0.51 | 0.17 | 0.62 | 0.79 | 0 |
| | 11 | 10 | 9 | 9 | 7 | 6 | 6 | 4 | |
| Percentage | 55 | 50 | 45 | 45 | 35 | 30 | 30 | 20 | |

The tumor over normal data for each of the eight candidate genes in each of the 20 WD prostate cancer patients is set forth in Table 10.

TABLE 10

| | \multicolumn{8}{c}{Tumor vs. Normal Ratios in Patients with WD Prostate Cancer} |

| Gene Symbol | FOLH1 | MAC1A | COL3A1 | STAG2 | COL1A1 | CAMK2N1 | SPARC | HPGD |
|---|---|---|---|---|---|---|---|---|
| Probe ID | 205860_x_at | 204388_s_at | 215076_s_at | 209022_at | 1556499_s_at | 218309_at | 200665_s_at | 203914_x_at |
| 298 | 1.32 | 0.33 | 0.03 | 0.53 | 0.01 | 0.27 | 0.08 | 1 | 0 |
| 318 | 9.55 | 15.53 | 1.45 | 2.19 | 0.39 | 0.22 | 0.71 | 1.69 | 2 |
| 343 | 3.57 | 7.41 | 1.05 | 8.46 | 0.88 | 1.81 | 0.74 | 1.02 | 3 |
| 349 | 1.72 | 1.22 | 6.81 | 0.89 | 5.24 | 1.21 | 2.56 | 1.12 | 3 |
| 359 | 1.75 | 1.4 | 0.06 | 1.05 | 0.25 | 0.98 | 0.19 | 1.04 | 0 |
| 376 | 6.07 | 2.3 | 1.01 | 0.42 | 0.31 | 2.71 | 0.58 | 0.85 | 2 |
| 430 | 0.2 | 0.68 | 1.13 | 0.87 | 2.98 | 1.33 | 1.34 | 1.05 | 1 |
| 455 | 1.28 | 0.77 | 0.45 | 0.56 | 0.65 | 0.36 | 0.37 | 1.05 | 0 |
| 458 | 0.04 | 0.41 | 0.23 | 0.39 | 0.33 | 0.79 | 0.54 | 1.25 | 0 |
| 479 | 1.97 | 1.74 | 1.02 | 2.12 | 0.18 | 1.29 | 0.93 | 1.06 | 0 |
| 480 | 4.61 | 0.55 | 4.7 | 2.54 | 0.83 | 0.6 | 0.77 | 1 | 3 |
| 488 | 0.83 | 1.16 | 1.39 | 0.76 | 8.5 | 0.75 | 1.15 | 1.01 | 1 |
| 504 | 0.78 | 1.11 | 0.1 | 0.64 | 0.33 | 0.49 | 0.11 | 1.08 | 0 |
| 506 | 0.32 | 1.88 | 0.72 | 1.4 | 0.58 | 1 | 0.51 | 1.07 | 0 |
| 521 | 0.04 | 1.88 | 0.73 | 1.73 | 0.45 | 1 | 0.7 | 0.96 | 0 |
| 532 | 4.23 | 5.19 | 2.7 | 1.94 | 1.31 | 1.73 | 1.52 | 1.03 | 3 |
| 553 | 1.35 | 1.8 | 1.35 | 3.9 | 0.38 | 0.74 | 0.7 | 1.01 | 1 |
| 589 | 0.54 | 0.09 | 0.29 | 0.22 | 0.15 | 0.37 | 0.39 | 1.21 | 0 |
| 618 | 0.21 | 0.79 | 1.33 | 1 | 1.02 | 0.62 | 0.77 | 1.08 | 0 |
| 704 | 0.76 | 3.26 | 1.33 | 1.73 | 1.28 | 0.7 | 0.43 | 0.98 | 1 |
| | 5 | 4 | 3 | 3 | 3 | 1 | 1 | 0 |
| Percentage | 25 | 20 | 15 | 15 | 15 | 5 | 5 | 0 |

Figure 11:
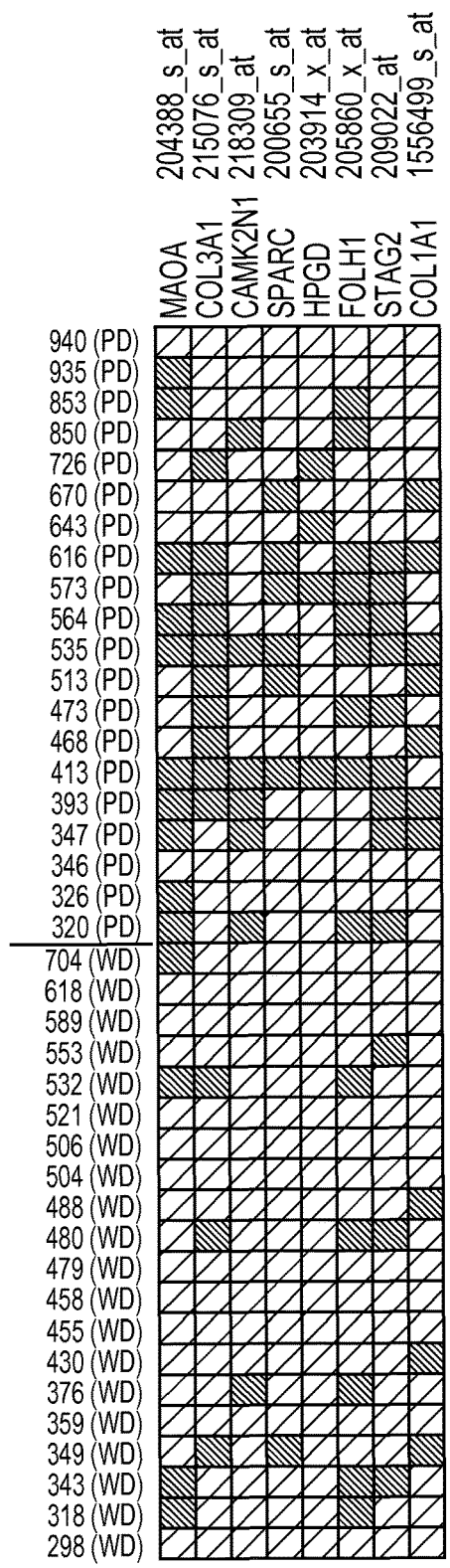
FIG. 11 shows a heatmap of a gene panel (MAOA, COL3A1, CAMK2N1, SPARC, HPGD, FOLH1, STAG2, and COL1A1) in the 40-patient cohort. Shaded boxes indicate an increased expression of at least 2.5 fold relative to a control sample.
Figure 12:
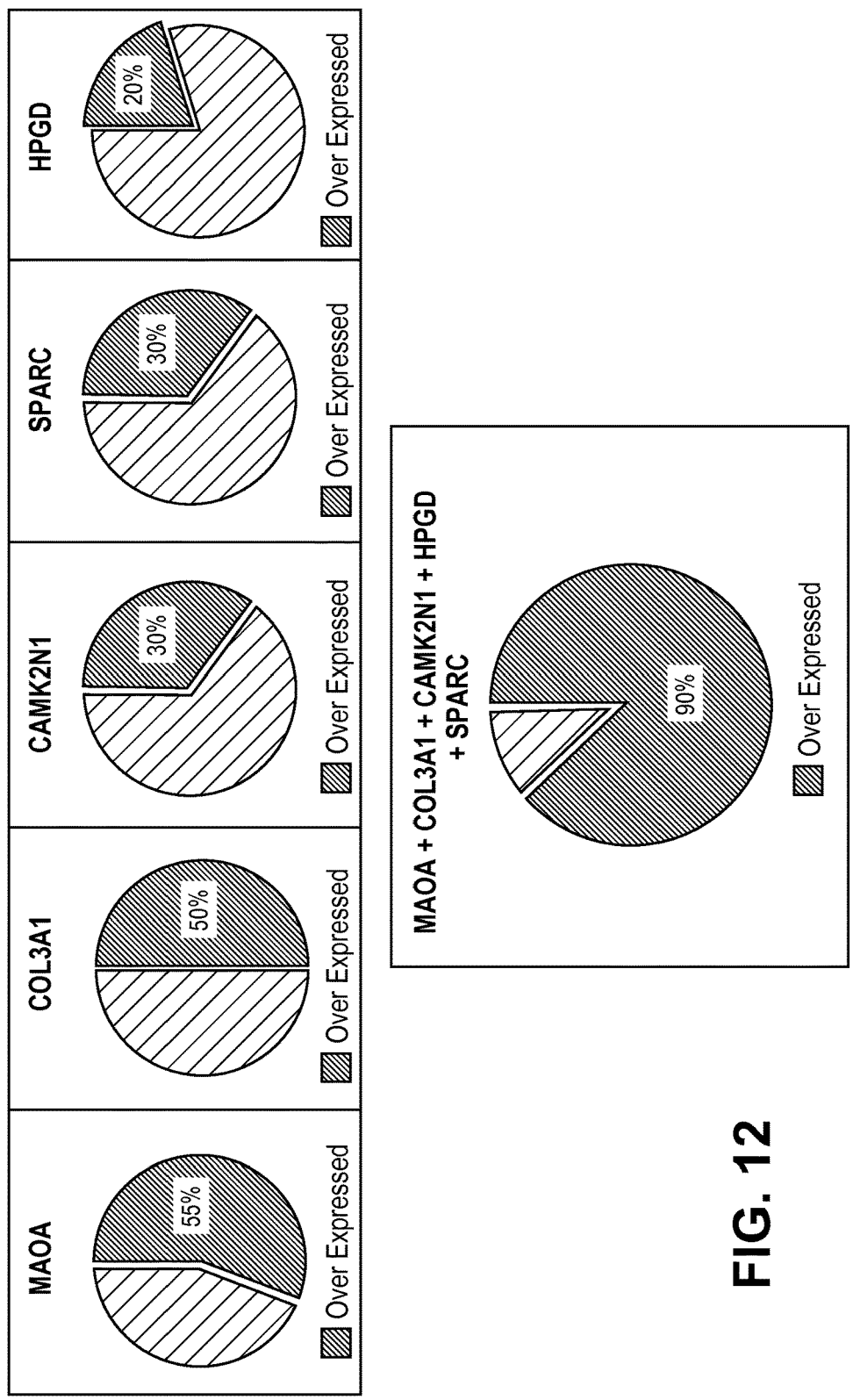
FIG. 12 shows the performance of a 5-gene panel (MAOA, COL3A1, CAMK2N1, SPARC, and HPGD) in patients with PD tumor (N=20). 90% of the patients over expressed at least one of the five genes.

A five-gene panel (CAMK2N1, MAOA, COL3A1, HPGD and SPARC) was identified as minimum prognostic gene panel with a performance of 90% over expression in PD tumors (FIG. 12). As a comparison, the same 5-gene panel has a 35% over expression in WD tumors. A heatmap was generated to illustrate the complementary nature of the gene panel in this cohort (FIG. 11).

REFERENCES

The following references are cited in the application and provide general information on the field of the invention and provide assays and other details discussed in the application. The following references are incorporated herein by reference in their entirety.

1. Punglia, R. S. et al. (2003) Effect of verification bias on screening for prostate cancer by measurement of prostate-specific antigen. N Engl J Med, 349, 335-42.
2. Sturgeon, C. M. et al. (2008) National Academy of Clinical Biochemistry laboratory medicine practice guidelines for use of tumor markers in testicular, prostate, colorectal, breast, and ovarian cancers. Clin Chem, 54, e11-79.
3. Catalona, W. J., et al. (1991) Measurement of prostate-specific antigen in serum as a screening test for prostate cancer. N Engl J Med, 324, 1156-61.
4. Groskopf, J., et al. (2006) APTIMA PCA3 molecular urine test: development of a method to aid in the diagnosis of prostate cancer. Clin Chem, 52, 1089-95.
5. Madden, T., et al. (2011) Infective complications after transrectal ultrasound-guided prostate biopsy following a new protocol for antibiotic prophylaxis aimed at reducing hospital-acquired infections. BJU Int.
6. Rubin, M. A., et al. (2002) alpha-Methylacyl coenzyme A racemase as a tissue biomarker for prostate cancer. JAMA.
7. CA DeRosa, et al. (2012) Elevated osteonectin/SPARC expression in primary prostate cancer predicts metastatic progression, Prostate Cancer and Prostatic Diseases, (15):150-56.
8. Ahmed A. Mohamed et al. (2011) ERG oncogene modulates prostaglandin signaling in prostate cancer cells, Cancer Biology & Therapy 11(4):1-8
9. Gary K Geiss, et al. (2008) Direct multiplexed measurement of gene expression with color-coded probe pairs, Nature Biotechnology 26:317-25.
10. Paolo Fortina and Saul Surrey, (2008) Digital mRNA Profiling, Nature Biotechnology 26:317-25.

What is claimed:

1. An array comprising (a) a substrate, and (b) at least ten different addressable elements, wherein each different addressable element comprises at least one polynucleotide probe for detecting the expression of an mRNA transcript of one of the following human genes: ERG, CLDN8, CACNA1D, HOXC6, TMEFF2, NPY, BICD1, OR51E1, OR51E2, and FOLH1, wherein the array comprises no more than 500 addressable elements.

2. The array of claim 1, wherein the array comprises no more than 1000 polynucleotide probes.

3. The array of claim 1, wherein the array comprises no more than 250 addressable elements.

4. The array of claim 1, wherein the array comprises no more than 100 addressable elements.

5. The array of claim 1, wherein the array comprises no more than 50 addressable elements.

6. The array of claim 1, wherein the array comprises no more than 25 addressable elements.

7. A method of detecting a combination of gene expression levels, which method comprises:
    measuring the expression level of the following human genes: ERG, CLDN8, CACNA1D, HOXC6, TMEFF2, NPY, BICD1, OR51E1, OR51E2, and FOLH1 in a biological sample to obtain a gene expression profile.

8. The method of claim 7, wherein the biological sample comprises prostate cells, prostate tissue, blood, serum, plasma, urine, saliva, or prostatic fluid.

9. The method of claim 7, wherein the measuring step comprises measuring nucleic acid levels.

10. The method of claim 7, wherein the measuring step comprises measuring protein levels.

11. The method of claim 10, wherein the protein levels are measured using immunohistochemistry.

* * * * *